US010221429B2

(12) United States Patent
Thayer et al.

(10) Patent No.: US 10,221,429 B2
(45) Date of Patent: Mar. 5, 2019

(54) TOXIN GENES AND METHODS FOR THEIR USE

(71) Applicants: BAYER CROPSCIENCE LP, Research Triangle Park, NC (US); Athenix Corp., Morrisville, NC (US)

(72) Inventors: Rebecca Thayer, Morrisville, NC (US); Kimberly S. Sampson, Durham, NC (US); Duane Lehtinen, Cary, NC (US); Cheryl Peters, Raleigh, NC (US); Kira Roberts, Bahama, NC (US); Leonardo Magalhaes, Durham, NC (US); Ethan Dunn, Durham, NC (US)

(73) Assignee: Bayer CropScience LP, Research Triangle Park, NC (US)

( * ) Notice: Subject to any disclaimer, the term of this patent is extended or adjusted under 35 U.S.C. 154(b) by 266 days.

(21) Appl. No.: 14/773,015

(22) PCT Filed: Mar. 6, 2014

(86) PCT No.: PCT/US2014/021021
§ 371 (c)(1),
(2) Date: Sep. 4, 2015

(87) PCT Pub. No.: WO2014/138339
PCT Pub. Date: Sep. 12, 2014

(65) Prior Publication Data

US 2016/0017363 A1 Jan. 21, 2016

Related U.S. Application Data

(60) Provisional application No. 61/774,110, filed on Mar. 7, 2013, provisional application No. 61/774,627, filed on Mar. 8, 2013, provisional application No. 61/774,629, filed on Mar. 8, 2013, provisional application No. 61/774,635, filed on Mar. 8, 2013, provisional application No. 61/774,638, filed on Mar. 8, 2013, provisional application No. 61/774,642, filed on Mar. 8, 2013, provisional application No. 61/774,645, filed on Mar. 8, 2013, provisional application No. 61/774,647, filed on Mar. 8, 2013, provisional application No. 61/774,650, filed on Mar. 8, 2013, provisional application No. 61/774,655, filed on Mar. 8, 2013, provisional application No. 61/774,659, filed on Mar. 8, 2013.

(51) Int. Cl.
*C12N 15/82* (2006.01)
*C07K 14/325* (2006.01)
*A01N 63/02* (2006.01)
*A01N 37/46* (2006.01)

(52) U.S. Cl.
CPC ......... *C12N 15/8286* (2013.01); *A01N 37/46* (2013.01); *A01N 63/02* (2013.01); *C07K 14/325* (2013.01); *Y02A 40/162* (2018.01)

(58) Field of Classification Search
None
See application file for complete search history.

(56) References Cited

U.S. PATENT DOCUMENTS

2011/0203015 A1* 8/2011 Sampson ............... A01N 37/46 800/279

OTHER PUBLICATIONS

Argôlo-Filho & Loguercio, Insects 5:62-91 (2014).*

* cited by examiner

Primary Examiner — Russell T Boggs

(57) ABSTRACT

Compositions and methods for conferring pesticidal activity to bacteria, plants, plant cells, tissues and seeds are provided. Compositions comprising a coding sequence for a toxin polypeptide are provided. The coding sequences can be used in DNA constructs or expression cassettes for transformation and expression in plants and bacteria. Compositions also comprise transformed bacteria, plants, plant cells, tissues, and seeds. In particular, isolated toxin nucleic acid molecules are provided. Additionally, amino acid sequences corresponding to the polynucleotides are encompassed, and antibodies specifically binding to those amino acid sequences. In particular, the present invention provides for isolated nucleic acid molecules comprising nucleotide sequences encoding the amino acid sequence shown in SEQ ID NO:21-74, or the nucleotide sequence set forth in SEQ ID NO: 1-20, as well as variants and fragments thereof.

18 Claims, No Drawings

Specification includes a Sequence Listing.

TOXIN GENES AND METHODS FOR THEIR USE

CROSS REFERENCE TO RELATED APPLICATIONS

This application claims the benefit of U.S. Provisional Application Ser. No. 61/774,110, filed Mar. 7, 2013 and U.S. Provisional Application Ser. Nos. 61/774,627; 61/774,629; 61/774,635; 61/774,638; 61/774,642; 61/774,645; 61/774,647; 61/774,650; 61/774,655; and 61/774,659, each of which was filed on Mar. 8, 2013, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "APA13-6008US01_SEQLIST.txt", created on Mar. 5, 2014, and having a size of 411 kilobytes and is filed concurrently with the specification. The sequence listing contained in this ASCII formatted document is part of the specification and is herein incorporated by reference in its entirety.

FIELD OF THE INVENTION

This invention relates to the field of molecular biology. Provided are novel genes that encode pesticidal proteins. These proteins and the nucleic acid sequences that encode them are useful in preparing pesticidal formulations and in the production of transgenic pest-resistant plants.

BACKGROUND OF THE INVENTION

*Bacillus thuringiensis* is a Gram-positive spore forming soil bacterium characterized by its ability to produce crystalline inclusions that are specifically toxic to certain orders and species of insects, but are harmless to plants and other non-targeted organisms. For this reason, compositions including *Bacillus thuringiensis* strains or their insecticidal proteins can be used as environmentally-acceptable insecticides to control agricultural insect pests or insect vectors for a variety of human or animal diseases.

Crystal (Cry) proteins (delta-endotoxins) from *Bacillus thuringiensis* have potent insecticidal activity against predominantly Lepidopteran, Hemipteran, Dipteran, and Coleopteran larvae. These proteins also have shown activity against Hymenoptera, Homoptera, Phthiraptera, Mallophaga, and Acari pest orders, as well as other invertebrate orders such as Nemathelminthes, Platyhelminthes, and Sarcomastigorphora (Feitelson (1993) The *Bacillus Thuringiensis* family tree. In Advanced Engineered Pesticides, Marcel Dekker, Inc., New York, N.Y.) These proteins were originally classified as CryI to CryV based primarily on their insecticidal activity. The major classes were Lepidoptera-specific (I), Lepidoptera- and Diptera-specific (II), Coleoptera-specific (III), Diptera-specific (IV), and nematode-specific (V) and (VI). The proteins were further classified into subfamilies; more highly related proteins within each family were assigned divisional letters such as Cry1A, Cry1B, Cry1C, etc. Even more closely related proteins within each division were given names such as Cry1C1, Cry1C2, etc.

A nomenclature was described for the Cry genes based upon amino acid sequence homology rather than insect target specificity (Crickmore et al. (1998) *Microbiol. Mol. Biol. Rev.* 62:807-813). In this classification, each toxin is assigned a unique name incorporating a primary rank (an Arabic number), a secondary rank (an uppercase letter), a tertiary rank (a lowercase letter), and a quaternary rank (another Arabic number). Roman numerals have been exchanged for Arabic numerals in the primary rank. Proteins with less than 45% sequence identity have different primary ranks, and the criteria for secondary and tertiary ranks are 78% and 95%, respectively.

The crystal protein does not exhibit insecticidal activity until it has been ingested and solubilized in the insect midgut. The ingested protoxin is hydrolyzed by proteases in the insect digestive tract to an active toxic molecule. (Höfte and Whiteley (1989) *Microbiol. Rev.* 53:242-255). This toxin binds to apical brush border receptors in the midgut of the target larvae and inserts into the apical membrane creating ion channels or pores, resulting in larval death.

Delta-endotoxins generally have five conserved sequence domains, and three conserved structural domains (see, for example, de Maagd et al. (2001) *Trends Genetics* 17:193-199). The first conserved structural domain consists of seven alpha helices and is involved in membrane insertion and pore formation. Domain II consists of three beta-sheets arranged in a Greek key configuration, and domain III consists of two antiparallel beta-sheets in "jelly-roll" formation (de Maagd et al., 2001, supra). Domains II and III are involved in receptor recognition and binding, and are therefore considered determinants of toxin specificity.

Aside from delta-endotoxins, there are several other known classes of pesticidal protein toxins. The VIP1/VIP2 toxins (see, for example, U.S. Pat. No. 5,770,696) are binary pesticidal toxins that exhibit strong activity on insects by a mechanism believed to involve receptor-mediated endocytosis followed by cellular toxification, similar to the mode of action of other binary ("A/B") toxins. A/B toxins such as VIP, C2, CDT, CST, or the *B. anthracis* edema and lethal toxins initially interact with target cells via a specific, receptor-mediated binding of "B" components as monomers. These monomers then form homoheptamers. The "B" heptamer-receptor complex then acts as a docking platform that subsequently binds and allows the translocation of an enzymatic "A" component(s) into the cytosol via receptor-mediated endocytosis. Once inside the cell's cytosol, "A" components inhibit normal cell function by, for example, ADP-ribosylation of G-actin, or increasing intracellular levels of cyclic AMP (cAMP). See Barth et al. (2004) *Microbiol Mol Biol Rev* 68:373-402.

The intensive use of *B. thuringiensis*-based insecticides has already given rise to resistance in field populations of the diamondback moth, *Plutella xylostella* (Ferre and Van Rie (2002) Annu Rev. Entomol. 47:501-533). The most common mechanism of resistance is the reduction of binding of the toxin to its specific midgut receptor(s). This may also confer cross-resistance to other toxins that share the same receptor (Ferre and Van Rie (2002)).

Because of the devastation that insects can confer, and the improvement in yield by controlling insect pests, there is a continual need to discover new forms of pesticidal toxins.

SUMMARY OF INVENTION

Compositions and methods for conferring pesticidal activity to bacteria, plants, plant cells, tissues and seeds are provided. Compositions include nucleic acid molecules encoding sequences for pesticidal and insectidal polypeptides, vectors comprising those nucleic acid molecules, and host cells comprising the vectors. Compositions also include the pesticidal polypeptide sequences and antibodies to those polypeptides. The nucleotide sequences can be used in DNA constructs or expression cassettes for transformation and expression in organisms, including microorganisms and plants. The nucleotide or amino acid sequences may be synthetic sequences that have been designed for expression in an organism including, but not limited to, a microorganism or a plant. Compositions also comprise bacteria, plants, plant cells, tissues, and seeds comprising the nucleotide sequence of the invention.

In particular, isolated or recombinant nucleic acid molecules are provided that encode a pesticidal protein. Additionally, amino acid sequences corresponding to the pesticidal protein are encompassed. In particular, the present invention provides for an isolated or recombinant nucleic acid molecule comprising a nucleotide sequence encoding the amino acid sequence shown in SEQ ID NO:21-74 or a nucleotide sequence set forth in SEQ ID NO:1-20, as well as biologically-active variants and fragments thereof. Nucleotide sequences that are complementary to a nucleotide sequence of the invention, or that hybridize to a sequence of the invention or a complement thereof are also encompassed. Further provided are vectors, host cells, plants, and seeds comprising the nucleotide sequences of the invention, or nucleotide sequences encoding the amino acid sequences of the invention, as well as biologically-active variants and fragments thereof.

Methods are provided for producing the polypeptides of the invention, and for using those polypeptides for controlling or killing a lepidopteran, hemipteran, coleopteran, nematode, or dipteran pest. Methods and kits for detecting the nucleic acids and polypeptides of the invention in a sample are also included.

The compositions and methods of the invention are useful for the production of organisms with enhanced pest resistance or tolerance. These organisms and compositions comprising the organisms are desirable for agricultural purposes. The compositions of the invention are also useful for generating altered or improved proteins that have pesticidal activity, or for detecting the presence of pesticidal proteins or nucleic acids in products or organisms.

DETAILED DESCRIPTION

The present invention is drawn to compositions and methods for regulating pest resistance or tolerance in organisms, particularly plants or plant cells. By "resistance" is intended that the pest (e.g., insect) is killed upon ingestion or other contact with the polypeptides of the invention. By "tolerance" is intended an impairment or reduction in the movement, feeding, reproduction, or other functions of the pest. The methods involve transforming organisms with a nucleotide sequence encoding a pesticidal protein of the invention. In particular, the nucleotide sequences of the invention are useful for preparing plants and microorganisms that possess pesticidal activity. Thus, transformed bacteria, plants, plant cells, plant tissues and seeds are provided. Compositions are pesticidal nucleic acids and proteins of *Bacillus* or other species. The sequences find use in the construction of expression vectors for subsequent transformation into organisms of interest, as probes for the isolation of other homologous (or partially homologous) genes, and for the generation of altered pesticidal proteins by methods known in the art, such as domain swapping or DNA shuffling, for example, with members of the Cry1, Cry2, and Cry9 families of endotoxins. The proteins find use in controlling or killing lepidopteran, hemipteran, coleopteran, dipteran, and nematode pest populations and for producing compositions with pesticidal activity.

By "pesticidal toxin" or "pesticidal protein" is intended a toxin that has toxic activity against one or more pests, including, but not limited to, members of the Lepidoptera, Diptera, and Coleoptera orders, or the Nematoda phylum, or a protein that has homology to such a protein. Pesticidal proteins have been isolated from organisms including, for example, *Bacillus* sp., *Clostridium bifermentans* and *Paenibacillus popilliae*. Pesticidal proteins include amino acid sequences deduced from the full-length nucleotide sequences disclosed herein, and amino acid sequences that are shorter than the full-length sequences, either due to the use of an alternate downstream start site, or due to processing that produces a shorter protein having pesticidal activity. Processing may occur in the organism the protein is expressed in, or in the pest after ingestion of the protein.

Pesticidal proteins encompass delta-endotoxins. Delta-endotoxins include proteins identified as cry1 through cry72, cyt1 and cyt2, and Cyt-like toxin. There are currently over 250 known species of delta-endotoxins with a wide range of specificities and toxicities. For an expansive list see Crickmore et al. (1998), *Microbiol. Mol. Biol. Rev.* 62:807-813, and for regular updates see Crickmore et al. (2003) "*Bacillus thuringiensis* toxin nomenclature," at www.biols.susx.ac.uk/Home/Neil_Crickmore/Bt/index.

Thus, provided herein are novel isolated or recombinant nucleotide sequences that confer pesticidal activity. These nucleotide sequences encode polypeptides with homology to known delta-endotoxins or binary toxins. Also provided are the amino acid sequences of the pesticidal proteins. The protein resulting from translation of this gene allows cells to control or kill pests that ingest it.

Nucleic Acid Molecules, and Variants and Fragments Thereof

One aspect of the invention pertains to isolated or recombinant nucleic acid molecules comprising nucleotide sequences encoding pesticidal proteins and polypeptides or biologically active portions thereof, as well as nucleic acid molecules sufficient for use as hybridization probes to identify nucleic acid molecules encoding proteins with regions of sequence homology. Also encompassed herein are nucleotide sequences capable of hybridizing to the nucleotide sequences of the invention under stringent conditions as defined elsewhere herein. As used herein, the term "nucleic acid molecule" is intended to include DNA molecules (e.g., recombinant DNA, cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. The term "recombinant" encompasses polynucleotides or polypeptides that have been manipulated with respect to the native polynucleotide or polypeptide, such that the polynucleotide or polypeptide differs (e.g., in chemical composition or structure) from what is occurring in nature. In another embodiment, a "recombinant" polynucleotide is free of internal sequences (i.e. introns) that naturally occur in the genomic DNA of the organism from which the polynucleotide is derived. A typical example of such polynucleotide is a so-called Complementary DNA (cDNA).

An isolated or recombinant nucleic acid (or DNA) is used herein to refer to a nucleic acid (or DNA) that is no longer in its natural environment, for example in an in vitro or in a recombinant bacterial or plant host cell. In some embodiments, an isolated or recombinant nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated delta-endotoxin encoding nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. In various embodiments, a delta-endotoxin protein that is substantially free of cellular material includes preparations of protein having less than about 30%, 20%, 10%, or 5% (by dry weight) of non-delta-endotoxin protein (also referred to herein as a "contaminating protein").

Nucleotide sequences encoding the proteins of the present invention include the sequence set forth in SEQ ID NO:1-20, and variants, fragments, and complements thereof. By "complement" is intended a nucleotide sequence that is sufficiently complementary to a given nucleotide sequence such that it can hybridize to the given nucleotide sequence to thereby form a stable duplex. The corresponding amino acid sequences for the pesticidal proteins encoded by these nucleotide sequences are set forth in SEQ ID NO:21-74.

Nucleic acid molecules that are fragments of these nucleotide sequences encoding pesticidal proteins are also encompassed by the present invention. By "fragment" is intended a portion of the nucleotide sequence encoding a pesticidal protein. A fragment of a nucleotide sequence may encode a biologically active portion of a pesticidal protein, or it may be a fragment that can be used as a hybridization probe or PCR primer using methods disclosed below. Nucleic acid molecules that are fragments of a nucleotide sequence encoding a pesticidal protein comprise at least about 50, 100, 200, 300, 400, 500, 600, 700, 800, 900, 1000, 1100, 1200, 1300, 1350, 1400 contiguous nucleotides, or up to the number of nucleotides present in a full-length nucleotide sequence encoding a pesticidal protein disclosed herein, depending upon the intended use. By "contiguous" nucleotides is intended nucleotide residues that are immediately adjacent to one another. Fragments of the nucleotide sequences of the present invention will encode protein fragments that retain the biological activity of the pesticidal protein and, hence, retain pesticidal activity. Thus, biologically-active fragments of the polypeptides disclosed herein are also encompassed. By "retains activity" is intended that the fragment will have at least about 30%, at least about 50%, at least about 70%, 80%, 90%, 95% or higher of the pesticidal activity of the pesticidal protein. In one embodiment, the pesticidal activity is coleoptericidal activity. In another embodiment, the pesticidal activity is lepidoptericidal activity. In another embodiment, the pesticidal activity is nematocidal activity. In another embodiment, the pesticidal activity is diptericidal activity. In another embodiment, the pesticidal activity is hemiptericidal activity. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

A fragment of a nucleotide sequence encoding a pesticidal protein that encodes a biologically active portion of a protein of the invention will encode at least about 15, 25, 30, 50, 75, 100, 125, 150, 175, 200, 250, 300, 350, 400, 450, 500, 550, 600, 650, 700, 750, 800, 850, 900, 950, 1000, 1050, 1100, 1150, 1200 contiguous amino acids, or up to the total number of amino acids present in a full-length pesticidal protein of the invention. In some embodiments, the fragment is a proteolytic cleavage fragment. For example, the proteolytic cleavage fragment may have an N-terminal or a C-terminal truncation of at least about 100 amino acids, about 120, about 130, about 140, about 150, or about 160 amino acids relative to SEQ ID NO:21-74. In some embodiments, the fragments encompassed herein result from the removal of the C-terminal crystallization domain, e.g., by proteolysis or by insertion of a stop codon in the coding sequence. See, for example, the truncated amino acid sequences set forth in SEQ ID NO: 25, 26, 39-45, 49-51, 58, 63-64, 66, 68, and 72-74. It will be understood that the truncation site may vary by 1, 2, 3, 4, 5, 6, 7, 8, 9, 10, 11, 12, 13, 14, 15, or more amino acids on either side of the truncation site represented by the terminus of SEQ ID NO:25, 26, 39-45, 49-51, 58, 63-64, 66, 68, or 72-74 (compared to the corresponding full-length sequence).

Preferred pesticidal proteins of the present invention are encoded by a nucleotide sequence sufficiently identical to the nucleotide sequence of SEQ ID NO:1-20, or the pesticidal proteins are sufficiently identical to the amino acid sequence set forth in SEQ ID NO:21-74. By "sufficiently identical" is intended an amino acid or nucleotide sequence that has at least about 60% or 65% sequence identity, about 70% or 75% sequence identity, about 80% or 85% sequence identity, about 90%, 91%, 92%, 93%, 94%, 95%, 96%, 97%, 98%, 99% or greater sequence identity compared to a reference sequence using one of the alignment programs described herein using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. In another embodiment, the percent identity is calculated across the entirety of the reference sequence (i.e., the sequence disclosed herein as any of SEQ ID NO:1-74). The percent identity between two sequences can be determined using techniques similar to those described below, with or without allowing gaps. In calculating percent identity, typically exact matches are counted. A gap, i.e. a position in an alignment where a residue is present in one sequence but not in the other, is regarded as a position with non-identical residues.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN and BLASTX programs of Altschul et al. (1990) *J. Mol. Biol.* 215:403. BLAST nucleotide searches can be performed with the BLASTN program, score=100, wordlength=12, to obtain nucleotide sequences homologous to pesticidal-like nucleic acid molecules of the invention. BLAST protein searches can be performed with the BLASTX program, score=50, wordlength=3, to obtain amino acid sequences homologous to pesticidal protein molecules of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. Alignment may also be performed manually by inspection.

Another non-limiting example of a mathematical algorithm utilized for the comparison of sequences is the ClustalW algorithm (Higgins et al. (1994) *Nucleic Acids Res.* 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, Calif.). After alignment of amino acid sequences with ClustalW, the percent amino acid identity can be assessed. A non-limiting example of a software program useful for analysis of ClustalW alignments is GENEDOC™. GENEDOC™ (Karl Nicholas) allows assessment of amino acid (or DNA) similarity and identity between multiple proteins. Another non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG Wisconsin Genetics Software Package, Version 10 (available from Accelrys, Inc., 9685 Scranton Rd., San Diego, Calif., USA). When utilizing the ALIGN program for comparing amino acid sequences, a PAM120 weight residue table, a gap length penalty of 12, and a gap penalty of 4 can be used.

Unless otherwise stated, GAP Version 10, which uses the algorithm of Needleman and Wunsch (1970) *J. Mol. Biol.* 48(3):443-453, will be used to determine sequence identity or similarity using the following parameters: % identity and % similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent programs may also be used. By "equivalent program" is intended any sequence comparison program that, for any two sequences in question, generates an alignment having identical nucleotide residue matches and an identical percent sequence identity when compared to the corresponding alignment generated by GAP Version 10.

The invention also encompasses variant nucleic acid molecules. "Variants" of the pesticidal protein encoding nucleotide sequences include those sequences that encode the pesticidal proteins disclosed herein but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the pesticidal proteins disclosed in the present invention as discussed below. Variant proteins encompassed by the present invention are biologically active, that is they continue to possess the desired biological activity of the native protein, that is, pesticidal activity. By "retains activity" is intended that the variant will have at least about 30%, at least about 50%, at least about 70%, or at least about 80% of the pesticidal activity of the native protein. Methods for measuring pesticidal activity are well known in the art. See, for example, Czapla and Lang (1990) *J. Econ. Entomol.* 83: 2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

The skilled artisan will further appreciate that changes can be introduced by mutation of the nucleotide sequences of the invention thereby leading to changes in the amino acid sequence of the encoded pesticidal proteins, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, conservative amino acid substitutions may be made at one or more, predicted, nonessential amino acid residues. A "nonessential" amino acid residue is a residue that can be altered from the wild-type sequence of a pesticidal protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Delta-endotoxins generally have five conserved sequence domains, and three conserved structural domains (see, for example, de Maagd et al. (2001) *Trends Genetics* 17:193-199). The first conserved structural domain consists of seven alpha helices and is involved in membrane insertion and pore formation. Domain II consists of three beta-sheets arranged in a Greek key configuration, and domain III consists of two antiparallel beta-sheets in "jelly-roll" formation (de Maagd et al., 2001, supra). Domains II and III are involved in receptor recognition and binding, and are therefore considered determinants of toxin specificity.

Amino acid substitutions may be made in nonconserved regions that retain function. In general, such substitutions would not be made for conserved amino acid residues, or for amino acid residues residing within a conserved motif, where such residues are essential for protein activity. Examples of residues that are conserved and that may be essential for protein activity include, for example, residues that are identical between all proteins contained in an alignment of similar or related toxins to the sequences of the invention (e.g., residues that are identical in an alignment of homologous proteins). Examples of residues that are conserved but that may allow conservative amino acid substitutions and still retain activity include, for example, residues that have only conservative substitutions between all proteins contained in an alignment of similar or related toxins to the sequences of the invention (e.g., residues that have only conservative substitutions between all proteins contained in the alignment homologous proteins). However, one of skill in the art would understand that functional variants may have minor conserved or nonconserved alterations in the conserved residues.

Alternatively, variant nucleotide sequences can be made by introducing mutations randomly along all or part of the coding sequence, such as by saturation mutagenesis, and the resultant mutants can be screened for ability to confer pesticidal activity to identify mutants that retain activity. Following mutagenesis, the encoded protein can be expressed recombinantly, and the activity of the protein can be determined using standard assay techniques.

Using methods such as PCR, hybridization, and the like corresponding pesticidal sequences can be identified, such sequences having substantial identity to the sequences of the invention (e.g., at least about 70%, at least about 75%, 80%, 85%, 90%, 95% or more sequence identity across the entirety of the reference sequence) and having or conferring pesticidal activity. See, for example, Sambrook and Russell (2001) *Molecular Cloning: A Laboratory Manual.* (Cold Spring Harbor Laboratory Press, Cold Spring Harbor, N.Y.) and Innis, et al. (1990) *PCR Protocols: A Guide to Methods and Applications* (Academic Press, NY).

In a hybridization method, all or part of the pesticidal nucleotide sequence can be used to screen cDNA or genomic libraries. Methods for construction of such cDNA and genomic libraries are generally known in the art and are disclosed in Sambrook and Russell, 2001, supra. The so-called hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known pesticidal protein-encoding nucleotide sequence disclosed herein. Degenerate primers designed on the basis of conserved nucleotides or amino acid residues in the nucleotide sequence or encoded amino acid sequence can additionally be used. The probe typically comprises a region of nucleotide sequence that hybridizes under stringent conditions to at least about 12, at least about 25, at least about 50, 75, 100, 125, 150, 175, or 200 consecutive nucleotides of nucleotide sequence encoding a pesticidal protein of the invention or a fragment or variant thereof. Methods for the preparation of probes for hybridization are generally known in the art and are disclosed in Sambrook and Russell, 2001, supra herein incorporated by reference.

For example, an entire pesticidal sequence disclosed herein, or one or more portions thereof, may be used as a probe capable of specifically hybridizing to corresponding pesticidal protein-like sequences and messenger RNAs. To achieve specific hybridization under a variety of conditions, such probes include sequences that are unique and are preferably at least about 10 nucleotides in length, or at least about 20 nucleotides in length. Such probes may be used to amplify corresponding pesticidal sequences from a chosen organism or sample by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Cold Spring Harbor, N.Y.).

Thus, the present invention encompasses probes for hybridization, as well as nucleotide sequences capable of hybridization to all or a portion of a nucleotide sequence of the invention (e.g., at least about 300 nucleotides, at least about 400, at least about 500, 1000, 1200, 1500, 2000, 2500, 3000, 3500, or up to the full length of a nucleotide sequence disclosed herein). Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Cold Spring Harbor, N.Y.).

Isolated Proteins and Variants and Fragments Thereof

Pesticidal proteins are also encompassed within the present invention. By “pesticidal protein” is intended a protein having the amino acid sequence set forth in SEQ ID NO:21-74. Fragments, biologically active portions, and variants thereof are also provided, and may be used to practice the methods of the present invention. A “recombinant protein” or “recombinant polypeptide” is used to refer to a protein that is no longer in its natural environment and has been manipulated with respect to the native protein, such that the recombinant protein or recombinant polypeptide differs (e.g., in chemical composition or structure) from what is occurring in nature.

“Fragments” or “biologically active portions” include polypeptide fragments comprising amino acid sequences sufficiently identical to the amino acid sequence set forth in SEQ ID NO:21-74, and that exhibit pesticidal activity. A biologically active portion of a pesticidal protein can be a polypeptide that is, for example, 10, 25, 50, 100, 150, 200, 250, 300, 350, 400, 450, 500, 550, 600, 650, 700, 750, 800, 850, 900, 950, 1000, 1050, 1100, 1150, 1200, or more amino acids in length. Such biologically active portions can be prepared by recombinant techniques and evaluated for pesticidal activity. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety. As used here, a fragment comprises at least 8 contiguous amino acids of SEQ ID NO:21-74. The invention encompasses other fragments, however, such as any fragment in the protein greater than about 10, 20, 30, 50, 100, 150, 200, 250, 300, 350, 400, 450, 500, 550, 600, 650, 700, 750, 800, 850, 900, 950, 1000, 1050, 1100, 1150, 1200, or more amino acids in length.

By “variants” is intended proteins or polypeptides having an amino acid sequence that is at least about 60%, 65%, about 70%, 75%, about 80%, 85%, about 90%, 91%, 92%, 93%, 94%, 95%, 96%, 97%, 98% or 99% identical to the amino acid sequence of any of SEQ ID NO:21-74. Variants also include polypeptides encoded by a nucleic acid molecule that hybridizes to the nucleic acid molecule of SEQ ID NO:1-20, or a complement thereof, under stringent conditions. Variants include polypeptides that differ in amino acid sequence due to mutagenesis. Variant proteins encompassed by the present invention are biologically active, that is they continue to possess the desired biological activity of the native protein, that is, retaining pesticidal activity. In some embodiments, the variants have improved activity relative to the native protein. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

Bacterial genes, such as the axmi genes of this invention, quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. On rare occasions, translation in bacterial systems can initiate at a TTG codon, though in this event the TTG encodes a methionine. Furthermore, it is not often determined a priori which of these codons are used naturally in the bacterium. Thus, it is understood that use of one of the alternate methionine codons may also lead to generation of pesticidal proteins. These pesticidal proteins are encompassed in the present invention and may be used in the methods of the present invention. It will be understood that, when expressed in plants, it will be necessary to alter the alternate start codon to ATG for proper translation.

In various embodiments of the present invention, pesticidal proteins include amino acid sequences deduced from the full-length nucleotide sequences disclosed herein, and amino acid sequences that are shorter than the full-length sequences due to the use of an alternate downstream start site. Thus, the nucleotide sequence of the invention and/or vectors, host cells, and plants comprising the nucleotide sequence of the invention (and methods of making and using the nucleotide sequence of the invention) may comprise a nucleotide sequence encoding an amino acid sequence corresponding to the amino acid sequences referenced in Table 1.

Antibodies to the polypeptides of the present invention, or to variants or fragments thereof, are also encompassed. Methods for producing antibodies are well known in the art (see, for example, Harlow and Lane (1988) *Antibodies: A Laboratory Manual*, Cold Spring Harbor Laboratory, Cold Spring Harbor, N.Y.; U.S. Pat. No. 4,196,265).

Thus, one aspect of the invention concerns antibodies, single-chain antigen binding molecules, or other proteins that specifically bind to one or more of the protein or peptide molecules of the invention and their homologs, fusions or fragments. In a particularly preferred embodiment, the antibody specifically binds to a protein having the amino acid sequence set forth in SEQ ID NO:21-74 or a fragment thereof. In another embodiment, the antibody specifically binds to a fusion protein comprising an amino acid sequence selected from the amino acid sequence set forth in SEQ ID NO:21-74 or a fragment thereof.

Antibodies of the invention may be used to quantitatively or qualitatively detect the protein or peptide molecules of the invention, or to detect post translational modifications of the proteins. As used herein, an antibody or peptide is said to "specifically bind" to a protein or peptide molecule of the invention if such binding is not competitively inhibited by the presence of non-related molecules.

The antibodies of the invention may be contained within a kit useful for detection of the protein or peptide molecules of the invention. The invention further comprises a method of detecting the protein or peptide molecule of the invention (particularly a protein encoded by the amino acid sequence set forth in SEQ ID NO:21-74, including variants or fragments thereof that are capable of specifically binding to the antibody of the invention) comprising contacting a sample with the antibody of the invention and determining whether the sample contains the protein or peptide molecule of the invention. Methods for utilizing antibodies for the detection of a protein or peptide of interest are known in the art.

Altered or Improved Variants

It is recognized that DNA sequences of a pesticidal protein may be altered by various methods, and that these alterations may result in DNA sequences encoding proteins with amino acid sequences different than that encoded by a pesticidal protein of the present invention. This protein may be altered in various ways including amino acid substitutions, deletions, truncations, and insertions of one or more amino acids of SEQ ID NO:21-74, including up to about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 100, about 105, about 110, about 115, about 120, about 125, about 130, about 135, about 140, about 145, about 150, about 155, or more amino acid substitutions, deletions or insertions. Methods for such manipulations are generally known in the art. For example, amino acid sequence variants of a pesticidal protein can be prepared by mutations in the DNA. This may also be accomplished by one of several forms of mutagenesis and/or in directed evolution. In some aspects, the changes encoded in the amino acid sequence will not substantially affect the function of the protein. Such variants will possess the desired pesticidal activity. However, it is understood that the ability of a pesticidal protein to confer pesticidal activity may be improved by the use of such techniques upon the compositions of this invention. For example, one may express a pesticidal protein in host cells that exhibit high rates of base misincorporation during DNA replication, such as XL-1 Red (Stratagene, La Jolla, Calif.). After propagation in such strains, one can isolate the DNA (for example by preparing plasmid DNA, or by amplifying by PCR and cloning the resulting PCR fragment into a vector), culture the pesticidal protein mutations in a non-mutagenic strain, and identify mutated genes with pesticidal activity, for example by performing an assay to test for pesticidal activity. Generally, the protein is mixed and used in feeding assays. See, for example Marrone et al. (1985) *J. of Economic Entomology* 78:290-293. Such assays can include contacting plants with one or more pests and determining the plant's ability to survive and/or cause the death of the pests. Examples of mutations that result in increased toxicity are found in Schnepf et al. (1998) *Microbiol. Mol. Biol. Rev.* 62:775-806.

Alternatively, alterations may be made to the protein sequence of many proteins at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity, or epitope to facilitate either protein purification, protein detection, or other experimental uses known in the art (3) target secretion or translation of a protein to a subcellular organelle, such as the periplasmic space of Gram-negative bacteria, or the endoplasmic reticulum of eukaryotic cells, the latter of which often results in glycosylation of the protein.

Variant nucleotide and amino acid sequences of the present invention also encompass sequences derived from mutagenic and recombinogenic procedures such as DNA shuffling. With such a procedure, one or more different pesticidal protein coding regions can be used to create a new pesticidal protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a pesticidal gene of the invention and other known pesticidal genes to obtain a new gene coding for a protein with an improved property of interest, such as an increased insecticidal activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Domain swapping or shuffling is another mechanism for generating altered pesticidal proteins. Domains may be swapped between pesticidal proteins, resulting in hybrid or chimeric toxins with improved pesticidal activity or target spectrum. Methods for generating recombinant proteins and testing them for pesticidal activity are well known in the art (see, for example, Naimov et al. (2001) *Appl. Environ. Microbiol.* 67:5328-5330; de Maagd et al. (1996) *Appl. Environ. Microbiol.* 62:1537-1543; Ge et al. (1991) *J. Biol. Chem.* 266:17954-17958; Schnepf et al. (1990) *J. Biol. Chem.* 265:20923-20930; Rang et al. 91999) *Appl. Environ. Microbiol.* 65:2918-2925).

In yet another embodiment, variant nucleotide and/or amino acid sequences can be obtained using one or more of error-prone PCR, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, gene site saturation mutagenesis, permutational mutagenesis, synthetic ligation reassembly (SLR), recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation, and the like.

Vectors

A pesticidal sequence of the invention may be provided in an expression cassette for expression in a plant of interest. By "plant expression cassette" is intended a DNA construct that is capable of resulting in the expression of a protein from an open reading frame in a plant cell. Typically these contain a promoter and a coding sequence. Often, such constructs will also contain a 3' untranslated region. Such constructs may contain a "signal sequence" or "leader sequence" to facilitate co-translational or post-translational transport of the peptide to certain intracellular structures such as the chloroplast (or other plastid), endoplasmic reticulum, or Golgi apparatus.

By "signal sequence" is intended a sequence that is known or suspected to result in cotranslational or post-translational peptide transport across the cell membrane. In eukaryotes, this typically involves secretion into the Golgi apparatus, with some resulting glycosylation. Insecticidal toxins of bacteria are often synthesized as protoxins, which are protolytically activated in the gut of the target pest (Chang (1987) *Methods Enzymol.* 153:507-516). In some embodiments of the present invention, the signal sequence is located in the native sequence, or may be derived from a sequence of the invention. By "leader sequence" is intended any sequence that when translated, results in an amino acid sequence sufficient to trigger co-translational transport of the peptide chain to a subcellular organelle. Thus, this includes leader sequences targeting transport and/or glycosylation by passage into the endoplasmic reticulum, passage to vacuoles, plastids including chloroplasts, mitochondria, and the like.

By "plant transformation vector" is intended a DNA molecule that is necessary for efficient transformation of a plant cell. Such a molecule may consist of one or more plant expression cassettes, and may be organized into more than one "vector" DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a nucleic acid construct designed for transfer between different host cells. "Expression vector" refers to a vector that has the ability to incorporate, integrate and express heterologous DNA sequences or fragments in a foreign cell. The cassette will include 5' and/or 3' regulatory sequences operably linked to a sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. In some embodiments, the nucleotide sequence is operably linked to a heterologous promoter capable of directing expression of said nucleotide sequence in a host cell, such as a microbial host cell or a plant host cell. The cassette may additionally contain at least one additional gene to be cotransformed into the organism. Alternatively, the additional gene(s) can be provided on multiple expression cassettes.

In various embodiments, the nucleotide sequence of the invention is operably linked to a promoter, e.g., a plant promoter. "Promoter" refers to a nucleic acid sequence that functions to direct transcription of a downstream coding sequence. The promoter together with other transcriptional and translational regulatory nucleic acid sequences (also termed "control sequences") are necessary for the expression of a DNA sequence of interest.

Such an expression cassette is provided with a plurality of restriction sites for insertion of the pesticidal sequence to be under the transcriptional regulation of the regulatory regions.

The expression cassette will include in the 5'-3' direction of transcription, a transcriptional and translational initiation region (i.e., a promoter), a DNA sequence of the invention, and a translational and transcriptional termination region (i.e., termination region) functional in plants. The promoter may be native or analogous, or foreign or heterologous, to the plant host and/or to the DNA sequence of the invention. Additionally, the promoter may be the natural sequence or alternatively a synthetic sequence. Where the promoter is "native" or "homologous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention.

The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof). Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed host cell. That is, the genes can be synthesized using host cell-preferred codons for improved expression, or may be synthesized using codons at a host-preferred codon usage frequency. Generally, the GC content of the gene will be increased. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, U.S. Patent Publication No. 20090137409, and Murray et al. (1989) *Nucleic Acids Res.* 17:477-498, herein incorporated by reference.

In one embodiment, the pesticidal protein is targeted to the chloroplast for expression. In this manner, where the pesticidal protein is not directly inserted into the chloroplast, the expression cassette will additionally contain a nucleic acid encoding a transit peptide to direct the pesticidal protein to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

The pesticidal gene to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Plant Transformation

Methods of the invention involve introducing a nucleotide construct into a plant. By "introducing" is intended to present to the plant the nucleotide construct in such a manner that the construct gains access to the interior of a cell of the plant. The methods of the invention do not require that a particular method for introducing a nucleotide construct to a plant is used, only that the nucleotide construct gains access to the interior of at least one cell of the plant. Methods for introducing nucleotide constructs into plants are known in the art including, but not limited to, stable transformation methods, transient transformation methods, and virus-mediated methods.

By "plant" is intended whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen).

"Transgenic plants" or "transformed plants" or "stably transformed" plants or cells or tissues refers to plants that have incorporated or integrated exogenous nucleic acid sequences or DNA fragments into the plant cell. These nucleic acid sequences include those that are exogenous, or not present in the untransformed plant cell, as well as those that may be endogenous, or present in the untransformed plant cell. "Heterologous" generally refers to the nucleic acid sequences that are not endogenous to the cell or part of the native genome in which they are present, and have been added to the cell by infection, transfection, microinjection, electroporation, microprojection, or the like.

The transgenic plants of the invention express one or more of the novel toxin sequences disclosed herein. In some embodiments, the protein or nucleotide sequence of the invention is advantageously combined in plants with other genes which encode proteins or RNAs that confer useful agronomic properties to such plants. Among the genes which encode proteins or RNAs that confer useful agronomic properties on the transformed plants, mention can be made of the DNA sequences encoding proteins which confer tolerance to one or more herbicides, and others which confer tolerance to certain insects, those which confer tolerance to certain diseases, DNAs that encodes RNAs that provide nematode or insect control, and the like. Such genes are in particular described in published PCT Patent Applications WO91/02071 and WO95/06128 and in U.S. Pat. No. 7,923,602 and US Patent Application Publication No. 20100166723, each of which is herein incorporated by reference in its entirety.

Among the DNA sequences encoding proteins which confer tolerance to certain herbicides on the transformed plant cells and plants, mention can be made of a bar or PAT gene or the *Streptomyces coelicolor* gene described in WO2009/152359 which confers tolerance to glufosinate herbicides, a gene encoding a suitable EPSPS which confers tolerance to herbicides having EPSPS as a target, such as glyphosate and its salts (U.S. Pat. Nos. 4,535,060, 4,769,061, 5,094,945, 4,940,835, 5,188,642, 4,971,908, 5,145,783, 5,310,667, 5,312,910, 5,627,061, 5,633,435), a gene encoding glyphosate-n-acetyltransferase (for example, U.S. Pat. Nos. 8,222,489, 8,088,972, 8,044,261, 8,021,857, 8,008,547, 7,999,152, 7,998,703, 7,863,503, 7,714,188, 7,709,702, 7,666,644, 7,666,643, 7,531,339, 7,527,955, and 7,405,074), a gene encoding glyphosate oxydoreductase (for example, U.S. Pat. No. 5,463,175), or a gene encoding an HPPD inhibitor-tolerant protein (for example, the HPPD inhibitor tolerance genes described in WO 2004/055191, WO 199638567, U.S. Pat. No. 6,791,014, WO2011/068567, WO2011/076345, WO2011/085221, WO2011/094205, WO2011/068567, WO2011/094199, WO2011/094205, WO2011/145015, WO2012056401, and PCT/US2013/59598).

Among the DNA sequences encoding a suitable EPSPS which confer tolerance to the herbicides which have EPSPS as a target, mention will more particularly be made of the gene which encodes a plant EPSPS, in particular maize EPSPS, particularly a maize EPSPS which comprises two mutations, particularly a mutation at amino acid position 102 and a mutation at amino acid position 106 (WO2004/074443), and which is described in U.S. Pat. No. 6,566,587, hereinafter named double mutant maize EPSPS or 2mEPSPS, or the gene which encodes an EPSPS isolated from *Agrobacterium* and which is described by sequence ID No. 2 and sequence ID No. 3 of U.S. Pat. No. 5,633,435, also named CP4.

Among the DNA sequences encoding a suitable EPSPS which confer tolerance to the herbicides which have EPSPS as a target, mention will more particularly be made of the gene which encodes an EPSPS GRG23 from *Arthrobacter globiformis*, but also the mutants GRG23 ACE1, GRG23 ACE2, or GRG23 ACE3, particularly the mutants or variants of GRG23 as described in WO2008/100353, such as GRG23 (ace3)R173K of SEQ ID No. 29 in WO2008/100353.

In the case of the DNA sequences encoding EPSPS, and more particularly encoding the above genes, the sequence encoding these enzymes is advantageously preceded by a sequence encoding a transit peptide, in particular the "optimized transit peptide" described in U.S. Pat. Nos. 5,510,471 or 5,633,448.

Exemplary herbicide tolerance traits that can be combined with the nucleic acid sequence of the invention further include at least one ALS (acetolactate synthase) inhibitor (WO2007/024782); a mutated *Arabidopsis* ALS/AHAS gene (U.S. Pat. No. 6,855,533); genes encoding 2,4-D-monooxygenases conferring tolerance to 2,4-D (2,4-dichlorophenoxyacetic acid) by metabolization (U.S. Pat. No. 6,153,401); and, genes encoding Dicamba monooxygenases conferring tolerance to dicamba (3,6-dichloro-2-methoxybenzoic acid) by metabolization (US 2008/0119361 and US 2008/0120739).

In various embodiments, the nucleic acid of the invention is stacked with one or more herbicide tolerant genes, including one or more HPPD inhibitor herbicide tolerant genes, and/or one or more genes tolerant to glyphosate and/or glufosinate.

Among the DNA sequences encoding proteins concerning properties of tolerance to insects, mention will more particularly be made of the Bt proteins widely described in the literature and well known to those skilled in the art. Mention will also be made of proteins extracted from bacteria such as *Photorhabdus* (WO97/17432 & WO98/08932).

Among such DNA sequences encoding proteins of interest which confer novel properties of tolerance to insects, mention will more particularly be made of the Bt Cry or VIP proteins widely described in the literature and well known to those skilled in the art. These include the Cry1F protein or hybrids derived from a Cry1F protein (e.g., the hybrid Cry1A-Cry1F proteins described in U.S. Pat. Nos. 6,326,169; 6,281,016; 6,218,188, or toxic fragments thereof), the CryI A-type proteins or toxic fragments thereof, preferably the Cry1Ac protein or hybrids derived from the Cry1Ac protein (e.g., the hybrid Cry1Ab-Cry1Ac protein described in U.S. Pat. No. 5,880,275) or the Cry1Ab or Bt2 protein or insecticidal fragments thereof as described in EP451878, the Cry2Ae, Cry2Af or Cry2Ag proteins as described in WO2002/057664 or toxic fragments thereof, the Cry1A.105 protein described in WO 2007/140256 (SEQ ID No. 7) or a toxic fragment thereof, the VIP3Aa19 protein of NCBI accession ABG20428, the VIP3Aa20 protein of NCBI accession ABG20429 (SEQ ID No. 2 in WO 2007/142840), the VIP3A proteins produced in the COT202 or COT203 cotton events (WO2005/054479 and WO2005/054480, respectively), the Cry proteins as described in WO2001/47952, the VIP3Aa protein or a toxic fragment thereof as described in Estruch et al. (1996), *Proc Natl Acad Sci USA*. 28; 93(11):5389-94 and U.S. Pat. No. 6,291,156, the insecticidal proteins from *Xenorhabdus* (as described in WO98/50427), *Serratia* (particularly from *S. entomophila*) or *Photorhabdus* species strains, such as Tc-proteins from *Photorhabdus* as described in WO98/08932 (e.g., Waterfield et al., 2001, Appl Environ Microbiol. 67(11):5017-24; Ffrench-Constant and Bowen, 2000, Cell Mol Life Sci.; 57(5):828-33). Also any variants or mutants of any one of these proteins differing in some (1-10, preferably 1-5) amino acids from any of the above sequences, particularly the sequence of their toxic fragment, or which are fused to a transit peptide, such as a plastid transit peptide, or another protein or peptide, is included herein.

In various embodiments, the nucleic acid of the invention can be combined in plants with one or more genes conferring a desirable trait, such as herbicide tolerance, insect tolerance, drought tolerance, nematode control, water use efficiency, nitrogen use efficiency, improved nutritional value, disease resistance, improved photosynthesis, improved fiber quality, stress tolerance, improved reproduction, and the like.

Particularly useful transgenic events which may be combined with the genes of the current invention in plants of the same species (e.g., by crossing or by re-transforming a plant containing another transgenic event with a chimeric gene of the invention), include Event 531/PV-GHBK04 (cotton, insect control, described in WO2002/040677), Event 1143-14A (cotton, insect control, not deposited, described in WO2006/128569); Event 1143-51B (cotton, insect control, not deposited, described in WO2006/128570); Event 1445 (cotton, herbicide tolerance, not deposited, described in US-A 2002-120964 or WO2002/034946Event 17053 (rice, herbicide tolerance, deposited as PTA-9843, described in WO2010/117737); Event 17314 (rice, herbicide tolerance, deposited as PTA-9844, described in WO2010/117735); Event 281-24-236 (cotton, insect control—herbicide tolerance, deposited as PTA-6233, described in WO2005/103266 or US-A 2005-216969); Event 3006-210-23 (cotton, insect control—herbicide tolerance, deposited as PTA-6233, described in US-A 2007-143876 or WO2005/103266); Event 3272 (corn, quality trait, deposited as PTA-9972, described in WO2006/098952 or US-A 2006-230473); Event 33391 (wheat, herbicide tolerance, deposited as PTA-2347, described in WO2002/027004), Event 40416 (corn, insect control—herbicide tolerance, deposited as ATCC PTA-11508, described in WO 11/075593); Event 43A47 (corn, insect control—herbicide tolerance, deposited as ATCC PTA-11509, described in WO2011/075595); Event 5307 (corn, insect control, deposited as ATCC PTA-9561, described in WO2010/077816); Event ASR-368 (bent grass, herbicide tolerance, deposited as ATCC PTA-4816, described in US-A 2006-162007 or WO2004/053062); Event B16 (corn, herbicide tolerance, not deposited, described in US-A 2003-126634); Event BPS-CV 127-9 (soybean, herbicide tolerance, deposited as NCIMB No. 41603, described in WO2010/080829); Event BLR1 (oilseed rape, restoration of male sterility, deposited as NCIMB 41193, described in WO2005/074671), Event CE43-67B (cotton, insect control, deposited as DSM ACC2724, described in US-A 2009-217423 or WO2006/128573); Event CE44-69D (cotton, insect control, not deposited, described in US-A 2010-0024077); Event CE44-69D (cotton, insect control, not deposited, described in WO2006/128571); Event CE46-02A (cotton, insect control, not deposited, described in WO2006/128572); Event COT102 (cotton, insect control, not deposited, described in US-A 2006-130175 or WO2004/039986); Event COT202 (cotton, insect control, not deposited, described in US-A 2007-067868 or WO2005/054479); Event COT203 (cotton, insect control, not deposited, described in WO2005/054480); Event DAS21606-3/1606 (soybean, herbicide tolerance, deposited as PTA-11028, described in WO2012/033794), Event DAS40278 (corn, herbicide tolerance, deposited as ATCC PTA-10244, described in WO2011/022469); Event DAS-44406-6/pDAB8264.44.06.1 (soybean, herbicide tolerance, deposited as PTA-11336, described in WO2012/075426), Event DAS-14536-7/pDAB8291.45.36.2 (soybean, herbicide tolerance, deposited as PTA-11335, described in WO2012/075429), Event DAS-59122-7 (corn, insect control—herbicide tolerance, deposited as ATCC PTA 11384, described in US-A 2006-070139); Event DAS-59132 (corn, insect control—herbicide tolerance, not deposited, described in WO2009/100188); Event DAS68416 (soybean, herbicide tolerance, deposited as ATCC PTA-10442, described in WO2011/066384 or WO2011/066360); Event DP-098140-6 (corn, herbicide tolerance, deposited as ATCC PTA-8296, described in US-A 2009-137395 or WO 08/112019); Event DP-305423-1 (soybean, quality trait, not deposited, described in US-A 2008-312082 or WO2008/054747); Event DP-32138-1 (corn, hybridization system, deposited as ATCC PTA-9158, described in US-A 2009-0210970 or WO2009/103049); Event DP-356043-5 (soybean, herbicide tolerance, deposited as ATCC PTA-8287, described in US-A 2010-0184079 or WO2008/002872); Event EE-1 (brinjal, insect control, not deposited, described in WO 07/091277); Event FI117 (corn, herbicide tolerance, deposited as ATCC 209031, described in US-A 2006-059581 or WO 98/044140); Event FG72 (soybean, herbicide tolerance, deposited as PTA-11041, described in WO2011/063413), Event GA21 (corn, herbicide tolerance, deposited as ATCC 209033, described in US-A 2005-086719 or WO 98/044140); Event GG25 (corn, herbicide tolerance, deposited as ATCC 209032, described in US-A 2005-188434 or WO 98/044140); Event GHB119 (cotton, insect control—herbicide tolerance, deposited as ATCC PTA-8398, described in WO2008/151780); Event GHB614 (cotton, herbicide tolerance, deposited as ATCC PTA-6878, described in US-A 2010-050282 or WO2007/017186); Event GJ11 (corn, herbicide tolerance, deposited as ATCC 209030, described in US-A 2005-188434 or WO98/044140); Event GM RZ13 (sugar beet, virus resistance, deposited as NCIMB-41601, described in WO2010/076212); Event H7-1 (sugar beet, herbicide tolerance, deposited as NCIMB 41158 or NCIMB 41159, described in US-A 2004-172669 or WO 2004/074492); Event JOPLIN1 (wheat, disease tolerance, not deposited, described in US-A 2008-064032); Event LL27 (soybean, herbicide tolerance, deposited as NCIMB41658, described in WO2006/108674 or US-A 2008-320616); Event LL55 (soybean, herbicide tolerance, deposited as NCIMB 41660, described in WO 2006/108675 or US-A 2008-196127); Event LLcotton25 (cotton, herbicide tolerance, deposited as ATCC PTA-3343, described in WO2003/013224 or US-A 2003-097687);

Event LLRICE06 (rice, herbicide tolerance, deposited as ATCC 203353, described in U.S. Pat. No. 6,468,747 or WO2000/026345); Event LLRice62 (rice, herbicide tolerance, deposited as ATCC 203352, described in WO2000/026345), Event LLRICE601 (rice, herbicide tolerance, deposited as ATCC PTA-2600, described in US-A 2008-2289060 or WO2000/026356); Event LY038 (corn, quality trait, deposited as ATCC PTA-5623, described in US-A 2007-028322 or WO2005/061720); Event MIR162 (corn, insect control, deposited as PTA-8166, described in US-A 2009-300784 or WO2007/142840); Event MIR604 (corn, insect control, not deposited, described in US-A 2008-167456 or WO2005/103301); Event MON15985 (cotton, insect control, deposited as ATCC PTA-2516, described in US-A 2004-250317 or WO2002/100163); Event MON810 (corn, insect control, not deposited, described in US-A 2002-102582); Event MON863 (corn, insect control, deposited as ATCC PTA-2605, described in WO2004/011601 or US-A 2006-095986); Event MON87427 (corn, pollination control, deposited as ATCC PTA-7899, described in WO2011/062904); Event MON87460 (corn, stress tolerance, deposited as ATCC PTA-8910, described in WO2009/111263 or US-A 2011-0138504); Event MON87701 (soybean, insect control, deposited as ATCC PTA-8194, described in US-A 2009-130071 or WO2009/064652); Event MON87705 (soybean, quality trait—herbicide tolerance, deposited as ATCC PTA-9241, described in US-A 2010-0080887 or WO2010/037016); Event MON87708 (soybean, herbicide tolerance, deposited as ATCC PTA-9670, described in WO2011/034704); Event MON87712 (soybean, yield, deposited as PTA-10296, described in WO2012/051199), Event MON87754 (soybean, quality trait, deposited as ATCC PTA-9385, described in WO2010/024976); Event MON87769 (soybean, quality trait, deposited as ATCC PTA-8911, described in US-A 2011-0067141 or WO2009/102873); Event MON88017 (corn, insect control—herbicide tolerance, deposited as ATCC PTA-5582, described in US-A 2008-028482 or WO2005/059103); Event MON88913 (cotton, herbicide tolerance, deposited as ATCC PTA-4854, described in WO2004/072235 or US-A 2006-059590); Event MON88302 (oilseed rape, herbicide tolerance, deposited as PTA-10955, described in WO2011/153186), Event MON88701 (cotton, herbicide tolerance, deposited as PTA-11754, described in WO2012/134808), Event MON89034 (corn, insect control, deposited as ATCC PTA-7455, described in WO 07/140256 or US-A 2008-260932); Event MON89788 (soybean, herbicide tolerance, deposited as ATCC PTA-6708, described in US-A 2006-282915 or WO2006/130436); Event MS11 (oilseed rape, pollination control-herbicide tolerance, deposited as ATCC PTA-850 or PTA-2485, described in WO2001/031042); Event MS8 (oilseed rape, pollination control—herbicide tolerance, deposited as ATCC PTA-730, described in WO2001/041558 or US-A 2003-188347); Event NK603 (corn, herbicide tolerance, deposited as ATCC PTA-2478, described in US-A 2007-292854); Event PE-7 (rice, insect control, not deposited, described in WO2008/114282); Event RF3 (oilseed rape, pollination control—herbicide tolerance, deposited as ATCC PTA-730, described in WO2001/041558 or US-A 2003-188347); Event RT73 (oilseed rape, herbicide tolerance, not deposited, described in WO2002/036831 or US-A 2008-070260); Event SYHT0H2/SYN-000H2-5 (soybean, herbicide tolerance, deposited as PTA-11226, described in WO2012/082548), Event T227-1 (sugar beet, herbicide tolerance, not deposited, described in WO2002/44407 or US-A 2009-265817); Event T25 (corn, herbicide tolerance, not deposited, described in US-A 2001-029014 or WO2001/051654); Event T304-40 (cotton, insect control—herbicide tolerance, deposited as ATCC PTA-8171, described in US-A 2010-077501 or WO2008/122406); Event T342-142 (cotton, insect control, not deposited, described in WO2006/128568); Event TC1507 (corn, insect control—herbicide tolerance, not deposited, described in US-A 2005-039226 or WO2004/099447); Event VIP1034 (corn, insect control—herbicide tolerance, deposited as ATCC PTA-3925., described in WO2003/052073), Event 32316 (corn, insect control-herbicide tolerance, deposited as PTA-11507, described in WO2011/084632), Event 4114 (corn, insect control-herbicide tolerance, deposited as PTA-11506, described in WO2011/084621), event EE-GM3/FG72 (soybean, herbicide tolerance, ATCC Accession No PTA-11041) optionally stacked with event EE-GM1/LL27 or event EE-GM2/LL55 (WO2011/063413A2), event DAS-68416-4 (soybean, herbicide tolerance, ATCC Accession No PTA-10442, WO2011/066360A1), event DAS-68416-4 (soybean, herbicide tolerance, ATCC Accession No PTA-10442, WO2011/066384A1), event DP-040416-8 (corn, insect control, ATCC Accession No PTA-11508, WO2011/075593A1), event DP-043A47-3 (corn, insect control, ATCC Accession No PTA-11509, WO2011/075595A1), event DP-004114-3 (corn, insect control, ATCC Accession No PTA-11506, WO2011/084621A1), event DP-032316-8 (corn, insect control, ATCC Accession No PTA-11507, WO2011/084632A1), event MON-88302-9 (oilseed rape, herbicide tolerance, ATCC Accession No PTA-10955, WO2011/153186A1), event DAS-21606-3 (soybean, herbicide tolerance, ATCC Accession No. PTA-11028, WO2012/033794A2), event MON-87712-4 (soybean, quality trait, ATCC Accession No. PTA-10296, WO2012/051199A2), event DAS-44406-6 (soybean, stacked herbicide tolerance, ATCC Accession No. PTA-11336, WO2012/075426A1), event DAS-14536-7 (soybean, stacked herbicide tolerance, ATCC Accession No. PTA-11335, WO2012/075429A1), event SYN-000H2-5 (soybean, herbicide tolerance, ATCC Accession No. PTA-11226, WO2012/082548A2), event DP-061061-7 (oilseed rape, herbicide tolerance, no deposit No available, WO2012071039A1), event DP-073496-4 (oilseed rape, herbicide tolerance, no deposit No available, US2012131692), event 8264.44.06.1 (soybean, stacked herbicide tolerance, Accession No PTA-11336, WO2012075426A2), event 8291.45.36.2 (soybean, stacked herbicide tolerance, Accession No. PTA-11335, WO2012075429A2), event SYHT0H2 (soybean, ATCC Accession No. PTA-11226, WO2012/082548A2), event MON88701 (cotton, ATCC Accession No PTA-11754, WO2012/134808A1), event KK179-2 (alfalfa, ATCC Accession No PTA-11833, WO2013/003558A1), event pDAB8264.42.32.1 (soybean, stacked herbicide tolerance, ATCC Accession No PTA-11993, WO2013/010094A1), event MZDT09Y (corn, ATCC Accession No PTA-13025, WO2013/012775A1).

Transformation of plant cells can be accomplished by one of several techniques known in the art. The pesticidal gene of the invention may be modified to obtain or enhance expression in plant cells. Typically a construct that expresses such a protein would contain a promoter to drive transcription of the gene, as well as a 3' untranslated region to allow transcription termination and polyadenylation. The organization of such constructs is well known in the art. In some instances, it may be useful to engineer the gene such that the resulting peptide is secreted, or otherwise targeted within the plant cell. For example, the gene can be engineered to contain a signal peptide to facilitate transfer of the peptide to the endoplasmic reticulum. It may also be preferable to engineer the plant expression cassette to contain an intron, such that mRNA processing of the intron is required for expression.

Typically this "plant expression cassette" will be inserted into a "plant transformation vector". This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as "binary vectors." Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the pesticidal gene are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux (2000) *Trends in Plant Science* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g. Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plants are found in Ayres and Park (1994) *Critical Reviews in Plant Science* 13:219-239 and Bommineni and Jauhar (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

Transformation protocols as well as protocols for introducing nucleotide sequences into plants may vary depending on the type of plant or plant cell, i.e., monocot or dicot, targeted for transformation. Generation of transgenic plants may be performed by one of several methods, including, but not limited to, microinjection, electroporation, direct gene transfer, introduction of heterologous DNA by *Agrobacterium* into plant cells (*Agrobacterium*-mediated transformation), bombardment of plant cells with heterologous foreign DNA adhered to particles, ballistic particle acceleration, aerosol beam transformation (U.S. Published Application No. 20010026941; U.S. Pat. No. 4,945,050; International Publication No. WO 91/00915; U.S. Published Application No. 2002015066), Lec1 transformation, and various other non-particle direct-mediated methods to transfer DNA.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

Following integration of heterologous foreign DNA into plant cells, one then applies a maximum threshold level of appropriate selection in the medium to kill the untransformed cells and separate and proliferate the putatively transformed cells that survive from this selection treatment by transferring regularly to a fresh medium. By continuous passage and challenge with appropriate selection, one identifies and proliferates the cells that are transformed with the plasmid vector. Molecular and biochemical methods can then be used to confirm the presence of the integrated heterologous gene of interest into the genome of the transgenic plant.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Evaluation of Plant Transformation

Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell (2001) *Molecular Cloning: A Laboratory Manual*. Cold Spring Harbor Laboratory Press, Cold Spring Harbor, N.Y.). PCR is carried out using oligonucleotide primers specific to the gene of interest or *Agrobacterium* vector background, etc.

Plant transformation may be confirmed by Southern blot analysis of genomic DNA (Sambrook and Russell, 2001, supra). In general, total DNA is extracted from the transformant, digested with appropriate restriction enzymes, fractionated in an agarose gel and transferred to a nitrocellulose or nylon membrane. The membrane or "blot" is then probed with, for example, radiolabeled $^{32}P$ target DNA fragment to confirm the integration of introduced gene into the plant genome according to standard techniques (Sambrook and Russell, 2001, supra).

In Northern blot analysis, RNA is isolated from specific tissues of transformant, fractionated in a formaldehyde agarose gel, and blotted onto a nylon filter according to standard procedures that are routinely used in the art (Sambrook and Russell, 2001, supra). Expression of RNA encoded by the pesticidal gene is then tested by hybridizing the filter to a radioactive probe derived from a pesticidal gene, by methods known in the art (Sambrook and Russell, 2001, supra).

Western blot, biochemical assays and the like may be carried out on the transgenic plants to confirm the presence of protein encoded by the pesticidal gene by standard procedures (Sambrook and Russell, 2001, supra) using antibodies that bind to one or more epitopes present on the pesticidal protein.

Pesticidal Activity in Plants

In another aspect of the invention, one may generate transgenic plants expressing a pesticidal protein that has pesticidal activity. Methods described above by way of example may be utilized to generate transgenic plants, but the manner in which the transgenic plant cells are generated is not critical to this invention. Methods known or described in the art such as *Agrobacterium*-mediated transformation, biolistic transformation, and non-particle-mediated methods may be used at the discretion of the experimenter. Plants expressing a pesticidal protein may be isolated by common methods described in the art, for example by transformation of callus, selection of transformed callus, and regeneration of fertile plants from such transgenic callus. In such process, one may use any gene as a selectable marker so long as its expression in plant cells confers ability to identify or select for transformed cells.

A number of markers have been developed for use with plant cells, such as resistance to chloramphenicol, the aminoglycoside G418, hygromycin, or the like. Other genes that encode a product involved in chloroplast metabolism may also be used as selectable markers. For example, genes that provide resistance to plant herbicides such as glyphosate, bromoxynil, or imidazolinone may find particular use. Such genes have been reported (Stalker et al. (1985) *J. Biol. Chem.* 263:6310-6314 (bromoxynil resistance nitrilase gene); and Sathasivan et al. (1990) *Nucl. Acids Res.* 18:2188 (AHAS imidazolinone resistance gene). Additionally, the genes disclosed herein are useful as markers to assess transformation of bacterial or plant cells. Methods for detecting the presence of a transgene in a plant, plant organ (e.g., leaves, stems, roots, etc.), seed, plant cell, propagule, embryo or progeny of the same are well known in the art. In one embodiment, the presence of the transgene is detected by testing for pesticidal activity.

Fertile plants expressing a pesticidal protein may be tested for pesticidal activity, and the plants showing optimal activity selected for further breeding. Methods are available in the art to assay for pest activity. Generally, the protein is mixed and used in feeding assays. See, for example Marrone et al. (1985) *J. of Economic Entomology* 78:290-293.

The present invention may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, ornamentals, and conifers.

Vegetables include, but are not limited to, tomatoes, lettuce, green beans, lima beans, peas, and members of the genus *Curcumis* such as cucumber, cantaloupe, and musk melon. Ornamentals include, but are not limited to, azalea, hydrangea, hibiscus, roses, tulips, daffodils, petunias, carnation, poinsettia, and chrysanthemum. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape., etc.).

Use in Pesticidal Control

General methods for employing strains comprising a nucleotide sequence of the present invention, or a variant thereof, in pest control or in engineering other organisms as pesticidal agents are known in the art. See, for example U.S. Pat. No. 5,039,523 and EP 0480762A2.

The *Bacillus* strains containing a nucleotide sequence of the present invention, or a variant thereof, or the microorganisms that have been genetically altered to contain a pesticidal gene of the invention and protein may be used for protecting agricultural crops and products from pests. In one aspect of the invention, whole, i.e., unlysed, cells of a toxin (pesticide)-producing organism are treated with reagents that prolong the activity of the toxin produced in the cell when the cell is applied to the environment of target pest(s).

Alternatively, the pesticide is produced by introducing a pesticidal gene into a cellular host. Expression of the pesticidal gene results, directly or indirectly, in the intracellular production and maintenance of the pesticide. In one aspect of this invention, these cells are then treated under conditions that prolong the activity of the toxin produced in the cell when the cell is applied to the environment of the target pest(s). The resulting product retains the toxicity of the toxin. These naturally encapsulated pesticides may then be formulated in accordance with conventional techniques for application to the environment hosting a target pest, e.g., soil, water, and foliage of plants. See, for example EPA 0192319, and the references cited therein. Alternatively, one may formulate the cells expressing a gene of this invention such as to allow application of the resulting material as a pesticide.

The active ingredients of the present invention are normally applied in the form of compositions and can be applied to the crop area or plant to be treated, simultaneously or in succession, with other compounds. These compounds can be fertilizers, weed killers, cryoprotectants, surfactants, detergents, pesticidal soaps, dormant oils, polymers, and/or time-release or biodegradable carrier formulations that permit long-term dosing of a target area following a single application of the formulation. They can also be selective herbicides, chemical insecticides, virucides, microbicides, amoebicides, pesticides, fungicides, bacteriocides, nematocides, molluscicides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. Likewise the formulations may be prepared into edible “baits” or fashioned into pest “traps” to permit feeding or ingestion by a target pest of the pesticidal formulation.

Methods of applying an active ingredient of the present invention or an agrochemical composition of the present invention that contains at least one of the pesticidal proteins produced by the bacterial strains of the present invention include leaf application, seed coating and soil application. The number of applications and the rate of application depend on the intensity of infestation by the corresponding pest.

The composition may be formulated as a powder, dust, pellet, granule, spray, emulsion, colloid, solution, or such like, and may be prepared by such conventional means as desiccation, lyophilization, homogenation, extraction, filtration, centrifugation, sedimentation, or concentration of a culture of cells comprising the polypeptide. In all such compositions that contain at least one such pesticidal polypeptide, the polypeptide may be present in a concentration of from about 1% to about 99% by weight.

Lepidopteran, hemipteran, dipteran, or coleopteran pests may be killed or reduced in numbers in a given area by the methods of the invention, or may be prophylactically applied to an environmental area to prevent infestation by a susceptible pest. Preferably the pest ingests, or is contacted with, a pesticidally-effective amount of the polypeptide. By “pesticidally-effective amount” is intended an amount of the pesticide that is able to bring about death to at least one pest, or to noticeably reduce pest growth, feeding, or normal physiological development. This amount will vary depending on such factors as, for example, the specific target pests to be controlled, the specific environment, location, plant, crop, or agricultural site to be treated, the environmental conditions, and the method, rate, concentration, stability, and quantity of application of the pesticidally-effective polypeptide composition. The formulations may also vary with respect to climatic conditions, environmental considerations, and/or frequency of application and/or severity of pest infestation.

The pesticide compositions described may be made by formulating either the bacterial cell, the crystal and/or the spore suspension, or the isolated protein component with the desired agriculturally-acceptable carrier. The compositions may be formulated prior to administration in an appropriate means such as lyophilized, freeze-dried, desiccated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term “agriculturally-acceptable carrier” covers all adjuvants, inert components, dispersants, surfactants, tackifiers, binders, etc. that are ordinarily used in pesticide formulation technology; these are well known to those skilled in pesticide formulation. The formulations may be mixed with one or more solid or liquid adjuvants and prepared by various means, e.g., by homogeneously mixing, blending and/or grinding the pesticidal composition with suitable adjuvants using conventional formulation techniques. Suitable formulations and application methods are described in U.S. Pat. No. 6,468,523, herein incorporated by reference.

“Pest” includes but is not limited to, insects, fungi, bacteria, nematodes, mites, ticks, and the like. Insect pests include insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Coleoptera, Lepidoptera, and Diptera.

The order Coleoptera includes the suborders Adephaga and Polyphaga. Suborder Adephaga includes the superfamilies Caraboidea and Gyrinoidea, while suborder Polyphaga includes the superfamilies Hydrophiloidea, Staphylinoidea, Cantharoidea, Cleroidea, Elateroidea, Dascilloidea, Dryopoidea, Byrrhoidea, Cucujoidea, Meloidea, Mordelloidea, Tenebrionoidea, Bostrichoidea, Scarabaeoidea, Cerambycoidea, Chrysomeloidea, and Curculionoidea. Superfamily Caraboidea includes the families Cicindelidae, Carabidae, and Dytiscidae. Superfamily Gyrinoidea includes the family Gyrinidae. Superfamily Hydrophiloidea includes the family Hydrophilidae. Superfamily Staphylinoidea includes the families Silphidae and Staphylinidae. Superfamily Cantharoidea includes the families Cantharidae and Lampyridae. Superfamily Cleroidea includes the families Cleridae and Dermestidae. Superfamily Elateroidea includes the families Elateridae and Buprestidae. Superfamily Cucujoidea includes the family Coccinellidae. Superfamily Meloidea includes the family Meloidae. Superfamily Tenebrionoidea includes the family Tenebrionidae. Superfamily Scarabaeoidea includes the families Passalidae and Scarabaeidae. Superfamily Cerambycoidea includes the family Cerambycidae. Superfamily Chrysomeloidea includes the family Chrysomelidae. Superfamily Curculionoidea includes the families Curculionidae and Scolytidae.

The order Diptera includes the Suborders Nematocera, Brachycera, and Cyclorrhapha. Suborder Nematocera includes the families Tipulidae, Psychodidae, Culicidae, Ceratopogonidae, Chironomidae, Simuliidae, Bibionidae, and Cecidomyiidae. Suborder Brachycera includes the families Stratiomyidae, Tabanidae, Therevidae, Asilidae, Mydidae, Bombyliidae, and Dolichopodidae. Suborder Cyclorrhapha includes the Divisions Aschiza and Aschiza. Division Aschiza includes the families Phoridae, Syrphidae, and Conopidae. Division Aschiza includes the Sections Acalyptratae and Calyptratae. Section Acalyptratae includes the families Otitidae, Tephritidae, Agromyzidae, and Drosophilidae. Section Calyptratae includes the families Hippoboscidae, Oestridae, Tachinidae, Anthomyiidae, Muscidae, Calliphoridae, and Sarcophagidae.

The order Lepidoptera includes the families Papilionidae, Pieridae, Lycaenidae, Nymphalidae, Danaidae, Satyridae, Hesperiidae, Sphingidae, Saturniidae, Geometridae, Arctiidae, Noctuidae, Lymantriidae, Sesiidae, and Tineidae.

Nematodes include parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp.

Hemipteran pests (which include species that are designated as Hemiptera, Homoptera, or Heteroptera) include, but are not limited to, *Lygus* spp., such as Western tarnished plant bug (*Lygus hesperus*), the tarnished plant bug (*Lygus lineolaris*), and green plant bug (*Lygus elisus*); aphids, such as the green peach aphid (*Myzus persicae*), cotton aphid (*Aphis gossypii*), cherry aphid or black cherry aphid (*Myzus cerasi*), soybean aphid (*Aphis glycines* Matsumura); brown plant hopper (*Nilaparvata lugens*), and rice green leafhopper (*Nephotettix* spp.); and stink bugs, such as green stink bug (*Acrosternum hilare*), brown marmorated stink bug (*Halyomorpha halys*), southern green stink bug (*Nezara viridula*), rice stink bug (*Oebalus pugnax*), forest bug (*Pentatoma rufipes*), European stink bug (*Rhaphigaster nebulosa*), and the shield bug *Troilus luridus*.

Insect pests of the invention for the major crops include: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm; *Diabrotica longicornis barberi*, northern corn rootworm; *Diabrotica undecimpunctata howardi*, southern corn rootworm; *Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; Anuraphis maidiradicis, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafminer; *Anaphothrips obscrurus*, grass *thrips; Solenopsis milesta*, thief ant; *Tetranychus urticae*, twospotted spider mite; Sorghum: *Chilo partellus*, sorghum borer; *Spodoptera frugiperda*, fall armyworm; *Spodoptera cosmioides; Spodoptera eridania; Helicoverpa zea*, corn earworm; *Elasmopalpus lignosellus*, lesser cornstalk borer; *Feltia subterranea*, granulate cutworm; *Phyllophaga crinita*, white grub; *Eleodes, Conoderus*, and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco *thrips; Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion *thrips; Franklinkiella fusca*, tobacco *thrips; Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Spodoptera cosmioides; Spodoptera eridania; Helicoverpa zea*, corn earworm; *Colaspis brunnea*, grape *colaspis; Lissorhoptrus oryzophilus*, rice water weevil; *Sitophilus oryzae*, rice weevil; *Nephotettix nigropictus*, rice leafhopper; *Blissus leucopterus leucopterus*, chinch bug; *Acrosternum hilare*, green stink bug; *Chilu suppressalis*, Asiatic rice borer; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Spodoptera* cosmioides; *Spodoptera eridania; Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean *thrips; Thrips tabaci*, onion *thrips; Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Euschistus heros*, neotropical brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; *Delia* ssp., Root maggots.

Methods for Increasing Plant Yield

Methods for increasing plant yield are provided. The methods comprise providing a plant or plant cell expressing a polynucleotide encoding the pesticidal polypeptide sequence disclosed herein and growing the plant or a seed thereof in a field infested with (or susceptible to infestation by) a pest against which said polypeptide has pesticidal activity. In some embodiments, the polypeptide has pesticidal activity against a lepidopteran, coleopteran, dipteran, hemipteran, or nematode pest, and said field is infested with a lepidopteran, hemipteran, coleopteran, dipteran, or nematode pest. As defined herein, the "yield" of the plant refers to the quality and/or quantity of biomass produced by the plant. By "biomass" is intended any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in yield compared to a plant not expressing the pesticidal sequence. In specific methods, plant yield is increased as a result of improved pest resistance of a plant expressing a pesticidal protein disclosed herein. Expression of the pesticidal protein results in a reduced ability of a pest to infest or feed.

The plants can also be treated with one or more chemical compositions, including one or more herbicide, insecticides, or fungicides. Exemplary chemical compositions include: Fruits/Vegetables Herbicides: Atrazine, Bromacil, Diuron, Glyphosate, Linuron, Metribuzin, Simazine, Trifluralin, Fluazifop, Glufosinate, Halosulfuron Gowan, Paraquat, Propyzamide, Sethoxydim, Butafenacil, Halosulfuron, Indaziflam; Fruits/Vegetables Insecticides: Aldicarb, *Bacillus thuriengiensis*, Carbaryl, Carbofuran, Chlorpyrifos, Cypermethrin, Deltamethrin, Abamectin, Cyfluthrin/beta-cyfluthrin, Esfenvalerate, Lambda-cyhalothrin, Acequinocyl, Bifenazate, Methoxyfenozide, Novaluron, Chromafenozide, Thiacloprid, Dinotefuran, Fluacrypyrim, Spirodiclofen, Gamma-cyhalothrin, Spiromesifen, Spinosad, Rynaxypyr, Cyazypyr, Triflumuron, Spirotetramat, Imidacloprid, Flubendiamide, Thiodicarb, Metaflumizone, Sulfoxaflor, Cyflumetofen, Cyanopyrafen, Clothianidin, Thiamethoxam, Spinotoram, Thiodicarb, Flonicamid, Methiocarb, Emamectin-benzoate, Indoxacarb, Fenamiphos, Pyriproxifen, Fenbutatin-oxid; Fruits/Vegetables Fungicides: Ametoctradin, Azoxystrobin, Benthiavalicarb, Boscalid, Captan, Carbendazim, Chlorothalonil, Copper, Cyazofamid, Cyflufenamid, Cymoxanil, Cyproconazole, Cyprodinil, Difenoconazole, Dimetomorph, Dithianon, Fenamidone, Fenhexamid, Fluazinam, Fludioxonil, Fluopicolide, Fluopyram, Fluoxastrobin, Fluxapyroxad, Folpet, Fosetyl, Iprodione, Iprovalicarb, Isopyrazam, Kresoxim-methyl, Mancozeb, Mandipropamid, Metalaxyl/mefenoxam, Metiram, Metrafenone, Myclobutanil, Penconazole, Penthiopyrad, Picoxystrobin, Propamocarb, Propiconazole, Propineb, Proquinazid, Prothioconazole, Pyraclostrobin, Pyrimethanil, Quinoxyfen, Spiroxamine, Sulphur, Tebuconazole, Thiophanate-methyl, Trifloxystrobin;

Cereals Herbicides:

2.4-D, Amidosulfuron, Bromoxynil, Carfentrazone-E, Chlorotoluron, Chlorsulfuron, Clodinafop-P, Clopyralid, Dicamba, Diclofop-M, Diflufenican, Fenoxaprop, Florasulam, Flucarbazone-NA, Flufenacet, Flupyrosulfuron-M, Fluroxypyr, Flurtamone, Glyphosate, Iodosulfuron, Ioxynil, Isoproturon, MCPA, Mesosulfuron, Metsulfuron, Pendimethalin, Pinoxaden, Propoxycarbazone, Prosulfocarb, Pyroxsulam, Sulfosulfuron, Thifensulfuron, Tralkoxydim, Triasulfuron, Tribenuron, Trifluralin, Tritosulfuron; Cereals Fungicides: Azoxystrobin, Bixafen, Boscalid, Carbendazim, Chlorothalonil, Cyflufenamid, Cyproconazole, Cyprodinil, Dimoxystrobin, Epoxiconazole, Fenpropidin, Fenpropimorph, Fluopyram, Fluoxastrobin, Fluquinconazole, Fluxapyroxad, Isopyrazam, Kresoxim-methyl, Metconazole, Metrafenone, Penthiopyrad, Picoxystrobin, Prochloraz, Propiconazole, Proquinazid, Prothioconazole, Pyraclostrobin, Quinoxyfen, Spiroxamine, Tebuconazole, Thiophanate-methyl, Trifloxystrobin; Cereals Insecticides: Dimethoate, Lambda-cyhalthrin, Deltamethrin, alpha-Cypermethrin, β-cyfluthrin, Bifenthrin, Imidacloprid, Clothianidin, Thiamethoxam, Thiacloprid, Acetamiprid, Dinetofuran, Clorphyriphos, Pirimicarb, Methiocarb, Sulfoxaflor; Maize Herbicides: Atrazine, Alachlor, Bromoxynil, Acetochlor, Dicamba, Clopyralid, (S-)Dimethenamid, Glufosinate, Glyphosate, Isoxaflutole, (S-) Metolachlor, Mesotrione, Nicosulfuron, Primisulfuron, Rimsulfuron, Sulcotrione, Foramsulfuron, Topramezone, Tembotrione, Saflufenacil, Thiencarbazone, Flufenacet, Pyroxasulfon; Maize Insecticides: Carbofuran, Chlorpyrifos, Bifenthrin, Fipronil, Imidacloprid, Lambda-Cyhalothrin, Tefluthrin, Terbufos, Thiamethoxam, Clothianidin, Spiromesifen, Flubendiamide, Triflumuron, Rynaxypyr, Deltamethrin, Thiodicarb, β-Cyfluthrin, Cypermethrin, Bifenthrin, Lufenuron, Tebupirimphos, Ethiprole, Cyazypyr, Thiacloprid, Acetamiprid, Dinetofuran, Avermectin; Maize Fungicides: Azoxystrobin, Bixafen, Boscalid, Cyproconazole, Dimoxystrobin, Epoxiconazole, Fenitropan, Fluopyram, Fluoxastrobin, Fluxapyroxad, Isopyrazam, Metconazole, Penthiopyrad, Picoxystrobin, Propiconazole, Prothioconazole, Pyraclostrobin, Tebuconazole, Trifloxystrobin; Rice Herbicides: Butachlor, Propanil, Azimsulfuron, Bensulfuron, Cyhalofop, Daimuron, Fentrazamide, Imazosulfuron, Mefenacet, Oxaziclomefone, Pyrazosulfuron, Pyributicarb, Quinclorac, Thiobencarb, Indanofan, Flufenacet, Fentrazamide, Halosulfuron, Oxaziclomefone, Benzobicyclon, Pyriftalid, Penoxsulam, Bispyribac, Oxadiargyl, Ethoxysulfuron, Pretilachlor, Mesotrione, Tefuryltrione, Oxadiazone, Fenoxaprop, Pyrimisulfan; Rice Insecticides: Diazinon, Fenobucarb, Benfuracarb, Buprofezin, Dinotefuran, Fipronil, Imidacloprid, Isoprocarb, Thiacloprid, Chromafenozide, Clothianidin, Ethiprole, Flubendiamide, Rynaxypyr, Deltamethrin, Acetamiprid, Thiamethoxam, Cyazypyr, Spinosad, Spinotoram, Emamectin-Benzoate, Cypermethrin, Chlorpyriphos, Etofenprox, Carbofuran, Benfuracarb, Sulfoxaflor; Rice Fungicides: Azoxystrobin, Carbendazim, Carpropamid, Diclocymet, Difenoconazole, Edifenphos, Ferimzone, Gentamycin, Hexaconazole, Hymexazol, Iprobenfos (IBP), Isoprothiolane, Isotianil, Kasugamycin, Mancozeb, Metominostrobin, Orysastrobin, Pencycuron, Probenazole, Propiconazole, Propineb, Pyroquilon, Tebuconazole, Thiophanate-methyl, Tiadinil, Tricyclazole, Trifloxystrobin, Validamycin; Cotton Herbicides: Diuron, Fluometuron, MSMA, Oxyfluorfen, Prometryn, Trifluralin, Carfentrazone, Clethodim, Fluazifop-butyl, Glyphosate, Norflurazon, Pendimethalin, Pyrithiobac-sodium, Trifloxysulfuron, Tepraloxydim, Glufosinate, Flumioxazin, Thidiazuron; Cotton Insecticides: Acephate, Aldicarb, Chlorpyrifos, Cypermethrin, Deltamethrin, Abamectin, Acetamiprid, Emamectin Benzoate, Imidacloprid, Indoxacarb, Lambda-Cyhalothrin, Spinosad, Thiodicarb, Gamma-Cyhalothrin, Spiromesifen, Pyridalyl, Flonicamid Flubendiamide, Triflumuron, Rynaxypyr, Beta-Cyfluthrin, Spirotetramat, Clothianidin, Thiamethoxam, Thiacloprid, Dinetofuran, Flubendiamide, Cyazypyr, Spinosad, Spinotoram, gamma Cyhalothrin, 4-[[(6-Chlorpyridin-3-yl)methyl](2,2-difluorethyl)amino]furan-2(5H)-on, Thiodicarb, Avermectin, Flonicamid, Pyridalyl, Spiromesifen, Sulfoxaflor; Cotton Fungicides: Azoxystrobin, Bixafen, Boscalid, Carbendazim, Chlorothalonil, Copper, Cyproconazole, Difenoconazole, Dimoxystrobin, Epoxiconazole, Fenamidone, Fluazinam, Fluopyram, Fluoxastrobin, Fluxapyroxad, Iprodione, Isopyrazam, Isotianil, Mancozeb, Maneb, Metominostrobin, Penthiopyrad, Picoxystrobin, Propineb, Prothioconazole, Pyraclostrobin, Quintozene, Tebuconazole, Tetraconazole, Thiophanate-methyl, Trifloxystrobin; Soybean Herbicides: Alachlor, Bentazone, Trifluralin, Chlorimuron-Ethyl, Cloransulam-Methyl, Fenoxaprop, Fomesafen, Fluazifop, Glyphosate, Imazamox, Imazaquin, Imazethapyr, (S-)Metolachlor, Metribuzin, Pendimethalin, Tepraloxydim, Glufosinate; Soybean Insecticides: Lambda-cyhalothrin, Methomyl, Imidacloprid, Clothianidin, Thiamethoxam, Thiacloprid, Acetamiprid, Dinetofuran, Flubendiamide, Rynaxypyr, Cyazypyr, Spinosad, Spinotoram, Emamectin-Benzoate, Fipronil, Ethiprole, Deltamethrin, β-Cyfluthrin, gamma and lambda Cyhalothrin, 4-[[(6-Chlorpyridin-3-yl)methyl](2,2-difluorethyl)amino]furan-2(5H)-on, Spirotetramat, Spinodiclofen, Triflumuron, Flonicamid, Thiodicarb, beta-Cyfluthrin; Soybean Fungicides: Azoxystrobin, Bixafen, Boscalid, Carbendazim, Chlorothalonil, Copper, Cyproconazole, Difenoconazole, Dimoxystrobin, Epoxiconazole, Fluazinam, Fluopyram, Fluoxastrobin, Flutriafol, Fluxapyroxad, Isopyrazam, Iprodione, Isotianil, Mancozeb, Maneb, Metconazole, Metominostrobin, Myclobutanil, Penthiopyrad, Picoxystrobin, Propiconazole, Propineb, Prothioconazole, Pyraclostrobin, Tebuconazole, Tetraconazole, Thiophanate-methyl, Trifloxystrobin; Sugarbeet Herbicides: Chloridazon, Desmedipham, Ethofumesate, Phenmedipham, Triallate, Clopyralid, Fluazifop, Lenacil, Metamitron, Quinmerac, Cycloxydim, Triflusulfuron, Tepraloxydim, Quizalofop; Sugarbeet Insecticides: Imidacloprid, Clothianidin, Thiamethoxam, Thiacloprid, Acetamiprid, Dinetofuran, Deltamethrin, β-Cyfluthrin, gamma/lambda Cyhalothrin, 4-[[(6-Chlorpyridin-3-yl)methyl](2,2-difluorethyl)amino]furan-2(5H)-on, Tefluthrin, Rynaxypyr, Cyaxypyr, Fipronil, Carbofuran; Canola Herbicides: Clopyralid, Diclofop, Fluazifop, Glufosinate, Glyphosate, Metazachlor, Trifluralin Ethametsulfuron, Quinmerac, Quizalofop, Clethodim, Tepraloxydim; Canola Fungicides: Azoxystrobin, Bixafen, Boscalid, Carbendazim, Cyproconazole, Difenoconazole, Dimoxystrobin, Epoxiconazole, Fluazinam, Fluopyram, Fluoxastrobin, Flusilazole, Fluxapyroxad, Iprodione, Isopyrazam, Mepiquat-chloride, Metconazole, Metominostrobin, Paclobutrazole, Penthiopyrad., Picoxystrobin, Prochloraz, Prothioconazole, Pyraclostrobin, Tebuconazole, Thiophanate-methyl, Trifloxystrobin, Vinclozolin; Canola Insecticides: Carbofuran, Thiacloprid, Deltamethrin, Imidacloprid, Clothianidin, Thiamethoxam, Acetamiprid, Dinetofuran, β-Cyfluthrin, gamma and lambda Cyhalothrin, tau-Fluvaleriate, Ethiprole, Spinosad, Spinotoram, Flubendiamide, Rynaxypyr, Cyazypyr, 4-[[(6-Chlorpyridin-3-yl)methyl](2,2-difluorethyl)amino]furan-2(5H)-on.

Methods of Introducing Gene of the Invention into Another Plant

Also provided herein are methods of introducing the nucleic acid of the invention into another plant. The nucleic acid of the invention, or a fragment thereof, can be introduced into second plant by recurrent selection, backcrossing, pedigree breeding, line selection, mass selection, mutation breeding and/or genetic marker enhanced selection.

Thus, in one embodiment, the methods of the invention comprise crossing a first plant comprising a nucleic acid of the invention with a second plant to produce F1 progeny plants and selecting F1 progeny plants that comprise the nucleic acid of the invention. The methods may further comprise crossing the selected progeny plants with the first plant comprising the nucleic acid of the invention to produce backcross progeny plants and selecting backcross progeny plants that comprise the nucleic acid of the invention. Methods for evaluating pesticidal activity are provided elsewhere herein. The methods may further comprise repeating these steps one or more times in succession to produce selected second or higher backcross progeny plants that comprise the nucleic acid of the invention.

Any breeding method involving selection of plants for the desired phenotype can be used in the method of the present invention. In some embodiments, The F1 plants may be self-pollinated to produce a segregating F2 generation. Individual plants may then be selected which represent the desired phenotype (e.g., pesticidal activity) in each generation (F3, F4, F5, etc.) until the traits are homozygous or fixed within a breeding population.

The second plant can be a plant having a desired trait, such as herbicide tolerance, insect tolerance, drought tolerance, nematode control, water use efficiency, nitrogen use efficiency, improved nutritional value, disease resistance, improved photosynthesis, improved fiber quality, stress tolerance, improved reproduction, and the like. The second plant may be an elite event as described elsewhere herein In various embodiments, plant parts (whole plants, plant organs (e.g., leaves, stems, roots, etc.), seeds, plant cells, propagules, embryos, and the like) can be harvested from the resulting cross and either propagated or collected for downstream use (such as food, feed, biofuel, oil, flour, meal, etc).

Methods of Obtaining a Plant Product

The present invention also relates to a process for obtaining a commodity product, comprising harvesting and/or milling the grains from a crop comprising a nucleic acid of the invention to obtain the commodity product. Agronomically and commercially important products and/or compositions of matter including but not limited to animal feed, commodities, and plant products and by-products that are intended for use as food for human consumption or for use in compositions and commodities that are intended for human consumption, particularly devitalized seed/grain products, including a (semi-)processed products produced from such grain/seeds, wherein said product is or comprises whole or processed seeds or grain, animal feed, corn or soy meal, corn or soy flour, corn, corn starch, soybean meal, soy flour, flakes, soy protein concentrate, soy protein isolates, texturized soy protein concentrate, cosmetics, hair care products, soy nut butter, natto, tempeh, hydrolyzed soy protein, whipped topping, shortening, lecithin, edible whole soybeans (raw, roasted, or as edamame), soy yogurt, soy cheese, tofu, yuba, as well as cooked, polished, steamed, baked or parboiled grain, and the like are intended to be within the scope of the present invention if these products and compositions of matter contain detectable amounts of the nucleotide and/or amino acid sequences set forth herein as being diagnostic for any plant containing such nucleotide sequences.

The following examples are offered by way of illustration and not by way of limitation.

EXPERIMENTAL EXAMPLES

Example 1

Discovery of Novel Pesticidal Genes from *Bacillus thuringiensis*

Novel pesticidal genes were identified from the bacterial strains listed in Table 1 using the following steps:

- Preparation of total DNA from the strain. Total DNA contains both genomic DNA and extrachromosomal DNA. Extrachromosomal DNA contains a mixture of some or all of the following: plasmids of various size; phage chromosomes; other uncharacterized extrachromosomal molecules.
- Sequencing of the DNA. Total DNA is sequenced via Next-Generation Sequencing methods.
- Identification of putative toxin genes via homology and/or other computational analyses.
- When required, sequence finishing of the gene of interest by one of several PCR or cloning strategies (e.g. TAIL-PCR).

TABLE 1

| Novel genes identified from bacterial strains | | | | | |
|---|---|---|---|---|---|
| Strain | Gene name | Molecular weight (kD) | Closest homolog | Nucleotide SEQ ID NO | Amino acid SEQ ID NO |
| ATX68363 | Axmi368 | 86.9 | 87.6% Cry13Aa1 | 1 | 21 |
| | Axmi368.2* | | | | 22 |
| ATX64783 | Axmi400 | 132.9 | 89% Cry1Da1 | 2 | 23 |
| | Axmi400.2* | | | | 24 |
| | Axmi400(trun) | | 87% Cry1Da1 | 3 | 25 |
| | Axmi400.2(trun)* | | | | 26 |
| ATX29161 | Axmi402 | 73.3 | 32% Axmi057, 31% Cry32Da1 | 4 | 27 |
| | Axmi402.2* | | | | 28 |
| | Axmi402.3* | | | | 29 |
| | Axmi402.4* | | | | 30 |
| | Axmi402.5* | | | | 31 |
| ATX29161 | Axmi403 | 139.7 | 60% Axmi103, 57% Cry32Aa1 | 5 | 32 |
| | Axmi403.2* | | | | 33 |
| | Axmi403.3* | | | | 34 |
| | Axmi403.4* | | | | 35 |
| | Axmi403.5* | | | | 36 |
| | Axmi403.6* | | | | 37 |
| | Axmi403.7* | | | | 38 |
| | Axmi403(trun) | | 58% Axmi103, 37% Cry32Aa1 | 6 | 39 |
| | Axmi403.2(trun)* | | | | 40 |
| | Axmi403.3(trun)* | | | | 41 |
| | Axmi403.4(trun)* | | | | 42 |
| | Axmi403.5(trun)* | | | | 43 |
| | Axmi403.6(trun)* | | | | 44 |
| | Axmi403.7(trun)* | | | | 45 |
| ATX67447 | Axmi404 | 137.1 | 68% Cry1Ah1 | 7 | 46 |
| | Axmi404.2* | | | | 47 |
| | Axmi404.3* | | | | 48 |
| | Axmi404(trun) | | 52% Cry1Ac1 | | 49 |
| | Axmi404.2(trun)* | | | 8 | 50 |
| | Axmi404.3(trun)* | | | | 51 |
| ATX52424 | Axmi405 | 87.6 | 48% Cry9Aa1 | 9 | 52 |
| | Axmi405.2* | | | 10 | 53 |
| | Axmi405.3* | | | | 54 |
| | Axmi405.4* | | | | 55 |
| | Axmi405.5* | | | | 56 |
| ATX66842 | Axmi416 | 133 | 71.3% Cry1Ai1 | 11 | 57 |
| | Axmi416(trun) | | 64.7% Cry1Ai1 | 12 | 58 |
| ATX68363 | Axmi417 | 35.9 | 56% Axmi194, 23% Cry55Aa2 | 13 | 59 |
| | Axmi417.2* | | | | 60 |
| | Axmi417.3* | | | | 61 |
| | Axmi417.4* | | | | 62 |
| | Axmi417(trun) | | | 14 | 63 |
| | Axmi417.2(trun)* | | | | 64 |
| ATX65158 | Axmi423 | 43.3 | 43% Cry15Aa1 | 15 | 65 |
| | Axmi423(trun) | | | 16 | 66 |
| ATX66410 | Axmi424 | 138.9 | 94% Axmi221z, 60% Cry1Aa9 | 17 | 67 |
| | Axmi424(trun) | | | 18 | 68 |
| ATX66854 | Axmi425 | 140 | 90% Cry1Ba1 | 19 | 69 |
| | Axmi425.2* | | | | 70 |
| | Axmi425.3* | | | | 71 |
| | Axmi425(trun) | | 95% Cry1Bal | 20 | 72 |
| | Axmi425.2(trun)* | | | | 73 |
| | Axmi425.3(trun)* | | | | 74 |

*Represents a protein that is encoded from a downstream start site and "(trun)" indicates that the protein has a C-terminal truncation.

Example 2

Expression and Purification

A gene encoding each of the amino acid sequences set forth in Table 2 was PCR amplified from the corresponding strain listed in Table 1 using HERCULASE® II Fusion DNA Polymerase with primers incorporating an AscI linker at the 3' end. Amplified PCR product was digested with AscI and ligated into the pMalC4X vector. The clone was confirmed by sequencing and the plasmid was transformed in B121 competent cells. A single colony was inoculated in LB media and grown at 37° C. until log phase, and induced with 0.5 mM IPTG at 20° C. for 18 hours. Purified protein was digested with Factor Xa at a 1:50 ratio at room temperature overnight. Purified protein was submitted to bioassay vs. selected insect pests according to standard protocol. The results are shown in Table 2 below. The pests are listed in Table 3 and the scoring system follows Table 3.

TABLE 2

| Bioassay results (stunt, mortality scores) | | | | | | | | | | | | | | |
|---|---|---|---|---|---|---|---|---|---|---|---|---|---|---|
| | SEQ ID NO | Ae | BCW | CA | DBM | ECB | FAW | Hv | Hz | SBA | SBL | SCB | SWCB | VBC |
| Axmi368 | 21 | | | | | | | | | 4, 4 | | | | |
| Axmi400(trun) | 25 | | | 2, 3 | 3, 4 | | | | | 2, 3 | 3, 4 | | | |
| Axmi402 | 27 | | | 3, 3 | | | | | | 2, 1 | | | 1, 1 | |
| Axmi403(trun) | 39 | | | 2, 3 | | | | | | 2, 3 | | | 1, 1 | |
| Axmi404.2(trun) | 50 | | | 4, 4 | 4, 4 | 4, 3 | 1, 0 | 2, 0 | 1, 0 | 2, 2 | 4, 4 | 1, 0 | 1, 1 | 1, 1 |
| Axmi405.2 | 53 | | | 2, 2 | 2, 2 | | | | | | | | 3, 1 | 2, 0 |
| Axmi416(trun) | 58 | | 3, 2 | | 4, 4 | 1, 0 | 2, 0 | 4, 2 | 2, 1 | | 4, 4 | 1, 1 | 4, 2 | 4, 2 |
| Axmi417(trun) | 63 | | | 3, 4 | 4, 4 | | | | | 3, 4 | | | | 3, 0 |
| Axmi423(trun) | 66 | | | | 4, 4 | 2, 2 | | 2, 1 | | | 4, 4 | 3, 4 | 3, 1 | 2, 0 |
| Axmi424(trun) | 68 | 2, 2 | | 3, 4 | 4, 4 | | | 3, 0 | 1, 0 | 3, 4 | 4, 4 | | | 4, 3 |
| Axmi425(trun) | 72 | | | | 4, 4 | 2, 2 | | 2, 1 | | | 3, 3 | 4, 4 | 3, 1 | 1, 0 |

TABLE 3

| Insects in bioassay panel | | |
|---|---|---|
| Ae | Yellow fever mosquito | *Aedes aegypti* |
| BCW | Black Cutworm | *Agrotis ipsilon* |
| CA | Cotton Aphid | *Aphis gossypil* |
| DBM | Diamondback Moth | *Plutella xylostella* |
| ECB | European Corn Borer | *Ostrinia nubilalis* |
| FAW | Fall Armyworm | *Spodoptera frugiperda* |
| Hv | Tobacco Budworm | *Heliothis virescens* |
| Hz | Corn Earworm | *Helicoverpa zea* |
| SBA | Soybean Aphid | *Aphis glycines* |
| SBL | Soybean Looper | *Pseudoplusia includens* |
| SCB | Sugarcane Borer | *Diatraea saccharalis* |
| SWCB | Southwestern Corn Borer | *Diatraea grandiosella* |
| VBC | Velvetbean Caterpillar | *Anticarsia gemmatalis* |

Stunting Scores:
0=No activity
1=Non-uniform stunt
2=Slight uniform stunt (75% the size of controls)
3=Strong uniform stunt (between 74-26% the size of the controls)
4=Severe uniform stunt (less than 25% the size of controls)
Mortality Scores:
0=No activity
1=up to 25% mortality
2=up to 50% mortality
3=up to 75% mortality
4=greater than 75% mortality

Example 3

Additional Assays for Pesticidal Activity

The nucleotide sequences of the invention can be tested for their ability to produce pesticidal proteins. The ability of a pesticidal protein to act as a pesticide upon a pest is often assessed in a number of ways. One way well known in the art is to perform a feeding assay. In such a feeding assay, one exposes the pest to a sample containing either compounds to be tested or control samples. Often this is performed by placing the material to be tested, or a suitable dilution of such material, onto a material that the pest will ingest, such as an artificial diet. The material to be tested may be composed of a liquid, solid, or slurry. The material to be tested may be placed upon the surface and then allowed to dry. Alternatively, the material to be tested may be mixed with a molten artificial diet, and then dispensed into the assay chamber. The assay chamber may be, for example, a cup, a dish, or a well of a microtiter plate.

Assays for sucking pests (for example aphids) may involve separating the test material from the insect by a partition, ideally a portion that can be pierced by the sucking mouth parts of the sucking insect, to allow ingestion of the test material. Often the test material is mixed with a feeding stimulant, such as sucrose, to promote ingestion of the test compound.

Other types of assays can include microinjection of the test material into the mouth, or gut of the pest, as well as development of transgenic plants, followed by test of the ability of the pest to feed upon the transgenic plant. Plant testing may involve isolation of the plant parts normally consumed, for example, small cages attached to a leaf, or isolation of entire plants in cages containing insects.

Other methods and approaches to assay pests are known in the art, and can be found, for example in Robertson and Preisler, eds. (1992) *Pesticide bioassays with arthropods*, CRC, Boca Raton, Fla. Alternatively, assays are commonly described in the journals *Arthropod Management Tests* and *Journal of Economic Entomology* or by discussion with members of the Entomological Society of America (ESA).

In some embodiments, the DNA regions encoding the toxin region of the pesticidal proteins disclosed herein are cloned into the *E. coli* expression vector pMAL-C4x behind the malE gene coding for Maltose binding protein (MBP). These in-frame fusions result in MBP-Axmi fusion proteins expression in *E. coli*.

For expression in *E. coli*, BL21*DE3 are transformed with individual plasmids. Single colonies are inoculated in LB supplemented with carbenicillin and glucose, and grown overnight at 37° C. The following day, fresh medium is inoculated with 1% of overnight culture and grown at 37° C. to logarithmic phase. Subsequently, cultures are induced with 0.3 mM IPTG overnight at 20° C. Each cell pellet is suspended in 20 mM Tris-Cl buffer, pH 7.4+200 mM NaCl+1 mM DTT+protease inhibitors and sonicated. Analysis by SDS-PAGE can be used to confirm expression of the fusion proteins.

Total cell free extracts are then run over amylose column attached to fast protein liquid chromatography (FPLC) for affinity purification of MBP-axmi fusion proteins. Bound fusion proteins are eluted from the resin with 10 mM maltose solution. Purified fusion proteins are then cleaved with either Factor Xa or trypsin to remove the amino terminal MBP tag from the Axmi protein. Cleavage and solubility of the proteins can be determined by SDS-PAGE Example 4

Vectoring of Genes for Plant Expression

The coding regions of the invention are connected with appropriate promoter and terminator sequences for expression in plants. Such sequences are well known in the art and may include the rice actin promoter or maize ubiquitin promoter for expression in monocots, the *Arabidopsis* UBQ3 promoter or CaMV 35S promoter for expression in dicots, and the nos or PinII terminators. Techniques for producing and confirming promoter—gene—terminator constructs also are well known in the art.

In one aspect of the invention, synthetic DNA sequences are designed and generated. These synthetic sequences have altered nucleotide sequence relative to the parent sequence, but encode proteins that are essentially identical to the parent sequence.

In another aspect of the invention, modified versions of the synthetic genes are designed such that the resulting peptide is targeted to a plant organelle, such as the endoplasmic reticulum or the apoplast. Peptide sequences known to result in targeting of fusion proteins to plant organelles are known in the art. For example, the N-terminal region of the acid phosphatase gene from the White Lupin *Lupinus albus* (GENBANK® ID GI:14276838, Miller et al. (2001) *Plant Physiology* 127: 594-606) is known in the art to result in endoplasmic reticulum targeting of heterologous proteins. If the resulting fusion protein also contains an endoplasmic reticulum retention sequence comprising the peptide N-terminus-lysine-aspartic acid-glutamic acid-leucine (i.e., the "KDEL" motif, SEQ ID NO:75) at the C-terminus, the fusion protein will be targeted to the endoplasmic reticulum. If the fusion protein lacks an endoplasmic reticulum targeting sequence at the C-terminus, the protein will be targeted to the endoplasmic reticulum, but will ultimately be sequestered in the apoplast.

Thus, this gene encodes a fusion protein that contains the N-terminal thirty-one amino acids of the acid phosphatase gene from the White Lupin *Lupinus albus* (GENBANK® ID GI:14276838, Miller et al., 2001, supra) fused to the N-terminus of the amino acid sequence of the invention, as well as the KDEL (SEQ ID NO:75) sequence at the C-terminus. Thus, the resulting protein is predicted to be targeted the plant endoplasmic reticulum upon expression in a plant cell.

The plant expression cassettes described above are combined with an appropriate plant selectable marker to aid in the selection of transformed cells and tissues, and ligated into plant transformation vectors. These may include binary vectors from *Agrobacterium*-mediated transformation or simple plasmid vectors for aerosol or biolistic transformation.

Example 5

Soybean Transformation

Soybean transformation is achieved using methods well known in the art, such as the one described using the *Agrobacterium tumefaciens* mediated transformation soybean half-seed explants using essentially the method described by Paz et al. (2006), Plant cell Rep. 25:206. Transformants are identified using tembotrione as selection marker. The appearance of green shoots was observed, and documented as an indicator of tolerance to the herbicide isoxaflutole or tembotrione. The tolerant transgenic shoots will show normal greening comparable to wild-type soybean shoots not treated with isoxaflutole or tembotrione, whereas wild-type soybean shoots treated with the same amount of isoxaflutole or tembotrione will be entirely bleached. This indicates that the presence of the HPPD protein enables the tolerance to HPPD inhibitor herbicides, like isoxaflutole or tembotrione.

Tolerant green shoots are transferred to rooting media or grafted. Rooted plantlets are transferred to the greenhouse after an acclimation period. Plants containing the transgene are then sprayed with HPPD inhibitor herbicides, as for example with tembotrione at a rate of 100 g AI/ha or with mesotrione at a rate of 300 g AI/ha supplemented with ammonium sulfate methyl ester rapeseed oil. Ten days after the application the symptoms due to the application of the herbicide are evaluated and compared to the symptoms observed on wild type plants under the same conditions.

Example 6

Cotton T0 Plant Establishment and Selection

Cotton transformation is achieved using methods well known in the art, especially preferred method in the one described in the PCT patent publication WO 00/71733. Regenerated plants are transferred to the greenhouse. Following an acclimation period, sufficiently grown plants are sprayed with HPPD inhibitor herbicides as for example tembotrione equivalent to 100 or 200 gAI/ha supplemented with ammonium sulfate and methyl ester rapeseed oil. Seven days after the spray application, the symptoms due to the treatment with the herbicide are evaluated and compared to the symptoms observed on wild type cotton plants subjected to the same treatment under the same conditions.

Example 7

Transformation of Maize Cells with the Pesticidal Protein Genes Described Herein Maize ears are best collected 8-12 days after pollination. Embryos are isolated from the ears, and those embryos 0.8-1.5 mm in size are preferred for use in transformation. Embryos are plated scutellum side-up on a suitable incubation media, such as DN62A5S media (3.98 g/L N6 Salts; 1 mL/L (of 1000× Stock) N6 Vitamins; 800 mg/L L-Asparagine; 100 mg/L Myo-inositol; 1.4 g/L L-Proline; 100 mg/L Casamino acids; 50 g/L sucrose; 1 mL/L (of 1 mg/mL Stock) 2,4-D). However, media and salts other than DN62A5S are suitable and are known in the art. Embryos are incubated overnight at 25° C. in the dark. However, it is not necessary per se to incubate the embryos overnight.

The resulting explants are transferred to mesh squares (30-40 per plate), transferred onto osmotic media for about 30-45 minutes, then transferred to a beaming plate (see, for example, PCT Publication No. WO/0138514 and U.S. Pat. No. 5,240,842).

DNA constructs designed to the genes of the invention in plant cells are accelerated into plant tissue using an aerosol beam accelerator, using conditions essentially as described in PCT Publication No. WO/0138514. After beaming, embryos are incubated for about 30 min on osmotic media, and placed onto incubation media overnight at 25° C. in the dark. To avoid unduly damaging beamed explants, they are incubated for at least 24 hours prior to transfer to recovery media. Embryos are then spread onto recovery period media, for about 5 days, 25° C. in the dark, then transferred to a selection media. Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated by methods known in the art. The resulting shoots are allowed to root on rooting media, and the resulting plants are transferred to nursery pots and propagated as transgenic plants.

Materials

DN62A5S Media

| Components | Per Liter | Source |
|---|---|---|
| Chu's N6 Basal Salt Mixture (Prod. No. C 416) | 3.98 g/L | Phytotechnology Labs |
| Chu's N6 Vitamin Solution (Prod. No. C 149) | 1 mL/L (of 1000x Stock) | Phytotechnology Labs |
| L-Asparagine | 800 mg/L | Phytotechnology Labs |
| Myo-inositol | 100 mg/L | Sigma |
| L-Proline | 1.4 g/L | Phytotechnology Labs |
| Casamino acids | 100 mg/L | Fisher Scientific |
| Sucrose | 50 g/L | Phytotechnology Labs |
| 2,4-D (Prod. No. D-7299) | 1 mL/L (of 1 mg/mL Stock) | Sigma |

The pH of the solution is adjusted to pH 5.8 with 1N KOH/1N KCl, Gelrite (Sigma) is added at a concentration up to 3 g/L, and the media is autoclaved. After cooling to 50° C., 2 ml/L of a 5 mg/ml stock solution of silver nitrate (Phytotechnology Labs) is added.

Example 8

Transformation of Genes of the Invention in Plant Cells by *Agrobacterium*-Mediated Transformation Ears are best collected 8-12 days after pollination. Embryos are isolated from the ears, and those embryos 0.8-1.5 mm in size are preferred for use in transformation. Embryos are plated scutellum side-up on a suitable incubation media, and incubated overnight at 25° C. in the dark. However, it is not necessary per se to incubate the embryos overnight. Embryos are contacted with an *Agrobacterium* strain containing the appropriate vectors for Ti plasmid mediated transfer for about 5-10 min, and then plated onto co-cultivation media for about 3 days (22° C. in the dark). After co-cultivation, explants are transferred to recovery period media for 5-10 days (at 25° C. in the dark). Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated as known in the art.

Example 9

Transformation of Rice

Immature rice seeds, containing embryos at the right developmental stage, are collected from donor plants grown under well controlled conditions in the greenhouse. After sterilization of the seeds, immature embryos are excised and preinduced on a solid medium for 3 days. After preinduction, embryos are immersed for several minutes in a suspension of *Agrobacterium* harboring the desired vectors. Then embryos are cocultivated on a solid medium containing acetosyringone and incubated in the dark for 4 days. Explants are then transferred to a first selective medium containing phosphinotricin as selective agent. After approximately 3 weeks, scutella with calli developing were cut into several smaller pieces and transferred to the same selective medium. Subsequent subcultures are performed approximately every 2 weeks. Upon each subculture, actively growing calli are cut into smaller pieces and incubated on a second selective medium. After several weeks calli clearly resistant to phosphinotricin are transferred to a selective regeneration medium. Plantlets generated are cultured on half strength MS for full elongation. The plants are eventually transferred to soil and grown in the greenhouse.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A construct comprising a heterologous promoter operably linked to a nucleotide sequence encoding an amino acid sequence having pesticidal activity, wherein said nucleotide sequence is selected from the group consisting of:

a) the nucleotide sequence set forth in SEQ ID NO:17 or 18; and b) a nucleotide sequence that encodes a polypeptide comprising the amino acid sequence of SEQ ID NO:67 or 68.

2. The construct of claim 1, wherein said nucleotide sequence has been optimized for expression in a plant.

3. The construct of claim 1, wherein said promoter is capable of directing expression of said nucleotide sequence in a plant cell.

4. An expression cassette comprising the construct of claim 1.

5. The expression cassette of claim 4, further comprising a nucleic acid molecule encoding a heterologous polypeptide.

6. A host cell that contains the construct of claim 1.

7. The host cell of claim 6 that is a bacterial host cell.

8. The host cell of claim 6 that is a plant cell.

9. A transgenic plant comprising the host cell of claim 8.

10. The transgenic plant of claim 9, wherein said plant is selected from the group consisting of maize, sorghum, wheat, cabbage, sunflower, tomato, crucifers, peppers, potato, cotton, rice, soybean, sugarbeet, sugarcane, tobacco, barley, and oilseed rape.

11. A transgenic seed comprising the construct of claim 1.

12. A recombinant polypeptide with pesticidal activity, wherein said polypeptide comprises a heterologous leader sequence or a transit peptide operably linked to a polypeptide comprising the amino acid sequence of SEQ ID NO:67 or 68.

13. The polypeptide of claim 12 further comprising heterologous amino acid sequences.

14. A composition comprising the polypeptide of claim 12.

15. The composition of claim 14, wherein said composition is selected from the group consisting of a powder, dust, pellet, granule, spray, emulsion, colloid, and solution.

16. The composition of claim 14, wherein said composition is prepared by desiccation, lyophilization, homogenization, extraction, filtration, centrifugation, sedimentation, or concentration of a culture of bacterial cells.

17. The composition of claim 14, comprising from about 1% to about 99% by weight of said polypeptide.

18. A plant or plant cell having stably incorporated into its genome a DNA construct comprising a nucleotide sequence that encodes a protein having pesticidal activity, wherein said nucleotide sequence is selected from the group consisting of:

a) the nucleotide sequence set forth in SEQ ID NO:17 or 18; and b) a nucleotide sequence that encodes a polypeptide comprising the amino acid sequence of SEQ ID NO:67 or 68.

* * * * *

SEQUENCE LISTING

```
<160> NUMBER OF SEQ ID NOS: 75

<210> SEQ ID NO 1
<211> LENGTH: 2382
<212> TYPE: DNA
<213> ORGANISM: Bacillus thuringiensis

<400> SEQUENCE: 1

atgacttgtc aattacaagc gcaaccactt attccctata acgtactagc aggagttcca      60

actagtaata caggtagtcc aatcggcaat gcaggtaatc aatttgatca gtttgagcaa     120

accgttaaag agctcaagga agcatgggaa gcgttccaaa aaaacggaag tttctcatta     180
```

```
gcagctcttg aaaagggatt tgatgcagca atcggaggag gatcctttga ttatttaggt    240
ttagttcaag ccggcctagg attagttggt acgctaggcg ccgcaatccc tggtgtttca    300
gtggcagtgc ctcttattag catgcttgtt ggtgtttttt ggccaaaggg cacaaacaac    360
caagaaaacc ttattacagt tattgataag gaagttcaga gaatactaga tgaaaagcta    420
tctgatcagt taataaagaa attgaacgca gatttaaatg cttttacgga cctagtaact    480
cgtttggaag aagtaataat agatgcaact ttcgagaatc acaagcctgt actacaagta    540
agtaaatcaa attatatgaa agtggattca gcatatttct caacaggagg tattcttact    600
cttggcatga gtgattttct tactgatacc tattcaaagc ttaccttccc attatatgta    660
ctaggcgcaa ctatgaaact ttcagcatat catagttata tacaattcgg aaatacatgg    720
cttaataaag tttatgattt atcatcagat gagggaaaaa caatgtcgca ggctttagca    780
cgagctaaac agcatatgcg ccaagacata gcattttata caagccaagc tttaaacatg    840
tttactggga atctcccttc attatcatct aataaatatg caattaatga ctataatgta    900
tacactcgag caatggtatt gaatggctta gatatagtag caacatggcc taccctatat    960
ccagatgact attcgtctca gataaaactg gagaaaacac gcgtgatctt ttcagatatg   1020
gtcgggcaaa gtgagagtag agatggcagc gtaacgatta aaaatatttt tgacaataca   1080
gattcacatc aacatggatc cataggtctc aattcaatct cttatttccc agatgagtta   1140
cagaaagcac aacttcgcat gtatgattat aatcacaaac cttattgtac ggactgtttc   1200
tgctggccgt atggagtgat tttaaactat aacaagaata cctttagata tggcgataat   1260
gatccaggtc tttcaggaga cgttcaactc ccagcaccta tgagtgtagt taatgcccaa   1320
actcaaacag cccaatatac agatggagaa aacatatgga cagatactgg ccgcagttgg   1380
ctttgtactc tacgtggcta ctgtactaca aactgttttc caggaagagg ttgttataat   1440
aatagtactg gatatggaga aagttgcaat caatcacttc caggtcaaaa aatacatgca   1500
ctatatcctt ttacacaaac aaatgtgctg ggacaatcag gcaaactagg attgctagca   1560
agtcatattc catatgacct aagtccgaac aatacgattg gtgacaaaga tacagattct   1620
acgaatattg tcgcaaaagg aattccagtg gaaaaagggt atgcatccag tggacaaaaa   1680
gttgaaatta tacgagagtg gataaatggt gcgaatgtag ttcaattatc tccaggccaa   1740
tcttggggaa tggattttac caatagcaca ggtggtcaat atatggtccg ctgtcgatat   1800
gcaagtacaa acgatactcc aatctttttt aatttagtgt atgacggggg atcgaatcct   1860
atttataacc agatgacatt ccctgctaca aaagagactc cagctcacga ttcagtagat   1920
aacaagatac taggcataaa aggaataaat ggaaattatt cactcatgaa tgtaaaagat   1980
tctgtcgaac ttccatctgg gaaatttcat gttttttca caaataatgg atcatctgct   2040
atttatttag atcgacttga gtttgttcct ttaggaaaac catcccctgg tgttttatat   2100
tctggttctt atgatcttat gggatcacag tatgctagcg ttctttttaa cgaccaaaat   2160
gcctcctata ccacagtttc tataaatggg gtatctgatg cacatagtac ctcaggaagt   2220
attactcttt ttaataatga gacattagta aaaggatttg atgtaccagg ttcaggtcaa   2280
agttatcaat attctaatgt aactgtgcct ccttataata gagtcaatat gacgaaaggc   2340
acctatgctg aactttcagg ttctgtaaca attaaaggaa at                       2382
```

<210> SEQ ID NO 2
<211> LENGTH: 3519
<212> TYPE: DNA
<213> ORGANISM: Bacillus thuringiensis -continued

<400> SEQUENCE: 2

```
gtgctaaaat taagaaaacg gaggtatttt atggagggaa ataatctaaa tcaatgcata     60
ccttacaatt gtttaagtaa tcctaaggac ataatattag gtgatgaaag gctagaaact    120
ggtaatactg tagcagacat taccttaggg attgtcaatc tattgttttc tgagtttgtt    180
cctggtggag gctttatact aggattactg gatttaatat gggggtctat aggtcgttcc    240
caatgggatc tatttctgga acagattgaa caattgatta agcaaagaat agaagaattt    300
gctaggaatc aggcaatttc aaggttggag gggctaagcg atctttataa gacctatgct    360
agagcgttta gcgattggga ggcagatccg actaatccag cattaaggga agaaatgcgt    420
atacaattta atgacatgaa tagtgctatc ataacggctc tcccactttt tagagttcaa    480
aattatgaag ttgctctttt atctgtttat gttcaagctg caaacttaca tttatctatt    540
ttaagagatg tttcagtctt tggagaaaga tggggatatg atacagcaac tatcaataat    600
cgctatagtg acttaactag ccttattcat gtttatacta atcattgtgt ggatacgtat    660
aatcagggat taaggcgttt ggaaggtcgt tttcttaccg attggattgt atataatcgt    720
ttccgaagac aattaacaat ttcagtatta gatattgttg catttttttcc aaattatgat    780
attcgaacat atccaattca aacagctact cagctaacga gggaaatcta tctggattta    840
ccttttatta atgaaaatct ttctcctgca gcaagctatc cctcattctc agatgctgaa    900
agtgctataa tcaggagtcc tcatttagtg gactttttaa atagcttcac tatttataca    960
gatagtcttg ctcgatattt atattgggga gggcatcggg tgaattttac ccgttcagga   1020
gttactactt ttatacaatc accactatat ggaagggaag gaaatgcaga gcgttctgta   1080
attatttcgg catcatctag cgtaccaata tttagaacac tttcatatgt tactggcctt   1140
gacaatgcaa atcctgtagc tggaattgaa ggagtggaat tccaaaatac tataagtaga   1200
agtatctatc gtaaaagtgg tccaattgat tcttttaatg aattaccacc tcaagatgcc   1260
agtgtatctc cttcaattgg gtatagtcac cgtttatgtc atgccacatt tttagaacgg   1320
attagtggac caagaattgc aggtgtcgtt ttttcctgga cacatcgtag tgctagccct   1380
actaatgaag taagttcatc tagaattaca caaattccat gggtaaaggc gcatactctt   1440
gcgtctggtg cctccgttat taaagggcct ggatttacag gtggagatat actaactagg   1500
aataccttag gcgaactggg aactttaaga gtaacttttg caggaagatt atcacaaagt   1560
tattatatac gtttccgtta tgcttccgta gctaatagga gtggtatatt tagctattca   1620
cagccaactt catatggaat ttcctttcca aaaactatgg atgcaaatga atcattaaca   1680
tctcgttcat ttgcacttgc tacacttgct acaccgctaa cctttagaag gcaagaagaa   1740
ttaaatctac aaataccatc aggtacttat atagatcgaa ttgagtttgt tccagtcgat   1800
gaaaccttta caacagaatc tgatctggat agagcacaac aggcggtgaa tgcgctgttt   1860
acttcttcca atcaaatcgg cttaaaaaca gatgtgacgg attatcatat tgatcaagta   1920
tccaatttag tggattgttt atcggatgaa ttttgtctgg atgaaaaaaa agaattgtcc   1980
gagaaagtca aacatgcgaa gcgacttagt gatgagcgga atttacttca agatccaaac   2040
tttagaggga tcaatagaca actagaccgt ggctggagtg gaagtacgga tattaccatc   2100
caaggaggag atgacgtatt caaagagaat tacgttacac taccaggtac ctttgatgag   2160
tgctatccaa cgtatttata tcaaaaaata gatgagtcga aattaaaagc ctatacccgt   2220
tatcaattaa gagggtatat cggggatagt caagacttag aaatctattt aattcgttac   2280
```

-continued

```
aatgcaaaac acgaaatagt aaatgtacca ggtacaggga gtttatggcc tctttctgta   2340
gaaaattcaa ttggaccttg tggagaaccg aatcgatgcg cgccacacct tgaatggaat   2400
cctaatctag agtgttcttg cagagaaggg gaaaaatgtg cccatcattc ccatcatttc   2460
tccttggaca ttgatgttgg atgtacagac ttaaatgagg acttaggtgt atgggcgata   2520
ttcaagatta agacgcaaga tggccatgca agactaggaa atctagagtt tctcgaagag   2580
aaaccattag taggggaagc actagctcgt gtgaaaagag cggagaaaaa atggagagac   2640
aaacgtgaaa aattggaatt ggaaacaaat attgtttata aagaggcaaa agaatctgta   2700
gatgctttat ttgtaaactc tcaatatgat agattacaag cggataccaa catcgcgatg   2760
attcatgcgg cagataaacg cgttcatagc attcgagaag catatcttcc agagttatct   2820
ataattccgg gtgtaaatgc gggcattttc gaagaattag agggacgtat ttacacagcc   2880
tactctctat atgatgcgag aaatgtcatt aaaaatggcg atttcgataa tggcttatta   2940
tgctggaacg tgaaagggca tgtagatgta gaagaacaaa acaatcaccg ttcagttctg   3000
gttatcccag aatgggaagc agaagtgtca caagaagttc gtgtctgtcc aggacgtggc   3060
tatatccttc gtgttacagc gtacaaagag ggatatggag agggctgcgt aacgatccat   3120
gagatcgaag acaatacaga cgaactgaaa ttcagcaact gtgtagaaga ggaagtatat   3180
ccaaacaaca cggtaacgtg taatgattat actgcgactc aagaagaata tgagggtacg   3240
tacacttctc gtaatcgagg atatgacgga gcctatgaaa gcaattcttc tgtaccagct   3300
gattatgcat cagcctatga agaaaaagcg tatacagatg gaagaagaga gaatccttgt   3360
gaatctaata gaggatatgg ggattacgcg ccactaccag ctggttatgt gacaaaggaa   3420
ttagagtact tcccagaaac cgataaggta tggattgaga tcggagaaac ggaaggaaca   3480
ttcattgtgg atagtgtgga attactcctt atggaggaa                          3519
```

<210> SEQ ID NO 3
<211> LENGTH: 1767
<212> TYPE: DNA
<213> ORGANISM: Bacillus thuringiensis

<400> SEQUENCE: 3

```
atggagggaa ataatctaaa tcaatgcata ccttacaatt gtttaagtaa tcctaaggac     60
ataatattag gtgatgaaag gctagaaact ggtaatactg tagcagacat taccttaggg    120
attgtcaatc tattgttttc tgagtttgtt cctggtggag gctttatact aggattactg    180
gatttaatat gggggtctat aggtcgttcc caatgggatc tatttctgga acagattgaa    240
caattgatta agcaaagaat agaagaattt gctaggaatc aggcaatttc aaggttggag    300
gggctaagcg atctttataa gacctatgct agagcgttta gcgattggga ggcagatccg    360
actaatccag cattaaggga agaaatgcgt atacaattta atgacatgaa tagtgctatc    420
ataacggctc tcccactttt tagagttcaa aattatgaag ttgctctttt atctgtttat    480
gttcaagctg caaacttaca tttatctatt ttaagagatg tttcagtctt tggagaaaga    540
tggggatatg atacagcaac tatcaataat cgctatagtg acttaactag ccttattcat    600
gtttatacta atcattgtgt ggatacgtat aatcagggat taaggcgttt ggaaggtcgt    660
tttcttaccg attggattgt atataatcgt ttccgaagac aattaacaat ttcagtatta    720
gatattgttg catttttccc aaattatgat attcgaacat atccaattca aacagctact    780
cagctaacga gggaaatcta tctggattta ccttttatta atgaaaatct ttctcctgca    840
gcaagctatc cctcattctc agatgctgaa agtgctataa tcaggagtcc tcatttagtg    900
```

```
gactttttaa atagcttcac tatttataca gatagtcttg ctcgatattt atattgggga    960

gggcatcggg tgaattttac ccgttcagga gttactactt ttatacaatc accactatat   1020

ggaagggaag gaaatgcaga gcgttctgta attatttcgg catcatctag cgtaccaata   1080

tttagaacac tttcatatgt tactggcctt gacaatgcaa atcctgtagc tggaattgaa   1140

ggagtggaat tccaaaatac tataagtaga agtatctatc gtaaaagtgg tccaattgat   1200

tcttttaatg aattaccacc tcaagatgcc agtgtatctc cttcaattgg gtatagtcac   1260

cgtttatgtc atgccacatt tttagaacgg attagtggac caagaattgc aggtgtcgtt   1320

ttttcctgga cacatcgtag tgctagccct actaatgaag taagttcatc tagaattaca   1380

caaattccat gggtaaaggc gcatactctt gcgtctggtg cctccgttat taaagggcct   1440

ggatttacag gtggagatat actaactagg aataccttag gcgaactggg aactttaaga   1500

gtaacttttg caggaagatt atcacaaagt tattatatac gtttccgtta tgcttccgta   1560

gctaatagga gtggtatatt tagctattca cagccaactt catatggaat ttcctttcca   1620

aaaactatgg atgcaaatga atcattaaca tctcgttcat ttgcacttgc tacacttgct   1680

acaccgctaa cctttagaag gcaagaagaa ttaaatctac aaataccatc aggtacttat   1740

atagatcgaa ttgagtttgt tccagtc                                       1767
```

<210> SEQ ID NO 4
<211> LENGTH: 1965
<212> TYPE: DNA
<213> ORGANISM: Bacillus thuringiensis

<400> SEQUENCE: 4

```
atgacccaca atgacaacaa taataaattc gaaatcaagg atactggtac caagccaagg     60

tcccccccttg caaatgcacc aggtcctaca tggcaaaata taaataatag agatgtagag  120

acatttggat caatagaaat tgcgggaaaa gtagtttcag gcgttataag ctcagttata    180

aaatctttaa gacaacaagc gcaaatagat aaaatagtag caatcgtcgt ggttgaagtc    240

tttgaagtgc tttggcctgt cctagaaggt atgtggtatg cgatgatgga tgctgtagaa    300

attatgattc aggaagccat tacaactgcg gtaagaagta aagcacaagc agaattaaat    360

ggcattcgca atgcccttgt actctttcaa caagctttcg acgactggga aaaaaattca    420

gataatccac aattacaaga tcgtgtaaga aggcaattta ctgcgacaaa tacattaatt    480

caattcgcca tgtcttcctt tgcagttcca ggttttcaag tcccattact cgttgtatat    540

gctcaagcgg ccaacctaca tttactgttt ttacgagagg ctgttgtact tggagaaaag    600

tgggggatga gtcgagaaga ggtagatgat tattataatg gagaacttgg actaactgag    660

ctcacacaat catacacgaa tcactgcaca aattggtatc atgagggatt agcgcaatca    720

atgaaattaa acccgagtgt aacaatacta gaacagtgga atttatataa tgactttaga    780

agagaaatga cgattatgat cttagatatt gtagcgttat ggccgacata tgatgtcaag    840

ttatatcccg caggaaccaa aacagagctc acacgaataa tatatacgcc attaatggga    900

gttttggaag atagtagttc tataagtgcc acaaggaaag aatatggtaa tatagcggct    960

ataaatcagc aagatggagc tacgacgatt ccaccagcat tatttatatg gttggagaaa   1020

caaattgtat atccgtataa caatctcata tatagttatc aaaatttcca aaaaaccaca   1080

tttggtaaag tgatgaatgg cactatattc ggaagtaata gcgagaaaca cctaacaaat   1140

cccataagta ttccgattga tgcagagtca tatgatgttt ataaagttga tacatcatat   1200
```

tcagcaaaga tggaaattaa aagttcacca attcataaac tagtatacta tcgctcaaaa 1260
gaacaacaag aaagtataat cagtaccaat acatcaaaag gtccaattga tcaggtgtct 1320
gaaatagcaa atgaaggata tcaagattat agtcattgtc ttgctcatat ggcggggtgg 1380
gtatcgattg cttacgggac gggtctgacc gagaagcctt atttagtccc atataattta 1440
gcactaggat ggacgtatgc aaatgttgat cccgtgaata gtatagcacc cgatgcaata 1500
acccaaattc cagcagtgaa aggggataaa gtaattggta ttccagaaga agaggctatt 1560
ttgggcgagg taactgcgat acaaggacct gggtttacag gaggaaattt agtaggattg 1620
ttcgctggtg ctgaattaca tatgaaagtt acaaatccag taagtaatgt tgcaggatat 1680
caaatgagaa ttcgttatgc gaacaatcac ccaacgatac ttgctgtcag ctatcaaggt 1740
gtagaaacat cctcaggtaa atttgacgtt ccagttacgt attctggtga ttttaaaact 1800
aagctaacat ataatgcctt taaatttaaa gaagctatta ttataccttc accattaaga 1860
gaagagattg ctgatatagt attgcgtaat gaaggtgata gcaatctcct tatcgataaa 1920
attgaactca tcccaatgga tttttggagg catgagcaat gcaat 1965

<210> SEQ ID NO 5
<211> LENGTH: 3717
<212> TYPE: DNA
<213> ORGANISM: Bacillus thuringiensis

<400> SEQUENCE: 5
atgaatcaac agcataacaa tgaatatgaa atcatgagta ctggcgacat gggctatcag 60
ccaaggtatc ccttttcgaa tgcacctggt gctgaattgc aacagatgca ttacaaagat 120
tggatggata tgtgtgcaga tggagagtcg ggaaaaacgt ttgcagacct tacagttcag 180
gagggagtca ctatagctgt aagtattgca gcggcaattc ttagtgtacc atttccagta 240
acagcagcgg gattaagtat tatctcttta ctagttccat actggtggcc agagacagca 300
gtaactcccg gtactccctc tgcgcaagtt acatgggaaa aatttatgag tgctgcggaa 360
aatctcagta atacacaaat tgtagcgagt aaacgatcag atgccattgc tagatggcaa 420
ggtatacaaa ccttaggaag agactatttt caagcgcaat gtgactggct acaagatcaa 480
aataatgaac tcaaaaaaag taaattacgg gaggcatttg atgacttcga agattattta 540
aaagtgtcaa tgccattctt tcgtgcgcaa ggctttgaaa ttcctatgtt agctatgtat 600
gcacaagctg cgaatatgca cttacttttg ctaagagagg ttgtccagaa tggtgtgggt 660
tgggggttcc agcaatacga agttgaccga tattattcca atacagaccc tttttttaggg 720 aaccctggac tattacaact attagaagga tatacggact attgtgtaaa atggtataat 780
gcaggtttac gacaacaata cgaaaataat agatacaatt gggatgcatt caatgatttc 840
cgtagagata tgattataat ggtattagat attgtatctt tatggccaac ttatgatccg 900
aagcgctatc ccctacctac aaaatcacaa cttacacgaa ctgtgtatac cgatttagta 960
ggtttttctg gaaatagcga gtacctacaa atagacattg aacgtgcaga acaagcgcta 1020
gtccagaaac ctggtctatt tacctggctg cgtgagctaa gtttcgagct ggggccactg 1080
tcgcgaatta attttgtaag aggaagacaa atagtcttca attataccgg aagttccgat 1140
aggtatgaag agaccaaggg gaatcttgga gaaactagag aaactgttgt tattccggca 1200
ccggatgtag gggatgacat ctggaggatt agcactcaag ttaacaccta tcagatacca 1260
aatgctactt ttgttagagg ctggaatttt tcttttactc aatcattaga tcaaaaaata 1320
gcttggcgga cagaatattc acccgaaata gtgatgcagg gattgtcttg tcacggacct 1380

-continued

```
tctgtgagtt cttgtaacct ttgtatcagt aacagtccgt gtagaagtat tactcctaac   1440
tatagctccc cttgtgatga caagttggtt tatagtcatc gattttcata tttaggagcc   1500
ggacttaaat ccgatttaac aacgttgatt tattttagct acggatggac ccatgtaagc   1560
gcagatgcaa acaatttgat agatcctaaa aagattaccc aaatcccagc cgtaaagggg   1620
gattatttag ggagaaatgc ccgtgttata aaaggacctg gaagtacagg tggagatcta   1680
gtccaacttt ccgatggaac cgaaagagga actctgggca tcaaactaac aaaaccacca   1740
ggaagtcaca gctatcgtgt aagaatacgt tatgcaagta atacgcgaac tcaacttgag   1800
attatttggg gagaagatta cgatagcgtt atagttcctg ctactacaac tgatataaca   1860
aatctcacct ataataaatt cgggtacttc gaaatccgcg tttttagtta taattcatca   1920
agcgaagaag aagacttaat aagagtggat gctacgggtt ctttcatcct cgacaaaatc   1980
gaattcattc caattgaggg atcagtggat gaatatcaag caaatcagga tctagaaaaa   2040
gcaaaaaagg ccgtgaatgc cttgtttaca ggtgatgcga aaagtgcgct aaaattgagc   2100
atcacaggct acatagtgga tcaagctgcc aactttgtgg aatgtgtatc agatgaattc   2160
catgcccaag aaaaaatgat cctattggat caagtgaaat tcgcgaaacg actgagtcaa   2220
gcacgcaatc tattaaacta tggggatttt gaatcctcag attggtcggg agagaatgga   2280
tggagaacca gtcctcatgt ccatgtggca tctaataatc caatctttaa agggcgctat   2340
ctccacatgc caggtgcgat gagccctcaa ttctctaaca atacctatcc aacgtatgcg   2400
tatcaaaaag tggatgagtc aaaattaaag tcctataccc gttacctcgt acgtggactt   2460
gttggaaata gtaaagatct agaattactg gtggaacgat atggaaaaga tgtacatgtg   2520
gaaatggatg taccaaatga tattcaatat acattaccaa cgaatgactg tggtggcttt   2580
gatcgatgta aaccagtatc gtatcaaaca ggaacttctt cgtacaaatc gtgtggatgc   2640
aagaacaacg acacgtatca gaatggaatg catctatcta aatcatgtgg ttgcaaaaaa   2700
gatccacatg tcttcaccta ccatattgac acaggatgcg tggatcaaga agaaaactta   2760
ggtctattct ttgcattaaa aatcgcaagt gaaaatggta tggcgaacat tgataacctg   2820
gaaatcattg aggcacagcc gttaaaaggg gaagccttgg ctcgtgtgaa aaaacgagaa   2880
cagaaatgga aacaggaaat ggcgcaaaaa cttttacgaa cagagaaagc tgtacaagca   2940
gcgaaagatg cactgcagac tctattcaca aacgcgcagt acaatcgtct caaatttgaa   3000
accctgttcc cacaaattgt ccatgcagag aaactcgtac agcagatccc atatgcgtac   3060
catccattct tgagcgggac gctgtcaact gtaccaggta tgaattttga aatcatccaa   3120
caactattgg cagtgattgg aaatgcccgt acattatacg agcaacgaaa tctcttgcgt   3180
actggtacat tcagctcagg taccggaagt tggaaagtga cagaaggtgt aaaggtgcag   3240
ccactgcaag acacatctgt tctggttctg tcggaatgga gtcatgaagc gtcccagcag   3300
ttacacatgg atccagatcg cggatatgta ttacgtgtaa cagcgcgaaa agaaggcgga   3360
ggaaaaggga ctgtcaccat gagtgactgt gcagactaca cggagacact gacctttaca   3420
tcatgtgact ataacacgta tggttcccaa acgatgacaa gtggtacatt atctggattt   3480
gtgacgaaga cgttagaaat tttcccagat acggatcgga ttcgaattga tattggggaa   3540
accgaaggaa cgttccaagt agaaagtgtg gaattgattt gtatggaaca gatggaggac   3600
gacttatata atatggcggg gaacgtggcg gaagagatgc aagttctaca gcaatctcgt   3660
tccggtagcc acacattaga tcctttatgt aacacaagaa ttggcgagtt cgattgt      3717
```

<210> SEQ ID NO 6
<211> LENGTH: 1995
<212> TYPE: DNA
<213> ORGANISM: Bacillus thuringiensis

<400> SEQUENCE: 6

```
atgaatcaac agcataacaa tgaatatgaa atcatgagta ctggcgacat gggctatcag     60

ccaaggtatc ccttttcgaa tgcacctggt gctgaattgc aacagatgca ttacaaagat    120

tggatggata tgtgtgcaga tggagagtcg ggaaaaacgt ttgcagacct tacagttcag    180

gagggagtca ctatagctgt aagtattgca gcggcaattc ttagtgtacc atttccagta    240

acagcagcgg gattaagtat tatctcttta ctagttccat actggtggcc agagacagca    300

gtaactcccg gtactccctc tgcgcaagtt acatgggaaa aatttatgag tgctgcggaa    360

aatctcagta atacacaaat tgtagcgagt aaacgatcag atgccattgc tagatggcaa    420

ggtatacaaa ccttaggaag agactatttt caagcgcaat gtgactggct acaagatcaa    480

aataatgaac tcaaaaaaag taaattacgg gaggcatttg atgacttcga agattattta    540

aaagtgtcaa tgccattctt tcgtgcgcaa ggctttgaaa ttcctatgtt agctatgtat    600

gcacaagctg cgaatatgca cttacttttg ctaagagagg ttgtccagaa tggtgtgggt    660

tgggggttcc agcaatacga agttgaccga tattattcca atacagaccc tttttttaggg    720

aaccctggac tattacaact attagaagga tatacggact attgtgtaaa atggtataat    780

gcaggtttac gacaacaata cgaaaataat agatacaatt gggatgcatt caatgatttc    840

cgtagagata tgattataat ggtattagat attgtatctt tatggccaac ttatgatccg    900

aagcgctatc ccctacctac aaaatcacaa cttacacgaa ctgtgtatac cgatttagta    960

ggtttttctg gaaatagcga gtacctacaa atagacattg aacgtgcaga acaagcgcta   1020

gtccagaaac ctggtctatt tacctggctg cgtgagctaa gtttcgagct ggggccactg   1080

tcgcgaatta attttgtaag aggaagacaa atagtcttca attataccgg aagttccgat   1140

aggtatgaag agaccaaggg gaatcttgga gaaactagag aaactgttgt tattccggca   1200

ccggatgtag ggatgacat ctggaggatt agcactcaag ttaacaccta tcagatacca   1260

aatgctactt ttgttagagg ctggaatttt tcttttactc aatcattaga tcaaaaaata   1320

gcttggcgga cagaatattc acccgaaata gtgatgcagg gattgtcttg tcacggacct   1380

tctgtgagtt cttgtaacct ttgtatcagt aacagtccgt gtagaagtat tactcctaac   1440

tatagctccc cttgtgatga caagttggtt tatagtcatc gattttcata tttaggagcc   1500

ggacttaaat ccgatttaac aacgttgatt tattttagct acggatggac ccatgtaagc   1560

gcagatgcaa acaatttgat agatcctaaa aagattaccc aaatcccagc cgtaaagggg   1620

gattatttag ggagaaatgc ccgtgttata aaaggacctg gaagtacagg tggagatcta   1680

gtccaacttt ccgatggaac cgaaagagga actctgggca tcaaactaac aaaaccacca   1740

ggaagtcaca gctatcgtgt aagaatacgt tatgcaagta atacgcgaac tcaacttgag   1800

attatttggg gagaagatta cgatagcgtt atagttcctg ctactacaac tgatataaca   1860

aatctcacct ataataaatt cgggtacttc gaaatccgcg tttttagtta taattcatca   1920

agcgaagaag aagacttaat aagagtggat gctacgggtt ctttcatcct cgacaaaatc   1980

gaattcattc caatt                                                    1995
```

<210> SEQ ID NO 7
<211> LENGTH: 3618

<212> TYPE: DNA
<213> ORGANISM: Bacillus thuringiensis

<400> SEQUENCE: 7
ttgaattggt taagtaaaaa atgcttatct actttaaatg taaacttgta taaatcacaa 60
ttccaggggg aatatatgga taacaatagt gaaaaccaat gcgtccctta taattgttta 120
agtaatctag aggagataac attgaatggg gaaagactct caacgaatag caccccaatt 180
aatatttcca tgtctgtttc aaagtttctc ctgactgaac ttattccagg tttagggttt 240
gtatttggat tacttgatgc aatatggggg tttataggac ctgatcaatg gacggaattt 300
attgaacata ttgaagaatt aataggtcaa agaataacag ttgtagtaag aaatacagca 360
attcgagaat tggaaggaat ggcacgcgtt tatcaaacct atgctactgc gtttgcggca 420
tgggaaaagg atcctaataa tccggaatta agagaggcat tacgtgcaca atttactgca 480
accgagacct atataagtgg aaggatatct gttttgacaa ttgaggatta ccaggtacaa 540
ctgttatctg tctatgctca agctacaaat ttacatttat ctttattaag agatgttgtg 600
ttttggggtc agaggtgggg cttttcgaca acgactttaa ataattatta tagtgattta 660
actagagaga ttaatgaata taccaattat gctgtccatt ggtacaatgt aggattagaa 720
caattacagg gaccaagctt tcaagagtgg gtcgcataca atcgctatag aagggaatta 780
acactaactg tattggatat tgttactctt ttccataatt atgatatcag gttgtaccca 840
atcccaacta ttagtcaact aacaagggaa gtctatacag acccaatagt tagtggaata 900
gggcagccta acagttggga ttttcctacc ttctcagaag cagaaaataa gtcaattaga 960
acccctcatc tgatggattt cttgaggaac ctcacgattt ttacagattc ggcccggtat 1020
ggtgcaatat accatttctg gggagggcat caaatatcct ctagccttgt agggggaagt 1080
aatataacat ttcccacgta tgggagtaat gtgtcccaag ggagtccttg gatattagtc 1140
acaaatggaa ttccaatata taggacatta tcaaatccct attacaggtt ccttttccaa 1200
tcagttggta gcgcccgttt acgttgtgtt ttgggtgtac aatttcacat ggataatcgt 1260
gcctttacgt atcgcgaaaa ggggacagtg gattcctttg atgaattacc acctacggat 1320
gcaagtgtgt cacctagtga aggatatagc caccgtttat gtcatgcaac actttttcaa 1380
gtaagaaccg gcgggggtgg ggctgtaagc ttttctagaa cagatggagt agtcttttcc 1440
tggacgcatc gtagtgcaac tcctacaaat acaattgatc caaatgttat tactcaaatt 1500
cctgcggtaa agggaagatc tctttttaat ggtgcagtaa ttaaaggacc aggatttact 1560
ggtggagatt tagttagatt aaataggaat aatggtaata ttcaaaatag aggtcatctt 1620
ccaattccaa tccaattctc gtcgcgttct accagatatc gagttcgttt acgttatgct 1680
tctgcaaccc caattcaagt caatgttcat tgggaaaata gcacaatttt ttcaggtata 1740
gtaccagcta cggctcagtc attagataaa ctacaatcaa acgattttgg ttactttgag 1800
atcgctaata ctatttcatc ttcattagat ggtatagtag gtattagaaa ttttagtgca 1860
aatgcagatt tgataataga cagatttgaa tttatcccag tgaatgcaac ctccgaggca 1920
gaatatgatt tagaaagagc gcaagaggcg gtgaatgctc tgtttacttc tacgaatcaa 1980
agaggactta aagcgaatgt aacagattat tacattgatc aagtatccaa tctagtagaa 2040
tgcctatcgg atgagttctg cctagatgaa aagagagaat tatccgagaa agtcaaacag 2100
gcgaagcgaa tcagtgatga gcggaatttg ctccaggatt caaacttcag atgtatcaat 2160
ggtgaagaag accgtggatg gagaggaagt acgcatatta ccatccaagg aggaaacgat 2220
gtattcaaga gaaattttgt tacattacca ggtgcctttg atgcgtgtta tccaacgtat 2280
ttgtatcaaa gaatagatga atcgaaatta aaagcctata cacgctataa attaagagga 2340
tatatagaag atagtcaaga cttggagatt tatttgatcc gttacaatgc gaaacatgaa 2400
acagtaaatg taccaggtac tgagtcccta tggtcgcttt gtactgagag cccaattgga 2460
acgtgtggag aaccaaatcg atgcgcacca caaattgaat ggaatcctga tctaaattgt 2520
tcctgcaaag ccggagaaaa atgtgcacat cattcccatc atttctcctt ggacattgat 2580
gttggatgta cagacttaaa tgaggactta ggtgtatggg tgatattcaa gattaagacg 2640
caggatggcc atgcaagatt aggaaatcta gagtttctcg aagagaaacc gttattagga 2700
gaagcgttag ctcgtgtgaa aagagctgag aaaaaatgga gagacaaacg tgaaaaattg 2760
cagtttgaaa cgaaaatcgt ttacaaagag gcaaaagaat ctgtagatgc tttattcgta 2820
gattctcaat ataatagatt acaagcggat acgaacatta cgatgattca tgcggcagat 2880
aaacgcgttc atcgaatccg agaagcgtat ctgccagagt tgtctgtgat tccgggtgtc 2940
aatgcggcta ttttcgaaga attagaaggt cttattttca ctgcattctc ctttatatgat 3000 gcgagaaatg tgataaaaaa cggagatttc aataatggtt tatcatgctg gaacgtaaaa 3060
gggcatgtag atgtacaaca gagccatcat cgttctgtcc ttgttctccc agaatgggaa 3120
gcagaagtgt cacaagaagt tcgtgtctgt ccaggtcgtg gctacatcct tcgtgttaca 3180
gcttacaaag aaggatatgg agaaggatgc gtaacgattc atgagattga gaatcatact 3240
gaaaaattga agtttagaaa ctgtgaagaa gaggacatct atccaaccaa tacggtaacg 3300
tgtcatgatt ataatgtgaa tcaaggcgca gaaggatgcg cagatacatg taattcacgt 3360
catcgtggat atgacgaaac ctatggaaat gattcttccg tatcagctga ttatatgcca 3420
gtttatgagg aagaagtata tacagatgga cgaagagata atccttgtga aatggaaaga 3480
ggttacacac ctttaccagt tgattatgtg acaaaagaat tagaatactt ccctgaaaca 3540
aatacagtat ggattgagat tggagaaacg gaaggaacat tcatcgtaga cagcgtggaa 3600
ttactcctta tggaagaa 3618

<210> SEQ ID NO 8
<211> LENGTH: 1827
<212> TYPE: DNA
<213> ORGANISM: Bacillus thuringiensis

<400> SEQUENCE: 8
atggataaca atagtgaaaa ccaatgcgtc ccttataatt gtttaagtaa tctagaggag 60
ataacattga atggggaaag actctcaacg aatagcaccc caattaatat ttccatgtct 120
gtttcaaagt ttctcctgac tgaacttatt ccaggtttag ggtttgtatt tggattactt 180
gatgcaatat gggggtttat aggacctgat caatggacgg aatttattga acatattgaa 240
gaattaatag gtcaaagaat aacagttgta gtaagaaata cagcaattcg agaattggaa 300
ggaatggcac gcgtttatca aacctatgct actgcgtttg cggcatggga aaaggatcct 360
aataatccgg aattaagaga ggcattacgt gcacaattta ctgcaaccga gacctatata 420
agtggaagga tatctgtttt gacaattgag gattaccagg tacaactgtt atctgtctat 480
gctcaagcta caaatttaca tttatcttta ttaagagatg ttgtgttttg ggtcagaggg 540
tggggctttt cgacaacgac tttaaataat tattatagtg atttaactag agagattaat 600
gaatatacca attatgctgt ccattggtac aatgtaggat tagaacaatt acagggacca 660
agctttcaag agtgggtcgc atacaatcgc tatagaaggg aattaacact aactgtattg 720
gatattgtta ctcttttcca taattatgat atcaggttgt acccaatccc aactattagt 780
caactaacaa gggaagtcta tacagaccca atagttagtg gaatagggca gcctaacagt 840
tgggattttc ctaccttctc agaagcagaa aataagtcaa ttagaacccc tcatctgatg 900
gatttcttga ggaacctcac gatttttaca gattcggccc ggtatggtgc aatataccat 960
ttctggggag ggcatcaaat atcctctagc cttgtagggg gaagtaatat aacatttccc 1020
acgtatggga gtaatgtgtc ccaagggagt ccttggatat tagtcacaaa tggaattcca 1080
atatatagga cattatcaaa tccctattac aggttccttt tccaatcagt tggtagcgcc 1140
cgtttacgtt gtgttttggg tgtacaattt cacatggata atcgtgcctt tacgtatcgc 1200
gaaaagggga cagtggattc ctttgatgaa ttaccaccta cggatgcaag tgtgtcacct 1260
agtgaaggat atagccaccg tttatgtcat gcaacacttt ttcaagtaag aaccggcggg 1320
ggtggggctg taagcttttc tagaacagat ggagtagtct tttcctggac gcatcgtagt 1380
gcaactccta caaatacaat tgatccaaat gttattactc aaattcctgc ggtaaaggga 1440
agatctcttt ttaatggtgc agtaattaaa ggaccaggat ttactggtgg agatttagtt 1500
agattaaata ggaataatgg taatattcaa aatagaggtc atcttccaat tccaatccaa 1560
ttctcgtcgc gttctaccag atatcgagtt cgtttacgtt atgcttctgc aaccccaatt 1620
caagtcaatg ttcattggga aaatagcaca attttttcag gtatagtacc agctacggct 1680
cagtcattag ataaactaca atcaaacgat tttggttact ttgagatcgc taatactatt 1740
tcatcttcat tagatggtat agtaggtatt agaaatttta gtgcaaatgc agatttgata 1800
atagacagat ttgaatttat cccagtg 1827

<210> SEQ ID NO 9
<211> LENGTH: 2370
<212> TYPE: DNA
<213> ORGANISM: Bacillus thuringiensis

<400> SEQUENCE: 9
gtgaaaaaga tgaattctta tcaaaataag aatgaatatg aaatactgga tgcttcagaa 60
aatactgtaa atgcgttaaa cagatatcct ttcgcaaata atccgtattc ttccattttt 120
agttcttgtc cacgcagtgg gcctggtaat tggattaata tactaggaaa tgcagttagc 180
gaagcagtat ctatttcgca agatataata tctcttctta cacagccttc tatctctggg 240
ataatttcaa tggcatttag tcttttaagt agaatgatag gtagtaatgg aaggtctata 300
tcggagttat ctatgtgtga cttactagct attattgatt tgcgggtaaa tcagagtgtt 360
ttggatgacg gagttgctga ttttaacggc tcgttagtta tatacagaaa ctatttagag 420
gctttacaaa ggtggaacaa taatcccaat cccgctaatg ccgaagaggt tcgtactcgt 480
tttagggaat ctgatacaat attcgatctc attttaacac aagggtcttt aacgaatggc 540
ggttcattag ccagaaataa tgctcaaata ttattattgc cttcttttgc aaatgctgca 600
tactttcatt tactgctatt aagagatgct aatgtatatg ggaataattg gggtttattt 660
ggggttacac ctaatataaa ttatgaatcg aaattactaa accttattag attatatact 720
aattattgca cacattggta taatcaagga ctaaatgaac taagaaatcg aggttccaat 780
gctacagctt ggttggaatt tcatagattt cgtagagata tgacattgat ggtattggat 840
atagtatcat cattttcaag tcttgatatt actagatatc caagagcaac agattttcaa 900
ttgagtagga taatttatac agatccaatt ggttttgtaa atcgtagtga ccctagcgca 960

-continued

```
ccaagaacct ggtttagttt tcacaatcaa gctaattttt cagcgttaga aagtggaata   1020

cctagtcctt cattctcaca attcttagat agtatgcgta tatctactgg cccgcttagt   1080

ttacctgctt ctcctaatat ccatagagca cgggtatggt atggtaatca aaataacttt   1140

aatggatcta gtagccaaac ttttggggaa ataacaaatg ataatcaaac catttcgggt   1200

ttaaatattt tcagaataga ttcacaggct gttaatctaa ataatactac gtttggagtt   1260

agtagagctg aattttatca tgatgctagt caaggctctc aaagatccat atatcaagga   1320

tttgttgata caggtggggc tagtaccgct gtagcccaga atattcaaac atttttcccg   1380

ggagaaaatt cgagtatacc aactccacaa gattatactc atatattaag taggtcaaca   1440

aatttaacag gaggacttcg acaagtagca tctggacgtc gttcttcttt agtattacac   1500

ggttggacac ataaaagtct gagtcgtcaa aatagagttg aaccaaatag aattactcaa   1560

gtgccggctg ttaaagcaag ttctccttcg aattgtactg taattgcagg acctggattt   1620

acaggtgggg atttagtcag aatgagttca aactgtagcg taagttacaa ttttacacca   1680

gctgatcagc aagttgtaat acgtctacgt tatgcttgtc aagggacagc ttcattaagg   1740

ataacgtttg gtaatggttc tagccaaata attccgcttg tttctacaac ttcatcaata   1800

aataatcttc aatatgaaaa ttttagtttt gcttctggtc caaatagcgt taacttttta   1860

tcagctggta cttcaataac tattcaaaat atcagtacaa attctaacgt agtgctagat   1920

agaattgaaa ttgtgccaga acaacctatt cctattattc caggggacta tcaaattgta   1980

acagctttaa ataatagtag tgtattcgat ttaaatagtg gaacccgagt tacattatgg   2040

tcgaataata gaggtgctca tcaaatttgg aatttcatgt atgatcagca aagaaatgca   2100

tatgtaatac gtaacgtaag taatccaagt ttagtcttaa cttgggattt tacaagtcct   2160

aatagtattg tatttgctgc cccttttttct ccaggaaggc aagagcaata ttggattgca   2220

gaaagttttc aaaatagcta tgtattcgaa aacctcagaa atacgaatat ggttttagat   2280

gtagccggag gatcaaccgc tattggtaca aatattatcg cattcccaag acataatgga   2340

aatgctcaaa gattcttcat cagaagacct                                     2370
```

```
<210> SEQ ID NO 10
<211> LENGTH: 2361
<212> TYPE: DNA
<213> ORGANISM: Bacillus thuringiensis

<400> SEQUENCE: 10

atgaattctt atcaaaataa gaatgaatat gaaatactgg atgcttcaga aaatactgta     60

aatgcgttaa acagatatcc tttcgcaaat aatccgtatt cttccatttt tagttcttgt    120

ccacgcagtg ggcctggtaa ttggattaat atactaggaa atgcagttag cgaagcagta    180

tctatttcgc aagatataat atctcttctt acacagcctt ctatctctgg gataatttca    240

atggcattta gtcttttaag tagaatgata ggtagtaatg gaaggtctat atcggagtta    300

tctatgtgtg acttactagc tattattgat ttgcgggtaa atcagagtgt tttggatgac    360

ggagttgctg attttaacgg ctcgttagtt atatacagaa actatttaga ggctttacaa    420

aggtggaaca ataatcccaa tcccgctaat gccgaagagg ttcgtactcg ttttagggaa    480

tctgatacaa tattcgatct cattttaaca caagggtctt taacgaatgg cggttcatta    540

gccagaaata atgctcaaat attattattg ccttcttttg caaatgctgc atactttcat    600

ttactgctat taagagatgc taatgtatat gggaataatt ggggtttatt tggggttaca    660

cctaatataa attatgaatc gaaattacta aaccttatta gattatatac taattattgc    720
```

acacattggt ataatcaagg actaaatgaa ctaagaaatc gaggttccaa tgctacagct 780
tggttggaat ttcatagatt tcgtagagat atgacattga tggtattgga tatagtatca 840
tcattttcaa gtcttgatat tactagatat ccaagagcaa cagattttca attgagtagg 900
ataatttata cagatccaat tggttttgta aatcgtagtg accctagcgc accaagaacc 960
tggtttagtt ttcacaatca agctaatttt tcagcgttag aaagtggaat acctagtcct 1020
tcattctcac aattcttaga tagtatgcgt atatctactg gcccgcttag tttacctgct 1080
tctcctaata tccatagagc acgggtatgg tatggtaatc aaaataactt taatggatct 1140
agtagccaaa cttttgggga aataacaaat gataatcaaa ccatttcggg tttaaatatt 1200
ttcagaatag attcacaggc tgttaatcta aataatacta cgtttggagt tagtagagct 1260
gaattttatc atgatgctag tcaaggctct caaagatcca tatatcaagg atttgttgat 1320
acaggtgggg ctagtaccgc tgtagcccag aatattcaaa catttttccc gggagaaaat 1380
tcgagtatac caactccaca agattatact catatattaa gtaggtcaac aaatttaaca 1440
ggaggacttc gacaagtagc atctggacgt cgttcttctt tagtattaca cggttggaca 1500
cataaaagtc tgagtcgtca aaatagagtt gaaccaaata gaattactca agtgccggct 1560
gttaaagcaa gttctccttc gaattgtact gtaattgcag gacctggatt tacaggtggg 1620
gatttagtca gaatgagttc aaactgtagc gtaagttaca attttacacc agctgatcag 1680
caagttgtaa tacgtctacg ttatgcttgt caagggacag cttcattaag gataacgttt 1740
ggtaatggtt ctagccaaat aattccgctt gtttctacaa cttcatcaat aaataatctt 1800
caatatgaaa attttagttt tgcttctggt ccaaatagcg ttaacttttt atcagctggt 1860
acttcaataa ctattcaaaa tatcagtaca aattctaacg tagtgctaga tagaattgaa 1920
attgtgccag aacaacctat tcctattatt ccaggggact atcaaattgt aacagcttta 1980
aataatagta gtgtattcga tttaaatagt ggaacccgag ttacattatg gtcgaataat 2040
agaggtgctc atcaaatttg gaatttcatg tatgatcagc aaagaaatgc atatgtaata 2100
cgtaacgtaa gtaatccaag tttagtctta acttgggatt ttacaagtcc taatagtatt 2160
gtatttgctg ccccttttc tccaggaagg caagagcaat attggattgc agaaagtttt 2220
caaaatagct atgtattcga aaacctcaga aatacgaata tggttttaga tgtagccgga 2280
ggatcaaccg ctattggtac aaatattatc gcattcccaa gacataatgg aaatgctcaa 2340
agattcttca tcagaagacc t 2361

<210> SEQ ID NO 11
<211> LENGTH: 3516
<212> TYPE: DNA
<213> ORGANISM: Bacillus thuringiensis

<400> SEQUENCE: 11
atggaggtaa ataatcaaaa tcaatgcgtg ccctataatt gtttgaataa tcctgaaatc 60
gaaatattag gaggagaaag aatatcagtt ggtaataccc caatcgatat ttctctgtcg 120
cttacgcagt ttcttttgag tgaatttgtc ccaggtgcgg ggtttgtatt agggttaatt 180
gatttaatat ggggattttt aggcccctct caatgggatg catttctttt gcaaattgaa 240
cagttaatta gccaaagaat agaggaattc gcaaggaacc aagcaatttc tagattagaa 300
gggctaagca atctttatcg catttacgca gaagctttta gagcgtggga agctgatcct 360
actaatctag cattaagaga agagatgcgt acgcaattta atgacatgaa cagtgctctt 420

-continued

```
gtaacagcta ttcctctttt ttcagttcaa aattatcaag tcccactttt atcagtatat    480
gttcaagctg caaatttaca tttatcggtt ttgagagatg tttcagtgtt tgggcaacgt    540
tggggatttg atgtagcaac aatcaatagt cgttataatg atttaactag gcttattggc    600
gaatatacgg attatgctgt acgctggtac aatacgggat tagatcgttt gcgaggttct    660
aatttccaag attggataag atacaatcgt tttagaagag aattaacact gactgtatta    720
gatatcgttt ctgtttttca aaactacgat tctagattat atccaattca aacatcatct    780
caattaacac gagaaattta ttcggattta cttttagcta atccatctgg agttggaagt    840
ttctctaatg tagatttcga tagtattcta attagacaac ctcatttaat agattttatg    900
agagtactta cgatttatac cgatcgacat aacgcaagta gacacaatat atattgggct    960
ggacatcaag tgactgccgt tgatactgct aatcgtacga ttgtgtatcc tgtaaatggt   1020
agtgcagcaa atttagaacc cccaagaact ttacgatttg aaagtccagt tgtagaaatt   1080
cgttcaaatc ctgtatggga tagaggatca actggaattg caggcagcta tgaatttttt   1140
ggggtgacaa gtgctttgtt tattacaatt ttgggatttg gttacactta tcgaagcgga   1200
tccaatacag aagttactgc attaccagac catcaagtga gtcatattgg ttattttaga   1260
cgttttacta caacgggtgc caccgctaga caaacgctaa caagtgcacc gatagtttcc   1320
tggacgcata gtagcgctga gccaccaaat agaatttatc agaatagaat tacccaaatc   1380
cctgctgtta aaggtaactt tctttttaat ggagctgtaa tctcaggacc aggatttact   1440
ggaggggact tagttagatt gaataggaat aatgataaca ttcaaaatag ggggtatatc   1500
gaagttccaa tccaattcgc gtcgacatct accagatatc gggttcgtgt acgttatgct   1560
tctacaaacg cgatcgaagt caatattaat tggggaaatg gatcaatttt tacgggcaca   1620
gcaccagcta cagctacatc attagataat ctacaatcaa acgattttgg ctattttgaa   1680
agtaccactg cttttgcacc ttcattaggt aatatagtag gtgttaggaa ttttagtgca   1740
aatgcagatg tgataataga cagatttgaa tttattccag ttactgcaac acttgaagca   1800
gaatatgacc tagaaagagc ggagaaggcg gtgaatgccc tgtttacttc cacaacccaa   1860
ttaggactaa aaacagatgt gacggattat catattgatc aggtatccaa tctagtagaa   1920
tgcctatcgg atgaattctg cctaaatgaa aagagagaat tatccgagaa agtcaaacat   1980
gcgaagcgac ttagtgataa aaggaattta ctccaagatc caaatttcac atccattaat   2040
gggcaactag accgtgggtg gagaggaagc acggatatta ctatccaagg aggcaatgac   2100
gtattcaaag agaattacgt gacactaccg ggcacctttg acgagtgcta tccaacgtat   2160
ttgtatcaaa aaatagatga gtcacaatta aaatcttata ctcgctatca attaagaggc   2220
tatatcgaag atagtcaaga tttagagatt tatttgattc gttacaatgc gaaacatgaa   2280
acattaagtg tgccaggtac tgagtcccca tggccatctt caggagtata tccaattgga   2340
aagtgcggag aaccgaatcg atgtgcacca cgaatcgaat ggaatcccga tctaggctgt   2400
tcctgcagat atggagagaa atgcgttcat cattcgcatc atttctcctt ggatattgat   2460
gttggatgta cagatttgaa tgaggatcta ggcgtatggg tgatatttaa gattaagacc   2520
caagatggcc atgcaaaact aggaaaccta gaattcatcg aagagaaacc attattagga   2580
gaagcgctgt cccgtgtgaa gagggccgag aaaaaatgga aagacaaatg tgaaaaactg   2640
caattggaaa cacaacgagt atatacagag gcaaaagaat ctgtggatgc tttattcata   2700
gattctcaat atgatagatt acaagcagat acaaacattg gtatgattca tgcggcagat   2760
aaacaggttc atcgaatccg agaagcgtat ctcccggaat tacacgcgat tccaggtgta   2820
```

```
aatgcggaaa ttttcgaaga attagaaaat ttccgcattt acactgcatt ctctctatat   2880

gatgcaagaa atgtcataaa aaatggcgat ttcaataatg gtttatcgtg ttggaacgta   2940

aaagggcatg tagatgtaca acagaaccat catcgctcgg tccttgttct ctcagaatgg   3000

gaagcagaag tgtcacaaaa ggtacgcgta tgtccagatc gaggctatat ccttcgtgtt   3060

acagcgtata aagagggata tggagaggga tgcgtaacga ttcatgaatt cgaagataat   3120

acggatgtac tgaagtttag aaactgtgta gaagaggaag tatatccaaa caacacggta   3180

acgtgtaatg attatactac gaatcaaagt gcagaaggat gtacggatgc atgtaattcc   3240

tataatcgtg gatatgagga tggatatgga aacaatcctt cagcaccagt taattacaca   3300

ccgacgtacg aagaaagaat gtatacagat acagatacac agggatataa tcattgtgta   3360

tctgacagag gatataggaa tcatacacca ttaccagcgg gctatgtaac gctagaatta   3420

gaatttttcc cagaaacaga gcaagtatgg atagagattg gggaaacaga aggaacattc   3480

atcgtggaca gtgtagaatt attccttatg gaggaa                             3516
```

<210> SEQ ID NO 12
<211> LENGTH: 1782
<212> TYPE: DNA
<213> ORGANISM: Bacillus thuringiensis

<400> SEQUENCE: 12

```
atggaggtaa ataatcaaaa tcaatgcgtg ccctataatt gtttgaataa tcctgaaatc     60

gaaatattag gaggagaaag aatatcagtt ggtaataccc caatcgatat ttctctgtcg    120

cttacgcagt ttcttttgag tgaatttgtc ccaggtgcgg ggtttgtatt agggttaatt    180

gatttaatat ggggattttt aggcccctct caatgggatg catttctttt gcaaattgaa    240

cagttaatta gccaaagaat agaggaattc gcaaggaacc aagcaatttc tagattagaa    300

gggctaagca atctttatcg catttacgca gaagctttta gagcgtggga agctgatcct    360

actaatctag cattaagaga agagatgcgt acgcaattta atgacatgaa cagtgctctt    420

gtaacagcta ttcctctttt ttcagttcaa aattatcaag tcccactttt atcagtatat    480

gttcaagctg caaatttaca tttatcggtt ttgagagatg tttcagtgtt tgggcaacgt    540

tggggatttg atgtagcaac aatcaatagt cgttataatg atttaactag gcttattggc    600

gaatatacgg attatgctgt acgctggtac aatacgggat tagatcgttt gcgaggttct    660

aatttccaag attggataag atacaatcgt tttagaagag aattaacact gactgtatta    720

gatatcgttt ctgtttttca aaactacgat tctagattat atccaattca aacatcatct    780

caattaacac gagaaattta ttcggattta cttttagcta atccatctgg agttggaagt    840

ttctctaatg tagatttcga tagtattcta attagacaac ctcatttaat agattttatg    900

agagtactta cgatttatac cgatcgacat aacgcaagta gacacaatat atattgggct    960

ggacatcaag tgactgccgt tgatactgct aatcgtacga ttgtgtatcc tgtaaatggt   1020

agtgcagcaa atttagaacc cccaagaact ttacgatttg aaagtccagt tgtagaaatt   1080

cgttcaaatc ctgtatggga tagaggatca actggaattg caggcagcta tgaatttttt   1140

ggggtgacaa gtgctttgtt tattacaatt ttgggatttg gttacactta tcgaagcgga   1200

tccaatacag aagttactgc attaccagac catcaagtga gtcatattgg ttattttaga   1260

cgttttacta caacgggtgc caccgctaga caaacgctaa caagtgcacc gatagtttcc   1320

tggacgcata gtagcgctga gccaccaaat agaatttatc agaatagaat tacccaaatc   1380
```

-continued

```
cctgctgtta aaggtaactt tctttttaat ggagctgtaa tctcaggacc aggatttact   1440

ggaggggact tagttagatt gaataggaat aatgataaca ttcaaaatag gggtatatc   1500

gaagttccaa tccaattcgc gtcgacatct accagatatc gggttcgtgt acgttatgct   1560

tctacaaacg cgatcgaagt caatattaat tggggaaatg gatcaatttt tacgggcaca   1620

gcaccagcta cagctacatc attagataat ctacaatcaa acgattttgg ctattttgaa   1680

agtaccactg cttttgcacc ttcattaggt aatatagtag gtgttaggaa ttttagtgca   1740

aatgcagatg tgataataga cagatttgaa tttattccag tt                      1782
```

<210> SEQ ID NO 13
<211> LENGTH: 999
<212> TYPE: DNA
<213> ORGANISM: Unknown
<220> FEATURE:
<223> OTHER INFORMATION: Isolated from soil sample

<400> SEQUENCE: 13

```
atgaaagtgt ataaaaaaat aacgaaaatg gcaccaatta tggcattaag tacagctgta     60

ttattgtctc caggatctac ttttgcagct gaaaaagcag ttgttacaaa atcaaatgta    120

tcttctctaa caactaatac agtaatgcaa tcaggaagta tcattcaagg atatctaatt    180

aaaaatggtg tcaaaacccc cgtatataac agtgaggtac aaactcggtc tacagcggta    240

aatgaagcac cctatccaga actttcaagt aatccaaatg atccagttcc ttcaaaagga    300

tccatcacaa gtgaaagtgg aaatgtagga tcggtactat atttttctaa atttaattcg    360

caaaaattac aaaatactgc ggaaccggtt tattggaaaa atgtatattt agaaaaaact    420

ccggatggga atattatttt tggaacgtat gatccgacaa ctttaaagcg gactcctaat    480

ctggttaata ttatgatgac tccttcaaag gtacaatatt accaatcctt ctttactgat    540

acaaaaataa aacgagaaac tgcgtatgaa aaaataggtg gaggaactcc acaacccaaa    600

aatacttcgt atacattttc aagtgctgtt acgtctggat tatctacatc agatgcaatc    660

ggtggttctc tgacattagg atataaatat agtgttaaag aaggtggtgg tgtacttcct    720

gttgaagcga cacaagaatt tagtttacaa ttaacggcaa gttataacca tacaatcact    780

gtttccagtc aaacaactaa tacacaaact tatagtgtag cacacgctgg agattcgtat    840

aaaaatgata aatatgtagc ggctatgtat cagttaaaat ctcattatac agttattcca    900

ggacctgcac taacacaatc gggaagtatt ttagctcaag aggcattcca atatgatgat    960

tcatctctgt atttagccgt gactcctggt gctggaatt                           999
```

<210> SEQ ID NO 14
<211> LENGTH: 915
<212> TYPE: DNA
<213> ORGANISM: Unknown
<220> FEATURE:
<223> OTHER INFORMATION: Isolated from soil sample

<400> SEQUENCE: 14

```
atggaaaaag cagttgttac aaaatcaaat gtatcttctc taacaactaa tacagtaatg     60

caatcaggaa gtatcattca aggatatcta attaaaaatg gtgtcaaaac ccccgtatat    120

aacagtgagg tacaaactcg gtctacagcg gtaaatgaag caccctatcc agaactttca    180

agtaatccaa atgatccagt tccttcaaaa ggatccatca caagtgaaag tggaaatgta    240

ggatcggtac tatatttttc taaatttaat tcgcaaaaat tacaaaatac tgcggaaccg    300

gtttattgga aaaatgtata tttagaaaaa actccggatg ggaatattat ttttggaacg    360
```

tatgatccga caactttaaa gcggactcct aatctggtta atattatgat gactccttca 420
aaggtacaat attaccaatc cttctttact gatacaaaaa taaaacgaga aactgcgtat 480
gaaaaaatag gtggaggaac tccacaaccc aaaaatactt cgtatacatt ttcaagtgct 540
gttacgtctg gattatctac atcagatgca atcggtggtt ctctgacatt aggatataaa 600
tatagtgtta aagaaggtgg tggtgtactt cctgttgaag cgacacaaga atttagttta 660
caattaacgg caagttataa ccatacaatc actgtttcca gtcaaacaac taatacacaa 720
acttatagtg tagcacacgc tggagattcg tataaaaatg ataaatatgt agcggctatg 780
tatcagttaa aatctcatta tacagttatt ccaggacctg cactaacaca atcgggaagt 840
attttagctc aagaggcatt ccaatatgat gattcatctc tgtatttagc cgtgactcct 900
ggtgctggaa tttag 915

<210> SEQ ID NO 15
<211> LENGTH: 1155
<212> TYPE: DNA
<213> ORGANISM: Unknown
<220> FEATURE:
<223> OTHER INFORMATION: Isolated from soil sample

<400> SEQUENCE: 15
atggcaatta taaatcaatc atcactaaat tcaagaatac atgatttacg tgaagattca 60
agaacagctc ttgaaaaagt ttatactagt aataatcctt ggggtttcgt aagtatacac 120
tctgaccgac ttgaaaatta tcaactaact aatgtaaatg ttagtcctag gaatcaagat 180
tttcaaacga ttcctagatt gcaacactct gctacacaaa taattgaaaa taacacaagt 240
gtaacacaat ctcaaaccat ttcttttaat gaaagaacaa cagacacttt tacaacatcg 300
gttactacgg gatttaaaac tggaactagt gtgaaatcta cgacaaaatt caaaatatct 360
gttggatttt tattagcagg cgaattagaa caatcagtgg aagtttctgt gaattttgag 420
tataattata gttcaacaac tacagagacg catagcgttg aaagaggatg gacaatttca 480
cagcctataa ttgctccccc acgaacaagg gtagaagcta ctcttctaat ttatgctgga 540
tctgttgatg taccaattga tttaaatgct accattgttg gtgatccaat tccatggcca 600
tcgtgggggc cggcagtata ttctggatct tttcttgcta atgatggtcg gatatggtcg 660
gctcctatac taccagagca actatcactg gcatcttcag cgtatacaac tgttggaagg 720
acagcaaatt ttagcggttt agcgactacc aacgtttcct caggcctgta ttctattgtt 780
cgtattgatg aaagtccttt accaggattt acaggagaaa caaggcgtta ttatttaccg 840
ccttcattag cgactacaaa tcaaatactt tcgacaaatg cgttaggaaa taatgtgcca 900
attattaatc cagttcctaa tggacattgc aaaaaagatc attctccaat tattattcat 960
aaaaatagag aggtgaagtg cgaacacaat tatgatgaag tgtatcctcg tcatgatcaa 1020
gtagagaagt gcgaacacaa ttatgatgaa gtgtatcctc gtcatgatca agtagagaag 1080
tgcgaacacg attatgatga agtgtatcct cgtcatgatc aagtagagaa gtacgaacac 1140
aattatgatg aagaa 1155

<210> SEQ ID NO 16
<211> LENGTH: 1002
<212> TYPE: DNA
<213> ORGANISM: Unknown
<220> FEATURE:
<223> OTHER INFORMATION: Isolated from soil sample
<400> SEQUENCE: 16
atggcaatta taaatcaatc atcactaaat tcaagaatac atgatttacg tgaagattca 60
agaacagctc ttgaaaaagt ttatactagt aataatcctt ggggtttcgt aagtatacac 120
tctgaccgac ttgaaaatta tcaactaact aatgtaaatg ttagtcctag gaatcaagat 180
tttcaaacga ttcctagatt gcaacactct gctacacaaa taattgaaaa taacacaagt 240
gtaacacaat ctcaaaccat ttcttttaat gaaagaacaa cagacacttt tacaacatcg 300
gttactacgg gatttaaaac tggaactagt gtgaaatcta cgacaaaatt caaaatatct 360
gttggatttt tattagcagg cgaattagaa caatcagtgg aagtttctgt gaattttgag 420
tataattata gttcaacaac tacagagacg catagcgttg aaagaggatg gacaatttca 480
cagcctataa ttgctccccc acgaacaagg gtagaagcta ctcttctaat ttatgctgga 540
tctgttgatg taccaattga tttaaatgct accattgttg gtgatccaat tccatggcca 600
tcgtgggggc cggcagtata ttctggatct tttcttgcta atgatggtcg gatatggtcg 660
gctcctatac taccagagca actatcactg gcatcttcag cgtatacaac tgttggaagg 720
acagcaaatt ttagcggttt agcgactacc aacgtttcct caggcctgta ttctattgtt 780
cgtattgatg aaagtccttt accaggattt acaggagaaa caaggcgtta ttatttaccg 840
ccttcattag cgactacaaa tcaaatactt tcgacaaatg cgttaggaaa taatgtgcca 900
attattaatc cagttcctaa tggacattgc aaaaaagatc attctccaat tattattcat 960
aaaaatagag aggtgaagtg cgaacacaat tatgatgaag aa 1002

<210> SEQ ID NO 17
<211> LENGTH: 3696
<212> TYPE: DNA
<213> ORGANISM: Bacillus thuringiensis
<400> SEQUENCE: 17
atgaataaaa ataatcaaaa tgaatatgaa attattgacg cttccaattg tggttgtgcg 60
tctgatgatg ttgcgagata tcctttagcc aacaatccgt attcatctgc tttaaattta 120
aattcttgtc aaaatagtag cattctcaat tggattaaca taataggaaa tgcagcaaaa 180
gaagcagtat ctattggatt aacaataaaa tctcttatca cagcaccttc tctcactgga 240
ttaatttcca tagcatataa tcttttgggg aaagtgctag gaggtagtag tggccaatcc 300
atatcagatt tgtctatatg tgacttatta tctattattg atttgcgggt aaatcagagt 360
gttttaaatg atgggattgc agattttaat ggttctttaa tcttatacag gaactatttg 420
gatgctctaa atagctggaa tgagaatcct aattctaatc gggctgaaga actccgtgcc 480
cgttttagaa tcgctgattc agaatttgat agaattttaa cacgggggtc tttaacgaat 540
ggtggttcgt tagctagaca agatgcccaa atattattat taccttcttt tgcaagtgct 600
gcatttttcc atttattact actaagggat gctgctagat atggaaatga ttgggatctt 660
tttggcgcta taccttttat aaattatcaa tccaaactag tagaacttat tgaactatat 720
actgattatt gcgtaaattg gtataatcaa ggtttcaacg aactaagaca acgaggcact 780
agtgctacag tttggttgga atttcataga tatcgtagag agatgacatt gacggtatta 840
gatatagtag catcattttc aagtcttgat attactaact acccaataga aacagatttt 900
cagttgagta ggattattta tacagatcca attggttttg tacatcgtag tagtcttagg 960
ggggagagtt ggtttagctt tattaataga gctaatttct cagagttaga aaatgcaata 1020
cctaacccta gaccgtcttg gtttttaaat aatatgatta tatctactgg ttcacttaca 1080

-continued

```
ttgcccgtta gtccaaatac tgatagagcg agagtatggt atgggagccg agatagaatt   1140
tcccctgcta attcacaagt aatttctgag ctgatttcgg ggcaacatac gaattctaca   1200
caaactattt tagggcgaaa tatatttaga atagattctc aagcatgtaa tttaaatgat   1260
accacatatg gagtaaacag ggctgtattt tatcatgatg ctagtgaagg ttctcaaaga   1320
tcagtgtacg aagggtttat tagaacaact ggaatagata atcctagagt tcagaatatt   1380
aatacttatt ttcctggaga aaattcaaat atcccaactc cagaagacta tactcattta   1440
ttaagtacaa cagtaaattt aacaggaggt cttagacaag tagcaaataa tcgtcgttca   1500
tctatagtaa tttatggttg gacacataaa agtctaactc gtaacaatac tattaatcca   1560
ggtattatta cacaaatccc aatggttaaa ttatccaatc tctcttcagg tactaatgtt   1620
gttagagggc caggatttac aggtggagat atccttcgta gaacgaatgc tggtaacttt   1680
ggagatgtac gagtcaatat tgctggatca ttatcccaaa gatatcgcgt aaggattcgt   1740
tatgcttcta ctacaaattt acaattccac acatcaatta acggaagagc tattaatcaa   1800
gcgaattttc cagcaactat gaatataggt gctagcttaa actatagaac ctttagaact   1860
gtaggattta caactccatt tactttttca gaagcatcaa gcatatttac attaagtact   1920
cattccttca gttcaggcaa tgcagtttat atagatcgaa ttgaatttgt cccggcagaa   1980
gtaacattcg aggcagaatc tgatctagaa agagcacaga aggcggtgaa tgcgctgttt   2040
acttcttcca atcaaatcgg cttaaaaaca gatgtgacgg actatcatat tgatcaagtt   2100
tccaatttag ttgcgtgttt atcggatgaa ttttgtctgg atgaaaagcg agagttgtcc   2160
gagaaagtca aacatgcgaa gcgactcagt gatgagcgaa atttacttca agatccaaac   2220
ttcagaggca tcaatagaca actagaccgt ggttggagag gaagtacgga tattaccatc   2280
caaggtggag atgacgtatt caaagagaat tacgtcacac tgccgggtac ctttgatgag   2340
tgctatccaa catatttata tcaaaaaata gatgagtcga aattaaaagc ctatacccgc   2400
tatgaattaa gagggtatat tgaagatagt caagacttag aagtctattt gatccgttac   2460
aatgcaaaac acgaaacgtt aaatgtgcca ggtacgggtt ccttatggcc acttgcagcc   2520
gaaagttcaa tcgggaggtg cggcgaaccg aatcgatgcg cgccacatat tgaatggaat   2580
cctgacctag attgttcgtg tagggatgga gaaaaatgtg cacatcattc tcatcatttc   2640
tccttggata ttgatgttgg atgtacagac ttaaatgagg atttaggtgt atgggtgata   2700
ttcaagatta agacgcaaga tggccacgca agacttggaa atctagagtt tctcgaagag   2760
aaaccattat taggagaagc gctagctcgt gtgaagagag cggagaaaaa atggagagac   2820
aaacgcgaca aattggaatt ggaaacaaat attgtttata aagaggcaaa agaatctgta   2880
gatgctttat tcgtagattc tcaatataat agattacaaa cggatacgaa cattgcgatg   2940
attcatgcgg cagataaacg cgttcatcga atccgagaag cgtatctgcc agagttgtct   3000
gtgattccgg gtgtcaatgc ggctattttc gaagaattag aaggtcttat tttcactgca   3060
ttctccctat atgatgcgag aaatgtcatt aaaaacggag atttcaatca tggtttatca   3120
tgctggaacg tgaaagggca tgtagatgta gaagaacaaa ataaccaccg ttcggtcctt   3180
gttgttccgg aatgggaagc agaagtgtca caagaagtcc gcgtatgtcc aggacgtggc   3240
tatatcctgc gtgttacagc gtacaaagag ggctacggag aaggatgcgt aacgatccat   3300
gaaattgaag atcatacaga cgaactgaaa tttagaaact gtgaagaaga ggaagtgtat   3360
ccgaataaca cggtaacgtg taatgattat ccagcaaatc aagaagaata caagggtgcg   3420
```

-continued tacccttctc gtaatggtgg atatgaggat acatatgaca cttcagcatc tgttcattac 3480
aacacaccaa cgtacgaaga agaaatagga acagatctac agagatataa tcagtgtgaa 3540
aataacagag gatatggaaa ttacacacca ctaccagcag gttatgtaac aaaagaatta 3600
gagtacttcc cagaaacaga taaagtatgg atagagattg gcgaaacgga aggaacattc 3660
atcgtagaca gtgtggaatt actcctcatg gaggaa 3696

<210> SEQ ID NO 18
<211> LENGTH: 1980
<212> TYPE: DNA
<213> ORGANISM: Bacillus thuringiensis

<400> SEQUENCE: 18
atgaataaaa ataatcaaaa tgaatatgaa attattgacg cttccaattg tggttgtgcg 60
tctgatgatg ttgcgagata tcctttagcc aacaatccgt attcatctgc tttaaattta 120
aattcttgtc aaaatagtag cattctcaat tggattaaca taataggaaa tgcagcaaaa 180
gaagcagtat ctattggatt aacaataaaa tctcttatca cagcaccttc tctcactgga 240
ttaatttcca tagcatataa tcttttgggg aaagtgctag gaggtagtag tggccaatcc 300
atatcagatt tgtctatatg tgacttatta tctattattg atttgcgggt aaatcagagt 360
gttttaaatg atgggattgc agattttaat ggttctttaa tcttatacag gaactatttg 420
gatgctctaa atagctggaa tgagaatcct aattctaatc gggctgaaga actccgtgcc 480
cgttttagaa tcgctgattc agaatttgat agaattttaa cacgggggtc tttaacgaat 540
ggtggttcgt tagctagaca agatgcccaa atattattat taccttcttt tgcaagtgct 600
gcatttttcc atttattact actaagggat gctgctagat atggaaatga ttgggatctt 660
tttggcgcta taccttttat aaattatcaa tccaaactag tagaacttat tgaactatat 720
actgattatt gcgtaaattg gtataatcaa ggtttcaacg aactaagaca acgaggcact 780
agtgctacag tttggttgga atttcataga tatcgtagag agatgacatt gacggtatta 840
gatatagtag catcattttc aagtcttgat attactaact acccaataga aacagatttt 900
cagttgagta ggattattta tacagatcca attggttttg tacatcgtag tagtcttagg 960
ggggagagtt ggtttagctt tattaataga gctaatttct cagagttaga aaatgcaata 1020
cctaacccta gaccgtcttg gtttttaaat aatatgatta tatctactgg ttcacttaca 1080
ttgcccgtta gtccaaatac tgatagagcg agagtatggt atgggagccg agatagaatt 1140
tcccctgcta attcacaagt aatttctgag ctgatttcgg ggcaacatac gaattctaca 1200
caaactattt tagggcgaaa tatatttaga atagattctc aagcatgtaa tttaaatgat 1260
accacatatg gagtaaacag ggctgtattt tatcatgatg ctagtgaagg ttctcaaaga 1320
tcagtgtacg aagggtttat tagaacaact ggaatagata atcctagagt tcagaatatt 1380
aatacttatt ttcctggaga aaattcaaat atcccaactc cagaagacta tactcattta 1440
ttaagtacaa cagtaaattt aacaggaggt cttagacaag tagcaaataa tcgtcgttca 1500
tctatagtaa tttatggttg gacacataaa agtctaactc gtaacaatac tattaatcca 1560
ggtattatta cacaaatccc aatggttaaa ttatccaatc tctcttcagg tactaatgtt 1620
gttagagggc caggatttac aggtggagat atccttcgta gaacgaatgc tggtaacttt 1680
ggagatgtac gagtcaatat tgctggatca ttatcccaaa gatatcgcgt aaggattcgt 1740
tatgcttcta ctacaaattt acaattccac acatcaatta acggaagagc tattaatcaa 1800
gcgaattttc cagcaactat gaatataggt gctagcttaa actatagaac ctttagaact 1860

-continued gtaggattta caactccatt tactttttca gaagcatcaa gcatatttac attaagtact 1920
cattccttca gttcaggcaa tgcagtttat atagatcgaa ttgaatttgt cccggcataa 1980

<210> SEQ ID NO 19
<211> LENGTH: 4008
<212> TYPE: DNA
<213> ORGANISM: Bacillus thuringiensis

<400> SEQUENCE: 19
aatataacct atatttatat atagacaatt aatatacttt attaaatata tataggctat 60
atatttatat tcataaaatt agtagaattt tatgaatatt ttcataaact gaaccatatg 120
atttaaactg aggtaaagat aaatggccct aaattatgaa ggtatatgtg ctaaagtcca 180
aaaaacggga ggtaattcat caaaaaatcg tactatacaa tttgcttagg taatgctgtg 240
ttgaaactac tcagtggaga aaaattaaat agttggtaat gtaagcacaa cgtaaaagga 300
ggagttatat tgacttcaaa taggaaaaat gagaatgaaa ttataaatgc tttatcgatt 360
ccagctgtat cgaatcattc cgcacaaatg gatctatcac cagatgctcg tattgaggat 420
agcttgtgta tagccgaggg gaacaatatc gatccatttg ttagcgcatc aacagtccaa 480
acgggtatta acatagctgg tagaatacta ggcgtattgg gcgtaccgtt tgctggacaa 540
ctagctagtt tttatagttt tcttgttggt gaattatggc ctagcggcag agatccatgg 600
gaaattttta tggaacatgt cgaacaactt gtaagacaac aaataacgga cagtgttagg 660
gataccgcta ttgctcgttt agaaggtcta ggaagagggt atagatctta ccagcaggct 720
cttgaaactt ggttagataa ccgaaatgat gcaagatcaa gaagcattat tcttgagaga 780
tatattgctt tagaacttga cattactact gctataccgc ttttcagcat acgaaatcaa 840
gaggttccat tattaatggt atatgctcaa gctgcaaatt tacacctatt attattgaga 900
gacgcatccc tttttggtag tgaatggggg atgtcatctg ccgatgttaa ccaatattac 960
caagaacaaa tcagatatac agaggaatat tctaaccatt gcgtgcaatg gtataatacg 1020
ggtctaaata acctaagagg gacaaatgct gaaagctggg tacggtataa tcaattccgc 1080
agagacctaa cattaggagt attagatcta gtggccctat tcccaagcta tgatactcgc 1140
acttatccaa taaatacgag tgctcagtta acaagagaag tttatacaga cgcaattgga 1200
gcaacagggg taaatatggc aaatatgaat tggtacaata ataatgcacc ttcgttctcc 1260
gctatagagg ctgcggttat cagaagcccg catctacttg attttctaga acaacttaca 1320
atttttagcg cttcatcacg atggagtaat actaggcata tgacttactg gcgggggcac 1380
acgattcaat ctcggccaat aggaggcgga ttaaacacct caacgtatgg gtctaccaat 1440
acttctatta atcctgtaac attacggttc acgtctcgag acgtctatag gacagaatca 1500
tgggcaggag tgcttctatg gggaatttac cttgaaccta ttcatggtgt ccctactgtt 1560
aggtttaatt ttacgaaccc tcagaatatt tatgatagag gtactgctaa ctatagtcaa 1620
ccgtacgagt cacctgggct tcaattaaaa gattcagaaa cggaattacc gccagaaaca 1680
acagaacgac caaattatga atcttacagt cataggttat ctcatatagg tataatttta 1740
caatccaggg tgaatgtacc ggtatattct tggacgcatc gtagtgcaga tcgtacgaat 1800
acgattggac caaatagaat cacccaaatc ccaatggtaa aagcatccga acttcctcaa 1860
ggtaccactg ttgttagagg accaggattt actggtgggg atattcttcg aagaacgaat 1920
actggtggat ttggaccgat aagagtaact gttaacggac cattaacaca aagatatcgt 1980
ataggattcc gctatgcttc aactgtagat tttgatttct ttgtatcacg tggaggtact 2040
actgtaaata attttagatt cctacgtaca atgaacagtg gagacgaact aaaatacgga 2100
aattttgtga gacgtgcttt tactacacct tttactttta cacaaattca agatataatt 2160
cgaacgtcta ttcaaggcct tagtggaaat ggggaagtgt atatagataa aattgaaatt 2220
attccagtta ctgcaacctt cgaagcagaa tatgatttag aaagagcgca agaggcggtg 2280
aatgctctgt ttactaatac gaatccaaga agattgaaaa cagatgtgac agattatcat 2340
attgatcaag tatccaattt agtggcgtgt ttatcggatg aattctgctt ggatgaaaag 2400
agagaattac ttgagaaagt gaaatatgcg aaacgactca gtgatgaaag aaacttactc 2460
caagatccaa acttcacatc catcaataag caaccagact tcatatctac taatgagcaa 2520
tcgaatttca catctatcca tgaacaatct gaacatggat ggtggggaag tgagaacatt 2580
accatccagg aaggaaatga cgtatttaaa gagaattacg tcacactacc gggtactttt 2640
aatgagtgtt atccgacgta tttatatcaa aaaatagggg agtcggaatt aaaagcttat 2700
actcgctacc aattaagagg ttatattgaa gatagtcaag atttagagat atatttgatt 2760
cgttataatg cgaaacctga aacattggat gttccaggta ccgagtccct atggccgctt 2820
tcagttgaaa gcccaatcgg aaggtgcgga gaaccgaatc gatgcgcacc acattttgaa 2880
tggaatcctg atctagattg ttcctgcaga gatggagaaa aatgtgcgca tcattcccat 2940
catttctctt tggatattga tgttggatgc acagacttgc atgagaatct aggcgtgtgg 3000
gtggtattca agattaagac gcaggaaggt catgcaagac tagggaatct ggaatttatt 3060
gaagagaaac cattattagg agaagcactg tctcgtgtga agagggcaga gaaaaaatgg 3120
agagacaaac gtgaaaaact acaattggaa acaaaacgag tatatacaga ggcaaaagaa 3180
gctgtggatg ctttattcgt agattctcaa tatgatagat tacaagcgga tacaaacatc 3240
ggcatgattc atgcggcaga taaacttgtt catcgaattc gagaggcgta tctttcagaa 3300
ttacctgtta tcccaggtgt aaatgcggaa atttttgaag aattagaagg tcacattatc 3360
actgcaatct ccttatacga tgcgagaaat gtcgttaaaa atggtgattt taataatgga 3420
ttaacatgtt ggaatgtaaa agggcatgta gatgtacaac agagccatca tcgttctgac 3480
cttgttatcc cagaatggga agcagaagtg tcacaagcag ttcgcgtctg tccggggtgt 3540
ggctatatcc ttcgtgtcac agcgtacaaa gagggatatg gagagggctg cgtaacgatc 3600
catgaaatcg agaacaatac agacgaacta aaatttaaaa accgtgaaga agaggaagtg 3660
tatccaacgg atacaggaac gtgtaatgat tatactgcac accaaggtac agctggatgc 3720
gcagatgcat gtaattcccg taatgctgga tatgaggatg catatgaagt tgatactaca 3780
gcatctgtta attacaaacc gacttatgaa gaagaaacgt atacagatgt aagaagagat 3840
aatcattgtg aatatgacag agggtatgtc aattatccac cagtaccagc tggttatgtg 3900
acaaaagaat tagaatactt cccagaaaca gatacagtat ggattgagat tggagaaacg 3960
gaaggaaagt ttattgtaga tagcgtggaa ttactcctca tggaagaa 4008

<210> SEQ ID NO 20
<211> LENGTH: 1920
<212> TYPE: DNA
<213> ORGANISM: Bacillus thuringiensis

<400> SEQUENCE: 20
atgacttcaa ataggaaaaa tgagaatgaa attataaatg ctttatcgat tccagctgta 60
tcgaatcatt ccgcacaaat ggatctatca ccagatgctc gtattgagga tagcttgtgt 120
atagccgagg ggaacaatat cgatccattt gttagcgcat caacagtcca aacgggtatt 180
aacatagctg gtagaatact aggcgtattg ggcgtaccgt ttgctggaca actagctagt 240
ttttatagtt ttcttgttgg tgaattatgg cctagcggca gagatccatg ggaaattttt 300
atggaacatg tcgaacaact tgtaagacaa caaataacgg acagtgttag ggataccgct 360
attgctcgtt tagaaggtct aggaagaggg tatagatctt accagcaggc tcttgaaact 420
tggttagata accgaaatga tgcaagatca agaagcatta ttcttgagag atatattgct 480
ttagaacttg acattactac tgctataccg cttttcagca tacgaaatca agaggttcca 540
ttattaatgg tatatgctca agctgcaaat ttacacctat tattattgag agacgcatcc 600
ctttttggta gtgaatgggg gatgtcatct gccgatgtta accaatatta ccaagaacaa 660
atcagatata cagaggaata ttctaaccat tgcgtgcaat ggtataatac gggtctaaat 720
aacctaagag ggacaaatgc tgaaagctgg gtacggtata atcaattccg cagagaccta 780
acattaggag tattagatct agtggcccta ttcccaagct atgatactcg cacttatcca 840
ataaatacga gtgctcagtt aacaagagaa gtttatacag acgcaattgg agcaacaggg 900
gtaaatatgg caaatatgaa ttggtacaat aataatgcac cttcgttctc cgctatagag 960
gctgcggtta tcagaagccc gcatctactt gattttctag aacaacttac aatttttagc 1020
gcttcatcac gatggagtaa tactaggcat atgacttact ggcgggggca cacgattcaa 1080
tctcggccaa taggaggcgg attaaacacc tcaacgtatg ggtctaccaa tacttctatt 1140
aatcctgtaa cattacggtt cacgtctcga gacgtctata ggacagaatc atgggcagga 1200
gtgcttctat ggggaattta ccttgaacct attcatggtg tccctactgt taggtttaat 1260
tttacgaacc ctcagaatat ttatgataga ggtactgcta actatagtca accgtacgag 1320
tcacctgggc ttcaattaaa agattcagaa acggaattac cgccagaaac aacagaacga 1380
ccaaattatg aatcttacag tcataggtta tctcatatag gtataatttt acaatccagg 1440
gtgaatgtac cggtatattc ttggacgcat cgtagtgcag atcgtacgaa tacgattgga 1500
ccaaatagaa tcacccaaat cccaatggta aaagcatccg aacttcctca aggtaccact 1560
gttgttagag gaccaggatt tactggtggg gatattcttc gaagaacgaa tactggtgga 1620
tttggaccga taagagtaac tgttaacgga ccattaacac aaagatatcg tataggattc 1680
cgctatgctt caactgtaga ttttgatttc tttgtatcac gtggaggtac tactgtaaat 1740
aattttagat tcctacgtac aatgaacagt ggagacgaac taaaatacgg aaattttgtg 1800
agacgtgctt ttactacacc ttttactttt acacaaattc aagatataat tcgaacgtct 1860
attcaaggcc ttagtggaaa tggggaagtg tatatagata aaattgaaat tattccagtt 1920

<210> SEQ ID NO 21
<211> LENGTH: 794
<212> TYPE: PRT
<213> ORGANISM: Bacillus thuringiensis

<400> SEQUENCE: 21

Met Thr Cys Gln Leu Gln Ala Gln Pro Leu Ile Pro Tyr Asn Val Leu
1 5 10 15

Ala Gly Val Pro Thr Ser Asn Thr Gly Ser Pro Ile Gly Asn Ala Gly
20 25 30

Asn Gln Phe Asp Gln Phe Glu Gln Thr Val Lys Glu Leu Lys Glu Ala
35 40 45

Trp Glu Ala Phe Gln Lys Asn Gly Ser Phe Ser Leu Ala Ala Leu Glu

```
    50                  55                  60

Lys Gly Phe Asp Ala Ala Ile Gly Gly Gly Ser Phe Asp Tyr Leu Gly
65                  70                  75                  80

Leu Val Gln Ala Gly Leu Gly Leu Val Gly Thr Leu Gly Ala Ala Ile
                85                  90                  95

Pro Gly Val Ser Val Ala Val Pro Leu Ile Ser Met Leu Val Gly Val
            100                 105                 110

Phe Trp Pro Lys Gly Thr Asn Asn Gln Glu Asn Leu Ile Thr Val Ile
        115                 120                 125

Asp Lys Glu Val Gln Arg Ile Leu Asp Glu Lys Leu Ser Asp Gln Leu
    130                 135                 140

Ile Lys Lys Leu Asn Ala Asp Leu Asn Ala Phe Thr Asp Leu Val Thr
145                 150                 155                 160

Arg Leu Glu Glu Val Ile Ile Asp Ala Thr Phe Glu Asn His Lys Pro
                165                 170                 175

Val Leu Gln Val Ser Lys Ser Asn Tyr Met Lys Val Asp Ser Ala Tyr
            180                 185                 190

Phe Ser Thr Gly Gly Ile Leu Thr Leu Gly Met Ser Asp Phe Leu Thr
        195                 200                 205

Asp Thr Tyr Ser Lys Leu Thr Phe Pro Leu Tyr Val Leu Gly Ala Thr
    210                 215                 220

Met Lys Leu Ser Ala Tyr His Ser Tyr Ile Gln Phe Gly Asn Thr Trp
225                 230                 235                 240

Leu Asn Lys Val Tyr Asp Leu Ser Ser Asp Glu Gly Lys Thr Met Ser
                245                 250                 255

Gln Ala Leu Ala Arg Ala Lys Gln His Met Arg Gln Asp Ile Ala Phe
            260                 265                 270

Tyr Thr Ser Gln Ala Leu Asn Met Phe Thr Gly Asn Leu Pro Ser Leu
        275                 280                 285

Ser Ser Asn Lys Tyr Ala Ile Asn Asp Tyr Asn Val Tyr Thr Arg Ala
    290                 295                 300

Met Val Leu Asn Gly Leu Asp Ile Val Ala Thr Trp Pro Thr Leu Tyr
305                 310                 315                 320

Pro Asp Asp Tyr Ser Ser Gln Ile Lys Leu Glu Lys Thr Arg Val Ile
                325                 330                 335

Phe Ser Asp Met Val Gly Gln Ser Glu Ser Arg Asp Gly Ser Val Thr
            340                 345                 350

Ile Lys Asn Ile Phe Asp Asn Thr Asp Ser His Gln His Gly Ser Ile
        355                 360                 365

Gly Leu Asn Ser Ile Ser Tyr Phe Pro Asp Glu Leu Gln Lys Ala Gln
    370                 375                 380

Leu Arg Met Tyr Asp Tyr Asn His Lys Pro Tyr Cys Thr Asp Cys Phe
385                 390                 395                 400

Cys Trp Pro Tyr Gly Val Ile Leu Asn Tyr Asn Lys Asn Thr Phe Arg
                405                 410                 415

Tyr Gly Asp Asn Asp Pro Gly Leu Ser Gly Asp Val Gln Leu Pro Ala
            420                 425                 430

Pro Met Ser Val Val Asn Ala Gln Thr Gln Thr Ala Gln Tyr Thr Asp
        435                 440                 445

Gly Glu Asn Ile Trp Thr Asp Thr Gly Arg Ser Trp Leu Cys Thr Leu
    450                 455                 460

Arg Gly Tyr Cys Thr Thr Asn Cys Phe Pro Gly Arg Gly Cys Tyr Asn
465                 470                 475                 480
```

```
Asn Ser Thr Gly Tyr Gly Glu Ser Cys Asn Gln Ser Leu Pro Gly Gln
                485                 490                 495

Lys Ile His Ala Leu Tyr Pro Phe Thr Gln Thr Asn Val Leu Gly Gln
            500                 505                 510

Ser Gly Lys Leu Gly Leu Leu Ala Ser His Ile Pro Tyr Asp Leu Ser
        515                 520                 525

Pro Asn Asn Thr Ile Gly Asp Lys Asp Thr Asp Ser Thr Asn Ile Val
    530                 535                 540

Ala Lys Gly Ile Pro Val Glu Lys Gly Tyr Ala Ser Ser Gly Gln Lys
545                 550                 555                 560

Val Glu Ile Ile Arg Glu Trp Ile Asn Gly Ala Asn Val Val Gln Leu
                565                 570                 575

Ser Pro Gly Gln Ser Trp Gly Met Asp Phe Thr Asn Ser Thr Gly Gly
            580                 585                 590

Gln Tyr Met Val Arg Cys Arg Tyr Ala Ser Thr Asn Asp Thr Pro Ile
        595                 600                 605

Phe Phe Asn Leu Val Tyr Asp Gly Gly Ser Asn Pro Ile Tyr Asn Gln
    610                 615                 620

Met Thr Phe Pro Ala Thr Lys Glu Thr Pro Ala His Asp Ser Val Asp
625                 630                 635                 640

Asn Lys Ile Leu Gly Ile Lys Gly Ile Asn Gly Asn Tyr Ser Leu Met
                645                 650                 655

Asn Val Lys Asp Ser Val Glu Leu Pro Ser Gly Lys Phe His Val Phe
            660                 665                 670

Phe Thr Asn Asn Gly Ser Ser Ala Ile Tyr Leu Asp Arg Leu Glu Phe
        675                 680                 685

Val Pro Leu Gly Lys Pro Ser Pro Gly Val Leu Tyr Ser Gly Ser Tyr
    690                 695                 700

Asp Leu Met Gly Ser Gln Tyr Ala Ser Val Leu Phe Asn Asp Gln Asn
705                 710                 715                 720

Ala Ser Tyr Thr Thr Val Ser Ile Asn Gly Val Ser Asp Ala His Ser
                725                 730                 735

Thr Ser Gly Ser Ile Thr Leu Phe Asn Asn Glu Thr Leu Val Lys Gly
            740                 745                 750

Phe Asp Val Pro Gly Ser Gly Gln Ser Tyr Gln Tyr Ser Asn Val Thr
        755                 760                 765

Val Pro Pro Tyr Asn Arg Val Asn Met Thr Lys Gly Thr Tyr Ala Glu
    770                 775                 780

Leu Ser Gly Ser Val Thr Ile Lys Gly Asn
785                 790


<210> SEQ ID NO 22
<211> LENGTH: 687
<212> TYPE: PRT
<213> ORGANISM: Bacillus thuringiensis

<400> SEQUENCE: 22

Met Leu Val Gly Val Phe Trp Pro Lys Gly Thr Asn Asn Gln Glu Asn
1               5                   10                  15

Leu Ile Thr Val Ile Asp Lys Glu Val Gln Arg Ile Leu Asp Glu Lys
            20                  25                  30

Leu Ser Asp Gln Leu Ile Lys Lys Leu Asn Ala Asp Leu Asn Ala Phe
        35                  40                  45

Thr Asp Leu Val Thr Arg Leu Glu Glu Val Ile Ile Asp Ala Thr Phe
```

```
    50                  55                  60

Glu Asn His Lys Pro Val Leu Gln Val Ser Lys Ser Asn Tyr Met Lys
65                  70                  75                  80

Val Asp Ser Ala Tyr Phe Ser Thr Gly Gly Ile Leu Thr Leu Gly Met
                85                  90                  95

Ser Asp Phe Leu Thr Asp Thr Tyr Ser Lys Leu Thr Phe Pro Leu Tyr
            100                 105                 110

Val Leu Gly Ala Thr Met Lys Leu Ser Ala Tyr His Ser Tyr Ile Gln
        115                 120                 125

Phe Gly Asn Thr Trp Leu Asn Lys Val Tyr Asp Leu Ser Ser Asp Glu
    130                 135                 140

Gly Lys Thr Met Ser Gln Ala Leu Ala Arg Ala Lys Gln His Met Arg
145                 150                 155                 160

Gln Asp Ile Ala Phe Tyr Thr Ser Gln Ala Leu Asn Met Phe Thr Gly
                165                 170                 175

Asn Leu Pro Ser Leu Ser Ser Asn Lys Tyr Ala Ile Asn Asp Tyr Asn
            180                 185                 190

Val Tyr Thr Arg Ala Met Val Leu Asn Gly Leu Asp Ile Val Ala Thr
        195                 200                 205

Trp Pro Thr Leu Tyr Pro Asp Asp Tyr Ser Ser Gln Ile Lys Leu Glu
    210                 215                 220

Lys Thr Arg Val Ile Phe Ser Asp Met Val Gly Gln Ser Glu Ser Arg
225                 230                 235                 240

Asp Gly Ser Val Thr Ile Lys Asn Ile Phe Asp Asn Thr Asp Ser His
                245                 250                 255

Gln His Gly Ser Ile Gly Leu Asn Ser Ile Ser Tyr Phe Pro Asp Glu
            260                 265                 270

Leu Gln Lys Ala Gln Leu Arg Met Tyr Asp Tyr Asn His Lys Pro Tyr
        275                 280                 285

Cys Thr Asp Cys Phe Cys Trp Pro Tyr Gly Val Ile Leu Asn Tyr Asn
    290                 295                 300

Lys Asn Thr Phe Arg Tyr Gly Asp Asn Asp Pro Gly Leu Ser Gly Asp
305                 310                 315                 320

Val Gln Leu Pro Ala Pro Met Ser Val Val Asn Ala Gln Thr Gln Thr
                325                 330                 335

Ala Gln Tyr Thr Asp Gly Glu Asn Ile Trp Thr Asp Thr Gly Arg Ser
            340                 345                 350

Trp Leu Cys Thr Leu Arg Gly Tyr Cys Thr Thr Asn Cys Phe Pro Gly
        355                 360                 365

Arg Gly Cys Tyr Asn Asn Ser Thr Gly Tyr Gly Glu Ser Cys Asn Gln
    370                 375                 380

Ser Leu Pro Gly Gln Lys Ile His Ala Leu Tyr Pro Phe Thr Gln Thr
385                 390                 395                 400

Asn Val Leu Gly Gln Ser Gly Lys Leu Gly Leu Leu Ala Ser His Ile
                405                 410                 415

Pro Tyr Asp Leu Ser Pro Asn Asn Thr Ile Gly Asp Lys Asp Thr Asp
            420                 425                 430

Ser Thr Asn Ile Val Ala Lys Gly Ile Pro Val Glu Lys Gly Tyr Ala
        435                 440                 445

Ser Ser Gly Gln Lys Val Glu Ile Ile Arg Glu Trp Ile Asn Gly Ala
    450                 455                 460

Asn Val Val Gln Leu Ser Pro Gly Gln Ser Trp Gly Met Asp Phe Thr
465                 470                 475                 480
```

```
Asn Ser Thr Gly Gly Gln Tyr Met Val Arg Cys Arg Tyr Ala Ser Thr
                485                 490                 495

Asn Asp Thr Pro Ile Phe Phe Asn Leu Val Tyr Asp Gly Gly Ser Asn
            500                 505                 510

Pro Ile Tyr Asn Gln Met Thr Phe Pro Ala Thr Lys Glu Thr Pro Ala
        515                 520                 525

His Asp Ser Val Asp Asn Lys Ile Leu Gly Ile Lys Gly Ile Asn Gly
    530                 535                 540

Asn Tyr Ser Leu Met Asn Val Lys Asp Ser Val Glu Leu Pro Ser Gly
545                 550                 555                 560

Lys Phe His Val Phe Phe Thr Asn Asn Gly Ser Ser Ala Ile Tyr Leu
                565                 570                 575

Asp Arg Leu Glu Phe Val Pro Leu Gly Lys Pro Ser Pro Gly Val Leu
            580                 585                 590

Tyr Ser Gly Ser Tyr Asp Leu Met Gly Ser Gln Tyr Ala Ser Val Leu
        595                 600                 605

Phe Asn Asp Gln Asn Ala Ser Tyr Thr Thr Val Ser Ile Asn Gly Val
    610                 615                 620

Ser Asp Ala His Ser Thr Ser Gly Ser Ile Thr Leu Phe Asn Asn Glu
625                 630                 635                 640

Thr Leu Val Lys Gly Phe Asp Val Pro Gly Ser Gly Gln Ser Tyr Gln
                645                 650                 655

Tyr Ser Asn Val Thr Val Pro Pro Tyr Asn Arg Val Asn Met Thr Lys
            660                 665                 670

Gly Thr Tyr Ala Glu Leu Ser Gly Ser Val Thr Ile Lys Gly Asn
        675                 680                 685
```

<210> SEQ ID NO 23
<211> LENGTH: 1173
<212> TYPE: PRT
<213> ORGANISM: Bacillus thuringiensis

<400> SEQUENCE: 23

```
Met Leu Lys Leu Arg Lys Arg Arg Tyr Phe Met Glu Gly Asn Asn Leu
1               5                   10                  15

Asn Gln Cys Ile Pro Tyr Asn Cys Leu Ser Asn Pro Lys Asp Ile Ile
            20                  25                  30

Leu Gly Asp Glu Arg Leu Glu Thr Gly Asn Thr Val Ala Asp Ile Thr
        35                  40                  45

Leu Gly Ile Val Asn Leu Leu Phe Ser Glu Phe Val Pro Gly Gly Gly
    50                  55                  60

Phe Ile Leu Gly Leu Leu Asp Leu Ile Trp Gly Ser Ile Gly Arg Ser
65                  70                  75                  80

Gln Trp Asp Leu Phe Leu Glu Gln Ile Glu Gln Leu Ile Lys Gln Arg
                85                  90                  95

Ile Glu Glu Phe Ala Arg Asn Gln Ala Ile Ser Arg Leu Glu Gly Leu
            100                 105                 110

Ser Asp Leu Tyr Lys Thr Tyr Ala Arg Ala Phe Ser Asp Trp Glu Ala
        115                 120                 125

Asp Pro Thr Asn Pro Ala Leu Arg Glu Glu Met Arg Ile Gln Phe Asn
    130                 135                 140

Asp Met Asn Ser Ala Ile Ile Thr Ala Leu Pro Leu Phe Arg Val Gln
145                 150                 155                 160

Asn Tyr Glu Val Ala Leu Leu Ser Val Tyr Val Gln Ala Ala Asn Leu
```

-continued

```
                165                 170                 175

His Leu Ser Ile Leu Arg Asp Val Ser Val Phe Gly Glu Arg Trp Gly
            180                 185                 190

Tyr Asp Thr Ala Thr Ile Asn Asn Arg Tyr Ser Asp Leu Thr Ser Leu
        195                 200                 205

Ile His Val Tyr Thr Asn His Cys Val Asp Thr Tyr Asn Gln Gly Leu
    210                 215                 220

Arg Arg Leu Glu Gly Arg Phe Leu Thr Asp Trp Ile Val Tyr Asn Arg
225                 230                 235                 240

Phe Arg Arg Gln Leu Thr Ile Ser Val Leu Asp Ile Val Ala Phe Phe
                245                 250                 255

Pro Asn Tyr Asp Ile Arg Thr Tyr Pro Ile Gln Thr Ala Thr Gln Leu
            260                 265                 270

Thr Arg Glu Ile Tyr Leu Asp Leu Pro Phe Ile Asn Glu Asn Leu Ser
        275                 280                 285

Pro Ala Ala Ser Tyr Pro Ser Phe Ser Asp Ala Glu Ser Ala Ile Ile
    290                 295                 300

Arg Ser Pro His Leu Val Asp Phe Leu Asn Ser Phe Thr Ile Tyr Thr
305                 310                 315                 320

Asp Ser Leu Ala Arg Tyr Leu Tyr Trp Gly Gly His Arg Val Asn Phe
                325                 330                 335

Thr Arg Ser Gly Val Thr Thr Phe Ile Gln Ser Pro Leu Tyr Gly Arg
            340                 345                 350

Glu Gly Asn Ala Glu Arg Ser Val Ile Ile Ser Ala Ser Ser Ser Val
        355                 360                 365

Pro Ile Phe Arg Thr Leu Ser Tyr Val Thr Gly Leu Asp Asn Ala Asn
    370                 375                 380

Pro Val Ala Gly Ile Glu Gly Val Glu Phe Gln Asn Thr Ile Ser Arg
385                 390                 395                 400

Ser Ile Tyr Arg Lys Ser Gly Pro Ile Asp Ser Phe Asn Glu Leu Pro
                405                 410                 415

Pro Gln Asp Ala Ser Val Ser Pro Ser Ile Gly Tyr Ser His Arg Leu
            420                 425                 430

Cys His Ala Thr Phe Leu Glu Arg Ile Ser Gly Pro Arg Ile Ala Gly
        435                 440                 445

Val Val Phe Ser Trp Thr His Arg Ser Ala Ser Pro Thr Asn Glu Val
    450                 455                 460

Ser Ser Ser Arg Ile Thr Gln Ile Pro Trp Val Lys Ala His Thr Leu
465                 470                 475                 480

Ala Ser Gly Ala Ser Val Ile Lys Gly Pro Gly Phe Thr Gly Gly Asp
                485                 490                 495

Ile Leu Thr Arg Asn Thr Leu Gly Glu Leu Gly Thr Leu Arg Val Thr
            500                 505                 510

Phe Ala Gly Arg Leu Ser Gln Ser Tyr Tyr Ile Arg Phe Arg Tyr Ala
        515                 520                 525

Ser Val Ala Asn Arg Ser Gly Ile Phe Ser Tyr Ser Gln Pro Thr Ser
    530                 535                 540

Tyr Gly Ile Ser Phe Pro Lys Thr Met Asp Ala Asn Glu Ser Leu Thr
545                 550                 555                 560

Ser Arg Ser Phe Ala Leu Ala Thr Leu Ala Thr Pro Leu Thr Phe Arg
                565                 570                 575

Arg Gln Glu Glu Leu Asn Leu Gln Ile Pro Ser Gly Thr Tyr Ile Asp
            580                 585                 590
```

```
Arg Ile Glu Phe Val Pro Val Asp Glu Thr Phe Thr Thr Glu Ser Asp
        595                 600                 605

Leu Asp Arg Ala Gln Gln Ala Val Asn Ala Leu Phe Thr Ser Ser Asn
    610                 615                 620

Gln Ile Gly Leu Lys Thr Asp Val Thr Asp Tyr His Ile Asp Gln Val
625                 630                 635                 640

Ser Asn Leu Val Asp Cys Leu Ser Asp Glu Phe Cys Leu Asp Glu Lys
                645                 650                 655

Lys Glu Leu Ser Glu Lys Val Lys His Ala Lys Arg Leu Ser Asp Glu
            660                 665                 670

Arg Asn Leu Leu Gln Asp Pro Asn Phe Arg Gly Ile Asn Arg Gln Leu
        675                 680                 685

Asp Arg Gly Trp Ser Gly Ser Thr Asp Ile Thr Ile Gln Gly Gly Asp
    690                 695                 700

Asp Val Phe Lys Glu Asn Tyr Val Thr Leu Pro Gly Thr Phe Asp Glu
705                 710                 715                 720

Cys Tyr Pro Thr Tyr Leu Tyr Gln Lys Ile Asp Glu Ser Lys Leu Lys
                725                 730                 735

Ala Tyr Thr Arg Tyr Gln Leu Arg Gly Tyr Ile Gly Asp Ser Gln Asp
            740                 745                 750

Leu Glu Ile Tyr Leu Ile Arg Tyr Asn Ala Lys His Glu Ile Val Asn
        755                 760                 765

Val Pro Gly Thr Gly Ser Leu Trp Pro Leu Ser Val Glu Asn Ser Ile
    770                 775                 780

Gly Pro Cys Gly Glu Pro Asn Arg Cys Ala Pro His Leu Glu Trp Asn
785                 790                 795                 800

Pro Asn Leu Glu Cys Ser Cys Arg Glu Gly Glu Lys Cys Ala His His
                805                 810                 815

Ser His His Phe Ser Leu Asp Ile Asp Val Gly Cys Thr Asp Leu Asn
            820                 825                 830

Glu Asp Leu Gly Val Trp Ala Ile Phe Lys Ile Lys Thr Gln Asp Gly
        835                 840                 845

His Ala Arg Leu Gly Asn Leu Glu Phe Leu Glu Glu Lys Pro Leu Val
    850                 855                 860

Gly Glu Ala Leu Ala Arg Val Lys Arg Ala Glu Lys Lys Trp Arg Asp
865                 870                 875                 880

Lys Arg Glu Lys Leu Glu Leu Glu Thr Asn Ile Val Tyr Lys Glu Ala
                885                 890                 895

Lys Glu Ser Val Asp Ala Leu Phe Val Asn Ser Gln Tyr Asp Arg Leu
            900                 905                 910

Gln Ala Asp Thr Asn Ile Ala Met Ile His Ala Ala Asp Lys Arg Val
        915                 920                 925

His Ser Ile Arg Glu Ala Tyr Leu Pro Glu Leu Ser Ile Ile Pro Gly
    930                 935                 940

Val Asn Ala Gly Ile Phe Glu Glu Leu Glu Gly Arg Ile Tyr Thr Ala
945                 950                 955                 960

Tyr Ser Leu Tyr Asp Ala Arg Asn Val Ile Lys Asn Gly Asp Phe Asp
                965                 970                 975

Asn Gly Leu Leu Cys Trp Asn Val Lys Gly His Val Asp Val Glu Glu
            980                 985                 990

Gln Asn Asn His Arg Ser Val Leu  Val Ile Pro Glu Trp  Glu Ala Glu
        995                 1000                1005
```

```
Val Ser  Gln Glu Val Arg Val  Cys Pro Gly Arg Gly  Tyr Ile Leu
    1010                 1015                 1020

Arg Val  Thr Ala Tyr Lys Glu  Gly Tyr Gly Glu Gly  Cys Val Thr
    1025                 1030                 1035

Ile His  Glu Ile Glu Asp Asn  Thr Asp Glu Leu Lys  Phe Ser Asn
    1040                 1045                 1050

Cys Val  Glu Glu Glu Val Tyr  Pro Asn Asn Thr Val  Thr Cys Asn
    1055                 1060                 1065

Asp Tyr  Thr Ala Thr Gln Glu  Glu Tyr Glu Gly Thr  Tyr Thr Ser
    1070                 1075                 1080

Arg Asn  Arg Gly Tyr Asp Gly  Ala Tyr Glu Ser Asn  Ser Ser Val
    1085                 1090                 1095

Pro Ala  Asp Tyr Ala Ser Ala  Tyr Glu Glu Lys Ala  Tyr Thr Asp
    1100                 1105                 1110

Gly Arg  Arg Glu Asn Pro Cys  Glu Ser Asn Arg Gly  Tyr Gly Asp
    1115                 1120                 1125

Tyr Ala  Pro Leu Pro Ala Gly  Tyr Val Thr Lys Glu  Leu Glu Tyr
    1130                 1135                 1140

Phe Pro  Glu Thr Asp Lys Val  Trp Ile Glu Ile Gly  Glu Thr Glu
    1145                 1150                 1155

Gly Thr  Phe Ile Val Asp Ser  Val Glu Leu Leu Leu  Met Glu Glu
    1160                 1165                 1170


<210> SEQ ID NO 24
<211> LENGTH: 1163
<212> TYPE: PRT
<213> ORGANISM: Bacillus thuringiensis

<400> SEQUENCE: 24

Met Glu Gly Asn Asn Leu Asn Gln Cys Ile Pro Tyr Asn Cys Leu Ser
1               5                   10                  15

Asn Pro Lys Asp Ile Ile Leu Gly Asp Glu Arg Leu Glu Thr Gly Asn
            20                  25                  30

Thr Val Ala Asp Ile Thr Leu Gly Ile Val Asn Leu Leu Phe Ser Glu
        35                  40                  45

Phe Val Pro Gly Gly Gly Phe Ile Leu Gly Leu Leu Asp Leu Ile Trp
    50                  55                  60

Gly Ser Ile Gly Arg Ser Gln Trp Asp Leu Phe Leu Glu Gln Ile Glu
65                  70                  75                  80

Gln Leu Ile Lys Gln Arg Ile Glu Glu Phe Ala Arg Asn Gln Ala Ile
                85                  90                  95

Ser Arg Leu Glu Gly Leu Ser Asp Leu Tyr Lys Thr Tyr Ala Arg Ala
            100                 105                 110

Phe Ser Asp Trp Glu Ala Asp Pro Thr Asn Pro Ala Leu Arg Glu Glu
        115                 120                 125

Met Arg Ile Gln Phe Asn Asp Met Asn Ser Ala Ile Ile Thr Ala Leu
    130                 135                 140

Pro Leu Phe Arg Val Gln Asn Tyr Glu Val Ala Leu Leu Ser Val Tyr
145                 150                 155                 160

Val Gln Ala Ala Asn Leu His Leu Ser Ile Leu Arg Asp Val Ser Val
                165                 170                 175

Phe Gly Glu Arg Trp Gly Tyr Asp Thr Ala Thr Ile Asn Asn Arg Tyr
            180                 185                 190

Ser Asp Leu Thr Ser Leu Ile His Val Tyr Thr Asn His Cys Val Asp
        195                 200                 205
```

-continued

```
Thr Tyr Asn Gln Gly Leu Arg Arg Leu Glu Gly Arg Phe Leu Thr Asp
    210                 215                 220

Trp Ile Val Tyr Asn Arg Phe Arg Arg Gln Leu Thr Ile Ser Val Leu
225                 230                 235                 240

Asp Ile Val Ala Phe Phe Pro Asn Tyr Asp Ile Arg Thr Tyr Pro Ile
                245                 250                 255

Gln Thr Ala Thr Gln Leu Thr Arg Glu Ile Tyr Leu Asp Leu Pro Phe
            260                 265                 270

Ile Asn Glu Asn Leu Ser Pro Ala Ala Ser Tyr Pro Ser Phe Ser Asp
        275                 280                 285

Ala Glu Ser Ala Ile Ile Arg Ser Pro His Leu Val Asp Phe Leu Asn
    290                 295                 300

Ser Phe Thr Ile Tyr Thr Asp Ser Leu Ala Arg Tyr Leu Tyr Trp Gly
305                 310                 315                 320

Gly His Arg Val Asn Phe Thr Arg Ser Gly Val Thr Thr Phe Ile Gln
                325                 330                 335

Ser Pro Leu Tyr Gly Arg Glu Gly Asn Ala Glu Arg Ser Val Ile Ile
            340                 345                 350

Ser Ala Ser Ser Ser Val Pro Ile Phe Arg Thr Leu Ser Tyr Val Thr
        355                 360                 365

Gly Leu Asp Asn Ala Asn Pro Val Ala Gly Ile Glu Gly Val Glu Phe
    370                 375                 380

Gln Asn Thr Ile Ser Arg Ser Ile Tyr Arg Lys Ser Gly Pro Ile Asp
385                 390                 395                 400

Ser Phe Asn Glu Leu Pro Pro Gln Asp Ala Ser Val Ser Pro Ser Ile
                405                 410                 415

Gly Tyr Ser His Arg Leu Cys His Ala Thr Phe Leu Glu Arg Ile Ser
            420                 425                 430

Gly Pro Arg Ile Ala Gly Val Val Phe Ser Trp Thr His Arg Ser Ala
        435                 440                 445

Ser Pro Thr Asn Glu Val Ser Ser Ser Arg Ile Thr Gln Ile Pro Trp
    450                 455                 460

Val Lys Ala His Thr Leu Ala Ser Gly Ala Ser Val Ile Lys Gly Pro
465                 470                 475                 480

Gly Phe Thr Gly Gly Asp Ile Leu Thr Arg Asn Thr Leu Gly Glu Leu
                485                 490                 495

Gly Thr Leu Arg Val Thr Phe Ala Gly Arg Leu Ser Gln Ser Tyr Tyr
            500                 505                 510

Ile Arg Phe Arg Tyr Ala Ser Val Ala Asn Arg Ser Gly Ile Phe Ser
        515                 520                 525

Tyr Ser Gln Pro Thr Ser Tyr Gly Ile Ser Phe Pro Lys Thr Met Asp
    530                 535                 540

Ala Asn Glu Ser Leu Thr Ser Arg Ser Phe Ala Leu Ala Thr Leu Ala
545                 550                 555                 560

Thr Pro Leu Thr Phe Arg Arg Gln Glu Glu Leu Asn Leu Gln Ile Pro
                565                 570                 575

Ser Gly Thr Tyr Ile Asp Arg Ile Glu Phe Val Pro Val Asp Glu Thr
            580                 585                 590

Phe Thr Thr Glu Ser Asp Leu Asp Arg Ala Gln Gln Ala Val Asn Ala
        595                 600                 605

Leu Phe Thr Ser Ser Asn Gln Ile Gly Leu Lys Thr Asp Val Thr Asp
    610                 615                 620
```

```
Tyr His Ile Asp Gln Val Ser Asn Leu Val Asp Cys Leu Ser Asp Glu
625                 630                 635                 640

Phe Cys Leu Asp Glu Lys Lys Glu Leu Ser Glu Lys Val Lys His Ala
                645                 650                 655

Lys Arg Leu Ser Asp Glu Arg Asn Leu Leu Gln Asp Pro Asn Phe Arg
            660                 665                 670

Gly Ile Asn Arg Gln Leu Asp Arg Gly Trp Ser Gly Ser Thr Asp Ile
        675                 680                 685

Thr Ile Gln Gly Gly Asp Asp Val Phe Lys Glu Asn Tyr Val Thr Leu
    690                 695                 700

Pro Gly Thr Phe Asp Glu Cys Tyr Pro Thr Tyr Leu Tyr Gln Lys Ile
705                 710                 715                 720

Asp Glu Ser Lys Leu Lys Ala Tyr Thr Arg Tyr Gln Leu Arg Gly Tyr
                725                 730                 735

Ile Gly Asp Ser Gln Asp Leu Glu Ile Tyr Leu Ile Arg Tyr Asn Ala
            740                 745                 750

Lys His Glu Ile Val Asn Val Pro Gly Thr Gly Ser Leu Trp Pro Leu
        755                 760                 765

Ser Val Glu Asn Ser Ile Gly Pro Cys Gly Glu Pro Asn Arg Cys Ala
    770                 775                 780

Pro His Leu Glu Trp Asn Pro Asn Leu Glu Cys Ser Cys Arg Glu Gly
785                 790                 795                 800

Glu Lys Cys Ala His His Ser His His Phe Ser Leu Asp Ile Asp Val
                805                 810                 815

Gly Cys Thr Asp Leu Asn Glu Asp Leu Gly Val Trp Ala Ile Phe Lys
            820                 825                 830

Ile Lys Thr Gln Asp Gly His Ala Arg Leu Gly Asn Leu Glu Phe Leu
        835                 840                 845

Glu Glu Lys Pro Leu Val Gly Glu Ala Leu Ala Arg Val Lys Arg Ala
    850                 855                 860

Glu Lys Lys Trp Arg Asp Lys Arg Glu Lys Leu Glu Leu Glu Thr Asn
865                 870                 875                 880

Ile Val Tyr Lys Glu Ala Lys Glu Ser Val Asp Ala Leu Phe Val Asn
                885                 890                 895

Ser Gln Tyr Asp Arg Leu Gln Ala Asp Thr Asn Ile Ala Met Ile His
            900                 905                 910

Ala Ala Asp Lys Arg Val His Ser Ile Arg Glu Ala Tyr Leu Pro Glu
        915                 920                 925

Leu Ser Ile Ile Pro Gly Val Asn Ala Gly Ile Phe Glu Glu Leu Glu
    930                 935                 940

Gly Arg Ile Tyr Thr Ala Tyr Ser Leu Tyr Asp Ala Arg Asn Val Ile
945                 950                 955                 960

Lys Asn Gly Asp Phe Asp Asn Gly Leu Leu Cys Trp Asn Val Lys Gly
                965                 970                 975

His Val Asp Val Glu Glu Gln Asn Asn His Arg Ser Val Leu Val Ile
            980                 985                 990

Pro Glu Trp Glu Ala Glu Val Ser  Gln Glu Val Arg Val  Cys Pro Gly
        995                 1000                1005

Arg Gly  Tyr Ile Leu Arg Val  Thr Ala Tyr Lys Glu  Gly Tyr Gly
    1010                1015                1020

Glu Gly  Cys Val Thr Ile His  Glu Ile Glu Asp Asn  Thr Asp Glu
    1025                1030                1035

Leu Lys  Phe Ser Asn Cys Val  Glu Glu Glu Val Tyr  Pro Asn Asn
```

```
    1040                1045                1050

Thr Val  Thr Cys Asn Asp Tyr  Thr Ala Thr Gln Glu  Glu Tyr Glu
    1055                1060                1065

Gly Thr  Tyr Thr Ser Arg Asn  Arg Gly Tyr Asp Gly  Ala Tyr Glu
    1070                1075                1080

Ser Asn  Ser Ser Val Pro Ala  Asp Tyr Ala Ser Ala  Tyr Glu Glu
    1085                1090                1095

Lys Ala  Tyr Thr Asp Gly Arg  Arg Glu Asn Pro Cys  Glu Ser Asn
    1100                1105                1110

Arg Gly  Tyr Gly Asp Tyr Ala  Pro Leu Pro Ala Gly  Tyr Val Thr
    1115                1120                1125

Lys Glu  Leu Glu Tyr Phe Pro  Glu Thr Asp Lys Val  Trp Ile Glu
    1130                1135                1140

Ile Gly  Glu Thr Glu Gly Thr  Phe Ile Val Asp Ser  Val Glu Leu
    1145                1150                1155

Leu Leu  Met Glu Glu
    1160


<210> SEQ ID NO 25
<211> LENGTH: 599
<212> TYPE: PRT
<213> ORGANISM: Bacillus thuringiensis

<400> SEQUENCE: 25

Met Leu Lys Leu Arg Lys Arg Arg Tyr Phe Met Glu Gly Asn Asn Leu
1               5                   10                  15

Asn Gln Cys Ile Pro Tyr Asn Cys Leu Ser Asn Pro Lys Asp Ile Ile
            20                  25                  30

Leu Gly Asp Glu Arg Leu Glu Thr Gly Asn Thr Val Ala Asp Ile Thr
        35                  40                  45

Leu Gly Ile Val Asn Leu Leu Phe Ser Glu Phe Val Pro Gly Gly Gly
    50                  55                  60

Phe Ile Leu Gly Leu Leu Asp Leu Ile Trp Gly Ser Ile Gly Arg Ser
65                  70                  75                  80

Gln Trp Asp Leu Phe Leu Glu Gln Ile Glu Gln Leu Ile Lys Gln Arg
                85                  90                  95

Ile Glu Glu Phe Ala Arg Asn Gln Ala Ile Ser Arg Leu Glu Gly Leu
            100                 105                 110

Ser Asp Leu Tyr Lys Thr Tyr Ala Arg Ala Phe Ser Asp Trp Glu Ala
        115                 120                 125

Asp Pro Thr Asn Pro Ala Leu Arg Glu Glu Met Arg Ile Gln Phe Asn
    130                 135                 140

Asp Met Asn Ser Ala Ile Ile Thr Ala Leu Pro Leu Phe Arg Val Gln
145                 150                 155                 160

Asn Tyr Glu Val Ala Leu Leu Ser Val Tyr Val Gln Ala Ala Asn Leu
                165                 170                 175

His Leu Ser Ile Leu Arg Asp Val Ser Val Phe Gly Glu Arg Trp Gly
            180                 185                 190

Tyr Asp Thr Ala Thr Ile Asn Asn Arg Tyr Ser Asp Leu Thr Ser Leu
        195                 200                 205

Ile His Val Tyr Thr Asn His Cys Val Asp Thr Tyr Asn Gln Gly Leu
    210                 215                 220

Arg Arg Leu Glu Gly Arg Phe Leu Thr Asp Trp Ile Val Tyr Asn Arg
225                 230                 235                 240
```

-continued

```
Phe Arg Arg Gln Leu Thr Ile Ser Val Leu Asp Ile Val Ala Phe Phe
                245                 250                 255

Pro Asn Tyr Asp Ile Arg Thr Tyr Pro Ile Gln Thr Ala Thr Gln Leu
            260                 265                 270

Thr Arg Glu Ile Tyr Leu Asp Leu Pro Phe Ile Asn Glu Asn Leu Ser
        275                 280                 285

Pro Ala Ala Ser Tyr Pro Ser Phe Ser Asp Ala Glu Ser Ala Ile Ile
    290                 295                 300

Arg Ser Pro His Leu Val Asp Phe Leu Asn Ser Phe Thr Ile Tyr Thr
305                 310                 315                 320

Asp Ser Leu Ala Arg Tyr Leu Tyr Trp Gly Gly His Arg Val Asn Phe
                325                 330                 335

Thr Arg Ser Gly Val Thr Thr Phe Ile Gln Ser Pro Leu Tyr Gly Arg
            340                 345                 350

Glu Gly Asn Ala Glu Arg Ser Val Ile Ile Ser Ala Ser Ser Ser Val
        355                 360                 365

Pro Ile Phe Arg Thr Leu Ser Tyr Val Thr Gly Leu Asp Asn Ala Asn
    370                 375                 380

Pro Val Ala Gly Ile Glu Gly Val Glu Phe Gln Asn Thr Ile Ser Arg
385                 390                 395                 400

Ser Ile Tyr Arg Lys Ser Gly Pro Ile Asp Ser Phe Asn Glu Leu Pro
                405                 410                 415

Pro Gln Asp Ala Ser Val Ser Pro Ser Ile Gly Tyr Ser His Arg Leu
            420                 425                 430

Cys His Ala Thr Phe Leu Glu Arg Ile Ser Gly Pro Arg Ile Ala Gly
        435                 440                 445

Val Val Phe Ser Trp Thr His Arg Ser Ala Ser Pro Thr Asn Glu Val
    450                 455                 460

Ser Ser Ser Arg Ile Thr Gln Ile Pro Trp Val Lys Ala His Thr Leu
465                 470                 475                 480

Ala Ser Gly Ala Ser Val Ile Lys Gly Pro Gly Phe Thr Gly Gly Asp
                485                 490                 495

Ile Leu Thr Arg Asn Thr Leu Gly Glu Leu Gly Thr Leu Arg Val Thr
            500                 505                 510

Phe Ala Gly Arg Leu Ser Gln Ser Tyr Tyr Ile Arg Phe Arg Tyr Ala
        515                 520                 525

Ser Val Ala Asn Arg Ser Gly Ile Phe Ser Tyr Ser Gln Pro Thr Ser
    530                 535                 540

Tyr Gly Ile Ser Phe Pro Lys Thr Met Asp Ala Asn Glu Ser Leu Thr
545                 550                 555                 560

Ser Arg Ser Phe Ala Leu Ala Thr Leu Ala Thr Pro Leu Thr Phe Arg
                565                 570                 575

Arg Gln Glu Glu Leu Asn Leu Gln Ile Pro Ser Gly Thr Tyr Ile Asp
            580                 585                 590

Arg Ile Glu Phe Val Pro Val
        595


<210> SEQ ID NO 26
<211> LENGTH: 589
<212> TYPE: PRT
<213> ORGANISM: Bacillus thuringiensis

<400> SEQUENCE: 26

Met Glu Gly Asn Asn Leu Asn Gln Cys Ile Pro Tyr Asn Cys Leu Ser
1               5                   10                  15
```

```
Asn Pro Lys Asp Ile Ile Leu Gly Asp Glu Arg Leu Glu Thr Gly Asn
            20                  25                  30

Thr Val Ala Asp Ile Thr Leu Gly Ile Val Asn Leu Leu Phe Ser Glu
        35                  40                  45

Phe Val Pro Gly Gly Gly Phe Ile Leu Gly Leu Leu Asp Leu Ile Trp
    50                  55                  60

Gly Ser Ile Gly Arg Ser Gln Trp Asp Leu Phe Leu Glu Gln Ile Glu
65                  70                  75                  80

Gln Leu Ile Lys Gln Arg Ile Glu Glu Phe Ala Arg Asn Gln Ala Ile
                85                  90                  95

Ser Arg Leu Glu Gly Leu Ser Asp Leu Tyr Lys Thr Tyr Ala Arg Ala
            100                 105                 110

Phe Ser Asp Trp Glu Ala Asp Pro Thr Asn Pro Ala Leu Arg Glu Glu
        115                 120                 125

Met Arg Ile Gln Phe Asn Asp Met Asn Ser Ala Ile Ile Thr Ala Leu
    130                 135                 140

Pro Leu Phe Arg Val Gln Asn Tyr Glu Val Ala Leu Leu Ser Val Tyr
145                 150                 155                 160

Val Gln Ala Ala Asn Leu His Leu Ser Ile Leu Arg Asp Val Ser Val
                165                 170                 175

Phe Gly Glu Arg Trp Gly Tyr Asp Thr Ala Thr Ile Asn Asn Arg Tyr
            180                 185                 190

Ser Asp Leu Thr Ser Leu Ile His Val Tyr Thr Asn His Cys Val Asp
        195                 200                 205

Thr Tyr Asn Gln Gly Leu Arg Arg Leu Glu Gly Arg Phe Leu Thr Asp
    210                 215                 220

Trp Ile Val Tyr Asn Arg Phe Arg Arg Gln Leu Thr Ile Ser Val Leu
225                 230                 235                 240

Asp Ile Val Ala Phe Phe Pro Asn Tyr Asp Ile Arg Thr Tyr Pro Ile
                245                 250                 255

Gln Thr Ala Thr Gln Leu Thr Arg Glu Ile Tyr Leu Asp Leu Pro Phe
            260                 265                 270

Ile Asn Glu Asn Leu Ser Pro Ala Ala Ser Tyr Pro Ser Phe Ser Asp
        275                 280                 285

Ala Glu Ser Ala Ile Ile Arg Ser Pro His Leu Val Asp Phe Leu Asn
    290                 295                 300

Ser Phe Thr Ile Tyr Thr Asp Ser Leu Ala Arg Tyr Leu Tyr Trp Gly
305                 310                 315                 320

Gly His Arg Val Asn Phe Thr Arg Ser Gly Val Thr Thr Phe Ile Gln
                325                 330                 335

Ser Pro Leu Tyr Gly Arg Glu Gly Asn Ala Glu Arg Ser Val Ile Ile
            340                 345                 350

Ser Ala Ser Ser Ser Val Pro Ile Phe Arg Thr Leu Ser Tyr Val Thr
        355                 360                 365

Gly Leu Asp Asn Ala Asn Pro Val Ala Gly Ile Glu Gly Val Glu Phe
    370                 375                 380

Gln Asn Thr Ile Ser Arg Ser Ile Tyr Arg Lys Ser Gly Pro Ile Asp
385                 390                 395                 400

Ser Phe Asn Glu Leu Pro Pro Gln Asp Ala Ser Val Ser Pro Ser Ile
                405                 410                 415

Gly Tyr Ser His Arg Leu Cys His Ala Thr Phe Leu Glu Arg Ile Ser
            420                 425                 430
```

-continued

```
Gly Pro Arg Ile Ala Gly Val Val Phe Ser Trp Thr His Arg Ser Ala
        435                 440                 445

Ser Pro Thr Asn Glu Val Ser Ser Ser Arg Ile Thr Gln Ile Pro Trp
    450                 455                 460

Val Lys Ala His Thr Leu Ala Ser Gly Ala Ser Val Ile Lys Gly Pro
465                 470                 475                 480

Gly Phe Thr Gly Gly Asp Ile Leu Thr Arg Asn Thr Leu Gly Glu Leu
                485                 490                 495

Gly Thr Leu Arg Val Thr Phe Ala Gly Arg Leu Ser Gln Ser Tyr Tyr
            500                 505                 510

Ile Arg Phe Arg Tyr Ala Ser Val Ala Asn Arg Ser Gly Ile Phe Ser
        515                 520                 525

Tyr Ser Gln Pro Thr Ser Tyr Gly Ile Ser Phe Pro Lys Thr Met Asp
    530                 535                 540

Ala Asn Glu Ser Leu Thr Ser Arg Ser Phe Ala Leu Ala Thr Leu Ala
545                 550                 555                 560

Thr Pro Leu Thr Phe Arg Arg Gln Glu Glu Leu Asn Leu Gln Ile Pro
                565                 570                 575

Ser Gly Thr Tyr Ile Asp Arg Ile Glu Phe Val Pro Val
            580                 585


<210> SEQ ID NO 27
<211> LENGTH: 655
<212> TYPE: PRT
<213> ORGANISM: Bacillus thuringiensis

<400> SEQUENCE: 27

Met Thr His Asn Asp Asn Asn Asn Lys Phe Glu Ile Lys Asp Thr Gly
1               5                   10                  15

Thr Lys Pro Arg Ser Pro Leu Ala Asn Ala Pro Gly Pro Thr Trp Gln
            20                  25                  30

Asn Ile Asn Asn Arg Asp Val Glu Thr Phe Gly Ser Ile Glu Ile Ala
        35                  40                  45

Gly Lys Val Val Ser Gly Val Ile Ser Ser Val Ile Lys Ser Leu Arg
    50                  55                  60

Gln Gln Ala Gln Ile Asp Lys Ile Val Ala Ile Val Val Val Glu Val
65                  70                  75                  80

Phe Glu Val Leu Trp Pro Val Leu Glu Gly Met Trp Tyr Ala Met Met
                85                  90                  95

Asp Ala Val Glu Ile Met Ile Gln Glu Ala Ile Thr Thr Ala Val Arg
            100                 105                 110

Ser Lys Ala Gln Ala Glu Leu Asn Gly Ile Arg Asn Ala Leu Val Leu
        115                 120                 125

Phe Gln Gln Ala Phe Asp Asp Trp Glu Lys Asn Ser Asp Asn Pro Gln
    130                 135                 140

Leu Gln Asp Arg Val Arg Arg Gln Phe Thr Ala Thr Asn Thr Leu Ile
145                 150                 155                 160

Gln Phe Ala Met Ser Ser Phe Ala Val Pro Gly Phe Gln Val Pro Leu
                165                 170                 175

Leu Val Val Tyr Ala Gln Ala Ala Asn Leu His Leu Leu Phe Leu Arg
            180                 185                 190

Glu Ala Val Val Leu Gly Glu Lys Trp Gly Met Ser Arg Glu Glu Val
        195                 200                 205

Asp Asp Tyr Tyr Asn Gly Glu Leu Gly Leu Thr Glu Leu Thr Gln Ser
    210                 215                 220
```

-continued

```
Tyr Thr Asn His Cys Thr Asn Trp Tyr His Glu Gly Leu Ala Gln Ser
225                 230                 235                 240

Met Lys Leu Asn Pro Ser Val Thr Ile Leu Glu Gln Trp Asn Leu Tyr
                245                 250                 255

Asn Asp Phe Arg Arg Glu Met Thr Ile Met Ile Leu Asp Ile Val Ala
            260                 265                 270

Leu Trp Pro Thr Tyr Asp Val Lys Leu Tyr Pro Ala Gly Thr Lys Thr
        275                 280                 285

Glu Leu Thr Arg Ile Ile Tyr Thr Pro Leu Met Gly Val Leu Glu Asp
    290                 295                 300

Ser Ser Ser Ile Ser Ala Thr Arg Lys Glu Tyr Gly Asn Ile Ala Ala
305                 310                 315                 320

Ile Asn Gln Gln Asp Gly Ala Thr Thr Ile Pro Pro Ala Leu Phe Ile
                325                 330                 335

Trp Leu Glu Lys Gln Ile Val Tyr Pro Tyr Asn Asn Leu Ile Tyr Ser
            340                 345                 350

Tyr Gln Asn Phe Gln Lys Thr Thr Phe Gly Lys Val Met Asn Gly Thr
        355                 360                 365

Ile Phe Gly Ser Asn Ser Glu Lys His Leu Thr Asn Pro Ile Ser Ile
    370                 375                 380

Pro Ile Asp Ala Glu Ser Tyr Asp Val Tyr Lys Val Asp Thr Ser Tyr
385                 390                 395                 400

Ser Ala Lys Met Glu Ile Lys Ser Ser Pro Ile His Lys Leu Val Tyr
                405                 410                 415

Tyr Arg Ser Lys Glu Gln Gln Glu Ser Ile Ile Ser Thr Asn Thr Ser
            420                 425                 430

Lys Gly Pro Ile Asp Gln Val Ser Glu Ile Ala Asn Glu Gly Tyr Gln
        435                 440                 445

Asp Tyr Ser His Cys Leu Ala His Met Ala Gly Trp Val Ser Ile Ala
    450                 455                 460

Tyr Gly Thr Gly Leu Thr Glu Lys Pro Tyr Leu Val Pro Tyr Asn Leu
465                 470                 475                 480

Ala Leu Gly Trp Thr Tyr Ala Asn Val Asp Pro Val Asn Ser Ile Ala
                485                 490                 495

Pro Asp Ala Ile Thr Gln Ile Pro Ala Val Lys Gly Asp Lys Val Ile
            500                 505                 510

Gly Ile Pro Glu Glu Glu Ala Ile Leu Gly Glu Val Thr Ala Ile Gln
        515                 520                 525

Gly Pro Gly Phe Thr Gly Gly Asn Leu Val Gly Leu Phe Ala Gly Ala
    530                 535                 540

Glu Leu His Met Lys Val Thr Asn Pro Val Ser Asn Val Ala Gly Tyr
545                 550                 555                 560

Gln Met Arg Ile Arg Tyr Ala Asn Asn His Pro Thr Ile Leu Ala Val
                565                 570                 575

Ser Tyr Gln Gly Val Glu Thr Ser Ser Gly Lys Phe Asp Val Pro Val
            580                 585                 590

Thr Tyr Ser Gly Asp Phe Lys Thr Lys Leu Thr Tyr Asn Ala Phe Lys
        595                 600                 605

Phe Lys Glu Ala Ile Ile Ile Pro Ser Pro Leu Arg Glu Glu Ile Ala
    610                 615                 620

Asp Ile Val Leu Arg Asn Glu Gly Asp Ser Asn Leu Leu Ile Asp Lys
625                 630                 635                 640
```

```
Ile Glu Leu Ile Pro Met Asp Phe Trp Arg His Glu Gln Cys Asn
                645                 650                 655


<210> SEQ ID NO 28
<211> LENGTH: 565
<212> TYPE: PRT
<213> ORGANISM: Bacillus thuringiensis

<400> SEQUENCE: 28

Met Trp Tyr Ala Met Met Asp Ala Val Glu Ile Met Ile Gln Glu Ala
1               5                   10                  15

Ile Thr Thr Ala Val Arg Ser Lys Ala Gln Ala Glu Leu Asn Gly Ile
            20                  25                  30

Arg Asn Ala Leu Val Leu Phe Gln Gln Ala Phe Asp Asp Trp Glu Lys
        35                  40                  45

Asn Ser Asp Asn Pro Gln Leu Gln Asp Arg Val Arg Arg Gln Phe Thr
    50                  55                  60

Ala Thr Asn Thr Leu Ile Gln Phe Ala Met Ser Ser Phe Ala Val Pro
65                  70                  75                  80

Gly Phe Gln Val Pro Leu Leu Val Val Tyr Ala Gln Ala Ala Asn Leu
                85                  90                  95

His Leu Leu Phe Leu Arg Glu Ala Val Val Leu Gly Glu Lys Trp Gly
            100                 105                 110

Met Ser Arg Glu Glu Val Asp Asp Tyr Tyr Asn Gly Glu Leu Gly Leu
        115                 120                 125

Thr Glu Leu Thr Gln Ser Tyr Thr Asn His Cys Thr Asn Trp Tyr His
    130                 135                 140

Glu Gly Leu Ala Gln Ser Met Lys Leu Asn Pro Ser Val Thr Ile Leu
145                 150                 155                 160

Glu Gln Trp Asn Leu Tyr Asn Asp Phe Arg Arg Glu Met Thr Ile Met
                165                 170                 175

Ile Leu Asp Ile Val Ala Leu Trp Pro Thr Tyr Asp Val Lys Leu Tyr
            180                 185                 190

Pro Ala Gly Thr Lys Thr Glu Leu Thr Arg Ile Ile Tyr Thr Pro Leu
        195                 200                 205

Met Gly Val Leu Glu Asp Ser Ser Ser Ile Ser Ala Thr Arg Lys Glu
    210                 215                 220

Tyr Gly Asn Ile Ala Ala Ile Asn Gln Gln Asp Gly Ala Thr Thr Ile
225                 230                 235                 240

Pro Pro Ala Leu Phe Ile Trp Leu Glu Lys Gln Ile Val Tyr Pro Tyr
                245                 250                 255

Asn Asn Leu Ile Tyr Ser Tyr Gln Asn Phe Gln Lys Thr Thr Phe Gly
            260                 265                 270

Lys Val Met Asn Gly Thr Ile Phe Gly Ser Asn Ser Glu Lys His Leu
        275                 280                 285

Thr Asn Pro Ile Ser Ile Pro Ile Asp Ala Glu Ser Tyr Asp Val Tyr
    290                 295                 300

Lys Val Asp Thr Ser Tyr Ser Ala Lys Met Glu Ile Lys Ser Ser Pro
305                 310                 315                 320

Ile His Lys Leu Val Tyr Tyr Arg Ser Lys Glu Gln Gln Glu Ser Ile
                325                 330                 335

Ile Ser Thr Asn Thr Ser Lys Gly Pro Ile Asp Gln Val Ser Glu Ile
            340                 345                 350

Ala Asn Glu Gly Tyr Gln Asp Tyr Ser His Cys Leu Ala His Met Ala
        355                 360                 365
```

```
Gly Trp Val Ser Ile Ala Tyr Gly Thr Gly Leu Thr Glu Lys Pro Tyr
    370                 375                 380

Leu Val Pro Tyr Asn Leu Ala Leu Gly Trp Thr Tyr Ala Asn Val Asp
385                 390                 395                 400

Pro Val Asn Ser Ile Ala Pro Asp Ala Ile Thr Gln Ile Pro Ala Val
                405                 410                 415

Lys Gly Asp Lys Val Ile Gly Ile Pro Glu Glu Glu Ala Ile Leu Gly
            420                 425                 430

Glu Val Thr Ala Ile Gln Gly Pro Gly Phe Thr Gly Gly Asn Leu Val
        435                 440                 445

Gly Leu Phe Ala Gly Ala Glu Leu His Met Lys Val Thr Asn Pro Val
    450                 455                 460

Ser Asn Val Ala Gly Tyr Gln Met Arg Ile Arg Tyr Ala Asn Asn His
465                 470                 475                 480

Pro Thr Ile Leu Ala Val Ser Tyr Gln Gly Val Glu Thr Ser Ser Gly
                485                 490                 495

Lys Phe Asp Val Pro Val Thr Tyr Ser Gly Asp Phe Lys Thr Lys Leu
            500                 505                 510

Thr Tyr Asn Ala Phe Lys Phe Lys Glu Ala Ile Ile Ile Pro Ser Pro
        515                 520                 525

Leu Arg Glu Glu Ile Ala Asp Ile Val Leu Arg Asn Glu Gly Asp Ser
    530                 535                 540

Asn Leu Leu Ile Asp Lys Ile Glu Leu Ile Pro Met Asp Phe Trp Arg
545                 550                 555                 560

His Glu Gln Cys Asn
                565


<210> SEQ ID NO 29
<211> LENGTH: 561
<212> TYPE: PRT
<213> ORGANISM: Bacillus thuringiensis

<400> SEQUENCE: 29

Met Met Asp Ala Val Glu Ile Met Ile Gln Glu Ala Ile Thr Thr Ala
1               5                   10                  15

Val Arg Ser Lys Ala Gln Ala Glu Leu Asn Gly Ile Arg Asn Ala Leu
            20                  25                  30

Val Leu Phe Gln Gln Ala Phe Asp Asp Trp Glu Lys Asn Ser Asp Asn
        35                  40                  45

Pro Gln Leu Gln Asp Arg Val Arg Arg Gln Phe Thr Ala Thr Asn Thr
    50                  55                  60

Leu Ile Gln Phe Ala Met Ser Ser Phe Ala Val Pro Gly Phe Gln Val
65                  70                  75                  80

Pro Leu Leu Val Val Tyr Ala Gln Ala Ala Asn Leu His Leu Leu Phe
                85                  90                  95

Leu Arg Glu Ala Val Val Leu Gly Glu Lys Trp Gly Met Ser Arg Glu
            100                 105                 110

Glu Val Asp Asp Tyr Tyr Asn Gly Glu Leu Gly Leu Thr Glu Leu Thr
        115                 120                 125

Gln Ser Tyr Thr Asn His Cys Thr Asn Trp Tyr His Glu Gly Leu Ala
    130                 135                 140

Gln Ser Met Lys Leu Asn Pro Ser Val Thr Ile Leu Glu Gln Trp Asn
145                 150                 155                 160

Leu Tyr Asn Asp Phe Arg Arg Glu Met Thr Ile Met Ile Leu Asp Ile
```

```
                165                 170                 175

Val Ala Leu Trp Pro Thr Tyr Asp Val Lys Leu Tyr Pro Ala Gly Thr
            180                 185                 190

Lys Thr Glu Leu Thr Arg Ile Ile Tyr Thr Pro Leu Met Gly Val Leu
        195                 200                 205

Glu Asp Ser Ser Ser Ile Ser Ala Thr Arg Lys Glu Tyr Gly Asn Ile
    210                 215                 220

Ala Ala Ile Asn Gln Gln Asp Gly Ala Thr Thr Ile Pro Pro Ala Leu
225                 230                 235                 240

Phe Ile Trp Leu Glu Lys Gln Ile Val Tyr Pro Tyr Asn Asn Leu Ile
                245                 250                 255

Tyr Ser Tyr Gln Asn Phe Gln Lys Thr Thr Phe Gly Lys Val Met Asn
            260                 265                 270

Gly Thr Ile Phe Gly Ser Asn Ser Glu Lys His Leu Thr Asn Pro Ile
        275                 280                 285

Ser Ile Pro Ile Asp Ala Glu Ser Tyr Asp Val Tyr Lys Val Asp Thr
    290                 295                 300

Ser Tyr Ser Ala Lys Met Glu Ile Lys Ser Ser Pro Ile His Lys Leu
305                 310                 315                 320

Val Tyr Tyr Arg Ser Lys Glu Gln Gln Glu Ser Ile Ile Ser Thr Asn
                325                 330                 335

Thr Ser Lys Gly Pro Ile Asp Gln Val Ser Glu Ile Ala Asn Glu Gly
            340                 345                 350

Tyr Gln Asp Tyr Ser His Cys Leu Ala His Met Ala Gly Trp Val Ser
        355                 360                 365

Ile Ala Tyr Gly Thr Gly Leu Thr Glu Lys Pro Tyr Leu Val Pro Tyr
    370                 375                 380

Asn Leu Ala Leu Gly Trp Thr Tyr Ala Asn Val Asp Pro Val Asn Ser
385                 390                 395                 400

Ile Ala Pro Asp Ala Ile Thr Gln Ile Pro Ala Val Lys Gly Asp Lys
                405                 410                 415

Val Ile Gly Ile Pro Glu Glu Glu Ala Ile Leu Gly Glu Val Thr Ala
            420                 425                 430

Ile Gln Gly Pro Gly Phe Thr Gly Gly Asn Leu Val Gly Leu Phe Ala
        435                 440                 445

Gly Ala Glu Leu His Met Lys Val Thr Asn Pro Val Ser Asn Val Ala
    450                 455                 460

Gly Tyr Gln Met Arg Ile Arg Tyr Ala Asn Asn His Pro Thr Ile Leu
465                 470                 475                 480

Ala Val Ser Tyr Gln Gly Val Glu Thr Ser Ser Gly Lys Phe Asp Val
                485                 490                 495

Pro Val Thr Tyr Ser Gly Asp Phe Lys Thr Lys Leu Thr Tyr Asn Ala
            500                 505                 510

Phe Lys Phe Lys Glu Ala Ile Ile Ile Pro Ser Pro Leu Arg Glu Glu
        515                 520                 525

Ile Ala Asp Ile Val Leu Arg Asn Glu Gly Asp Ser Asn Leu Leu Ile
    530                 535                 540

Asp Lys Ile Glu Leu Ile Pro Met Asp Phe Trp Arg His Glu Gln Cys
545                 550                 555                 560

Asn
```

<210> SEQ ID NO 30
<211> LENGTH: 560

<212> TYPE: PRT
<213> ORGANISM: Bacillus thuringiensis

<400> SEQUENCE: 30

Met Asp Ala Val Glu Ile Met Ile Gln Glu Ala Ile Thr Thr Ala Val
1 5 10 15

Arg Ser Lys Ala Gln Ala Glu Leu Asn Gly Ile Arg Asn Ala Leu Val
20 25 30

Leu Phe Gln Gln Ala Phe Asp Asp Trp Glu Lys Asn Ser Asp Asn Pro
35 40 45

Gln Leu Gln Asp Arg Val Arg Arg Gln Phe Thr Ala Thr Asn Thr Leu
50 55 60

Ile Gln Phe Ala Met Ser Ser Phe Ala Val Pro Gly Phe Gln Val Pro
65 70 75 80

Leu Leu Val Val Tyr Ala Gln Ala Ala Asn Leu His Leu Leu Phe Leu
85 90 95

Arg Glu Ala Val Val Leu Gly Glu Lys Trp Gly Met Ser Arg Glu Glu
100 105 110

Val Asp Asp Tyr Tyr Asn Gly Glu Leu Gly Leu Thr Glu Leu Thr Gln
115 120 125

Ser Tyr Thr Asn His Cys Thr Asn Trp Tyr His Glu Gly Leu Ala Gln
130 135 140

Ser Met Lys Leu Asn Pro Ser Val Thr Ile Leu Glu Gln Trp Asn Leu
145 150 155 160

Tyr Asn Asp Phe Arg Arg Glu Met Thr Ile Met Ile Leu Asp Ile Val
165 170 175

Ala Leu Trp Pro Thr Tyr Asp Val Lys Leu Tyr Pro Ala Gly Thr Lys
180 185 190

Thr Glu Leu Thr Arg Ile Ile Tyr Thr Pro Leu Met Gly Val Leu Glu
195 200 205

Asp Ser Ser Ser Ile Ser Ala Thr Arg Lys Glu Tyr Gly Asn Ile Ala
210 215 220

Ala Ile Asn Gln Gln Asp Gly Ala Thr Thr Ile Pro Pro Ala Leu Phe
225 230 235 240

Ile Trp Leu Glu Lys Gln Ile Val Tyr Pro Tyr Asn Asn Leu Ile Tyr
245 250 255

Ser Tyr Gln Asn Phe Gln Lys Thr Thr Phe Gly Lys Val Met Asn Gly
260 265 270

Thr Ile Phe Gly Ser Asn Ser Glu Lys His Leu Thr Asn Pro Ile Ser
275 280 285

Ile Pro Ile Asp Ala Glu Ser Tyr Asp Val Tyr Lys Val Asp Thr Ser
290 295 300

Tyr Ser Ala Lys Met Glu Ile Lys Ser Ser Pro Ile His Lys Leu Val
305 310 315 320

Tyr Tyr Arg Ser Lys Glu Gln Gln Glu Ser Ile Ile Ser Thr Asn Thr
325 330 335

Ser Lys Gly Pro Ile Asp Gln Val Ser Glu Ile Ala Asn Glu Gly Tyr
340 345 350

Gln Asp Tyr Ser His Cys Leu Ala His Met Ala Gly Trp Val Ser Ile
355 360 365

Ala Tyr Gly Thr Gly Leu Thr Glu Lys Pro Tyr Leu Val Pro Tyr Asn
370 375 380

Leu Ala Leu Gly Trp Thr Tyr Ala Asn Val Asp Pro Val Asn Ser Ile
385 390 395 400

Ala Pro Asp Ala Ile Thr Gln Ile Pro Ala Val Lys Gly Asp Lys Val
405 410 415

Ile Gly Ile Pro Glu Glu Glu Ala Ile Leu Gly Glu Val Thr Ala Ile
420 425 430

Gln Gly Pro Gly Phe Thr Gly Gly Asn Leu Val Gly Leu Phe Ala Gly
435 440 445

Ala Glu Leu His Met Lys Val Thr Asn Pro Val Ser Asn Val Ala Gly
450 455 460

Tyr Gln Met Arg Ile Arg Tyr Ala Asn Asn His Pro Thr Ile Leu Ala
465 470 475 480

Val Ser Tyr Gln Gly Val Glu Thr Ser Ser Gly Lys Phe Asp Val Pro
485 490 495

Val Thr Tyr Ser Gly Asp Phe Lys Thr Lys Leu Thr Tyr Asn Ala Phe
500 505 510

Lys Phe Lys Glu Ala Ile Ile Ile Pro Ser Pro Leu Arg Glu Glu Ile
515 520 525

Ala Asp Ile Val Leu Arg Asn Glu Gly Asp Ser Asn Leu Leu Ile Asp
530 535 540

Lys Ile Glu Leu Ile Pro Met Asp Phe Trp Arg His Glu Gln Cys Asn
545 550 555 560

<210> SEQ ID NO 31
<211> LENGTH: 554
<212> TYPE: PRT
<213> ORGANISM: Bacillus thuringiensis

<400> SEQUENCE: 31

Met Ile Gln Glu Ala Ile Thr Thr Ala Val Arg Ser Lys Ala Gln Ala
1 5 10 15

Glu Leu Asn Gly Ile Arg Asn Ala Leu Val Leu Phe Gln Gln Ala Phe
20 25 30

Asp Asp Trp Glu Lys Asn Ser Asp Asn Pro Gln Leu Gln Asp Arg Val
35 40 45

Arg Arg Gln Phe Thr Ala Thr Asn Thr Leu Ile Gln Phe Ala Met Ser
50 55 60

Ser Phe Ala Val Pro Gly Phe Gln Val Pro Leu Leu Val Val Tyr Ala
65 70 75 80

Gln Ala Ala Asn Leu His Leu Leu Phe Leu Arg Glu Ala Val Val Leu
85 90 95

Gly Glu Lys Trp Gly Met Ser Arg Glu Glu Val Asp Asp Tyr Tyr Asn
100 105 110

Gly Glu Leu Gly Leu Thr Glu Leu Thr Gln Ser Tyr Thr Asn His Cys
115 120 125

Thr Asn Trp Tyr His Glu Gly Leu Ala Gln Ser Met Lys Leu Asn Pro
130 135 140

Ser Val Thr Ile Leu Glu Gln Trp Asn Leu Tyr Asn Asp Phe Arg Arg
145 150 155 160

Glu Met Thr Ile Met Ile Leu Asp Ile Val Ala Leu Trp Pro Thr Tyr
165 170 175

Asp Val Lys Leu Tyr Pro Ala Gly Thr Lys Thr Glu Leu Thr Arg Ile
180 185 190

Ile Tyr Thr Pro Leu Met Gly Val Leu Glu Asp Ser Ser Ser Ile Ser
195 200 205

Ala Thr Arg Lys Glu Tyr Gly Asn Ile Ala Ala Ile Asn Gln Gln Asp

```
    210                 215                 220

Gly Ala Thr Thr Ile Pro Pro Ala Leu Phe Ile Trp Leu Glu Lys Gln
225                 230                 235                 240

Ile Val Tyr Pro Tyr Asn Asn Leu Ile Tyr Ser Tyr Gln Asn Phe Gln
                245                 250                 255

Lys Thr Thr Phe Gly Lys Val Met Asn Gly Thr Ile Phe Gly Ser Asn
            260                 265                 270

Ser Glu Lys His Leu Thr Asn Pro Ile Ser Ile Pro Ile Asp Ala Glu
        275                 280                 285

Ser Tyr Asp Val Tyr Lys Val Asp Thr Ser Tyr Ser Ala Lys Met Glu
    290                 295                 300

Ile Lys Ser Ser Pro Ile His Lys Leu Val Tyr Tyr Arg Ser Lys Glu
305                 310                 315                 320

Gln Gln Glu Ser Ile Ile Ser Thr Asn Thr Ser Lys Gly Pro Ile Asp
                325                 330                 335

Gln Val Ser Glu Ile Ala Asn Glu Gly Tyr Gln Asp Tyr Ser His Cys
            340                 345                 350

Leu Ala His Met Ala Gly Trp Val Ser Ile Ala Tyr Gly Thr Gly Leu
        355                 360                 365

Thr Glu Lys Pro Tyr Leu Val Pro Tyr Asn Leu Ala Leu Gly Trp Thr
    370                 375                 380

Tyr Ala Asn Val Asp Pro Val Asn Ser Ile Ala Pro Asp Ala Ile Thr
385                 390                 395                 400

Gln Ile Pro Ala Val Lys Gly Asp Lys Val Ile Gly Ile Pro Glu Glu
                405                 410                 415

Glu Ala Ile Leu Gly Glu Val Thr Ala Ile Gln Gly Pro Gly Phe Thr
            420                 425                 430

Gly Gly Asn Leu Val Gly Leu Phe Ala Gly Ala Glu Leu His Met Lys
        435                 440                 445

Val Thr Asn Pro Val Ser Asn Val Ala Gly Tyr Gln Met Arg Ile Arg
    450                 455                 460

Tyr Ala Asn Asn His Pro Thr Ile Leu Ala Val Ser Tyr Gln Gly Val
465                 470                 475                 480

Glu Thr Ser Ser Gly Lys Phe Asp Val Pro Val Thr Tyr Ser Gly Asp
                485                 490                 495

Phe Lys Thr Lys Leu Thr Tyr Asn Ala Phe Lys Phe Lys Glu Ala Ile
            500                 505                 510

Ile Ile Pro Ser Pro Leu Arg Glu Glu Ile Ala Asp Ile Val Leu Arg
        515                 520                 525

Asn Glu Gly Asp Ser Asn Leu Leu Ile Asp Lys Ile Glu Leu Ile Pro
    530                 535                 540

Met Asp Phe Trp Arg His Glu Gln Cys Asn
545                 550


<210> SEQ ID NO 32
<211> LENGTH: 1239
<212> TYPE: PRT
<213> ORGANISM: Bacillus thuringiensis

<400> SEQUENCE: 32

Met Asn Gln Gln His Asn Asn Glu Tyr Glu Ile Met Ser Thr Gly Asp
1               5                   10                  15

Met Gly Tyr Gln Pro Arg Tyr Pro Phe Ser Asn Ala Pro Gly Ala Glu
            20                  25                  30
```

-continued

```
Leu Gln Gln Met His Tyr Lys Asp Trp Met Asp Met Cys Ala Asp Gly
        35                  40                  45

Glu Ser Gly Lys Thr Phe Ala Asp Leu Thr Val Gln Glu Gly Val Thr
    50                  55                  60

Ile Ala Val Ser Ile Ala Ala Ala Ile Leu Ser Val Pro Phe Pro Val
65                  70                  75                  80

Thr Ala Ala Gly Leu Ser Ile Ile Ser Leu Leu Val Pro Tyr Trp Trp
                85                  90                  95

Pro Glu Thr Ala Val Thr Pro Gly Thr Pro Ser Ala Gln Val Thr Trp
            100                 105                 110

Glu Lys Phe Met Ser Ala Ala Glu Asn Leu Ser Asn Thr Gln Ile Val
        115                 120                 125

Ala Ser Lys Arg Ser Asp Ala Ile Ala Arg Trp Gln Gly Ile Gln Thr
    130                 135                 140

Leu Gly Arg Asp Tyr Phe Gln Ala Gln Cys Asp Trp Leu Gln Asp Gln
145                 150                 155                 160

Asn Asn Glu Leu Lys Lys Ser Lys Leu Arg Glu Ala Phe Asp Asp Phe
                165                 170                 175

Glu Asp Tyr Leu Lys Val Ser Met Pro Phe Phe Arg Ala Gln Gly Phe
            180                 185                 190

Glu Ile Pro Met Leu Ala Met Tyr Ala Gln Ala Ala Asn Met His Leu
        195                 200                 205

Leu Leu Leu Arg Glu Val Val Gln Asn Gly Val Gly Trp Gly Phe Gln
    210                 215                 220

Gln Tyr Glu Val Asp Arg Tyr Tyr Ser Asn Thr Asp Pro Phe Leu Gly
225                 230                 235                 240

Asn Pro Gly Leu Leu Gln Leu Leu Glu Gly Tyr Thr Asp Tyr Cys Val
                245                 250                 255

Lys Trp Tyr Asn Ala Gly Leu Arg Gln Gln Tyr Glu Asn Asn Arg Tyr
            260                 265                 270

Asn Trp Asp Ala Phe Asn Asp Phe Arg Arg Asp Met Ile Ile Met Val
        275                 280                 285

Leu Asp Ile Val Ser Leu Trp Pro Thr Tyr Asp Pro Lys Arg Tyr Pro
    290                 295                 300

Leu Pro Thr Lys Ser Gln Leu Thr Arg Thr Val Tyr Thr Asp Leu Val
305                 310                 315                 320

Gly Phe Ser Gly Asn Ser Glu Tyr Leu Gln Ile Asp Ile Glu Arg Ala
                325                 330                 335

Glu Gln Ala Leu Val Gln Lys Pro Gly Leu Phe Thr Trp Leu Arg Glu
            340                 345                 350

Leu Ser Phe Glu Leu Gly Pro Leu Ser Arg Ile Asn Phe Val Arg Gly
        355                 360                 365

Arg Gln Ile Val Phe Asn Tyr Thr Gly Ser Ser Asp Arg Tyr Glu Glu
    370                 375                 380

Thr Lys Gly Asn Leu Gly Glu Thr Arg Glu Thr Val Val Ile Pro Ala
385                 390                 395                 400

Pro Asp Val Gly Asp Asp Ile Trp Arg Ile Ser Thr Gln Val Asn Thr
                405                 410                 415

Tyr Gln Ile Pro Asn Ala Thr Phe Val Arg Gly Trp Asn Phe Ser Phe
            420                 425                 430

Thr Gln Ser Leu Asp Gln Lys Ile Ala Trp Arg Thr Glu Tyr Ser Pro
        435                 440                 445

Glu Ile Val Met Gln Gly Leu Ser Cys His Gly Pro Ser Val Ser Ser
```

```
    450                 455                 460

Cys Asn Leu Cys Ile Ser Asn Ser Pro Cys Arg Ser Ile Thr Pro Asn
465                 470                 475                 480

Tyr Ser Ser Pro Cys Asp Asp Lys Leu Val Tyr Ser His Arg Phe Ser
                485                 490                 495

Tyr Leu Gly Ala Gly Leu Lys Ser Asp Leu Thr Thr Leu Ile Tyr Phe
            500                 505                 510

Ser Tyr Gly Trp Thr His Val Ser Ala Asp Ala Asn Asn Leu Ile Asp
        515                 520                 525

Pro Lys Lys Ile Thr Gln Ile Pro Ala Val Lys Gly Asp Tyr Leu Gly
    530                 535                 540

Arg Asn Ala Arg Val Ile Lys Gly Pro Gly Ser Thr Gly Gly Asp Leu
545                 550                 555                 560

Val Gln Leu Ser Asp Gly Thr Glu Arg Gly Thr Leu Gly Ile Lys Leu
                565                 570                 575

Thr Lys Pro Pro Gly Ser His Ser Tyr Arg Val Arg Ile Arg Tyr Ala
            580                 585                 590

Ser Asn Thr Arg Thr Gln Leu Glu Ile Ile Trp Gly Glu Asp Tyr Asp
        595                 600                 605

Ser Val Ile Val Pro Ala Thr Thr Thr Asp Ile Thr Asn Leu Thr Tyr
    610                 615                 620

Asn Lys Phe Gly Tyr Phe Glu Ile Arg Val Phe Ser Tyr Asn Ser Ser
625                 630                 635                 640

Ser Glu Glu Glu Asp Leu Ile Arg Val Asp Ala Thr Gly Ser Phe Ile
                645                 650                 655

Leu Asp Lys Ile Glu Phe Ile Pro Ile Glu Gly Ser Val Asp Glu Tyr
            660                 665                 670

Gln Ala Asn Gln Asp Leu Glu Lys Ala Lys Lys Ala Val Asn Ala Leu
        675                 680                 685

Phe Thr Gly Asp Ala Lys Ser Ala Leu Lys Leu Ser Ile Thr Gly Tyr
    690                 695                 700

Ile Val Asp Gln Ala Ala Asn Phe Val Glu Cys Val Ser Asp Glu Phe
705                 710                 715                 720

His Ala Gln Glu Lys Met Ile Leu Leu Asp Gln Val Lys Phe Ala Lys
                725                 730                 735

Arg Leu Ser Gln Ala Arg Asn Leu Leu Asn Tyr Gly Asp Phe Glu Ser
            740                 745                 750

Ser Asp Trp Ser Gly Glu Asn Gly Trp Arg Thr Ser Pro His Val His
        755                 760                 765

Val Ala Ser Asn Asn Pro Ile Phe Lys Gly Arg Tyr Leu His Met Pro
    770                 775                 780

Gly Ala Met Ser Pro Gln Phe Ser Asn Asn Thr Tyr Pro Thr Tyr Ala
785                 790                 795                 800

Tyr Gln Lys Val Asp Glu Ser Lys Leu Lys Ser Tyr Thr Arg Tyr Leu
                805                 810                 815

Val Arg Gly Leu Val Gly Asn Ser Lys Asp Leu Glu Leu Leu Val Glu
            820                 825                 830

Arg Tyr Gly Lys Asp Val His Val Glu Met Asp Val Pro Asn Asp Ile
        835                 840                 845

Gln Tyr Thr Leu Pro Thr Asn Asp Cys Gly Gly Phe Asp Arg Cys Lys
    850                 855                 860

Pro Val Ser Tyr Gln Thr Gly Thr Ser Ser Tyr Lys Ser Cys Gly Cys
865                 870                 875                 880
```

-continued

```
Lys Asn Asn Asp Thr Tyr Gln Asn Gly Met His Leu Ser Lys Ser Cys
                885                 890                 895

Gly Cys Lys Lys Asp Pro His Val Phe Thr Tyr His Ile Asp Thr Gly
            900                 905                 910

Cys Val Asp Gln Glu Glu Asn Leu Gly Leu Phe Phe Ala Leu Lys Ile
        915                 920                 925

Ala Ser Glu Asn Gly Met Ala Asn Ile Asp Asn Leu Glu Ile Ile Glu
    930                 935                 940

Ala Gln Pro Leu Lys Gly Glu Ala Leu Ala Arg Val Lys Lys Arg Glu
945                 950                 955                 960

Gln Lys Trp Lys Gln Glu Met Ala Gln Lys Leu Leu Arg Thr Glu Lys
                965                 970                 975

Ala Val Gln Ala Ala Lys Asp Ala Leu Gln Thr Leu Phe Thr Asn Ala
            980                 985                 990

Gln Tyr Asn Arg Leu Lys Phe Glu  Thr Leu Phe Pro Gln  Ile Val His
        995                 1000                1005

Ala Glu  Lys Leu Val Gln Gln  Ile Pro Tyr Ala Tyr  His Pro Phe
    1010                 1015                 1020

Leu Ser  Gly Thr Leu Ser Thr  Val Pro Gly Met Asn  Phe Glu Ile
    1025                 1030                 1035

Ile Gln  Gln Leu Leu Ala Val  Ile Gly Asn Ala Arg  Thr Leu Tyr
    1040                 1045                 1050

Glu Gln  Arg Asn Leu Leu Arg  Thr Gly Thr Phe Ser  Ser Gly Thr
    1055                 1060                 1065

Gly Ser  Trp Lys Val Thr Glu  Gly Val Lys Val Gln  Pro Leu Gln
    1070                 1075                 1080

Asp Thr  Ser Val Leu Val Leu  Ser Glu Trp Ser His  Glu Ala Ser
    1085                 1090                 1095

Gln Gln  Leu His Met Asp Pro  Asp Arg Gly Tyr Val  Leu Arg Val
    1100                 1105                 1110

Thr Ala  Arg Lys Glu Gly Gly  Gly Lys Gly Thr Val  Thr Met Ser
    1115                 1120                 1125

Asp Cys  Ala Asp Tyr Thr Glu  Thr Leu Thr Phe Thr  Ser Cys Asp
    1130                 1135                 1140

Tyr Asn  Thr Tyr Gly Ser Gln  Thr Met Thr Ser Gly  Thr Leu Ser
    1145                 1150                 1155

Gly Phe  Val Thr Lys Thr Leu  Glu Ile Phe Pro Asp  Thr Asp Arg
    1160                 1165                 1170

Ile Arg  Ile Asp Ile Gly Glu  Thr Glu Gly Thr Phe  Gln Val Glu
    1175                 1180                 1185

Ser Val  Glu Leu Ile Cys Met  Glu Gln Met Glu Asp  Asp Leu Tyr
    1190                 1195                 1200

Asn Met  Ala Gly Asn Val Ala  Glu Glu Met Gln Val  Leu Gln Gln
    1205                 1210                 1215

Ser Arg  Ser Gly Ser His Thr  Leu Asp Pro Leu Cys  Asn Thr Arg
    1220                 1225                 1230

Ile Gly  Glu Phe Asp Cys
    1235
```

<210> SEQ ID NO 33
<211> LENGTH: 1228
<212> TYPE: PRT
<213> ORGANISM: Bacillus thuringiensis

<400> SEQUENCE: 33

Met Ser Thr Gly Asp Met Gly Tyr Gln Pro Arg Tyr Pro Phe Ser Asn
1 5 10 15

Ala Pro Gly Ala Glu Leu Gln Gln Met His Tyr Lys Asp Trp Met Asp
20 25 30

Met Cys Ala Asp Gly Glu Ser Gly Lys Thr Phe Ala Asp Leu Thr Val
35 40 45

Gln Glu Gly Val Thr Ile Ala Val Ser Ile Ala Ala Ile Leu Ser
50 55 60

Val Pro Phe Pro Val Thr Ala Ala Gly Leu Ser Ile Ile Ser Leu Leu
65 70 75 80

Val Pro Tyr Trp Trp Pro Glu Thr Ala Val Thr Pro Gly Thr Pro Ser
85 90 95

Ala Gln Val Thr Trp Glu Lys Phe Met Ser Ala Ala Glu Asn Leu Ser
100 105 110

Asn Thr Gln Ile Val Ala Ser Lys Arg Ser Asp Ala Ile Ala Arg Trp
115 120 125

Gln Gly Ile Gln Thr Leu Gly Arg Asp Tyr Phe Gln Ala Gln Cys Asp
130 135 140

Trp Leu Gln Asp Gln Asn Asn Glu Leu Lys Lys Ser Lys Leu Arg Glu
145 150 155 160

Ala Phe Asp Asp Phe Glu Asp Tyr Leu Lys Val Ser Met Pro Phe Phe
165 170 175

Arg Ala Gln Gly Phe Glu Ile Pro Met Leu Ala Met Tyr Ala Gln Ala
180 185 190

Ala Asn Met His Leu Leu Leu Leu Arg Glu Val Val Gln Asn Gly Val
195 200 205

Gly Trp Gly Phe Gln Gln Tyr Glu Val Asp Arg Tyr Tyr Ser Asn Thr
210 215 220

Asp Pro Phe Leu Gly Asn Pro Gly Leu Leu Gln Leu Leu Glu Gly Tyr
225 230 235 240

Thr Asp Tyr Cys Val Lys Trp Tyr Asn Ala Gly Leu Arg Gln Gln Tyr
245 250 255

Glu Asn Asn Arg Tyr Asn Trp Asp Ala Phe Asn Asp Phe Arg Arg Asp
260 265 270

Met Ile Ile Met Val Leu Asp Ile Val Ser Leu Trp Pro Thr Tyr Asp
275 280 285

Pro Lys Arg Tyr Pro Leu Pro Thr Lys Ser Gln Leu Thr Arg Thr Val
290 295 300

Tyr Thr Asp Leu Val Gly Phe Ser Gly Asn Ser Glu Tyr Leu Gln Ile
305 310 315 320

Asp Ile Glu Arg Ala Glu Gln Ala Leu Val Gln Lys Pro Gly Leu Phe
325 330 335

Thr Trp Leu Arg Glu Leu Ser Phe Glu Leu Gly Pro Leu Ser Arg Ile
340 345 350

Asn Phe Val Arg Gly Arg Gln Ile Val Phe Asn Tyr Thr Gly Ser Ser
355 360 365

Asp Arg Tyr Glu Glu Thr Lys Gly Asn Leu Gly Glu Thr Arg Glu Thr
370 375 380

Val Val Ile Pro Ala Pro Asp Val Gly Asp Asp Ile Trp Arg Ile Ser
385 390 395 400

Thr Gln Val Asn Thr Tyr Gln Ile Pro Asn Ala Thr Phe Val Arg Gly
405 410 415

-continued

```
Trp Asn Phe Ser Phe Thr Gln Ser Leu Asp Gln Lys Ile Ala Trp Arg
            420                 425                 430

Thr Glu Tyr Ser Pro Glu Ile Val Met Gln Gly Leu Ser Cys His Gly
        435                 440                 445

Pro Ser Val Ser Ser Cys Asn Leu Cys Ile Ser Asn Ser Pro Cys Arg
    450                 455                 460

Ser Ile Thr Pro Asn Tyr Ser Ser Pro Cys Asp Asp Lys Leu Val Tyr
465                 470                 475                 480

Ser His Arg Phe Ser Tyr Leu Gly Ala Gly Leu Lys Ser Asp Leu Thr
                485                 490                 495

Thr Leu Ile Tyr Phe Ser Tyr Gly Trp Thr His Val Ser Ala Asp Ala
            500                 505                 510

Asn Asn Leu Ile Asp Pro Lys Lys Ile Thr Gln Ile Pro Ala Val Lys
        515                 520                 525

Gly Asp Tyr Leu Gly Arg Asn Ala Arg Val Ile Lys Gly Pro Gly Ser
    530                 535                 540

Thr Gly Gly Asp Leu Val Gln Leu Ser Asp Gly Thr Glu Arg Gly Thr
545                 550                 555                 560

Leu Gly Ile Lys Leu Thr Lys Pro Pro Gly Ser His Ser Tyr Arg Val
                565                 570                 575

Arg Ile Arg Tyr Ala Ser Asn Thr Arg Thr Gln Leu Glu Ile Ile Trp
            580                 585                 590

Gly Glu Asp Tyr Asp Ser Val Ile Val Pro Ala Thr Thr Thr Asp Ile
        595                 600                 605

Thr Asn Leu Thr Tyr Asn Lys Phe Gly Tyr Phe Glu Ile Arg Val Phe
    610                 615                 620

Ser Tyr Asn Ser Ser Ser Glu Glu Glu Asp Leu Ile Arg Val Asp Ala
625                 630                 635                 640

Thr Gly Ser Phe Ile Leu Asp Lys Ile Glu Phe Ile Pro Ile Glu Gly
                645                 650                 655

Ser Val Asp Glu Tyr Gln Ala Asn Gln Asp Leu Glu Lys Ala Lys Lys
            660                 665                 670

Ala Val Asn Ala Leu Phe Thr Gly Asp Ala Lys Ser Ala Leu Lys Leu
        675                 680                 685

Ser Ile Thr Gly Tyr Ile Val Asp Gln Ala Ala Asn Phe Val Glu Cys
    690                 695                 700

Val Ser Asp Glu Phe His Ala Gln Glu Lys Met Ile Leu Leu Asp Gln
705                 710                 715                 720

Val Lys Phe Ala Lys Arg Leu Ser Gln Ala Arg Asn Leu Leu Asn Tyr
                725                 730                 735

Gly Asp Phe Glu Ser Ser Asp Trp Ser Gly Glu Asn Gly Trp Arg Thr
            740                 745                 750

Ser Pro His Val His Val Ala Ser Asn Asn Pro Ile Phe Lys Gly Arg
        755                 760                 765

Tyr Leu His Met Pro Gly Ala Met Ser Pro Gln Phe Ser Asn Asn Thr
    770                 775                 780

Tyr Pro Thr Tyr Ala Tyr Gln Lys Val Asp Glu Ser Lys Leu Lys Ser
785                 790                 795                 800

Tyr Thr Arg Tyr Leu Val Arg Gly Leu Val Gly Asn Ser Lys Asp Leu
                805                 810                 815

Glu Leu Leu Val Glu Arg Tyr Gly Lys Asp Val His Val Glu Met Asp
            820                 825                 830
```

-continued

```
Val Pro Asn Asp Ile Gln Tyr Thr Leu Pro Thr Asn Asp Cys Gly Gly
        835                 840                 845

Phe Asp Arg Cys Lys Pro Val Ser Tyr Gln Thr Gly Thr Ser Ser Tyr
    850                 855                 860

Lys Ser Cys Gly Cys Lys Asn Asn Asp Thr Tyr Gln Asn Gly Met His
865                 870                 875                 880

Leu Ser Lys Ser Cys Gly Cys Lys Lys Asp Pro His Val Phe Thr Tyr
                885                 890                 895

His Ile Asp Thr Gly Cys Val Asp Gln Glu Glu Asn Leu Gly Leu Phe
            900                 905                 910

Phe Ala Leu Lys Ile Ala Ser Glu Asn Gly Met Ala Asn Ile Asp Asn
        915                 920                 925

Leu Glu Ile Ile Glu Ala Gln Pro Leu Lys Gly Glu Ala Leu Ala Arg
    930                 935                 940

Val Lys Lys Arg Glu Gln Lys Trp Lys Gln Glu Met Ala Gln Lys Leu
945                 950                 955                 960

Leu Arg Thr Glu Lys Ala Val Gln Ala Ala Lys Asp Ala Leu Gln Thr
                965                 970                 975

Leu Phe Thr Asn Ala Gln Tyr Asn Arg Leu Lys Phe Glu Thr Leu Phe
            980                 985                 990

Pro Gln Ile Val His Ala Glu Lys  Leu Val Gln Gln Ile  Pro Tyr Ala
        995                 1000                 1005

Tyr His  Pro Phe Leu Ser Gly  Thr Leu Ser Thr Val  Pro Gly Met
    1010                 1015                 1020

Asn Phe  Glu Ile Ile Gln Gln  Leu Leu Ala Val Ile  Gly Asn Ala
    1025                 1030                 1035

Arg Thr  Leu Tyr Glu Gln Arg  Asn Leu Leu Arg Thr  Gly Thr Phe
    1040                 1045                 1050

Ser Ser  Gly Thr Gly Ser Trp  Lys Val Thr Glu Gly  Val Lys Val
    1055                 1060                 1065

Gln Pro  Leu Gln Asp Thr Ser  Val Leu Val Leu Ser  Glu Trp Ser
    1070                 1075                 1080

His Glu  Ala Ser Gln Gln Leu  His Met Asp Pro Asp  Arg Gly Tyr
    1085                 1090                 1095

Val Leu  Arg Val Thr Ala Arg  Lys Glu Gly Gly Gly  Lys Gly Thr
    1100                 1105                 1110

Val Thr  Met Ser Asp Cys Ala  Asp Tyr Thr Glu Thr  Leu Thr Phe
    1115                 1120                 1125

Thr Ser  Cys Asp Tyr Asn Thr  Tyr Gly Ser Gln Thr  Met Thr Ser
    1130                 1135                 1140

Gly Thr  Leu Ser Gly Phe Val  Thr Lys Thr Leu Glu  Ile Phe Pro
    1145                 1150                 1155

Asp Thr  Asp Arg Ile Arg Ile  Asp Ile Gly Glu Thr  Glu Gly Thr
    1160                 1165                 1170

Phe Gln  Val Glu Ser Val Glu  Leu Ile Cys Met Glu  Gln Met Glu
    1175                 1180                 1185

Asp Asp  Leu Tyr Asn Met Ala  Gly Asn Val Ala Glu  Glu Met Gln
    1190                 1195                 1200

Val Leu  Gln Gln Ser Arg Ser  Gly Ser His Thr Leu  Asp Pro Leu
    1205                 1210                 1215

Cys Asn  Thr Arg Ile Gly Glu  Phe Asp Cys
    1220                 1225
```

<210> SEQ ID NO 34
<211> LENGTH: 1223
<212> TYPE: PRT
<213> ORGANISM: Bacillus thuringiensis

<400> SEQUENCE: 34

```
Met Gly Tyr Gln Pro Arg Tyr Pro Phe Ser Asn Ala Pro Gly Ala Glu
1               5                   10                  15

Leu Gln Gln Met His Tyr Lys Asp Trp Met Asp Met Cys Ala Asp Gly
            20                  25                  30

Glu Ser Gly Lys Thr Phe Ala Asp Leu Thr Val Gln Glu Gly Val Thr
        35                  40                  45

Ile Ala Val Ser Ile Ala Ala Ala Ile Leu Ser Val Pro Phe Pro Val
    50                  55                  60

Thr Ala Ala Gly Leu Ser Ile Ile Ser Leu Leu Val Pro Tyr Trp Trp
65                  70                  75                  80

Pro Glu Thr Ala Val Thr Pro Gly Thr Pro Ser Ala Gln Val Thr Trp
                85                  90                  95

Glu Lys Phe Met Ser Ala Ala Glu Asn Leu Ser Asn Thr Gln Ile Val
            100                 105                 110

Ala Ser Lys Arg Ser Asp Ala Ile Ala Arg Trp Gln Gly Ile Gln Thr
        115                 120                 125

Leu Gly Arg Asp Tyr Phe Gln Ala Gln Cys Asp Trp Leu Gln Asp Gln
    130                 135                 140

Asn Asn Glu Leu Lys Lys Ser Lys Leu Arg Glu Ala Phe Asp Asp Phe
145                 150                 155                 160

Glu Asp Tyr Leu Lys Val Ser Met Pro Phe Phe Arg Ala Gln Gly Phe
                165                 170                 175

Glu Ile Pro Met Leu Ala Met Tyr Ala Gln Ala Ala Asn Met His Leu
            180                 185                 190

Leu Leu Leu Arg Glu Val Val Gln Asn Gly Val Gly Trp Gly Phe Gln
        195                 200                 205

Gln Tyr Glu Val Asp Arg Tyr Tyr Ser Asn Thr Asp Pro Phe Leu Gly
    210                 215                 220

Asn Pro Gly Leu Leu Gln Leu Leu Glu Gly Tyr Thr Asp Tyr Cys Val
225                 230                 235                 240

Lys Trp Tyr Asn Ala Gly Leu Arg Gln Gln Tyr Glu Asn Asn Arg Tyr
                245                 250                 255

Asn Trp Asp Ala Phe Asn Asp Phe Arg Arg Asp Met Ile Ile Met Val
            260                 265                 270

Leu Asp Ile Val Ser Leu Trp Pro Thr Tyr Asp Pro Lys Arg Tyr Pro
        275                 280                 285

Leu Pro Thr Lys Ser Gln Leu Thr Arg Thr Val Tyr Thr Asp Leu Val
    290                 295                 300

Gly Phe Ser Gly Asn Ser Glu Tyr Leu Gln Ile Asp Ile Glu Arg Ala
305                 310                 315                 320

Glu Gln Ala Leu Val Gln Lys Pro Gly Leu Phe Thr Trp Leu Arg Glu
                325                 330                 335

Leu Ser Phe Glu Leu Gly Pro Leu Ser Arg Ile Asn Phe Val Arg Gly
            340                 345                 350

Arg Gln Ile Val Phe Asn Tyr Thr Gly Ser Ser Asp Arg Tyr Glu Glu
        355                 360                 365

Thr Lys Gly Asn Leu Gly Glu Thr Arg Glu Thr Val Val Ile Pro Ala
    370                 375                 380
```

```
Pro Asp Val Gly Asp Asp Ile Trp Arg Ile Ser Thr Gln Val Asn Thr
385                 390                 395                 400

Tyr Gln Ile Pro Asn Ala Thr Phe Val Arg Gly Trp Asn Phe Ser Phe
                405                 410                 415

Thr Gln Ser Leu Asp Gln Lys Ile Ala Trp Arg Thr Glu Tyr Ser Pro
            420                 425                 430

Glu Ile Val Met Gln Gly Leu Ser Cys His Gly Pro Ser Val Ser Ser
        435                 440                 445

Cys Asn Leu Cys Ile Ser Asn Ser Pro Cys Arg Ser Ile Thr Pro Asn
    450                 455                 460

Tyr Ser Ser Pro Cys Asp Asp Lys Leu Val Tyr Ser His Arg Phe Ser
465                 470                 475                 480

Tyr Leu Gly Ala Gly Leu Lys Ser Asp Leu Thr Thr Leu Ile Tyr Phe
                485                 490                 495

Ser Tyr Gly Trp Thr His Val Ser Ala Asp Ala Asn Asn Leu Ile Asp
            500                 505                 510

Pro Lys Lys Ile Thr Gln Ile Pro Ala Val Lys Gly Asp Tyr Leu Gly
        515                 520                 525

Arg Asn Ala Arg Val Ile Lys Gly Pro Gly Ser Thr Gly Gly Asp Leu
    530                 535                 540

Val Gln Leu Ser Asp Gly Thr Glu Arg Gly Thr Leu Gly Ile Lys Leu
545                 550                 555                 560

Thr Lys Pro Pro Gly Ser His Ser Tyr Arg Val Arg Ile Arg Tyr Ala
                565                 570                 575

Ser Asn Thr Arg Thr Gln Leu Glu Ile Ile Trp Gly Glu Asp Tyr Asp
            580                 585                 590

Ser Val Ile Val Pro Ala Thr Thr Thr Asp Ile Thr Asn Leu Thr Tyr
        595                 600                 605

Asn Lys Phe Gly Tyr Phe Glu Ile Arg Val Phe Ser Tyr Asn Ser Ser
    610                 615                 620

Ser Glu Glu Glu Asp Leu Ile Arg Val Asp Ala Thr Gly Ser Phe Ile
625                 630                 635                 640

Leu Asp Lys Ile Glu Phe Ile Pro Ile Glu Gly Ser Val Asp Glu Tyr
                645                 650                 655

Gln Ala Asn Gln Asp Leu Glu Lys Ala Lys Lys Ala Val Asn Ala Leu
            660                 665                 670

Phe Thr Gly Asp Ala Lys Ser Ala Leu Lys Leu Ser Ile Thr Gly Tyr
        675                 680                 685

Ile Val Asp Gln Ala Ala Asn Phe Val Glu Cys Val Ser Asp Glu Phe
    690                 695                 700

His Ala Gln Glu Lys Met Ile Leu Leu Asp Gln Val Lys Phe Ala Lys
705                 710                 715                 720

Arg Leu Ser Gln Ala Arg Asn Leu Leu Asn Tyr Gly Asp Phe Glu Ser
                725                 730                 735

Ser Asp Trp Ser Gly Glu Asn Gly Trp Arg Thr Ser Pro His Val His
            740                 745                 750

Val Ala Ser Asn Asn Pro Ile Phe Lys Gly Arg Tyr Leu His Met Pro
        755                 760                 765

Gly Ala Met Ser Pro Gln Phe Ser Asn Asn Thr Tyr Pro Thr Tyr Ala
    770                 775                 780

Tyr Gln Lys Val Asp Glu Ser Lys Leu Lys Ser Tyr Thr Arg Tyr Leu
785                 790                 795                 800

Val Arg Gly Leu Val Gly Asn Ser Lys Asp Leu Glu Leu Leu Val Glu
```

```
                805                 810                 815

Arg Tyr Gly Lys Asp Val His Val Glu Met Asp Val Pro Asn Asp Ile
            820                 825                 830

Gln Tyr Thr Leu Pro Thr Asn Asp Cys Gly Gly Phe Asp Arg Cys Lys
        835                 840                 845

Pro Val Ser Tyr Gln Thr Gly Thr Ser Ser Tyr Lys Ser Cys Gly Cys
    850                 855                 860

Lys Asn Asn Asp Thr Tyr Gln Asn Gly Met His Leu Ser Lys Ser Cys
865                 870                 875                 880

Gly Cys Lys Lys Asp Pro His Val Phe Thr Tyr His Ile Asp Thr Gly
                885                 890                 895

Cys Val Asp Gln Glu Glu Asn Leu Gly Leu Phe Phe Ala Leu Lys Ile
            900                 905                 910

Ala Ser Glu Asn Gly Met Ala Asn Ile Asp Asn Leu Glu Ile Ile Glu
        915                 920                 925

Ala Gln Pro Leu Lys Gly Glu Ala Leu Ala Arg Val Lys Lys Arg Glu
    930                 935                 940

Gln Lys Trp Lys Gln Glu Met Ala Gln Lys Leu Leu Arg Thr Glu Lys
945                 950                 955                 960

Ala Val Gln Ala Ala Lys Asp Ala Leu Gln Thr Leu Phe Thr Asn Ala
                965                 970                 975

Gln Tyr Asn Arg Leu Lys Phe Glu Thr Leu Phe Pro Gln Ile Val His
            980                 985                 990

Ala Glu Lys Leu Val Gln Gln Ile  Pro Tyr Ala Tyr His  Pro Phe Leu
        995                 1000                1005

Ser Gly  Thr Leu Ser Thr Val  Pro Gly Met Asn Phe  Glu Ile Ile
    1010                1015                1020

Gln Gln  Leu Leu Ala Val Ile  Gly Asn Ala Arg Thr  Leu Tyr Glu
    1025                1030                1035

Gln Arg  Asn Leu Leu Arg Thr  Gly Thr Phe Ser Ser  Gly Thr Gly
    1040                1045                1050

Ser Trp  Lys Val Thr Glu Gly  Val Lys Val Gln Pro  Leu Gln Asp
    1055                1060                1065

Thr Ser  Val Leu Val Leu Ser  Glu Trp Ser His Glu  Ala Ser Gln
    1070                1075                1080

Gln Leu  His Met Asp Pro Asp  Arg Gly Tyr Val Leu  Arg Val Thr
    1085                1090                1095

Ala Arg  Lys Glu Gly Gly Gly  Lys Gly Thr Val Thr  Met Ser Asp
    1100                1105                1110

Cys Ala  Asp Tyr Thr Glu Thr  Leu Thr Phe Thr Ser  Cys Asp Tyr
    1115                1120                1125

Asn Thr  Tyr Gly Ser Gln Thr  Met Thr Ser Gly Thr  Leu Ser Gly
    1130                1135                1140

Phe Val  Thr Lys Thr Leu Glu  Ile Phe Pro Asp Thr  Asp Arg Ile
    1145                1150                1155

Arg Ile  Asp Ile Gly Glu Thr  Glu Gly Thr Phe Gln  Val Glu Ser
    1160                1165                1170

Val Glu  Leu Ile Cys Met Glu  Gln Met Glu Asp Asp  Leu Tyr Asn
    1175                1180                1185

Met Ala  Gly Asn Val Ala Glu  Glu Met Gln Val Leu  Gln Gln Ser
    1190                1195                1200

Arg Ser  Gly Ser His Thr Leu  Asp Pro Leu Cys Asn  Thr Arg Ile
    1205                1210                1215
```

```
Gly Glu  Phe Asp Cys
    1220


<210> SEQ ID NO 35
<211> LENGTH: 1204
<212> TYPE: PRT
<213> ORGANISM: Bacillus thuringiensis

<400> SEQUENCE: 35

Met His Tyr Lys Asp Trp Met Asp Met Cys Ala Asp Gly Glu Ser Gly
1               5                   10                  15

Lys Thr Phe Ala Asp Leu Thr Val Gln Glu Gly Val Thr Ile Ala Val
            20                  25                  30

Ser Ile Ala Ala Ala Ile Leu Ser Val Pro Phe Pro Val Thr Ala Ala
        35                  40                  45

Gly Leu Ser Ile Ile Ser Leu Leu Val Pro Tyr Trp Trp Pro Glu Thr
    50                  55                  60

Ala Val Thr Pro Gly Thr Pro Ser Ala Gln Val Thr Trp Glu Lys Phe
65                  70                  75                  80

Met Ser Ala Ala Glu Asn Leu Ser Asn Thr Gln Ile Val Ala Ser Lys
                85                  90                  95

Arg Ser Asp Ala Ile Ala Arg Trp Gln Gly Ile Gln Thr Leu Gly Arg
            100                 105                 110

Asp Tyr Phe Gln Ala Gln Cys Asp Trp Leu Gln Asp Gln Asn Asn Glu
        115                 120                 125

Leu Lys Lys Ser Lys Leu Arg Glu Ala Phe Asp Asp Phe Glu Asp Tyr
    130                 135                 140

Leu Lys Val Ser Met Pro Phe Phe Arg Ala Gln Gly Phe Glu Ile Pro
145                 150                 155                 160

Met Leu Ala Met Tyr Ala Gln Ala Ala Asn Met His Leu Leu Leu Leu
                165                 170                 175

Arg Glu Val Val Gln Asn Gly Val Gly Trp Gly Phe Gln Gln Tyr Glu
            180                 185                 190

Val Asp Arg Tyr Tyr Ser Asn Thr Asp Pro Phe Leu Gly Asn Pro Gly
        195                 200                 205

Leu Leu Gln Leu Leu Glu Gly Tyr Thr Asp Tyr Cys Val Lys Trp Tyr
    210                 215                 220

Asn Ala Gly Leu Arg Gln Gln Tyr Glu Asn Asn Arg Tyr Asn Trp Asp
225                 230                 235                 240

Ala Phe Asn Asp Phe Arg Arg Asp Met Ile Ile Met Val Leu Asp Ile
                245                 250                 255

Val Ser Leu Trp Pro Thr Tyr Asp Pro Lys Arg Tyr Pro Leu Pro Thr
            260                 265                 270

Lys Ser Gln Leu Thr Arg Thr Val Tyr Thr Asp Leu Val Gly Phe Ser
        275                 280                 285

Gly Asn Ser Glu Tyr Leu Gln Ile Asp Ile Glu Arg Ala Glu Gln Ala
    290                 295                 300

Leu Val Gln Lys Pro Gly Leu Phe Thr Trp Leu Arg Glu Leu Ser Phe
305                 310                 315                 320

Glu Leu Gly Pro Leu Ser Arg Ile Asn Phe Val Arg Gly Arg Gln Ile
                325                 330                 335

Val Phe Asn Tyr Thr Gly Ser Ser Asp Arg Tyr Glu Glu Thr Lys Gly
            340                 345                 350

Asn Leu Gly Glu Thr Arg Glu Thr Val Val Ile Pro Ala Pro Asp Val
```

-continued

```
        355                 360                 365

Gly Asp Asp Ile Trp Arg Ile Ser Thr Gln Val Asn Thr Tyr Gln Ile
    370                 375                 380

Pro Asn Ala Thr Phe Val Arg Gly Trp Asn Phe Ser Phe Thr Gln Ser
385                 390                 395                 400

Leu Asp Gln Lys Ile Ala Trp Arg Thr Glu Tyr Ser Pro Glu Ile Val
                405                 410                 415

Met Gln Gly Leu Ser Cys His Gly Pro Ser Val Ser Ser Cys Asn Leu
            420                 425                 430

Cys Ile Ser Asn Ser Pro Cys Arg Ser Ile Thr Pro Asn Tyr Ser Ser
        435                 440                 445

Pro Cys Asp Asp Lys Leu Val Tyr Ser His Arg Phe Ser Tyr Leu Gly
    450                 455                 460

Ala Gly Leu Lys Ser Asp Leu Thr Thr Leu Ile Tyr Phe Ser Tyr Gly
465                 470                 475                 480

Trp Thr His Val Ser Ala Asp Ala Asn Asn Leu Ile Asp Pro Lys Lys
                485                 490                 495

Ile Thr Gln Ile Pro Ala Val Lys Gly Asp Tyr Leu Gly Arg Asn Ala
            500                 505                 510

Arg Val Ile Lys Gly Pro Gly Ser Thr Gly Gly Asp Leu Val Gln Leu
        515                 520                 525

Ser Asp Gly Thr Glu Arg Gly Thr Leu Gly Ile Lys Leu Thr Lys Pro
    530                 535                 540

Pro Gly Ser His Ser Tyr Arg Val Arg Ile Arg Tyr Ala Ser Asn Thr
545                 550                 555                 560

Arg Thr Gln Leu Glu Ile Ile Trp Gly Glu Asp Tyr Asp Ser Val Ile
                565                 570                 575

Val Pro Ala Thr Thr Thr Asp Ile Thr Asn Leu Thr Tyr Asn Lys Phe
            580                 585                 590

Gly Tyr Phe Glu Ile Arg Val Phe Ser Tyr Asn Ser Ser Ser Glu Glu
        595                 600                 605

Glu Asp Leu Ile Arg Val Asp Ala Thr Gly Ser Phe Ile Leu Asp Lys
    610                 615                 620

Ile Glu Phe Ile Pro Ile Glu Gly Ser Val Asp Glu Tyr Gln Ala Asn
625                 630                 635                 640

Gln Asp Leu Glu Lys Ala Lys Lys Ala Val Asn Ala Leu Phe Thr Gly
                645                 650                 655

Asp Ala Lys Ser Ala Leu Lys Leu Ser Ile Thr Gly Tyr Ile Val Asp
            660                 665                 670

Gln Ala Ala Asn Phe Val Glu Cys Val Ser Asp Glu Phe His Ala Gln
        675                 680                 685

Glu Lys Met Ile Leu Leu Asp Gln Val Lys Phe Ala Lys Arg Leu Ser
    690                 695                 700

Gln Ala Arg Asn Leu Leu Asn Tyr Gly Asp Phe Glu Ser Ser Asp Trp
705                 710                 715                 720

Ser Gly Glu Asn Gly Trp Arg Thr Ser Pro His Val His Val Ala Ser
                725                 730                 735

Asn Asn Pro Ile Phe Lys Gly Arg Tyr Leu His Met Pro Gly Ala Met
            740                 745                 750

Ser Pro Gln Phe Ser Asn Asn Thr Tyr Pro Thr Tyr Ala Tyr Gln Lys
        755                 760                 765

Val Asp Glu Ser Lys Leu Lys Ser Tyr Thr Arg Tyr Leu Val Arg Gly
    770                 775                 780
```

```
Leu Val Gly Asn Ser Lys Asp Leu Glu Leu Leu Val Glu Arg Tyr Gly
785                 790                 795                 800

Lys Asp Val His Val Glu Met Asp Val Pro Asn Asp Ile Gln Tyr Thr
                805                 810                 815

Leu Pro Thr Asn Asp Cys Gly Gly Phe Asp Arg Cys Lys Pro Val Ser
            820                 825                 830

Tyr Gln Thr Gly Thr Ser Ser Tyr Lys Ser Cys Gly Cys Lys Asn Asn
        835                 840                 845

Asp Thr Tyr Gln Asn Gly Met His Leu Ser Lys Ser Cys Gly Cys Lys
    850                 855                 860

Lys Asp Pro His Val Phe Thr Tyr His Ile Asp Thr Gly Cys Val Asp
865                 870                 875                 880

Gln Glu Glu Asn Leu Gly Leu Phe Phe Ala Leu Lys Ile Ala Ser Glu
                885                 890                 895

Asn Gly Met Ala Asn Ile Asp Asn Leu Glu Ile Ile Glu Ala Gln Pro
            900                 905                 910

Leu Lys Gly Glu Ala Leu Ala Arg Val Lys Lys Arg Glu Gln Lys Trp
        915                 920                 925

Lys Gln Glu Met Ala Gln Lys Leu Leu Arg Thr Glu Lys Ala Val Gln
    930                 935                 940

Ala Ala Lys Asp Ala Leu Gln Thr Leu Phe Thr Asn Ala Gln Tyr Asn
945                 950                 955                 960

Arg Leu Lys Phe Glu Thr Leu Phe Pro Gln Ile Val His Ala Glu Lys
                965                 970                 975

Leu Val Gln Gln Ile Pro Tyr Ala Tyr His Pro Phe Leu Ser Gly Thr
            980                 985                 990

Leu Ser Thr Val Pro Gly Met Asn  Phe Glu Ile Ile Gln  Gln Leu Leu
        995                 1000                1005

Ala Val  Ile Gly Asn Ala Arg  Thr Leu Tyr Glu Gln  Arg Asn Leu
    1010                 1015                 1020

Leu Arg  Thr Gly Thr Phe Ser  Ser Gly Thr Gly Ser  Trp Lys Val
    1025                 1030                 1035

Thr Glu  Gly Val Lys Val Gln  Pro Leu Gln Asp Thr  Ser Val Leu
    1040                 1045                 1050

Val Leu  Ser Glu Trp Ser His  Glu Ala Ser Gln Gln  Leu His Met
    1055                 1060                 1065

Asp Pro  Asp Arg Gly Tyr Val  Leu Arg Val Thr Ala  Arg Lys Glu
    1070                 1075                 1080

Gly Gly  Gly Lys Gly Thr Val  Thr Met Ser Asp Cys  Ala Asp Tyr
    1085                 1090                 1095

Thr Glu  Thr Leu Thr Phe Thr  Ser Cys Asp Tyr Asn  Thr Tyr Gly
    1100                 1105                 1110

Ser Gln  Thr Met Thr Ser Gly  Thr Leu Ser Gly Phe  Val Thr Lys
    1115                 1120                 1125

Thr Leu  Glu Ile Phe Pro Asp  Thr Asp Arg Ile Arg  Ile Asp Ile
    1130                 1135                 1140

Gly Glu  Thr Glu Gly Thr Phe  Gln Val Glu Ser Val  Glu Leu Ile
    1145                 1150                 1155

Cys Met  Glu Gln Met Glu Asp  Asp Leu Tyr Asn Met  Ala Gly Asn
    1160                 1165                 1170

Val Ala  Glu Glu Met Gln Val  Leu Gln Gln Ser Arg  Ser Gly Ser
    1175                 1180                 1185
```

-continued

```
His Thr  Leu Asp Pro Leu Cys  Asn Thr Arg Ile Gly  Glu Phe Asp
    1190                 1195                 1200

Cys


<210> SEQ ID NO 36
<211> LENGTH: 1198
<212> TYPE: PRT
<213> ORGANISM: Bacillus thuringiensis

<400> SEQUENCE: 36

Met Asp Met Cys Ala Asp Gly Glu Ser Gly Lys Thr Phe Ala Asp Leu
1               5                   10                  15

Thr Val Gln Glu Gly Val Thr Ile Ala Val Ser Ile Ala Ala Ala Ile
            20                  25                  30

Leu Ser Val Pro Phe Pro Val Thr Ala Ala Gly Leu Ser Ile Ile Ser
        35                  40                  45

Leu Leu Val Pro Tyr Trp Trp Pro Glu Thr Ala Val Thr Pro Gly Thr
    50                  55                  60

Pro Ser Ala Gln Val Thr Trp Glu Lys Phe Met Ser Ala Ala Glu Asn
65                  70                  75                  80

Leu Ser Asn Thr Gln Ile Val Ala Ser Lys Arg Ser Asp Ala Ile Ala
                85                  90                  95

Arg Trp Gln Gly Ile Gln Thr Leu Gly Arg Asp Tyr Phe Gln Ala Gln
            100                 105                 110

Cys Asp Trp Leu Gln Asp Gln Asn Asn Glu Leu Lys Lys Ser Lys Leu
        115                 120                 125

Arg Glu Ala Phe Asp Asp Phe Glu Asp Tyr Leu Lys Val Ser Met Pro
    130                 135                 140

Phe Phe Arg Ala Gln Gly Phe Glu Ile Pro Met Leu Ala Met Tyr Ala
145                 150                 155                 160

Gln Ala Ala Asn Met His Leu Leu Leu Leu Arg Glu Val Val Gln Asn
                165                 170                 175

Gly Val Gly Trp Gly Phe Gln Gln Tyr Glu Val Asp Arg Tyr Tyr Ser
            180                 185                 190

Asn Thr Asp Pro Phe Leu Gly Asn Pro Gly Leu Leu Gln Leu Leu Glu
        195                 200                 205

Gly Tyr Thr Asp Tyr Cys Val Lys Trp Tyr Asn Ala Gly Leu Arg Gln
    210                 215                 220

Gln Tyr Glu Asn Asn Arg Tyr Asn Trp Asp Ala Phe Asn Asp Phe Arg
225                 230                 235                 240

Arg Asp Met Ile Ile Met Val Leu Asp Ile Val Ser Leu Trp Pro Thr
                245                 250                 255

Tyr Asp Pro Lys Arg Tyr Pro Leu Pro Thr Lys Ser Gln Leu Thr Arg
            260                 265                 270

Thr Val Tyr Thr Asp Leu Val Gly Phe Ser Gly Asn Ser Glu Tyr Leu
        275                 280                 285

Gln Ile Asp Ile Glu Arg Ala Glu Gln Ala Leu Val Gln Lys Pro Gly
    290                 295                 300

Leu Phe Thr Trp Leu Arg Glu Leu Ser Phe Glu Leu Gly Pro Leu Ser
305                 310                 315                 320

Arg Ile Asn Phe Val Arg Gly Arg Gln Ile Val Phe Asn Tyr Thr Gly
                325                 330                 335

Ser Ser Asp Arg Tyr Glu Glu Thr Lys Gly Asn Leu Gly Glu Thr Arg
            340                 345                 350
```

-continued

```
Glu Thr Val Val Ile Pro Ala Pro Asp Val Gly Asp Asp Ile Trp Arg
        355                 360                 365

Ile Ser Thr Gln Val Asn Thr Tyr Gln Ile Pro Asn Ala Thr Phe Val
    370                 375                 380

Arg Gly Trp Asn Phe Ser Phe Thr Gln Ser Leu Asp Gln Lys Ile Ala
385                 390                 395                 400

Trp Arg Thr Glu Tyr Ser Pro Glu Ile Val Met Gln Gly Leu Ser Cys
                405                 410                 415

His Gly Pro Ser Val Ser Ser Cys Asn Leu Cys Ile Ser Asn Ser Pro
            420                 425                 430

Cys Arg Ser Ile Thr Pro Asn Tyr Ser Ser Pro Cys Asp Asp Lys Leu
        435                 440                 445

Val Tyr Ser His Arg Phe Ser Tyr Leu Gly Ala Gly Leu Lys Ser Asp
    450                 455                 460

Leu Thr Thr Leu Ile Tyr Phe Ser Tyr Gly Trp Thr His Val Ser Ala
465                 470                 475                 480

Asp Ala Asn Asn Leu Ile Asp Pro Lys Lys Ile Thr Gln Ile Pro Ala
                485                 490                 495

Val Lys Gly Asp Tyr Leu Gly Arg Asn Ala Arg Val Ile Lys Gly Pro
            500                 505                 510

Gly Ser Thr Gly Gly Asp Leu Val Gln Leu Ser Asp Gly Thr Glu Arg
        515                 520                 525

Gly Thr Leu Gly Ile Lys Leu Thr Lys Pro Pro Gly Ser His Ser Tyr
    530                 535                 540

Arg Val Arg Ile Arg Tyr Ala Ser Asn Thr Arg Thr Gln Leu Glu Ile
545                 550                 555                 560

Ile Trp Gly Glu Asp Tyr Asp Ser Val Ile Val Pro Ala Thr Thr Thr
                565                 570                 575

Asp Ile Thr Asn Leu Thr Tyr Asn Lys Phe Gly Tyr Phe Glu Ile Arg
            580                 585                 590

Val Phe Ser Tyr Asn Ser Ser Ser Glu Glu Glu Asp Leu Ile Arg Val
        595                 600                 605

Asp Ala Thr Gly Ser Phe Ile Leu Asp Lys Ile Glu Phe Ile Pro Ile
    610                 615                 620

Glu Gly Ser Val Asp Glu Tyr Gln Ala Asn Gln Asp Leu Glu Lys Ala
625                 630                 635                 640

Lys Lys Ala Val Asn Ala Leu Phe Thr Gly Asp Ala Lys Ser Ala Leu
                645                 650                 655

Lys Leu Ser Ile Thr Gly Tyr Ile Val Asp Gln Ala Ala Asn Phe Val
            660                 665                 670

Glu Cys Val Ser Asp Glu Phe His Ala Gln Glu Lys Met Ile Leu Leu
        675                 680                 685

Asp Gln Val Lys Phe Ala Lys Arg Leu Ser Gln Ala Arg Asn Leu Leu
    690                 695                 700

Asn Tyr Gly Asp Phe Glu Ser Ser Asp Trp Ser Gly Glu Asn Gly Trp
705                 710                 715                 720

Arg Thr Ser Pro His Val His Val Ala Ser Asn Asn Pro Ile Phe Lys
                725                 730                 735

Gly Arg Tyr Leu His Met Pro Gly Ala Met Ser Pro Gln Phe Ser Asn
            740                 745                 750

Asn Thr Tyr Pro Thr Tyr Ala Tyr Gln Lys Val Asp Glu Ser Lys Leu
        755                 760                 765

Lys Ser Tyr Thr Arg Tyr Leu Val Arg Gly Leu Val Gly Asn Ser Lys
```

-continued

```
    770                 775                 780

Asp Leu Glu Leu Leu Val Glu Arg Tyr Gly Lys Asp Val His Val Glu
785                 790                 795                 800

Met Asp Val Pro Asn Asp Ile Gln Tyr Thr Leu Pro Thr Asn Asp Cys
                805                 810                 815

Gly Gly Phe Asp Arg Cys Lys Pro Val Ser Tyr Gln Thr Gly Thr Ser
            820                 825                 830

Ser Tyr Lys Ser Cys Gly Cys Lys Asn Asn Asp Thr Tyr Gln Asn Gly
        835                 840                 845

Met His Leu Ser Lys Ser Cys Gly Cys Lys Lys Asp Pro His Val Phe
    850                 855                 860

Thr Tyr His Ile Asp Thr Gly Cys Val Asp Gln Glu Glu Asn Leu Gly
865                 870                 875                 880

Leu Phe Phe Ala Leu Lys Ile Ala Ser Glu Asn Gly Met Ala Asn Ile
                885                 890                 895

Asp Asn Leu Glu Ile Ile Glu Ala Gln Pro Leu Lys Gly Glu Ala Leu
            900                 905                 910

Ala Arg Val Lys Lys Arg Glu Gln Lys Trp Lys Gln Glu Met Ala Gln
        915                 920                 925

Lys Leu Leu Arg Thr Glu Lys Ala Val Gln Ala Ala Lys Asp Ala Leu
    930                 935                 940

Gln Thr Leu Phe Thr Asn Ala Gln Tyr Asn Arg Leu Lys Phe Glu Thr
945                 950                 955                 960

Leu Phe Pro Gln Ile Val His Ala Glu Lys Leu Val Gln Gln Ile Pro
                965                 970                 975

Tyr Ala Tyr His Pro Phe Leu Ser Gly Thr Leu Ser Thr Val Pro Gly
            980                 985                 990

Met Asn Phe Glu Ile Ile Gln Gln  Leu Leu Ala Val Ile  Gly Asn Ala
        995                 1000                1005

Arg Thr  Leu Tyr Glu Gln Arg  Asn Leu Leu Arg Thr  Gly Thr Phe
    1010                1015                1020

Ser Ser  Gly Thr Gly Ser Trp  Lys Val Thr Glu Gly  Val Lys Val
    1025                1030                1035

Gln Pro  Leu Gln Asp Thr Ser  Val Leu Val Leu Ser  Glu Trp Ser
    1040                1045                1050

His Glu  Ala Ser Gln Gln Leu  His Met Asp Pro Asp  Arg Gly Tyr
    1055                1060                1065

Val Leu  Arg Val Thr Ala Arg  Lys Glu Gly Gly Gly  Lys Gly Thr
    1070                1075                1080

Val Thr  Met Ser Asp Cys Ala  Asp Tyr Thr Glu Thr  Leu Thr Phe
    1085                1090                1095

Thr Ser  Cys Asp Tyr Asn Thr  Tyr Gly Ser Gln Thr  Met Thr Ser
    1100                1105                1110

Gly Thr  Leu Ser Gly Phe Val  Thr Lys Thr Leu Glu  Ile Phe Pro
    1115                1120                1125

Asp Thr  Asp Arg Ile Arg Ile  Asp Ile Gly Glu Thr  Glu Gly Thr
    1130                1135                1140

Phe Gln  Val Glu Ser Val Glu  Leu Ile Cys Met Glu  Gln Met Glu
    1145                1150                1155

Asp Asp  Leu Tyr Asn Met Ala  Gly Asn Val Ala Glu  Glu Met Gln
    1160                1165                1170

Val Leu  Gln Gln Ser Arg Ser  Gly Ser His Thr Leu  Asp Pro Leu
    1175                1180                1185
```

```
Cys Asn  Thr Arg Ile Gly Glu  Phe Asp Cys
    1190                 1195


<210> SEQ ID NO 37
<211> LENGTH: 1196
<212> TYPE: PRT
<213> ORGANISM: Bacillus thuringiensis

<400> SEQUENCE: 37

Met Cys Ala Asp Gly Glu Ser Gly Lys Thr Phe Ala Asp Leu Thr Val
1               5                   10                  15

Gln Glu Gly Val Thr Ile Ala Val Ser Ile Ala Ala Ala Ile Leu Ser
            20                  25                  30

Val Pro Phe Pro Val Thr Ala Ala Gly Leu Ser Ile Ile Ser Leu Leu
        35                  40                  45

Val Pro Tyr Trp Trp Pro Glu Thr Ala Val Thr Pro Gly Thr Pro Ser
    50                  55                  60

Ala Gln Val Thr Trp Glu Lys Phe Met Ser Ala Ala Glu Asn Leu Ser
65                  70                  75                  80

Asn Thr Gln Ile Val Ala Ser Lys Arg Ser Asp Ala Ile Ala Arg Trp
                85                  90                  95

Gln Gly Ile Gln Thr Leu Gly Arg Asp Tyr Phe Gln Ala Gln Cys Asp
            100                 105                 110

Trp Leu Gln Asp Gln Asn Asn Glu Leu Lys Lys Ser Lys Leu Arg Glu
        115                 120                 125

Ala Phe Asp Asp Phe Glu Asp Tyr Leu Lys Val Ser Met Pro Phe Phe
    130                 135                 140

Arg Ala Gln Gly Phe Glu Ile Pro Met Leu Ala Met Tyr Ala Gln Ala
145                 150                 155                 160

Ala Asn Met His Leu Leu Leu Leu Arg Glu Val Val Gln Asn Gly Val
                165                 170                 175

Gly Trp Gly Phe Gln Gln Tyr Glu Val Asp Arg Tyr Tyr Ser Asn Thr
            180                 185                 190

Asp Pro Phe Leu Gly Asn Pro Gly Leu Leu Gln Leu Leu Glu Gly Tyr
        195                 200                 205

Thr Asp Tyr Cys Val Lys Trp Tyr Asn Ala Gly Leu Arg Gln Gln Tyr
    210                 215                 220

Glu Asn Asn Arg Tyr Asn Trp Asp Ala Phe Asn Asp Phe Arg Arg Asp
225                 230                 235                 240

Met Ile Ile Met Val Leu Asp Ile Val Ser Leu Trp Pro Thr Tyr Asp
                245                 250                 255

Pro Lys Arg Tyr Pro Leu Pro Thr Lys Ser Gln Leu Thr Arg Thr Val
            260                 265                 270

Tyr Thr Asp Leu Val Gly Phe Ser Gly Asn Ser Glu Tyr Leu Gln Ile
        275                 280                 285

Asp Ile Glu Arg Ala Glu Gln Ala Leu Val Gln Lys Pro Gly Leu Phe
    290                 295                 300

Thr Trp Leu Arg Glu Leu Ser Phe Glu Leu Gly Pro Leu Ser Arg Ile
305                 310                 315                 320

Asn Phe Val Arg Gly Arg Gln Ile Val Phe Asn Tyr Thr Gly Ser Ser
                325                 330                 335

Asp Arg Tyr Glu Glu Thr Lys Gly Asn Leu Gly Glu Thr Arg Glu Thr
            340                 345                 350

Val Val Ile Pro Ala Pro Asp Val Gly Asp Asp Ile Trp Arg Ile Ser
```

```
        355                 360                 365

Thr Gln Val Asn Thr Tyr Gln Ile Pro Asn Ala Thr Phe Val Arg Gly
    370                 375                 380

Trp Asn Phe Ser Phe Thr Gln Ser Leu Asp Gln Lys Ile Ala Trp Arg
385                 390                 395                 400

Thr Glu Tyr Ser Pro Glu Ile Val Met Gln Gly Leu Ser Cys His Gly
                405                 410                 415

Pro Ser Val Ser Ser Cys Asn Leu Cys Ile Ser Asn Ser Pro Cys Arg
            420                 425                 430

Ser Ile Thr Pro Asn Tyr Ser Ser Pro Cys Asp Asp Lys Leu Val Tyr
        435                 440                 445

Ser His Arg Phe Ser Tyr Leu Gly Ala Gly Leu Lys Ser Asp Leu Thr
    450                 455                 460

Thr Leu Ile Tyr Phe Ser Tyr Gly Trp Thr His Val Ser Ala Asp Ala
465                 470                 475                 480

Asn Asn Leu Ile Asp Pro Lys Lys Ile Thr Gln Ile Pro Ala Val Lys
                485                 490                 495

Gly Asp Tyr Leu Gly Arg Asn Ala Arg Val Ile Lys Gly Pro Gly Ser
            500                 505                 510

Thr Gly Gly Asp Leu Val Gln Leu Ser Asp Gly Thr Glu Arg Gly Thr
        515                 520                 525

Leu Gly Ile Lys Leu Thr Lys Pro Pro Gly Ser His Ser Tyr Arg Val
    530                 535                 540

Arg Ile Arg Tyr Ala Ser Asn Thr Arg Thr Gln Leu Glu Ile Ile Trp
545                 550                 555                 560

Gly Glu Asp Tyr Asp Ser Val Ile Val Pro Ala Thr Thr Thr Asp Ile
                565                 570                 575

Thr Asn Leu Thr Tyr Asn Lys Phe Gly Tyr Phe Glu Ile Arg Val Phe
            580                 585                 590

Ser Tyr Asn Ser Ser Ser Glu Glu Glu Asp Leu Ile Arg Val Asp Ala
        595                 600                 605

Thr Gly Ser Phe Ile Leu Asp Lys Ile Glu Phe Ile Pro Ile Glu Gly
    610                 615                 620

Ser Val Asp Glu Tyr Gln Ala Asn Gln Asp Leu Glu Lys Ala Lys Lys
625                 630                 635                 640

Ala Val Asn Ala Leu Phe Thr Gly Asp Ala Lys Ser Ala Leu Lys Leu
                645                 650                 655

Ser Ile Thr Gly Tyr Ile Val Asp Gln Ala Ala Asn Phe Val Glu Cys
            660                 665                 670

Val Ser Asp Glu Phe His Ala Gln Glu Lys Met Ile Leu Leu Asp Gln
        675                 680                 685

Val Lys Phe Ala Lys Arg Leu Ser Gln Ala Arg Asn Leu Leu Asn Tyr
    690                 695                 700

Gly Asp Phe Glu Ser Ser Asp Trp Ser Gly Glu Asn Gly Trp Arg Thr
705                 710                 715                 720

Ser Pro His Val His Val Ala Ser Asn Asn Pro Ile Phe Lys Gly Arg
                725                 730                 735

Tyr Leu His Met Pro Gly Ala Met Ser Pro Gln Phe Ser Asn Asn Thr
            740                 745                 750

Tyr Pro Thr Tyr Ala Tyr Gln Lys Val Asp Glu Ser Lys Leu Lys Ser
        755                 760                 765

Tyr Thr Arg Tyr Leu Val Arg Gly Leu Val Gly Asn Ser Lys Asp Leu
    770                 775                 780
```

-continued

Glu Leu Leu Val Glu Arg Tyr Gly Lys Asp Val His Val Glu Met Asp
785 790 795 800

Val Pro Asn Asp Ile Gln Tyr Thr Leu Pro Thr Asn Asp Cys Gly Gly
805 810 815

Phe Asp Arg Cys Lys Pro Val Ser Tyr Gln Thr Gly Thr Ser Ser Tyr
820 825 830

Lys Ser Cys Gly Cys Lys Asn Asn Asp Thr Tyr Gln Asn Gly Met His
835 840 845

Leu Ser Lys Ser Cys Gly Cys Lys Lys Asp Pro His Val Phe Thr Tyr
850 855 860

His Ile Asp Thr Gly Cys Val Asp Gln Glu Glu Asn Leu Gly Leu Phe
865 870 875 880

Phe Ala Leu Lys Ile Ala Ser Glu Asn Gly Met Ala Asn Ile Asp Asn
885 890 895

Leu Glu Ile Ile Glu Ala Gln Pro Leu Lys Gly Glu Ala Leu Ala Arg
900 905 910

Val Lys Lys Arg Glu Gln Lys Trp Lys Gln Glu Met Ala Gln Lys Leu
915 920 925

Leu Arg Thr Glu Lys Ala Val Gln Ala Ala Lys Asp Ala Leu Gln Thr
930 935 940

Leu Phe Thr Asn Ala Gln Tyr Asn Arg Leu Lys Phe Glu Thr Leu Phe
945 950 955 960

Pro Gln Ile Val His Ala Glu Lys Leu Val Gln Gln Ile Pro Tyr Ala
965 970 975

Tyr His Pro Phe Leu Ser Gly Thr Leu Ser Thr Val Pro Gly Met Asn
980 985 990

Phe Glu Ile Ile Gln Gln Leu Leu Ala Val Ile Gly Asn Ala Arg Thr
995 1000 1005

Leu Tyr Glu Gln Arg Asn Leu Leu Arg Thr Gly Thr Phe Ser Ser
1010 1015 1020

Gly Thr Gly Ser Trp Lys Val Thr Glu Gly Val Lys Val Gln Pro
1025 1030 1035

Leu Gln Asp Thr Ser Val Leu Val Leu Ser Glu Trp Ser His Glu
1040 1045 1050

Ala Ser Gln Gln Leu His Met Asp Pro Asp Arg Gly Tyr Val Leu
1055 1060 1065

Arg Val Thr Ala Arg Lys Glu Gly Gly Gly Lys Gly Thr Val Thr
1070 1075 1080

Met Ser Asp Cys Ala Asp Tyr Thr Glu Thr Leu Thr Phe Thr Ser
1085 1090 1095

Cys Asp Tyr Asn Thr Tyr Gly Ser Gln Thr Met Thr Ser Gly Thr
1100 1105 1110

Leu Ser Gly Phe Val Thr Lys Thr Leu Glu Ile Phe Pro Asp Thr
1115 1120 1125

Asp Arg Ile Arg Ile Asp Ile Gly Glu Thr Glu Gly Thr Phe Gln
1130 1135 1140

Val Glu Ser Val Glu Leu Ile Cys Met Glu Gln Met Glu Asp Asp
1145 1150 1155

Leu Tyr Asn Met Ala Gly Asn Val Ala Glu Glu Met Gln Val Leu
1160 1165 1170

Gln Gln Ser Arg Ser Gly Ser His Thr Leu Asp Pro Leu Cys Asn
1175 1180 1185

```
Thr Arg  Ile Gly Glu Phe Asp  Cys
    1190                 1195


<210> SEQ ID NO 38
<211> LENGTH: 1124
<212> TYPE: PRT
<213> ORGANISM: Bacillus thuringiensis

<400> SEQUENCE: 38

Met Ser Ala Ala Glu Asn Leu Ser Asn Thr Gln Ile Val Ala Ser Lys
1               5                   10                  15

Arg Ser Asp Ala Ile Ala Arg Trp Gln Gly Ile Gln Thr Leu Gly Arg
            20                  25                  30

Asp Tyr Phe Gln Ala Gln Cys Asp Trp Leu Gln Asp Gln Asn Asn Glu
        35                  40                  45

Leu Lys Lys Ser Lys Leu Arg Glu Ala Phe Asp Asp Phe Glu Asp Tyr
    50                  55                  60

Leu Lys Val Ser Met Pro Phe Phe Arg Ala Gln Gly Phe Glu Ile Pro
65                  70                  75                  80

Met Leu Ala Met Tyr Ala Gln Ala Ala Asn Met His Leu Leu Leu Leu
                85                  90                  95

Arg Glu Val Val Gln Asn Gly Val Gly Trp Gly Phe Gln Gln Tyr Glu
            100                 105                 110

Val Asp Arg Tyr Tyr Ser Asn Thr Asp Pro Phe Leu Gly Asn Pro Gly
        115                 120                 125

Leu Leu Gln Leu Leu Glu Gly Tyr Thr Asp Tyr Cys Val Lys Trp Tyr
    130                 135                 140

Asn Ala Gly Leu Arg Gln Gln Tyr Glu Asn Asn Arg Tyr Asn Trp Asp
145                 150                 155                 160

Ala Phe Asn Asp Phe Arg Arg Asp Met Ile Ile Met Val Leu Asp Ile
                165                 170                 175

Val Ser Leu Trp Pro Thr Tyr Asp Pro Lys Arg Tyr Pro Leu Pro Thr
            180                 185                 190

Lys Ser Gln Leu Thr Arg Thr Val Tyr Thr Asp Leu Val Gly Phe Ser
        195                 200                 205

Gly Asn Ser Glu Tyr Leu Gln Ile Asp Ile Glu Arg Ala Glu Gln Ala
    210                 215                 220

Leu Val Gln Lys Pro Gly Leu Phe Thr Trp Leu Arg Glu Leu Ser Phe
225                 230                 235                 240

Glu Leu Gly Pro Leu Ser Arg Ile Asn Phe Val Arg Gly Arg Gln Ile
                245                 250                 255

Val Phe Asn Tyr Thr Gly Ser Ser Asp Arg Tyr Glu Glu Thr Lys Gly
            260                 265                 270

Asn Leu Gly Glu Thr Arg Glu Thr Val Val Ile Pro Ala Pro Asp Val
        275                 280                 285

Gly Asp Asp Ile Trp Arg Ile Ser Thr Gln Val Asn Thr Tyr Gln Ile
    290                 295                 300

Pro Asn Ala Thr Phe Val Arg Gly Trp Asn Phe Ser Phe Thr Gln Ser
305                 310                 315                 320

Leu Asp Gln Lys Ile Ala Trp Arg Thr Glu Tyr Ser Pro Glu Ile Val
                325                 330                 335

Met Gln Gly Leu Ser Cys His Gly Pro Ser Val Ser Ser Cys Asn Leu
            340                 345                 350

Cys Ile Ser Asn Ser Pro Cys Arg Ser Ile Thr Pro Asn Tyr Ser Ser
        355                 360                 365
```

-continued

```
Pro Cys Asp Asp Lys Leu Val Tyr Ser His Arg Phe Ser Tyr Leu Gly
    370                 375                 380

Ala Gly Leu Lys Ser Asp Leu Thr Thr Leu Ile Tyr Phe Ser Tyr Gly
385                 390                 395                 400

Trp Thr His Val Ser Ala Asp Ala Asn Asn Leu Ile Asp Pro Lys Lys
                405                 410                 415

Ile Thr Gln Ile Pro Ala Val Lys Gly Asp Tyr Leu Gly Arg Asn Ala
            420                 425                 430

Arg Val Ile Lys Gly Pro Gly Ser Thr Gly Gly Asp Leu Val Gln Leu
        435                 440                 445

Ser Asp Gly Thr Glu Arg Gly Thr Leu Gly Ile Lys Leu Thr Lys Pro
    450                 455                 460

Pro Gly Ser His Ser Tyr Arg Val Arg Ile Arg Tyr Ala Ser Asn Thr
465                 470                 475                 480

Arg Thr Gln Leu Glu Ile Ile Trp Gly Glu Asp Tyr Asp Ser Val Ile
                485                 490                 495

Val Pro Ala Thr Thr Thr Asp Ile Thr Asn Leu Thr Tyr Asn Lys Phe
            500                 505                 510

Gly Tyr Phe Glu Ile Arg Val Phe Ser Tyr Asn Ser Ser Ser Glu Glu
        515                 520                 525

Glu Asp Leu Ile Arg Val Asp Ala Thr Gly Ser Phe Ile Leu Asp Lys
    530                 535                 540

Ile Glu Phe Ile Pro Ile Glu Gly Ser Val Asp Glu Tyr Gln Ala Asn
545                 550                 555                 560

Gln Asp Leu Glu Lys Ala Lys Lys Ala Val Asn Ala Leu Phe Thr Gly
                565                 570                 575

Asp Ala Lys Ser Ala Leu Lys Leu Ser Ile Thr Gly Tyr Ile Val Asp
            580                 585                 590

Gln Ala Ala Asn Phe Val Glu Cys Val Ser Asp Glu Phe His Ala Gln
        595                 600                 605

Glu Lys Met Ile Leu Leu Asp Gln Val Lys Phe Ala Lys Arg Leu Ser
    610                 615                 620

Gln Ala Arg Asn Leu Leu Asn Tyr Gly Asp Phe Glu Ser Ser Asp Trp
625                 630                 635                 640

Ser Gly Glu Asn Gly Trp Arg Thr Ser Pro His Val His Val Ala Ser
                645                 650                 655

Asn Asn Pro Ile Phe Lys Gly Arg Tyr Leu His Met Pro Gly Ala Met
            660                 665                 670

Ser Pro Gln Phe Ser Asn Asn Thr Tyr Pro Thr Tyr Ala Tyr Gln Lys
        675                 680                 685

Val Asp Glu Ser Lys Leu Lys Ser Tyr Thr Arg Tyr Leu Val Arg Gly
    690                 695                 700

Leu Val Gly Asn Ser Lys Asp Leu Glu Leu Leu Val Glu Arg Tyr Gly
705                 710                 715                 720

Lys Asp Val His Val Glu Met Asp Val Pro Asn Asp Ile Gln Tyr Thr
                725                 730                 735

Leu Pro Thr Asn Asp Cys Gly Gly Phe Asp Arg Cys Lys Pro Val Ser
            740                 745                 750

Tyr Gln Thr Gly Thr Ser Ser Tyr Lys Ser Cys Gly Cys Lys Asn Asn
        755                 760                 765

Asp Thr Tyr Gln Asn Gly Met His Leu Ser Lys Ser Cys Gly Cys Lys
    770                 775                 780
```

```
Lys Asp Pro His Val Phe Thr Tyr His Ile Asp Thr Gly Cys Val Asp
785                 790                 795                 800

Gln Glu Glu Asn Leu Gly Leu Phe Phe Ala Leu Lys Ile Ala Ser Glu
                805                 810                 815

Asn Gly Met Ala Asn Ile Asp Asn Leu Glu Ile Ile Glu Ala Gln Pro
            820                 825                 830

Leu Lys Gly Glu Ala Leu Ala Arg Val Lys Lys Arg Glu Gln Lys Trp
        835                 840                 845

Lys Gln Glu Met Ala Gln Lys Leu Leu Arg Thr Glu Lys Ala Val Gln
    850                 855                 860

Ala Ala Lys Asp Ala Leu Gln Thr Leu Phe Thr Asn Ala Gln Tyr Asn
865                 870                 875                 880

Arg Leu Lys Phe Glu Thr Leu Phe Pro Gln Ile Val His Ala Glu Lys
                885                 890                 895

Leu Val Gln Gln Ile Pro Tyr Ala Tyr His Pro Phe Leu Ser Gly Thr
            900                 905                 910

Leu Ser Thr Val Pro Gly Met Asn Phe Glu Ile Ile Gln Gln Leu Leu
        915                 920                 925

Ala Val Ile Gly Asn Ala Arg Thr Leu Tyr Glu Gln Arg Asn Leu Leu
    930                 935                 940

Arg Thr Gly Thr Phe Ser Ser Gly Thr Gly Ser Trp Lys Val Thr Glu
945                 950                 955                 960

Gly Val Lys Val Gln Pro Leu Gln Asp Thr Ser Val Leu Val Leu Ser
                965                 970                 975

Glu Trp Ser His Glu Ala Ser Gln Gln Leu His Met Asp Pro Asp Arg
            980                 985                 990

Gly Tyr Val Leu Arg Val Thr Ala  Arg Lys Glu Gly Gly  Gly Lys Gly
        995                 1000                1005

Thr Val  Thr Met Ser Asp Cys  Ala Asp Tyr Thr Glu  Thr Leu Thr
    1010                1015                1020

Phe Thr  Ser Cys Asp Tyr Asn  Thr Tyr Gly Ser Gln  Thr Met Thr
    1025                1030                1035

Ser Gly  Thr Leu Ser Gly Phe  Val Thr Lys Thr Leu  Glu Ile Phe
    1040                1045                1050

Pro Asp  Thr Asp Arg Ile Arg  Ile Asp Ile Gly Glu  Thr Glu Gly
    1055                1060                1065

Thr Phe  Gln Val Glu Ser Val  Glu Leu Ile Cys Met  Glu Gln Met
    1070                1075                1080

Glu Asp  Asp Leu Tyr Asn Met  Ala Gly Asn Val Ala  Glu Glu Met
    1085                1090                1095

Gln Val  Leu Gln Gln Ser Arg  Ser Gly Ser His Thr  Leu Asp Pro
    1100                1105                1110

Leu Cys  Asn Thr Arg Ile Gly  Glu Phe Asp Cys
    1115                1120
```

<210> SEQ ID NO 39
<211> LENGTH: 665
<212> TYPE: PRT
<213> ORGANISM: Bacillus thuringiensis

<400> SEQUENCE: 39

```
Met Asn Gln Gln His Asn Asn Glu Tyr Glu Ile Met Ser Thr Gly Asp
1               5                   10                  15

Met Gly Tyr Gln Pro Arg Tyr Pro Phe Ser Asn Ala Pro Gly Ala Glu
            20                  25                  30
```

-continued

```
Leu Gln Gln Met His Tyr Lys Asp Trp Met Asp Met Cys Ala Asp Gly
        35                  40                  45

Glu Ser Gly Lys Thr Phe Ala Asp Leu Thr Val Gln Glu Gly Val Thr
    50                  55                  60

Ile Ala Val Ser Ile Ala Ala Ala Ile Leu Ser Val Pro Phe Pro Val
65                  70                  75                  80

Thr Ala Ala Gly Leu Ser Ile Ile Ser Leu Leu Val Pro Tyr Trp Trp
                85                  90                  95

Pro Glu Thr Ala Val Thr Pro Gly Thr Pro Ser Ala Gln Val Thr Trp
            100                 105                 110

Glu Lys Phe Met Ser Ala Ala Glu Asn Leu Ser Asn Thr Gln Ile Val
        115                 120                 125

Ala Ser Lys Arg Ser Asp Ala Ile Ala Arg Trp Gln Gly Ile Gln Thr
    130                 135                 140

Leu Gly Arg Asp Tyr Phe Gln Ala Gln Cys Asp Trp Leu Gln Asp Gln
145                 150                 155                 160

Asn Asn Glu Leu Lys Lys Ser Lys Leu Arg Glu Ala Phe Asp Asp Phe
                165                 170                 175

Glu Asp Tyr Leu Lys Val Ser Met Pro Phe Phe Arg Ala Gln Gly Phe
            180                 185                 190

Glu Ile Pro Met Leu Ala Met Tyr Ala Gln Ala Ala Asn Met His Leu
        195                 200                 205

Leu Leu Leu Arg Glu Val Val Gln Asn Gly Val Gly Trp Gly Phe Gln
    210                 215                 220

Gln Tyr Glu Val Asp Arg Tyr Tyr Ser Asn Thr Asp Pro Phe Leu Gly
225                 230                 235                 240

Asn Pro Gly Leu Leu Gln Leu Leu Glu Gly Tyr Thr Asp Tyr Cys Val
                245                 250                 255

Lys Trp Tyr Asn Ala Gly Leu Arg Gln Gln Tyr Glu Asn Asn Arg Tyr
            260                 265                 270

Asn Trp Asp Ala Phe Asn Asp Phe Arg Arg Asp Met Ile Ile Met Val
        275                 280                 285

Leu Asp Ile Val Ser Leu Trp Pro Thr Tyr Asp Pro Lys Arg Tyr Pro
    290                 295                 300

Leu Pro Thr Lys Ser Gln Leu Thr Arg Thr Val Tyr Thr Asp Leu Val
305                 310                 315                 320

Gly Phe Ser Gly Asn Ser Glu Tyr Leu Gln Ile Asp Ile Glu Arg Ala
                325                 330                 335

Glu Gln Ala Leu Val Gln Lys Pro Gly Leu Phe Thr Trp Leu Arg Glu
            340                 345                 350

Leu Ser Phe Glu Leu Gly Pro Leu Ser Arg Ile Asn Phe Val Arg Gly
        355                 360                 365

Arg Gln Ile Val Phe Asn Tyr Thr Gly Ser Ser Asp Arg Tyr Glu Glu
    370                 375                 380

Thr Lys Gly Asn Leu Gly Glu Thr Arg Glu Thr Val Val Ile Pro Ala
385                 390                 395                 400

Pro Asp Val Gly Asp Asp Ile Trp Arg Ile Ser Thr Gln Val Asn Thr
                405                 410                 415

Tyr Gln Ile Pro Asn Ala Thr Phe Val Arg Gly Trp Asn Phe Ser Phe
            420                 425                 430

Thr Gln Ser Leu Asp Gln Lys Ile Ala Trp Arg Thr Glu Tyr Ser Pro
        435                 440                 445
```

```
Glu Ile Val Met Gln Gly Leu Ser Cys His Gly Pro Ser Val Ser Ser
    450                 455                 460

Cys Asn Leu Cys Ile Ser Asn Ser Pro Cys Arg Ser Ile Thr Pro Asn
465                 470                 475                 480

Tyr Ser Ser Pro Cys Asp Asp Lys Leu Val Tyr Ser His Arg Phe Ser
                485                 490                 495

Tyr Leu Gly Ala Gly Leu Lys Ser Asp Leu Thr Thr Leu Ile Tyr Phe
            500                 505                 510

Ser Tyr Gly Trp Thr His Val Ser Ala Asp Ala Asn Asn Leu Ile Asp
        515                 520                 525

Pro Lys Lys Ile Thr Gln Ile Pro Ala Val Lys Gly Asp Tyr Leu Gly
    530                 535                 540

Arg Asn Ala Arg Val Ile Lys Gly Pro Gly Ser Thr Gly Gly Asp Leu
545                 550                 555                 560

Val Gln Leu Ser Asp Gly Thr Glu Arg Gly Thr Leu Gly Ile Lys Leu
                565                 570                 575

Thr Lys Pro Pro Gly Ser His Ser Tyr Arg Val Arg Ile Arg Tyr Ala
            580                 585                 590

Ser Asn Thr Arg Thr Gln Leu Glu Ile Ile Trp Gly Glu Asp Tyr Asp
        595                 600                 605

Ser Val Ile Val Pro Ala Thr Thr Thr Asp Ile Thr Asn Leu Thr Tyr
    610                 615                 620

Asn Lys Phe Gly Tyr Phe Glu Ile Arg Val Phe Ser Tyr Asn Ser Ser
625                 630                 635                 640

Ser Glu Glu Glu Asp Leu Ile Arg Val Asp Ala Thr Gly Ser Phe Ile
                645                 650                 655

Leu Asp Lys Ile Glu Phe Ile Pro Ile
            660                 665


<210> SEQ ID NO 40
<211> LENGTH: 654
<212> TYPE: PRT
<213> ORGANISM: Bacillus thuringiensis

<400> SEQUENCE: 40

Met Ser Thr Gly Asp Met Gly Tyr Gln Pro Arg Tyr Pro Phe Ser Asn
1               5                   10                  15

Ala Pro Gly Ala Glu Leu Gln Gln Met His Tyr Lys Asp Trp Met Asp
            20                  25                  30

Met Cys Ala Asp Gly Glu Ser Gly Lys Thr Phe Ala Asp Leu Thr Val
        35                  40                  45

Gln Glu Gly Val Thr Ile Ala Val Ser Ile Ala Ala Ala Ile Leu Ser
    50                  55                  60

Val Pro Phe Pro Val Thr Ala Ala Gly Leu Ser Ile Ile Ser Leu Leu
65                  70                  75                  80

Val Pro Tyr Trp Trp Pro Glu Thr Ala Val Thr Pro Gly Thr Pro Ser
                85                  90                  95

Ala Gln Val Thr Trp Glu Lys Phe Met Ser Ala Ala Glu Asn Leu Ser
            100                 105                 110

Asn Thr Gln Ile Val Ala Ser Lys Arg Ser Asp Ala Ile Ala Arg Trp
        115                 120                 125

Gln Gly Ile Gln Thr Leu Gly Arg Asp Tyr Phe Gln Ala Gln Cys Asp
    130                 135                 140

Trp Leu Gln Asp Gln Asn Asn Glu Leu Lys Lys Ser Lys Leu Arg Glu
145                 150                 155                 160
```

```
Ala Phe Asp Asp Phe Glu Asp Tyr Leu Lys Val Ser Met Pro Phe Phe
                165                 170                 175

Arg Ala Gln Gly Phe Glu Ile Pro Met Leu Ala Met Tyr Ala Gln Ala
            180                 185                 190

Ala Asn Met His Leu Leu Leu Leu Arg Glu Val Val Gln Asn Gly Val
        195                 200                 205

Gly Trp Gly Phe Gln Gln Tyr Glu Val Asp Arg Tyr Tyr Ser Asn Thr
    210                 215                 220

Asp Pro Phe Leu Gly Asn Pro Gly Leu Leu Gln Leu Leu Glu Gly Tyr
225                 230                 235                 240

Thr Asp Tyr Cys Val Lys Trp Tyr Asn Ala Gly Leu Arg Gln Gln Tyr
                245                 250                 255

Glu Asn Asn Arg Tyr Asn Trp Asp Ala Phe Asn Asp Phe Arg Arg Asp
            260                 265                 270

Met Ile Ile Met Val Leu Asp Ile Val Ser Leu Trp Pro Thr Tyr Asp
        275                 280                 285

Pro Lys Arg Tyr Pro Leu Pro Thr Lys Ser Gln Leu Thr Arg Thr Val
    290                 295                 300

Tyr Thr Asp Leu Val Gly Phe Ser Gly Asn Ser Glu Tyr Leu Gln Ile
305                 310                 315                 320

Asp Ile Glu Arg Ala Glu Gln Ala Leu Val Gln Lys Pro Gly Leu Phe
                325                 330                 335

Thr Trp Leu Arg Glu Leu Ser Phe Glu Leu Gly Pro Leu Ser Arg Ile
            340                 345                 350

Asn Phe Val Arg Gly Arg Gln Ile Val Phe Asn Tyr Thr Gly Ser Ser
        355                 360                 365

Asp Arg Tyr Glu Glu Thr Lys Gly Asn Leu Gly Glu Thr Arg Glu Thr
    370                 375                 380

Val Val Ile Pro Ala Pro Asp Val Gly Asp Asp Ile Trp Arg Ile Ser
385                 390                 395                 400

Thr Gln Val Asn Thr Tyr Gln Ile Pro Asn Ala Thr Phe Val Arg Gly
                405                 410                 415

Trp Asn Phe Ser Phe Thr Gln Ser Leu Asp Gln Lys Ile Ala Trp Arg
            420                 425                 430

Thr Glu Tyr Ser Pro Glu Ile Val Met Gln Gly Leu Ser Cys His Gly
        435                 440                 445

Pro Ser Val Ser Ser Cys Asn Leu Cys Ile Ser Asn Ser Pro Cys Arg
    450                 455                 460

Ser Ile Thr Pro Asn Tyr Ser Ser Pro Cys Asp Asp Lys Leu Val Tyr
465                 470                 475                 480

Ser His Arg Phe Ser Tyr Leu Gly Ala Gly Leu Lys Ser Asp Leu Thr
                485                 490                 495

Thr Leu Ile Tyr Phe Ser Tyr Gly Trp Thr His Val Ser Ala Asp Ala
            500                 505                 510

Asn Asn Leu Ile Asp Pro Lys Lys Ile Thr Gln Ile Pro Ala Val Lys
        515                 520                 525

Gly Asp Tyr Leu Gly Arg Asn Ala Arg Val Ile Lys Gly Pro Gly Ser
    530                 535                 540

Thr Gly Gly Asp Leu Val Gln Leu Ser Asp Gly Thr Glu Arg Gly Thr
545                 550                 555                 560

Leu Gly Ile Lys Leu Thr Lys Pro Pro Gly Ser His Ser Tyr Arg Val
                565                 570                 575
```

-continued

Arg Ile Arg Tyr Ala Ser Asn Thr Arg Thr Gln Leu Glu Ile Ile Trp
580 585 590

Gly Glu Asp Tyr Asp Ser Val Ile Val Pro Ala Thr Thr Thr Asp Ile
595 600 605

Thr Asn Leu Thr Tyr Asn Lys Phe Gly Tyr Phe Glu Ile Arg Val Phe
610 615 620

Ser Tyr Asn Ser Ser Ser Glu Glu Glu Asp Leu Ile Arg Val Asp Ala
625 630 635 640

Thr Gly Ser Phe Ile Leu Asp Lys Ile Glu Phe Ile Pro Ile
645 650

<210> SEQ ID NO 41
<211> LENGTH: 649
<212> TYPE: PRT
<213> ORGANISM: Bacillus thuringiensis

<400> SEQUENCE: 41

Met Gly Tyr Gln Pro Arg Tyr Pro Phe Ser Asn Ala Pro Gly Ala Glu
1 5 10 15

Leu Gln Gln Met His Tyr Lys Asp Trp Met Asp Met Cys Ala Asp Gly
20 25 30

Glu Ser Gly Lys Thr Phe Ala Asp Leu Thr Val Gln Glu Gly Val Thr
35 40 45

Ile Ala Val Ser Ile Ala Ala Ala Ile Leu Ser Val Pro Phe Pro Val
50 55 60

Thr Ala Ala Gly Leu Ser Ile Ile Ser Leu Leu Val Pro Tyr Trp Trp
65 70 75 80

Pro Glu Thr Ala Val Thr Pro Gly Thr Pro Ser Ala Gln Val Thr Trp
85 90 95

Glu Lys Phe Met Ser Ala Ala Glu Asn Leu Ser Asn Thr Gln Ile Val
100 105 110

Ala Ser Lys Arg Ser Asp Ala Ile Ala Arg Trp Gln Gly Ile Gln Thr
115 120 125

Leu Gly Arg Asp Tyr Phe Gln Ala Gln Cys Asp Trp Leu Gln Asp Gln
130 135 140

Asn Asn Glu Leu Lys Lys Ser Lys Leu Arg Glu Ala Phe Asp Asp Phe
145 150 155 160

Glu Asp Tyr Leu Lys Val Ser Met Pro Phe Phe Arg Ala Gln Gly Phe
165 170 175

Glu Ile Pro Met Leu Ala Met Tyr Ala Gln Ala Ala Asn Met His Leu
180 185 190

Leu Leu Leu Arg Glu Val Val Gln Asn Gly Val Gly Trp Gly Phe Gln
195 200 205

Gln Tyr Glu Val Asp Arg Tyr Tyr Ser Asn Thr Asp Pro Phe Leu Gly
210 215 220

Asn Pro Gly Leu Leu Gln Leu Leu Glu Gly Tyr Thr Asp Tyr Cys Val
225 230 235 240

Lys Trp Tyr Asn Ala Gly Leu Arg Gln Gln Tyr Glu Asn Asn Arg Tyr
245 250 255

Asn Trp Asp Ala Phe Asn Asp Phe Arg Arg Asp Met Ile Ile Met Val
260 265 270

Leu Asp Ile Val Ser Leu Trp Pro Thr Tyr Asp Pro Lys Arg Tyr Pro
275 280 285

Leu Pro Thr Lys Ser Gln Leu Thr Arg Thr Val Tyr Thr Asp Leu Val
290 295 300

-continued

Gly Phe Ser Gly Asn Ser Glu Tyr Leu Gln Ile Asp Ile Glu Arg Ala
305 310 315 320

Glu Gln Ala Leu Val Gln Lys Pro Gly Leu Phe Thr Trp Leu Arg Glu
325 330 335

Leu Ser Phe Glu Leu Gly Pro Leu Ser Arg Ile Asn Phe Val Arg Gly
340 345 350

Arg Gln Ile Val Phe Asn Tyr Thr Gly Ser Ser Asp Arg Tyr Glu Glu
355 360 365

Thr Lys Gly Asn Leu Gly Glu Thr Arg Glu Thr Val Val Ile Pro Ala
370 375 380

Pro Asp Val Gly Asp Asp Ile Trp Arg Ile Ser Thr Gln Val Asn Thr
385 390 395 400

Tyr Gln Ile Pro Asn Ala Thr Phe Val Arg Gly Trp Asn Phe Ser Phe
405 410 415

Thr Gln Ser Leu Asp Gln Lys Ile Ala Trp Arg Thr Glu Tyr Ser Pro
420 425 430

Glu Ile Val Met Gln Gly Leu Ser Cys His Gly Pro Ser Val Ser Ser
435 440 445

Cys Asn Leu Cys Ile Ser Asn Ser Pro Cys Arg Ser Ile Thr Pro Asn
450 455 460

Tyr Ser Ser Pro Cys Asp Asp Lys Leu Val Tyr Ser His Arg Phe Ser
465 470 475 480

Tyr Leu Gly Ala Gly Leu Lys Ser Asp Leu Thr Thr Leu Ile Tyr Phe
485 490 495

Ser Tyr Gly Trp Thr His Val Ser Ala Asp Ala Asn Asn Leu Ile Asp
500 505 510

Pro Lys Lys Ile Thr Gln Ile Pro Ala Val Lys Gly Asp Tyr Leu Gly
515 520 525

Arg Asn Ala Arg Val Ile Lys Gly Pro Gly Ser Thr Gly Gly Asp Leu
530 535 540

Val Gln Leu Ser Asp Gly Thr Glu Arg Gly Thr Leu Gly Ile Lys Leu
545 550 555 560

Thr Lys Pro Pro Gly Ser His Ser Tyr Arg Val Arg Ile Arg Tyr Ala
565 570 575

Ser Asn Thr Arg Thr Gln Leu Glu Ile Ile Trp Gly Glu Asp Tyr Asp
580 585 590

Ser Val Ile Val Pro Ala Thr Thr Thr Asp Ile Thr Asn Leu Thr Tyr
595 600 605

Asn Lys Phe Gly Tyr Phe Glu Ile Arg Val Phe Ser Tyr Asn Ser Ser
610 615 620

Ser Glu Glu Glu Asp Leu Ile Arg Val Asp Ala Thr Gly Ser Phe Ile
625 630 635 640

Leu Asp Lys Ile Glu Phe Ile Pro Ile
645

<210> SEQ ID NO 42
<211> LENGTH: 630
<212> TYPE: PRT
<213> ORGANISM: Bacillus thuringiensis

<400> SEQUENCE: 42

Met His Tyr Lys Asp Trp Met Asp Met Cys Ala Asp Gly Glu Ser Gly
1 5 10 15

Lys Thr Phe Ala Asp Leu Thr Val Gln Glu Gly Val Thr Ile Ala Val

-continued

```
                20                  25                  30

Ser Ile Ala Ala Ala Ile Leu Ser Val Pro Phe Pro Val Thr Ala Ala
            35                  40                  45

Gly Leu Ser Ile Ile Ser Leu Leu Val Pro Tyr Trp Trp Pro Glu Thr
    50                  55                  60

Ala Val Thr Pro Gly Thr Pro Ser Ala Gln Val Thr Trp Glu Lys Phe
65                  70                  75                  80

Met Ser Ala Ala Glu Asn Leu Ser Asn Thr Gln Ile Val Ala Ser Lys
                85                  90                  95

Arg Ser Asp Ala Ile Ala Arg Trp Gln Gly Ile Gln Thr Leu Gly Arg
            100                 105                 110

Asp Tyr Phe Gln Ala Gln Cys Asp Trp Leu Gln Asp Gln Asn Asn Glu
        115                 120                 125

Leu Lys Lys Ser Lys Leu Arg Glu Ala Phe Asp Asp Phe Glu Asp Tyr
    130                 135                 140

Leu Lys Val Ser Met Pro Phe Phe Arg Ala Gln Gly Phe Glu Ile Pro
145                 150                 155                 160

Met Leu Ala Met Tyr Ala Gln Ala Ala Asn Met His Leu Leu Leu Leu
                165                 170                 175

Arg Glu Val Val Gln Asn Gly Val Gly Trp Gly Phe Gln Gln Tyr Glu
            180                 185                 190

Val Asp Arg Tyr Tyr Ser Asn Thr Asp Pro Phe Leu Gly Asn Pro Gly
        195                 200                 205

Leu Leu Gln Leu Leu Glu Gly Tyr Thr Asp Tyr Cys Val Lys Trp Tyr
    210                 215                 220

Asn Ala Gly Leu Arg Gln Gln Tyr Glu Asn Asn Arg Tyr Asn Trp Asp
225                 230                 235                 240

Ala Phe Asn Asp Phe Arg Arg Asp Met Ile Ile Met Val Leu Asp Ile
                245                 250                 255

Val Ser Leu Trp Pro Thr Tyr Asp Pro Lys Arg Tyr Pro Leu Pro Thr
            260                 265                 270

Lys Ser Gln Leu Thr Arg Thr Val Tyr Thr Asp Leu Val Gly Phe Ser
        275                 280                 285

Gly Asn Ser Glu Tyr Leu Gln Ile Asp Ile Glu Arg Ala Glu Gln Ala
    290                 295                 300

Leu Val Gln Lys Pro Gly Leu Phe Thr Trp Leu Arg Glu Leu Ser Phe
305                 310                 315                 320

Glu Leu Gly Pro Leu Ser Arg Ile Asn Phe Val Arg Gly Arg Gln Ile
                325                 330                 335

Val Phe Asn Tyr Thr Gly Ser Ser Asp Arg Tyr Glu Glu Thr Lys Gly
            340                 345                 350

Asn Leu Gly Glu Thr Arg Glu Thr Val Val Ile Pro Ala Pro Asp Val
        355                 360                 365

Gly Asp Asp Ile Trp Arg Ile Ser Thr Gln Val Asn Thr Tyr Gln Ile
    370                 375                 380

Pro Asn Ala Thr Phe Val Arg Gly Trp Asn Phe Ser Phe Thr Gln Ser
385                 390                 395                 400

Leu Asp Gln Lys Ile Ala Trp Arg Thr Glu Tyr Ser Pro Glu Ile Val
                405                 410                 415

Met Gln Gly Leu Ser Cys His Gly Pro Ser Val Ser Ser Cys Asn Leu
            420                 425                 430

Cys Ile Ser Asn Ser Pro Cys Arg Ser Ile Thr Pro Asn Tyr Ser Ser
        435                 440                 445
```

```
Pro Cys Asp Asp Lys Leu Val Tyr Ser His Arg Phe Ser Tyr Leu Gly
    450                 455                 460

Ala Gly Leu Lys Ser Asp Leu Thr Thr Leu Ile Tyr Phe Ser Tyr Gly
465                 470                 475                 480

Trp Thr His Val Ser Ala Asp Ala Asn Asn Leu Ile Asp Pro Lys Lys
                485                 490                 495

Ile Thr Gln Ile Pro Ala Val Lys Gly Asp Tyr Leu Gly Arg Asn Ala
            500                 505                 510

Arg Val Ile Lys Gly Pro Gly Ser Thr Gly Gly Asp Leu Val Gln Leu
        515                 520                 525

Ser Asp Gly Thr Glu Arg Gly Thr Leu Gly Ile Lys Leu Thr Lys Pro
    530                 535                 540

Pro Gly Ser His Ser Tyr Arg Val Arg Ile Arg Tyr Ala Ser Asn Thr
545                 550                 555                 560

Arg Thr Gln Leu Glu Ile Ile Trp Gly Glu Asp Tyr Asp Ser Val Ile
                565                 570                 575

Val Pro Ala Thr Thr Thr Asp Ile Thr Asn Leu Thr Tyr Asn Lys Phe
            580                 585                 590

Gly Tyr Phe Glu Ile Arg Val Phe Ser Tyr Asn Ser Ser Ser Glu Glu
        595                 600                 605

Glu Asp Leu Ile Arg Val Asp Ala Thr Gly Ser Phe Ile Leu Asp Lys
    610                 615                 620

Ile Glu Phe Ile Pro Ile
625                 630


<210> SEQ ID NO 43
<211> LENGTH: 624
<212> TYPE: PRT
<213> ORGANISM: Bacillus thuringiensis

<400> SEQUENCE: 43

Met Asp Met Cys Ala Asp Gly Glu Ser Gly Lys Thr Phe Ala Asp Leu
1               5                   10                  15

Thr Val Gln Glu Gly Val Thr Ile Ala Val Ser Ile Ala Ala Ala Ile
            20                  25                  30

Leu Ser Val Pro Phe Pro Val Thr Ala Ala Gly Leu Ser Ile Ile Ser
        35                  40                  45

Leu Leu Val Pro Tyr Trp Trp Pro Glu Thr Ala Val Thr Pro Gly Thr
    50                  55                  60

Pro Ser Ala Gln Val Thr Trp Glu Lys Phe Met Ser Ala Ala Glu Asn
65                  70                  75                  80

Leu Ser Asn Thr Gln Ile Val Ala Ser Lys Arg Ser Asp Ala Ile Ala
                85                  90                  95

Arg Trp Gln Gly Ile Gln Thr Leu Gly Arg Asp Tyr Phe Gln Ala Gln
            100                 105                 110

Cys Asp Trp Leu Gln Asp Gln Asn Asn Glu Leu Lys Lys Ser Lys Leu
        115                 120                 125

Arg Glu Ala Phe Asp Asp Phe Glu Asp Tyr Leu Lys Val Ser Met Pro
    130                 135                 140

Phe Phe Arg Ala Gln Gly Phe Glu Ile Pro Met Leu Ala Met Tyr Ala
145                 150                 155                 160

Gln Ala Ala Asn Met His Leu Leu Leu Leu Arg Glu Val Val Gln Asn
                165                 170                 175

Gly Val Gly Trp Gly Phe Gln Gln Tyr Glu Val Asp Arg Tyr Tyr Ser
```

-continued

```
            180                 185                 190

Asn Thr Asp Pro Phe Leu Gly Asn Pro Gly Leu Leu Gln Leu Leu Glu
        195                 200                 205

Gly Tyr Thr Asp Tyr Cys Val Lys Trp Tyr Asn Ala Gly Leu Arg Gln
    210                 215                 220

Gln Tyr Glu Asn Asn Arg Tyr Asn Trp Asp Ala Phe Asn Asp Phe Arg
225                 230                 235                 240

Arg Asp Met Ile Ile Met Val Leu Asp Ile Val Ser Leu Trp Pro Thr
                245                 250                 255

Tyr Asp Pro Lys Arg Tyr Pro Leu Pro Thr Lys Ser Gln Leu Thr Arg
            260                 265                 270

Thr Val Tyr Thr Asp Leu Val Gly Phe Ser Gly Asn Ser Glu Tyr Leu
        275                 280                 285

Gln Ile Asp Ile Glu Arg Ala Glu Gln Ala Leu Val Gln Lys Pro Gly
    290                 295                 300

Leu Phe Thr Trp Leu Arg Glu Leu Ser Phe Glu Leu Gly Pro Leu Ser
305                 310                 315                 320

Arg Ile Asn Phe Val Arg Gly Arg Gln Ile Val Phe Asn Tyr Thr Gly
                325                 330                 335

Ser Ser Asp Arg Tyr Glu Glu Thr Lys Gly Asn Leu Gly Glu Thr Arg
            340                 345                 350

Glu Thr Val Val Ile Pro Ala Pro Asp Val Gly Asp Asp Ile Trp Arg
        355                 360                 365

Ile Ser Thr Gln Val Asn Thr Tyr Gln Ile Pro Asn Ala Thr Phe Val
    370                 375                 380

Arg Gly Trp Asn Phe Ser Phe Thr Gln Ser Leu Asp Gln Lys Ile Ala
385                 390                 395                 400

Trp Arg Thr Glu Tyr Ser Pro Glu Ile Val Met Gln Gly Leu Ser Cys
                405                 410                 415

His Gly Pro Ser Val Ser Ser Cys Asn Leu Cys Ile Ser Asn Ser Pro
            420                 425                 430

Cys Arg Ser Ile Thr Pro Asn Tyr Ser Ser Pro Cys Asp Asp Lys Leu
        435                 440                 445

Val Tyr Ser His Arg Phe Ser Tyr Leu Gly Ala Gly Leu Lys Ser Asp
    450                 455                 460

Leu Thr Thr Leu Ile Tyr Phe Ser Tyr Gly Trp Thr His Val Ser Ala
465                 470                 475                 480

Asp Ala Asn Asn Leu Ile Asp Pro Lys Lys Ile Thr Gln Ile Pro Ala
                485                 490                 495

Val Lys Gly Asp Tyr Leu Gly Arg Asn Ala Arg Val Ile Lys Gly Pro
            500                 505                 510

Gly Ser Thr Gly Gly Asp Leu Val Gln Leu Ser Asp Gly Thr Glu Arg
        515                 520                 525

Gly Thr Leu Gly Ile Lys Leu Thr Lys Pro Pro Gly Ser His Ser Tyr
    530                 535                 540

Arg Val Arg Ile Arg Tyr Ala Ser Asn Thr Arg Thr Gln Leu Glu Ile
545                 550                 555                 560

Ile Trp Gly Glu Asp Tyr Asp Ser Val Ile Val Pro Ala Thr Thr Thr
                565                 570                 575

Asp Ile Thr Asn Leu Thr Tyr Asn Lys Phe Gly Tyr Phe Glu Ile Arg
            580                 585                 590

Val Phe Ser Tyr Asn Ser Ser Ser Glu Glu Glu Asp Leu Ile Arg Val
        595                 600                 605
```

Asp Ala Thr Gly Ser Phe Ile Leu Asp Lys Ile Glu Phe Ile Pro Ile
610 615 620

<210> SEQ ID NO 44
<211> LENGTH: 622
<212> TYPE: PRT
<213> ORGANISM: Bacillus thuringiensis

<400> SEQUENCE: 44

Met Cys Ala Asp Gly Glu Ser Gly Lys Thr Phe Ala Asp Leu Thr Val
1 5 10 15

Gln Glu Gly Val Thr Ile Ala Val Ser Ile Ala Ala Ala Ile Leu Ser
20 25 30

Val Pro Phe Pro Val Thr Ala Ala Gly Leu Ser Ile Ile Ser Leu Leu
35 40 45

Val Pro Tyr Trp Trp Pro Glu Thr Ala Val Thr Pro Gly Thr Pro Ser
50 55 60

Ala Gln Val Thr Trp Glu Lys Phe Met Ser Ala Ala Glu Asn Leu Ser
65 70 75 80

Asn Thr Gln Ile Val Ala Ser Lys Arg Ser Asp Ala Ile Ala Arg Trp
85 90 95

Gln Gly Ile Gln Thr Leu Gly Arg Asp Tyr Phe Gln Ala Gln Cys Asp
100 105 110

Trp Leu Gln Asp Gln Asn Asn Glu Leu Lys Lys Ser Lys Leu Arg Glu
115 120 125

Ala Phe Asp Asp Phe Glu Asp Tyr Leu Lys Val Ser Met Pro Phe Phe
130 135 140

Arg Ala Gln Gly Phe Glu Ile Pro Met Leu Ala Met Tyr Ala Gln Ala
145 150 155 160

Ala Asn Met His Leu Leu Leu Leu Arg Glu Val Val Gln Asn Gly Val
165 170 175

Gly Trp Gly Phe Gln Gln Tyr Glu Val Asp Arg Tyr Tyr Ser Asn Thr
180 185 190

Asp Pro Phe Leu Gly Asn Pro Gly Leu Leu Gln Leu Leu Glu Gly Tyr
195 200 205

Thr Asp Tyr Cys Val Lys Trp Tyr Asn Ala Gly Leu Arg Gln Gln Tyr
210 215 220

Glu Asn Asn Arg Tyr Asn Trp Asp Ala Phe Asn Asp Phe Arg Arg Asp
225 230 235 240

Met Ile Ile Met Val Leu Asp Ile Val Ser Leu Trp Pro Thr Tyr Asp
245 250 255

Pro Lys Arg Tyr Pro Leu Pro Thr Lys Ser Gln Leu Thr Arg Thr Val
260 265 270

Tyr Thr Asp Leu Val Gly Phe Ser Gly Asn Ser Glu Tyr Leu Gln Ile
275 280 285

Asp Ile Glu Arg Ala Glu Gln Ala Leu Val Gln Lys Pro Gly Leu Phe
290 295 300

Thr Trp Leu Arg Glu Leu Ser Phe Glu Leu Gly Pro Leu Ser Arg Ile
305 310 315 320

Asn Phe Val Arg Gly Arg Gln Ile Val Phe Asn Tyr Thr Gly Ser Ser
325 330 335

Asp Arg Tyr Glu Glu Thr Lys Gly Asn Leu Gly Glu Thr Arg Glu Thr
340 345 350

Val Val Ile Pro Ala Pro Asp Val Gly Asp Asp Ile Trp Arg Ile Ser

-continued

```
        355                 360                 365

Thr Gln Val Asn Thr Tyr Gln Ile Pro Asn Ala Thr Phe Val Arg Gly
    370                 375                 380

Trp Asn Phe Ser Phe Thr Gln Ser Leu Asp Gln Lys Ile Ala Trp Arg
385                 390                 395                 400

Thr Glu Tyr Ser Pro Glu Ile Val Met Gln Gly Leu Ser Cys His Gly
                405                 410                 415

Pro Ser Val Ser Ser Cys Asn Leu Cys Ile Ser Asn Ser Pro Cys Arg
            420                 425                 430

Ser Ile Thr Pro Asn Tyr Ser Ser Pro Cys Asp Asp Lys Leu Val Tyr
        435                 440                 445

Ser His Arg Phe Ser Tyr Leu Gly Ala Gly Leu Lys Ser Asp Leu Thr
    450                 455                 460

Thr Leu Ile Tyr Phe Ser Tyr Gly Trp Thr His Val Ser Ala Asp Ala
465                 470                 475                 480

Asn Asn Leu Ile Asp Pro Lys Lys Ile Thr Gln Ile Pro Ala Val Lys
                485                 490                 495

Gly Asp Tyr Leu Gly Arg Asn Ala Arg Val Ile Lys Gly Pro Gly Ser
            500                 505                 510

Thr Gly Gly Asp Leu Val Gln Leu Ser Asp Gly Thr Glu Arg Gly Thr
        515                 520                 525

Leu Gly Ile Lys Leu Thr Lys Pro Pro Gly Ser His Ser Tyr Arg Val
    530                 535                 540

Arg Ile Arg Tyr Ala Ser Asn Thr Arg Thr Gln Leu Glu Ile Ile Trp
545                 550                 555                 560

Gly Glu Asp Tyr Asp Ser Val Ile Val Pro Ala Thr Thr Thr Asp Ile
                565                 570                 575

Thr Asn Leu Thr Tyr Asn Lys Phe Gly Tyr Phe Glu Ile Arg Val Phe
            580                 585                 590

Ser Tyr Asn Ser Ser Ser Glu Glu Glu Asp Leu Ile Arg Val Asp Ala
        595                 600                 605

Thr Gly Ser Phe Ile Leu Asp Lys Ile Glu Phe Ile Pro Ile
    610                 615                 620


<210> SEQ ID NO 45
<211> LENGTH: 550
<212> TYPE: PRT
<213> ORGANISM: Bacillus thuringiensis

<400> SEQUENCE: 45

Met Ser Ala Ala Glu Asn Leu Ser Asn Thr Gln Ile Val Ala Ser Lys
1               5                   10                  15

Arg Ser Asp Ala Ile Ala Arg Trp Gln Gly Ile Gln Thr Leu Gly Arg
            20                  25                  30

Asp Tyr Phe Gln Ala Gln Cys Asp Trp Leu Gln Asp Gln Asn Asn Glu
        35                  40                  45

Leu Lys Lys Ser Lys Leu Arg Glu Ala Phe Asp Asp Phe Glu Asp Tyr
    50                  55                  60

Leu Lys Val Ser Met Pro Phe Phe Arg Ala Gln Gly Phe Glu Ile Pro
65                  70                  75                  80

Met Leu Ala Met Tyr Ala Gln Ala Ala Asn Met His Leu Leu Leu Leu
                85                  90                  95

Arg Glu Val Val Gln Asn Gly Val Gly Trp Gly Phe Gln Gln Tyr Glu
            100                 105                 110
```

-continued

```
Val Asp Arg Tyr Tyr Ser Asn Thr Asp Pro Phe Leu Gly Asn Pro Gly
        115                 120                 125

Leu Leu Gln Leu Leu Glu Gly Tyr Thr Asp Tyr Cys Val Lys Trp Tyr
    130                 135                 140

Asn Ala Gly Leu Arg Gln Gln Tyr Glu Asn Asn Arg Tyr Asn Trp Asp
145                 150                 155                 160

Ala Phe Asn Asp Phe Arg Arg Asp Met Ile Ile Met Val Leu Asp Ile
                165                 170                 175

Val Ser Leu Trp Pro Thr Tyr Asp Pro Lys Arg Tyr Pro Leu Pro Thr
            180                 185                 190

Lys Ser Gln Leu Thr Arg Thr Val Tyr Thr Asp Leu Val Gly Phe Ser
        195                 200                 205

Gly Asn Ser Glu Tyr Leu Gln Ile Asp Ile Glu Arg Ala Glu Gln Ala
    210                 215                 220

Leu Val Gln Lys Pro Gly Leu Phe Thr Trp Leu Arg Glu Leu Ser Phe
225                 230                 235                 240

Glu Leu Gly Pro Leu Ser Arg Ile Asn Phe Val Arg Gly Arg Gln Ile
                245                 250                 255

Val Phe Asn Tyr Thr Gly Ser Ser Asp Arg Tyr Glu Glu Thr Lys Gly
            260                 265                 270

Asn Leu Gly Glu Thr Arg Glu Thr Val Val Ile Pro Ala Pro Asp Val
        275                 280                 285

Gly Asp Asp Ile Trp Arg Ile Ser Thr Gln Val Asn Thr Tyr Gln Ile
    290                 295                 300

Pro Asn Ala Thr Phe Val Arg Gly Trp Asn Phe Ser Phe Thr Gln Ser
305                 310                 315                 320

Leu Asp Gln Lys Ile Ala Trp Arg Thr Glu Tyr Ser Pro Glu Ile Val
                325                 330                 335

Met Gln Gly Leu Ser Cys His Gly Pro Ser Val Ser Ser Cys Asn Leu
            340                 345                 350

Cys Ile Ser Asn Ser Pro Cys Arg Ser Ile Thr Pro Asn Tyr Ser Ser
        355                 360                 365

Pro Cys Asp Asp Lys Leu Val Tyr Ser His Arg Phe Ser Tyr Leu Gly
    370                 375                 380

Ala Gly Leu Lys Ser Asp Leu Thr Thr Leu Ile Tyr Phe Ser Tyr Gly
385                 390                 395                 400

Trp Thr His Val Ser Ala Asp Ala Asn Asn Leu Ile Asp Pro Lys Lys
                405                 410                 415

Ile Thr Gln Ile Pro Ala Val Lys Gly Asp Tyr Leu Gly Arg Asn Ala
            420                 425                 430

Arg Val Ile Lys Gly Pro Gly Ser Thr Gly Gly Asp Leu Val Gln Leu
        435                 440                 445

Ser Asp Gly Thr Glu Arg Gly Thr Leu Gly Ile Lys Leu Thr Lys Pro
    450                 455                 460

Pro Gly Ser His Ser Tyr Arg Val Arg Ile Arg Tyr Ala Ser Asn Thr
465                 470                 475                 480

Arg Thr Gln Leu Glu Ile Ile Trp Gly Glu Asp Tyr Asp Ser Val Ile
                485                 490                 495

Val Pro Ala Thr Thr Thr Asp Ile Thr Asn Leu Thr Tyr Asn Lys Phe
            500                 505                 510

Gly Tyr Phe Glu Ile Arg Val Phe Ser Tyr Asn Ser Ser Ser Glu Glu
        515                 520                 525

Glu Asp Leu Ile Arg Val Asp Ala Thr Gly Ser Phe Ile Leu Asp Lys
```

```
    530                 535                 540

Ile Glu Phe Ile Pro Ile
545                 550


<210> SEQ ID NO 46
<211> LENGTH: 1206
<212> TYPE: PRT
<213> ORGANISM: Bacillus thuringiensis

<400> SEQUENCE: 46

Met Asn Trp Leu Ser Lys Lys Cys Leu Ser Thr Leu Asn Val Asn Leu
1               5                   10                  15

Tyr Lys Ser Gln Phe Gln Gly Glu Tyr Met Asp Asn Asn Ser Glu Asn
            20                  25                  30

Gln Cys Val Pro Tyr Asn Cys Leu Ser Asn Leu Glu Glu Ile Thr Leu
        35                  40                  45

Asn Gly Glu Arg Leu Ser Thr Asn Ser Thr Pro Ile Asn Ile Ser Met
    50                  55                  60

Ser Val Ser Lys Phe Leu Leu Thr Glu Leu Ile Pro Gly Leu Gly Phe
65                  70                  75                  80

Val Phe Gly Leu Leu Asp Ala Ile Trp Gly Phe Ile Gly Pro Asp Gln
                85                  90                  95

Trp Thr Glu Phe Ile Glu His Ile Glu Glu Leu Ile Gly Gln Arg Ile
            100                 105                 110

Thr Val Val Val Arg Asn Thr Ala Ile Arg Glu Leu Glu Gly Met Ala
        115                 120                 125

Arg Val Tyr Gln Thr Tyr Ala Thr Ala Phe Ala Ala Trp Glu Lys Asp
    130                 135                 140

Pro Asn Asn Pro Glu Leu Arg Glu Ala Leu Arg Ala Gln Phe Thr Ala
145                 150                 155                 160

Thr Glu Thr Tyr Ile Ser Gly Arg Ile Ser Val Leu Thr Ile Glu Asp
                165                 170                 175

Tyr Gln Val Gln Leu Leu Ser Val Tyr Ala Gln Ala Thr Asn Leu His
            180                 185                 190

Leu Ser Leu Leu Arg Asp Val Val Phe Trp Gly Gln Arg Trp Gly Phe
        195                 200                 205

Ser Thr Thr Thr Leu Asn Asn Tyr Tyr Ser Asp Leu Thr Arg Glu Ile
    210                 215                 220

Asn Glu Tyr Thr Asn Tyr Ala Val His Trp Tyr Asn Val Gly Leu Glu
225                 230                 235                 240

Gln Leu Gln Gly Pro Ser Phe Gln Glu Trp Val Ala Tyr Asn Arg Tyr
                245                 250                 255

Arg Arg Glu Leu Thr Leu Thr Val Leu Asp Ile Val Thr Leu Phe His
            260                 265                 270

Asn Tyr Asp Ile Arg Leu Tyr Pro Ile Pro Thr Ile Ser Gln Leu Thr
        275                 280                 285

Arg Glu Val Tyr Thr Asp Pro Ile Val Ser Gly Ile Gly Gln Pro Asn
    290                 295                 300

Ser Trp Asp Phe Pro Thr Phe Ser Glu Ala Glu Asn Lys Ser Ile Arg
305                 310                 315                 320

Thr Pro His Leu Met Asp Phe Leu Arg Asn Leu Thr Ile Phe Thr Asp
                325                 330                 335

Ser Ala Arg Tyr Gly Ala Ile Tyr His Phe Trp Gly Gly His Gln Ile
            340                 345                 350
```

-continued

```
Ser Ser Ser Leu Val Gly Gly Ser Asn Ile Thr Phe Pro Thr Tyr Gly
        355                 360                 365

Ser Asn Val Ser Gln Gly Ser Pro Trp Ile Leu Val Thr Asn Gly Ile
    370                 375                 380

Pro Ile Tyr Arg Thr Leu Ser Asn Pro Tyr Tyr Arg Phe Leu Phe Gln
385                 390                 395                 400

Ser Val Gly Ser Ala Arg Leu Arg Cys Val Leu Gly Val Gln Phe His
                405                 410                 415

Met Asp Asn Arg Ala Phe Thr Tyr Arg Glu Lys Gly Thr Val Asp Ser
            420                 425                 430

Phe Asp Glu Leu Pro Pro Thr Asp Ala Ser Val Ser Pro Ser Glu Gly
        435                 440                 445

Tyr Ser His Arg Leu Cys His Ala Thr Leu Phe Gln Val Arg Thr Gly
    450                 455                 460

Gly Gly Gly Ala Val Ser Phe Ser Arg Thr Asp Gly Val Val Phe Ser
465                 470                 475                 480

Trp Thr His Arg Ser Ala Thr Pro Thr Asn Thr Ile Asp Pro Asn Val
                485                 490                 495

Ile Thr Gln Ile Pro Ala Val Lys Gly Arg Ser Leu Phe Asn Gly Ala
            500                 505                 510

Val Ile Lys Gly Pro Gly Phe Thr Gly Gly Asp Leu Val Arg Leu Asn
        515                 520                 525

Arg Asn Asn Gly Asn Ile Gln Asn Arg Gly His Leu Pro Ile Pro Ile
    530                 535                 540

Gln Phe Ser Ser Arg Ser Thr Arg Tyr Arg Val Arg Leu Arg Tyr Ala
545                 550                 555                 560

Ser Ala Thr Pro Ile Gln Val Asn Val His Trp Glu Asn Ser Thr Ile
                565                 570                 575

Phe Ser Gly Ile Val Pro Ala Thr Ala Gln Ser Leu Asp Lys Leu Gln
            580                 585                 590

Ser Asn Asp Phe Gly Tyr Phe Glu Ile Ala Asn Thr Ile Ser Ser Ser
        595                 600                 605

Leu Asp Gly Ile Val Gly Ile Arg Asn Phe Ser Ala Asn Ala Asp Leu
    610                 615                 620

Ile Ile Asp Arg Phe Glu Phe Ile Pro Val Asn Ala Thr Ser Glu Ala
625                 630                 635                 640

Glu Tyr Asp Leu Glu Arg Ala Gln Glu Ala Val Asn Ala Leu Phe Thr
                645                 650                 655

Ser Thr Asn Gln Arg Gly Leu Lys Ala Asn Val Thr Asp Tyr Tyr Ile
            660                 665                 670

Asp Gln Val Ser Asn Leu Val Glu Cys Leu Ser Asp Glu Phe Cys Leu
        675                 680                 685

Asp Glu Lys Arg Glu Leu Ser Glu Lys Val Lys Gln Ala Lys Arg Ile
    690                 695                 700

Ser Asp Glu Arg Asn Leu Leu Gln Asp Ser Asn Phe Arg Cys Ile Asn
705                 710                 715                 720

Gly Glu Glu Asp Arg Gly Trp Arg Gly Ser Thr His Ile Thr Ile Gln
                725                 730                 735

Gly Gly Asn Asp Val Phe Lys Arg Asn Phe Val Thr Leu Pro Gly Ala
            740                 745                 750

Phe Asp Ala Cys Tyr Pro Thr Tyr Leu Tyr Gln Arg Ile Asp Glu Ser
        755                 760                 765

Lys Leu Lys Ala Tyr Thr Arg Tyr Lys Leu Arg Gly Tyr Ile Glu Asp
```

770 775 780

Ser Gln Asp Leu Glu Ile Tyr Leu Ile Arg Tyr Asn Ala Lys His Glu
785 790 795 800

Thr Val Asn Val Pro Gly Thr Glu Ser Leu Trp Ser Leu Cys Thr Glu
805 810 815

Ser Pro Ile Gly Thr Cys Gly Glu Pro Asn Arg Cys Ala Pro Gln Ile
820 825 830

Glu Trp Asn Pro Asp Leu Asn Cys Ser Cys Lys Ala Gly Glu Lys Cys
835 840 845

Ala His His Ser His His Phe Ser Leu Asp Ile Asp Val Gly Cys Thr
850 855 860

Asp Leu Asn Glu Asp Leu Gly Val Trp Val Ile Phe Lys Ile Lys Thr
865 870 875 880

Gln Asp Gly His Ala Arg Leu Gly Asn Leu Glu Phe Leu Glu Glu Lys
885 890 895

Pro Leu Leu Gly Glu Ala Leu Ala Arg Val Lys Arg Ala Glu Lys Lys
900 905 910

Trp Arg Asp Lys Arg Glu Lys Leu Gln Phe Glu Thr Lys Ile Val Tyr
915 920 925

Lys Glu Ala Lys Glu Ser Val Asp Ala Leu Phe Val Asp Ser Gln Tyr
930 935 940

Asn Arg Leu Gln Ala Asp Thr Asn Ile Thr Met Ile His Ala Ala Asp
945 950 955 960

Lys Arg Val His Arg Ile Arg Glu Ala Tyr Leu Pro Glu Leu Ser Val
965 970 975

Ile Pro Gly Val Asn Ala Ala Ile Phe Glu Glu Leu Glu Gly Leu Ile
980 985 990

Phe Thr Ala Phe Ser Leu Tyr Asp Ala Arg Asn Val Ile Lys Asn Gly
995 1000 1005

Asp Phe Asn Asn Gly Leu Ser Cys Trp Asn Val Lys Gly His Val
1010 1015 1020

Asp Val Gln Gln Ser His His Arg Ser Val Leu Val Leu Pro Glu
1025 1030 1035

Trp Glu Ala Glu Val Ser Gln Glu Val Arg Val Cys Pro Gly Arg
1040 1045 1050

Gly Tyr Ile Leu Arg Val Thr Ala Tyr Lys Glu Gly Tyr Gly Glu
1055 1060 1065

Gly Cys Val Thr Ile His Glu Ile Glu Asn His Thr Glu Lys Leu
1070 1075 1080

Lys Phe Arg Asn Cys Glu Glu Glu Asp Ile Tyr Pro Thr Asn Thr
1085 1090 1095

Val Thr Cys His Asp Tyr Asn Val Asn Gln Gly Ala Glu Gly Cys
1100 1105 1110

Ala Asp Thr Cys Asn Ser Arg His Arg Gly Tyr Asp Glu Thr Tyr
1115 1120 1125

Gly Asn Asp Ser Ser Val Ser Ala Asp Tyr Met Pro Val Tyr Glu
1130 1135 1140

Glu Glu Val Tyr Thr Asp Gly Arg Arg Asp Asn Pro Cys Glu Met
1145 1150 1155

Glu Arg Gly Tyr Thr Pro Leu Pro Val Asp Tyr Val Thr Lys Glu
1160 1165 1170

Leu Glu Tyr Phe Pro Glu Thr Asn Thr Val Trp Ile Glu Ile Gly
1175 1180 1185

```
Glu Thr  Glu Gly Thr Phe Ile  Val Asp Ser Val Glu  Leu Leu Leu
    1190                 1195                 1200

Met Glu  Glu
    1205


<210> SEQ ID NO 47
<211> LENGTH: 1181
<212> TYPE: PRT
<213> ORGANISM: Bacillus thuringiensis

<400> SEQUENCE: 47

Met Asp Asn Asn Ser Glu Asn Gln Cys Val Pro Tyr Asn Cys Leu Ser
1               5                   10                  15

Asn Leu Glu Glu Ile Thr Leu Asn Gly Glu Arg Leu Ser Thr Asn Ser
            20                  25                  30

Thr Pro Ile Asn Ile Ser Met Ser Val Ser Lys Phe Leu Leu Thr Glu
        35                  40                  45

Leu Ile Pro Gly Leu Gly Phe Val Phe Gly Leu Leu Asp Ala Ile Trp
    50                  55                  60

Gly Phe Ile Gly Pro Asp Gln Trp Thr Glu Phe Ile Glu His Ile Glu
65                  70                  75                  80

Glu Leu Ile Gly Gln Arg Ile Thr Val Val Val Arg Asn Thr Ala Ile
                85                  90                  95

Arg Glu Leu Glu Gly Met Ala Arg Val Tyr Gln Thr Tyr Ala Thr Ala
            100                 105                 110

Phe Ala Ala Trp Glu Lys Asp Pro Asn Asn Pro Glu Leu Arg Glu Ala
        115                 120                 125

Leu Arg Ala Gln Phe Thr Ala Thr Glu Thr Tyr Ile Ser Gly Arg Ile
    130                 135                 140

Ser Val Leu Thr Ile Glu Asp Tyr Gln Val Gln Leu Leu Ser Val Tyr
145                 150                 155                 160

Ala Gln Ala Thr Asn Leu His Leu Ser Leu Leu Arg Asp Val Val Phe
                165                 170                 175

Trp Gly Gln Arg Trp Gly Phe Ser Thr Thr Thr Leu Asn Asn Tyr Tyr
            180                 185                 190

Ser Asp Leu Thr Arg Glu Ile Asn Glu Tyr Thr Asn Tyr Ala Val His
        195                 200                 205

Trp Tyr Asn Val Gly Leu Glu Gln Leu Gln Gly Pro Ser Phe Gln Glu
    210                 215                 220

Trp Val Ala Tyr Asn Arg Tyr Arg Arg Glu Leu Thr Leu Thr Val Leu
225                 230                 235                 240

Asp Ile Val Thr Leu Phe His Asn Tyr Asp Ile Arg Leu Tyr Pro Ile
                245                 250                 255

Pro Thr Ile Ser Gln Leu Thr Arg Glu Val Tyr Thr Asp Pro Ile Val
            260                 265                 270

Ser Gly Ile Gly Gln Pro Asn Ser Trp Asp Phe Pro Thr Phe Ser Glu
        275                 280                 285

Ala Glu Asn Lys Ser Ile Arg Thr Pro His Leu Met Asp Phe Leu Arg
    290                 295                 300

Asn Leu Thr Ile Phe Thr Asp Ser Ala Arg Tyr Gly Ala Ile Tyr His
305                 310                 315                 320

Phe Trp Gly Gly His Gln Ile Ser Ser Ser Leu Val Gly Gly Ser Asn
                325                 330                 335

Ile Thr Phe Pro Thr Tyr Gly Ser Asn Val Ser Gln Gly Ser Pro Trp
```

```
            340                 345                 350

Ile Leu Val Thr Asn Gly Ile Pro Ile Tyr Arg Thr Leu Ser Asn Pro
        355                 360                 365

Tyr Tyr Arg Phe Leu Phe Gln Ser Val Gly Ser Ala Arg Leu Arg Cys
    370                 375                 380

Val Leu Gly Val Gln Phe His Met Asp Asn Arg Ala Phe Thr Tyr Arg
385                 390                 395                 400

Glu Lys Gly Thr Val Asp Ser Phe Asp Glu Leu Pro Pro Thr Asp Ala
                405                 410                 415

Ser Val Ser Pro Ser Glu Gly Tyr Ser His Arg Leu Cys His Ala Thr
            420                 425                 430

Leu Phe Gln Val Arg Thr Gly Gly Gly Gly Ala Val Ser Phe Ser Arg
        435                 440                 445

Thr Asp Gly Val Val Phe Ser Trp Thr His Arg Ser Ala Thr Pro Thr
    450                 455                 460

Asn Thr Ile Asp Pro Asn Val Ile Thr Gln Ile Pro Ala Val Lys Gly
465                 470                 475                 480

Arg Ser Leu Phe Asn Gly Ala Val Ile Lys Gly Pro Gly Phe Thr Gly
                485                 490                 495

Gly Asp Leu Val Arg Leu Asn Arg Asn Asn Gly Asn Ile Gln Asn Arg
            500                 505                 510

Gly His Leu Pro Ile Pro Ile Gln Phe Ser Ser Arg Ser Thr Arg Tyr
        515                 520                 525

Arg Val Arg Leu Arg Tyr Ala Ser Ala Thr Pro Ile Gln Val Asn Val
    530                 535                 540

His Trp Glu Asn Ser Thr Ile Phe Ser Gly Ile Val Pro Ala Thr Ala
545                 550                 555                 560

Gln Ser Leu Asp Lys Leu Gln Ser Asn Asp Phe Gly Tyr Phe Glu Ile
                565                 570                 575

Ala Asn Thr Ile Ser Ser Ser Leu Asp Gly Ile Val Gly Ile Arg Asn
            580                 585                 590

Phe Ser Ala Asn Ala Asp Leu Ile Ile Asp Arg Phe Glu Phe Ile Pro
        595                 600                 605

Val Asn Ala Thr Ser Glu Ala Glu Tyr Asp Leu Glu Arg Ala Gln Glu
    610                 615                 620

Ala Val Asn Ala Leu Phe Thr Ser Thr Asn Gln Arg Gly Leu Lys Ala
625                 630                 635                 640

Asn Val Thr Asp Tyr Tyr Ile Asp Gln Val Ser Asn Leu Val Glu Cys
                645                 650                 655

Leu Ser Asp Glu Phe Cys Leu Asp Glu Lys Arg Glu Leu Ser Glu Lys
            660                 665                 670

Val Lys Gln Ala Lys Arg Ile Ser Asp Glu Arg Asn Leu Leu Gln Asp
        675                 680                 685

Ser Asn Phe Arg Cys Ile Asn Gly Glu Glu Asp Arg Gly Trp Arg Gly
    690                 695                 700

Ser Thr His Ile Thr Ile Gln Gly Gly Asn Asp Val Phe Lys Arg Asn
705                 710                 715                 720

Phe Val Thr Leu Pro Gly Ala Phe Asp Ala Cys Tyr Pro Thr Tyr Leu
                725                 730                 735

Tyr Gln Arg Ile Asp Glu Ser Lys Leu Lys Ala Tyr Thr Arg Tyr Lys
            740                 745                 750

Leu Arg Gly Tyr Ile Glu Asp Ser Gln Asp Leu Glu Ile Tyr Leu Ile
        755                 760                 765
```

```
Arg Tyr Asn Ala Lys His Glu Thr Val Asn Val Pro Gly Thr Glu Ser
    770                 775                 780

Leu Trp Ser Leu Cys Thr Glu Ser Pro Ile Gly Thr Cys Gly Glu Pro
785                 790                 795                 800

Asn Arg Cys Ala Pro Gln Ile Glu Trp Asn Pro Asp Leu Asn Cys Ser
                805                 810                 815

Cys Lys Ala Gly Glu Lys Cys Ala His His Ser His His Phe Ser Leu
            820                 825                 830

Asp Ile Asp Val Gly Cys Thr Asp Leu Asn Glu Asp Leu Gly Val Trp
        835                 840                 845

Val Ile Phe Lys Ile Lys Thr Gln Asp Gly His Ala Arg Leu Gly Asn
    850                 855                 860

Leu Glu Phe Leu Glu Glu Lys Pro Leu Leu Gly Glu Ala Leu Ala Arg
865                 870                 875                 880

Val Lys Arg Ala Glu Lys Lys Trp Arg Asp Lys Arg Glu Lys Leu Gln
                885                 890                 895

Phe Glu Thr Lys Ile Val Tyr Lys Glu Ala Lys Glu Ser Val Asp Ala
            900                 905                 910

Leu Phe Val Asp Ser Gln Tyr Asn Arg Leu Gln Ala Asp Thr Asn Ile
        915                 920                 925

Thr Met Ile His Ala Ala Asp Lys Arg Val His Arg Ile Arg Glu Ala
    930                 935                 940

Tyr Leu Pro Glu Leu Ser Val Ile Pro Gly Val Asn Ala Ala Ile Phe
945                 950                 955                 960

Glu Glu Leu Glu Gly Leu Ile Phe Thr Ala Phe Ser Leu Tyr Asp Ala
                965                 970                 975

Arg Asn Val Ile Lys Asn Gly Asp Phe Asn Asn Gly Leu Ser Cys Trp
            980                 985                 990

Asn Val Lys Gly His Val Asp Val  Gln Gln Ser His His  Arg Ser Val
        995                 1000                1005

Leu Val  Leu Pro Glu Trp Glu  Ala Glu Val Ser Gln  Glu Val Arg
    1010                1015                1020

Val Cys  Pro Gly Arg Gly Tyr  Ile Leu Arg Val Thr  Ala Tyr Lys
    1025                1030                1035

Glu Gly  Tyr Gly Glu Gly Cys  Val Thr Ile His Glu  Ile Glu Asn
    1040                1045                1050

His Thr  Glu Lys Leu Lys Phe  Arg Asn Cys Glu Glu  Glu Asp Ile
    1055                1060                1065

Tyr Pro  Thr Asn Thr Val Thr  Cys His Asp Tyr Asn  Val Asn Gln
    1070                1075                1080

Gly Ala  Glu Gly Cys Ala Asp  Thr Cys Asn Ser Arg  His Arg Gly
    1085                1090                1095

Tyr Asp  Glu Thr Tyr Gly Asn  Asp Ser Ser Val Ser  Ala Asp Tyr
    1100                1105                1110

Met Pro  Val Tyr Glu Glu Glu  Val Tyr Thr Asp Gly  Arg Arg Asp
    1115                1120                1125

Asn Pro  Cys Glu Met Glu Arg  Gly Tyr Thr Pro Leu  Pro Val Asp
    1130                1135                1140

Tyr Val  Thr Lys Glu Leu Glu  Tyr Phe Pro Glu Thr  Asn Thr Val
    1145                1150                1155

Trp Ile  Glu Ile Gly Glu Thr  Glu Gly Thr Phe Ile  Val Asp Ser
    1160                1165                1170
```

```
Val Glu  Leu Leu Leu Met Glu  Glu
    1175                 1180


<210> SEQ ID NO 48
<211> LENGTH: 1143
<212> TYPE: PRT
<213> ORGANISM: Bacillus thuringiensis

<400> SEQUENCE: 48

Met Ser Val Ser Lys Phe Leu Leu Thr Glu Leu Ile Pro Gly Leu Gly
1               5                   10                  15

Phe Val Phe Gly Leu Leu Asp Ala Ile Trp Gly Phe Ile Gly Pro Asp
            20                  25                  30

Gln Trp Thr Glu Phe Ile Glu His Ile Glu Glu Leu Ile Gly Gln Arg
        35                  40                  45

Ile Thr Val Val Val Arg Asn Thr Ala Ile Arg Glu Leu Glu Gly Met
    50                  55                  60

Ala Arg Val Tyr Gln Thr Tyr Ala Thr Ala Phe Ala Ala Trp Glu Lys
65                  70                  75                  80

Asp Pro Asn Asn Pro Glu Leu Arg Glu Ala Leu Arg Ala Gln Phe Thr
                85                  90                  95

Ala Thr Glu Thr Tyr Ile Ser Gly Arg Ile Ser Val Leu Thr Ile Glu
            100                 105                 110

Asp Tyr Gln Val Gln Leu Leu Ser Val Tyr Ala Gln Ala Thr Asn Leu
        115                 120                 125

His Leu Ser Leu Leu Arg Asp Val Val Phe Trp Gly Gln Arg Trp Gly
    130                 135                 140

Phe Ser Thr Thr Thr Leu Asn Asn Tyr Tyr Ser Asp Leu Thr Arg Glu
145                 150                 155                 160

Ile Asn Glu Tyr Thr Asn Tyr Ala Val His Trp Tyr Asn Val Gly Leu
                165                 170                 175

Glu Gln Leu Gln Gly Pro Ser Phe Gln Glu Trp Val Ala Tyr Asn Arg
            180                 185                 190

Tyr Arg Arg Glu Leu Thr Leu Thr Val Leu Asp Ile Val Thr Leu Phe
        195                 200                 205

His Asn Tyr Asp Ile Arg Leu Tyr Pro Ile Pro Thr Ile Ser Gln Leu
    210                 215                 220

Thr Arg Glu Val Tyr Thr Asp Pro Ile Val Ser Gly Ile Gly Gln Pro
225                 230                 235                 240

Asn Ser Trp Asp Phe Pro Thr Phe Ser Glu Ala Glu Asn Lys Ser Ile
                245                 250                 255

Arg Thr Pro His Leu Met Asp Phe Leu Arg Asn Leu Thr Ile Phe Thr
            260                 265                 270

Asp Ser Ala Arg Tyr Gly Ala Ile Tyr His Phe Trp Gly Gly His Gln
        275                 280                 285

Ile Ser Ser Ser Leu Val Gly Gly Ser Asn Ile Thr Phe Pro Thr Tyr
    290                 295                 300

Gly Ser Asn Val Ser Gln Gly Ser Pro Trp Ile Leu Val Thr Asn Gly
305                 310                 315                 320

Ile Pro Ile Tyr Arg Thr Leu Ser Asn Pro Tyr Tyr Arg Phe Leu Phe
                325                 330                 335

Gln Ser Val Gly Ser Ala Arg Leu Arg Cys Val Leu Gly Val Gln Phe
            340                 345                 350

His Met Asp Asn Arg Ala Phe Thr Tyr Arg Glu Lys Gly Thr Val Asp
        355                 360                 365
```

-continued

```
Ser Phe Asp Glu Leu Pro Pro Thr Asp Ala Ser Val Ser Pro Ser Glu
    370                 375                 380

Gly Tyr Ser His Arg Leu Cys His Ala Thr Leu Phe Gln Val Arg Thr
385                 390                 395                 400

Gly Gly Gly Gly Ala Val Ser Phe Ser Arg Thr Asp Gly Val Val Phe
                405                 410                 415

Ser Trp Thr His Arg Ser Ala Thr Pro Thr Asn Thr Ile Asp Pro Asn
            420                 425                 430

Val Ile Thr Gln Ile Pro Ala Val Lys Gly Arg Ser Leu Phe Asn Gly
        435                 440                 445

Ala Val Ile Lys Gly Pro Gly Phe Thr Gly Gly Asp Leu Val Arg Leu
    450                 455                 460

Asn Arg Asn Asn Gly Asn Ile Gln Asn Arg Gly His Leu Pro Ile Pro
465                 470                 475                 480

Ile Gln Phe Ser Ser Arg Ser Thr Arg Tyr Arg Val Arg Leu Arg Tyr
                485                 490                 495

Ala Ser Ala Thr Pro Ile Gln Val Asn Val His Trp Glu Asn Ser Thr
            500                 505                 510

Ile Phe Ser Gly Ile Val Pro Ala Thr Ala Gln Ser Leu Asp Lys Leu
        515                 520                 525

Gln Ser Asn Asp Phe Gly Tyr Phe Glu Ile Ala Asn Thr Ile Ser Ser
    530                 535                 540

Ser Leu Asp Gly Ile Val Gly Ile Arg Asn Phe Ser Ala Asn Ala Asp
545                 550                 555                 560

Leu Ile Ile Asp Arg Phe Glu Phe Ile Pro Val Asn Ala Thr Ser Glu
                565                 570                 575

Ala Glu Tyr Asp Leu Glu Arg Ala Gln Glu Ala Val Asn Ala Leu Phe
            580                 585                 590

Thr Ser Thr Asn Gln Arg Gly Leu Lys Ala Asn Val Thr Asp Tyr Tyr
        595                 600                 605

Ile Asp Gln Val Ser Asn Leu Val Glu Cys Leu Ser Asp Glu Phe Cys
    610                 615                 620

Leu Asp Glu Lys Arg Glu Leu Ser Glu Lys Val Lys Gln Ala Lys Arg
625                 630                 635                 640

Ile Ser Asp Glu Arg Asn Leu Leu Gln Asp Ser Asn Phe Arg Cys Ile
                645                 650                 655

Asn Gly Glu Glu Asp Arg Gly Trp Arg Gly Ser Thr His Ile Thr Ile
            660                 665                 670

Gln Gly Gly Asn Asp Val Phe Lys Arg Asn Phe Val Thr Leu Pro Gly
        675                 680                 685

Ala Phe Asp Ala Cys Tyr Pro Thr Tyr Leu Tyr Gln Arg Ile Asp Glu
    690                 695                 700

Ser Lys Leu Lys Ala Tyr Thr Arg Tyr Lys Leu Arg Gly Tyr Ile Glu
705                 710                 715                 720

Asp Ser Gln Asp Leu Glu Ile Tyr Leu Ile Arg Tyr Asn Ala Lys His
                725                 730                 735

Glu Thr Val Asn Val Pro Gly Thr Glu Ser Leu Trp Ser Leu Cys Thr
            740                 745                 750

Glu Ser Pro Ile Gly Thr Cys Gly Glu Pro Asn Arg Cys Ala Pro Gln
        755                 760                 765

Ile Glu Trp Asn Pro Asp Leu Asn Cys Ser Cys Lys Ala Gly Glu Lys
    770                 775                 780
```

```
Cys Ala His His Ser His His Phe Ser Leu Asp Ile Asp Val Gly Cys
785                 790                 795                 800

Thr Asp Leu Asn Glu Asp Leu Gly Val Trp Val Ile Phe Lys Ile Lys
                805                 810                 815

Thr Gln Asp Gly His Ala Arg Leu Gly Asn Leu Glu Phe Leu Glu Glu
            820                 825                 830

Lys Pro Leu Leu Gly Glu Ala Leu Ala Arg Val Lys Arg Ala Glu Lys
        835                 840                 845

Lys Trp Arg Asp Lys Arg Glu Lys Leu Gln Phe Glu Thr Lys Ile Val
    850                 855                 860

Tyr Lys Glu Ala Lys Glu Ser Val Asp Ala Leu Phe Val Asp Ser Gln
865                 870                 875                 880

Tyr Asn Arg Leu Gln Ala Asp Thr Asn Ile Thr Met Ile His Ala Ala
                885                 890                 895

Asp Lys Arg Val His Arg Ile Arg Glu Ala Tyr Leu Pro Glu Leu Ser
            900                 905                 910

Val Ile Pro Gly Val Asn Ala Ala Ile Phe Glu Glu Leu Glu Gly Leu
        915                 920                 925

Ile Phe Thr Ala Phe Ser Leu Tyr Asp Ala Arg Asn Val Ile Lys Asn
    930                 935                 940

Gly Asp Phe Asn Asn Gly Leu Ser Cys Trp Asn Val Lys Gly His Val
945                 950                 955                 960

Asp Val Gln Gln Ser His His Arg Ser Val Leu Val Leu Pro Glu Trp
                965                 970                 975

Glu Ala Glu Val Ser Gln Glu Val Arg Val Cys Pro Gly Arg Gly Tyr
            980                 985                 990

Ile Leu Arg Val Thr Ala Tyr Lys  Glu Gly Tyr Gly Glu  Gly Cys Val
        995                 1000                 1005

Thr Ile  His Glu Ile Glu Asn  His Thr Glu Lys Leu  Lys Phe Arg
    1010                 1015                 1020

Asn Cys  Glu Glu Glu Asp Ile  Tyr Pro Thr Asn Thr  Val Thr Cys
    1025                 1030                 1035

His Asp  Tyr Asn Val Asn Gln  Gly Ala Glu Gly Cys  Ala Asp Thr
    1040                 1045                 1050

Cys Asn  Ser Arg His Arg Gly  Tyr Asp Glu Thr Tyr  Gly Asn Asp
    1055                 1060                 1065

Ser Ser  Val Ser Ala Asp Tyr  Met Pro Val Tyr Glu  Glu Glu Val
    1070                 1075                 1080

Tyr Thr  Asp Gly Arg Arg Asp  Asn Pro Cys Glu Met  Glu Arg Gly
    1085                 1090                 1095

Tyr Thr  Pro Leu Pro Val Asp  Tyr Val Thr Lys Glu  Leu Glu Tyr
    1100                 1105                 1110

Phe Pro  Glu Thr Asn Thr Val  Trp Ile Glu Ile Gly  Glu Thr Glu
    1115                 1120                 1125

Gly Thr  Phe Ile Val Asp Ser  Val Glu Leu Leu Leu  Met Glu Glu
    1130                 1135                 1140


<210> SEQ ID NO 49
<211> LENGTH: 634
<212> TYPE: PRT
<213> ORGANISM: Bacillus thuringiensis

<400> SEQUENCE: 49

Met Asn Trp Leu Ser Lys Lys Cys Leu Ser Thr Leu Asn Val Asn Leu
1               5                   10                  15
```

-continued

```
Tyr Lys Ser Gln Phe Gln Gly Glu Tyr Met Asp Asn Asn Ser Glu Asn
            20                  25                  30

Gln Cys Val Pro Tyr Asn Cys Leu Ser Asn Leu Glu Glu Ile Thr Leu
        35                  40                  45

Asn Gly Glu Arg Leu Ser Thr Asn Ser Thr Pro Ile Asn Ile Ser Met
    50                  55                  60

Ser Val Ser Lys Phe Leu Leu Thr Glu Leu Ile Pro Gly Leu Gly Phe
65                  70                  75                  80

Val Phe Gly Leu Leu Asp Ala Ile Trp Gly Phe Ile Gly Pro Asp Gln
                85                  90                  95

Trp Thr Glu Phe Ile Glu His Ile Glu Glu Leu Ile Gly Gln Arg Ile
            100                 105                 110

Thr Val Val Val Arg Asn Thr Ala Ile Arg Glu Leu Glu Gly Met Ala
        115                 120                 125

Arg Val Tyr Gln Thr Tyr Ala Thr Ala Phe Ala Ala Trp Glu Lys Asp
    130                 135                 140

Pro Asn Asn Pro Glu Leu Arg Glu Ala Leu Arg Ala Gln Phe Thr Ala
145                 150                 155                 160

Thr Glu Thr Tyr Ile Ser Gly Arg Ile Ser Val Leu Thr Ile Glu Asp
                165                 170                 175

Tyr Gln Val Gln Leu Leu Ser Val Tyr Ala Gln Ala Thr Asn Leu His
            180                 185                 190

Leu Ser Leu Leu Arg Asp Val Val Phe Trp Gly Gln Arg Trp Gly Phe
        195                 200                 205

Ser Thr Thr Thr Leu Asn Asn Tyr Tyr Ser Asp Leu Thr Arg Glu Ile
    210                 215                 220

Asn Glu Tyr Thr Asn Tyr Ala Val His Trp Tyr Asn Val Gly Leu Glu
225                 230                 235                 240

Gln Leu Gln Gly Pro Ser Phe Gln Glu Trp Val Ala Tyr Asn Arg Tyr
                245                 250                 255

Arg Arg Glu Leu Thr Leu Thr Val Leu Asp Ile Val Thr Leu Phe His
            260                 265                 270

Asn Tyr Asp Ile Arg Leu Tyr Pro Ile Pro Thr Ile Ser Gln Leu Thr
        275                 280                 285

Arg Glu Val Tyr Thr Asp Pro Ile Val Ser Gly Ile Gly Gln Pro Asn
    290                 295                 300

Ser Trp Asp Phe Pro Thr Phe Ser Glu Ala Glu Asn Lys Ser Ile Arg
305                 310                 315                 320

Thr Pro His Leu Met Asp Phe Leu Arg Asn Leu Thr Ile Phe Thr Asp
                325                 330                 335

Ser Ala Arg Tyr Gly Ala Ile Tyr His Phe Trp Gly Gly His Gln Ile
            340                 345                 350

Ser Ser Ser Leu Val Gly Gly Ser Asn Ile Thr Phe Pro Thr Tyr Gly
        355                 360                 365

Ser Asn Val Ser Gln Gly Ser Pro Trp Ile Leu Val Thr Asn Gly Ile
    370                 375                 380

Pro Ile Tyr Arg Thr Leu Ser Asn Pro Tyr Tyr Arg Phe Leu Phe Gln
385                 390                 395                 400

Ser Val Gly Ser Ala Arg Leu Arg Cys Val Leu Gly Val Gln Phe His
                405                 410                 415

Met Asp Asn Arg Ala Phe Thr Tyr Arg Glu Lys Gly Thr Val Asp Ser
            420                 425                 430
```

```
Phe Asp Glu Leu Pro Pro Thr Asp Ala Ser Val Ser Pro Ser Glu Gly
        435                 440                 445

Tyr Ser His Arg Leu Cys His Ala Thr Leu Phe Gln Val Arg Thr Gly
    450                 455                 460

Gly Gly Gly Ala Val Ser Phe Ser Arg Thr Asp Gly Val Val Phe Ser
465                 470                 475                 480

Trp Thr His Arg Ser Ala Thr Pro Thr Asn Thr Ile Asp Pro Asn Val
                485                 490                 495

Ile Thr Gln Ile Pro Ala Val Lys Gly Arg Ser Leu Phe Asn Gly Ala
            500                 505                 510

Val Ile Lys Gly Pro Gly Phe Thr Gly Gly Asp Leu Val Arg Leu Asn
        515                 520                 525

Arg Asn Asn Gly Asn Ile Gln Asn Arg Gly His Leu Pro Ile Pro Ile
    530                 535                 540

Gln Phe Ser Ser Arg Ser Thr Arg Tyr Arg Val Arg Leu Arg Tyr Ala
545                 550                 555                 560

Ser Ala Thr Pro Ile Gln Val Asn Val His Trp Glu Asn Ser Thr Ile
                565                 570                 575

Phe Ser Gly Ile Val Pro Ala Thr Ala Gln Ser Leu Asp Lys Leu Gln
            580                 585                 590

Ser Asn Asp Phe Gly Tyr Phe Glu Ile Ala Asn Thr Ile Ser Ser Ser
        595                 600                 605

Leu Asp Gly Ile Val Gly Ile Arg Asn Phe Ser Ala Asn Ala Asp Leu
    610                 615                 620

Ile Ile Asp Arg Phe Glu Phe Ile Pro Val
625                 630


<210> SEQ ID NO 50
<211> LENGTH: 609
<212> TYPE: PRT
<213> ORGANISM: Bacillus thuringiensis

<400> SEQUENCE: 50

Met Asp Asn Asn Ser Glu Asn Gln Cys Val Pro Tyr Asn Cys Leu Ser
1               5                   10                  15

Asn Leu Glu Glu Ile Thr Leu Asn Gly Glu Arg Leu Ser Thr Asn Ser
            20                  25                  30

Thr Pro Ile Asn Ile Ser Met Ser Val Ser Lys Phe Leu Leu Thr Glu
        35                  40                  45

Leu Ile Pro Gly Leu Gly Phe Val Phe Gly Leu Leu Asp Ala Ile Trp
    50                  55                  60

Gly Phe Ile Gly Pro Asp Gln Trp Thr Glu Phe Ile Glu His Ile Glu
65                  70                  75                  80

Glu Leu Ile Gly Gln Arg Ile Thr Val Val Val Arg Asn Thr Ala Ile
                85                  90                  95

Arg Glu Leu Glu Gly Met Ala Arg Val Tyr Gln Thr Tyr Ala Thr Ala
            100                 105                 110

Phe Ala Ala Trp Glu Lys Asp Pro Asn Asn Pro Glu Leu Arg Glu Ala
        115                 120                 125

Leu Arg Ala Gln Phe Thr Ala Thr Glu Thr Tyr Ile Ser Gly Arg Ile
    130                 135                 140

Ser Val Leu Thr Ile Glu Asp Tyr Gln Val Gln Leu Leu Ser Val Tyr
145                 150                 155                 160

Ala Gln Ala Thr Asn Leu His Leu Ser Leu Leu Arg Asp Val Val Phe
                165                 170                 175
```

```
Trp Gly Gln Arg Trp Gly Phe Ser Thr Thr Thr Leu Asn Asn Tyr Tyr
            180                 185                 190

Ser Asp Leu Thr Arg Glu Ile Asn Glu Tyr Thr Asn Tyr Ala Val His
        195                 200                 205

Trp Tyr Asn Val Gly Leu Glu Gln Leu Gln Gly Pro Ser Phe Gln Glu
    210                 215                 220

Trp Val Ala Tyr Asn Arg Tyr Arg Arg Glu Leu Thr Leu Thr Val Leu
225                 230                 235                 240

Asp Ile Val Thr Leu Phe His Asn Tyr Asp Ile Arg Leu Tyr Pro Ile
                245                 250                 255

Pro Thr Ile Ser Gln Leu Thr Arg Glu Val Tyr Thr Asp Pro Ile Val
            260                 265                 270

Ser Gly Ile Gly Gln Pro Asn Ser Trp Asp Phe Pro Thr Phe Ser Glu
        275                 280                 285

Ala Glu Asn Lys Ser Ile Arg Thr Pro His Leu Met Asp Phe Leu Arg
    290                 295                 300

Asn Leu Thr Ile Phe Thr Asp Ser Ala Arg Tyr Gly Ala Ile Tyr His
305                 310                 315                 320

Phe Trp Gly Gly His Gln Ile Ser Ser Ser Leu Val Gly Gly Ser Asn
                325                 330                 335

Ile Thr Phe Pro Thr Tyr Gly Ser Asn Val Ser Gln Gly Ser Pro Trp
            340                 345                 350

Ile Leu Val Thr Asn Gly Ile Pro Ile Tyr Arg Thr Leu Ser Asn Pro
        355                 360                 365

Tyr Tyr Arg Phe Leu Phe Gln Ser Val Gly Ser Ala Arg Leu Arg Cys
    370                 375                 380

Val Leu Gly Val Gln Phe His Met Asp Asn Arg Ala Phe Thr Tyr Arg
385                 390                 395                 400

Glu Lys Gly Thr Val Asp Ser Phe Asp Glu Leu Pro Pro Thr Asp Ala
                405                 410                 415

Ser Val Ser Pro Ser Glu Gly Tyr Ser His Arg Leu Cys His Ala Thr
            420                 425                 430

Leu Phe Gln Val Arg Thr Gly Gly Gly Gly Ala Val Ser Phe Ser Arg
        435                 440                 445

Thr Asp Gly Val Val Phe Ser Trp Thr His Arg Ser Ala Thr Pro Thr
    450                 455                 460

Asn Thr Ile Asp Pro Asn Val Ile Thr Gln Ile Pro Ala Val Lys Gly
465                 470                 475                 480

Arg Ser Leu Phe Asn Gly Ala Val Ile Lys Gly Pro Gly Phe Thr Gly
                485                 490                 495

Gly Asp Leu Val Arg Leu Asn Arg Asn Asn Gly Asn Ile Gln Asn Arg
            500                 505                 510

Gly His Leu Pro Ile Pro Ile Gln Phe Ser Ser Arg Ser Thr Arg Tyr
        515                 520                 525

Arg Val Arg Leu Arg Tyr Ala Ser Ala Thr Pro Ile Gln Val Asn Val
    530                 535                 540

His Trp Glu Asn Ser Thr Ile Phe Ser Gly Ile Val Pro Ala Thr Ala
545                 550                 555                 560

Gln Ser Leu Asp Lys Leu Gln Ser Asn Asp Phe Gly Tyr Phe Glu Ile
                565                 570                 575

Ala Asn Thr Ile Ser Ser Ser Leu Asp Gly Ile Val Gly Ile Arg Asn
            580                 585                 590
```

-continued

Phe Ser Ala Asn Ala Asp Leu Ile Ile Asp Arg Phe Glu Phe Ile Pro
595 600 605

Val

<210> SEQ ID NO 51
<211> LENGTH: 571
<212> TYPE: PRT
<213> ORGANISM: Bacillus thuringiensis

<400> SEQUENCE: 51

Met Ser Val Ser Lys Phe Leu Leu Thr Glu Leu Ile Pro Gly Leu Gly
1 5 10 15

Phe Val Phe Gly Leu Leu Asp Ala Ile Trp Gly Phe Ile Gly Pro Asp
20 25 30

Gln Trp Thr Glu Phe Ile Glu His Ile Glu Glu Leu Ile Gly Gln Arg
35 40 45

Ile Thr Val Val Val Arg Asn Thr Ala Ile Arg Glu Leu Glu Gly Met
50 55 60

Ala Arg Val Tyr Gln Thr Tyr Ala Thr Ala Phe Ala Ala Trp Glu Lys
65 70 75 80

Asp Pro Asn Asn Pro Glu Leu Arg Glu Ala Leu Arg Ala Gln Phe Thr
85 90 95

Ala Thr Glu Thr Tyr Ile Ser Gly Arg Ile Ser Val Leu Thr Ile Glu
100 105 110

Asp Tyr Gln Val Gln Leu Leu Ser Val Tyr Ala Gln Ala Thr Asn Leu
115 120 125

His Leu Ser Leu Leu Arg Asp Val Val Phe Trp Gly Gln Arg Trp Gly
130 135 140

Phe Ser Thr Thr Thr Leu Asn Asn Tyr Tyr Ser Asp Leu Thr Arg Glu
145 150 155 160

Ile Asn Glu Tyr Thr Asn Tyr Ala Val His Trp Tyr Asn Val Gly Leu
165 170 175

Glu Gln Leu Gln Gly Pro Ser Phe Gln Glu Trp Val Ala Tyr Asn Arg
180 185 190

Tyr Arg Arg Glu Leu Thr Leu Thr Val Leu Asp Ile Val Thr Leu Phe
195 200 205

His Asn Tyr Asp Ile Arg Leu Tyr Pro Ile Pro Thr Ile Ser Gln Leu
210 215 220

Thr Arg Glu Val Tyr Thr Asp Pro Ile Val Ser Gly Ile Gly Gln Pro
225 230 235 240

Asn Ser Trp Asp Phe Pro Thr Phe Ser Glu Ala Glu Asn Lys Ser Ile
245 250 255

Arg Thr Pro His Leu Met Asp Phe Leu Arg Asn Leu Thr Ile Phe Thr
260 265 270

Asp Ser Ala Arg Tyr Gly Ala Ile Tyr His Phe Trp Gly Gly His Gln
275 280 285

Ile Ser Ser Ser Leu Val Gly Gly Ser Asn Ile Thr Phe Pro Thr Tyr
290 295 300

Gly Ser Asn Val Ser Gln Gly Ser Pro Trp Ile Leu Val Thr Asn Gly
305 310 315 320

Ile Pro Ile Tyr Arg Thr Leu Ser Asn Pro Tyr Tyr Arg Phe Leu Phe
325 330 335

Gln Ser Val Gly Ser Ala Arg Leu Arg Cys Val Leu Gly Val Gln Phe
340 345 350

```
His Met Asp Asn Arg Ala Phe Thr Tyr Arg Glu Lys Gly Thr Val Asp
        355                 360                 365

Ser Phe Asp Glu Leu Pro Pro Thr Asp Ala Ser Val Ser Pro Ser Glu
    370                 375                 380

Gly Tyr Ser His Arg Leu Cys His Ala Thr Leu Phe Gln Val Arg Thr
385                 390                 395                 400

Gly Gly Gly Gly Ala Val Ser Phe Ser Arg Thr Asp Gly Val Val Phe
                405                 410                 415

Ser Trp Thr His Arg Ser Ala Thr Pro Thr Asn Thr Ile Asp Pro Asn
            420                 425                 430

Val Ile Thr Gln Ile Pro Ala Val Lys Gly Arg Ser Leu Phe Asn Gly
        435                 440                 445

Ala Val Ile Lys Gly Pro Gly Phe Thr Gly Gly Asp Leu Val Arg Leu
    450                 455                 460

Asn Arg Asn Asn Gly Asn Ile Gln Asn Arg Gly His Leu Pro Ile Pro
465                 470                 475                 480

Ile Gln Phe Ser Ser Arg Ser Thr Arg Tyr Arg Val Arg Leu Arg Tyr
                485                 490                 495

Ala Ser Ala Thr Pro Ile Gln Val Asn Val His Trp Glu Asn Ser Thr
            500                 505                 510

Ile Phe Ser Gly Ile Val Pro Ala Thr Ala Gln Ser Leu Asp Lys Leu
        515                 520                 525

Gln Ser Asn Asp Phe Gly Tyr Phe Glu Ile Ala Asn Thr Ile Ser Ser
    530                 535                 540

Ser Leu Asp Gly Ile Val Gly Ile Arg Asn Phe Ser Ala Asn Ala Asp
545                 550                 555                 560

Leu Ile Ile Asp Arg Phe Glu Phe Ile Pro Val
                565                 570


<210> SEQ ID NO 52
<211> LENGTH: 790
<212> TYPE: PRT
<213> ORGANISM: Bacillus thuringiensis

<400> SEQUENCE: 52

Met Lys Lys Met Asn Ser Tyr Gln Asn Lys Asn Glu Tyr Glu Ile Leu
1               5                   10                  15

Asp Ala Ser Glu Asn Thr Val Asn Ala Leu Asn Arg Tyr Pro Phe Ala
            20                  25                  30

Asn Asn Pro Tyr Ser Ser Ile Phe Ser Ser Cys Pro Arg Ser Gly Pro
        35                  40                  45

Gly Asn Trp Ile Asn Ile Leu Gly Asn Ala Val Ser Glu Ala Val Ser
    50                  55                  60

Ile Ser Gln Asp Ile Ile Ser Leu Leu Thr Gln Pro Ser Ile Ser Gly
65                  70                  75                  80

Ile Ile Ser Met Ala Phe Ser Leu Leu Ser Arg Met Ile Gly Ser Asn
                85                  90                  95

Gly Arg Ser Ile Ser Glu Leu Ser Met Cys Asp Leu Leu Ala Ile Ile
            100                 105                 110

Asp Leu Arg Val Asn Gln Ser Val Leu Asp Asp Gly Val Ala Asp Phe
        115                 120                 125

Asn Gly Ser Leu Val Ile Tyr Arg Asn Tyr Leu Glu Ala Leu Gln Arg
    130                 135                 140

Trp Asn Asn Asn Pro Asn Pro Ala Asn Ala Glu Glu Val Arg Thr Arg
145                 150                 155                 160
```

```
Phe Arg Glu Ser Asp Thr Ile Phe Asp Leu Ile Leu Thr Gln Gly Ser
                165                 170                 175

Leu Thr Asn Gly Gly Ser Leu Ala Arg Asn Asn Ala Gln Ile Leu Leu
            180                 185                 190

Leu Pro Ser Phe Ala Asn Ala Ala Tyr Phe His Leu Leu Leu Leu Arg
        195                 200                 205

Asp Ala Asn Val Tyr Gly Asn Asn Trp Gly Leu Phe Gly Val Thr Pro
    210                 215                 220

Asn Ile Asn Tyr Glu Ser Lys Leu Leu Asn Leu Ile Arg Leu Tyr Thr
225                 230                 235                 240

Asn Tyr Cys Thr His Trp Tyr Asn Gln Gly Leu Asn Glu Leu Arg Asn
                245                 250                 255

Arg Gly Ser Asn Ala Thr Ala Trp Leu Glu Phe His Arg Phe Arg Arg
            260                 265                 270

Asp Met Thr Leu Met Val Leu Asp Ile Val Ser Ser Phe Ser Ser Leu
        275                 280                 285

Asp Ile Thr Arg Tyr Pro Arg Ala Thr Asp Phe Gln Leu Ser Arg Ile
    290                 295                 300

Ile Tyr Thr Asp Pro Ile Gly Phe Val Asn Arg Ser Asp Pro Ser Ala
305                 310                 315                 320

Pro Arg Thr Trp Phe Ser Phe His Asn Gln Ala Asn Phe Ser Ala Leu
                325                 330                 335

Glu Ser Gly Ile Pro Ser Pro Ser Phe Ser Gln Phe Leu Asp Ser Met
            340                 345                 350

Arg Ile Ser Thr Gly Pro Leu Ser Leu Pro Ala Ser Pro Asn Ile His
        355                 360                 365

Arg Ala Arg Val Trp Tyr Gly Asn Gln Asn Asn Phe Asn Gly Ser Ser
    370                 375                 380

Ser Gln Thr Phe Gly Glu Ile Thr Asn Asp Asn Gln Thr Ile Ser Gly
385                 390                 395                 400

Leu Asn Ile Phe Arg Ile Asp Ser Gln Ala Val Asn Leu Asn Asn Thr
                405                 410                 415

Thr Phe Gly Val Ser Arg Ala Glu Phe Tyr His Asp Ala Ser Gln Gly
            420                 425                 430

Ser Gln Arg Ser Ile Tyr Gln Gly Phe Val Asp Thr Gly Gly Ala Ser
        435                 440                 445

Thr Ala Val Ala Gln Asn Ile Gln Thr Phe Phe Pro Gly Glu Asn Ser
    450                 455                 460

Ser Ile Pro Thr Pro Gln Asp Tyr Thr His Ile Leu Ser Arg Ser Thr
465                 470                 475                 480

Asn Leu Thr Gly Gly Leu Arg Gln Val Ala Ser Gly Arg Arg Ser Ser
                485                 490                 495

Leu Val Leu His Gly Trp Thr His Lys Ser Leu Ser Arg Gln Asn Arg
            500                 505                 510

Val Glu Pro Asn Arg Ile Thr Gln Val Pro Ala Val Lys Ala Ser Ser
        515                 520                 525

Pro Ser Asn Cys Thr Val Ile Ala Gly Pro Gly Phe Thr Gly Gly Asp
    530                 535                 540

Leu Val Arg Met Ser Ser Asn Cys Ser Val Ser Tyr Asn Phe Thr Pro
545                 550                 555                 560

Ala Asp Gln Gln Val Val Ile Arg Leu Arg Tyr Ala Cys Gln Gly Thr
                565                 570                 575
```

-continued

```
Ala Ser Leu Arg Ile Thr Phe Gly Asn Gly Ser Ser Gln Ile Ile Pro
            580                 585                 590

Leu Val Ser Thr Thr Ser Ser Ile Asn Asn Leu Gln Tyr Glu Asn Phe
        595                 600                 605

Ser Phe Ala Ser Gly Pro Asn Ser Val Asn Phe Leu Ser Ala Gly Thr
    610                 615                 620

Ser Ile Thr Ile Gln Asn Ile Ser Thr Asn Ser Asn Val Val Leu Asp
625                 630                 635                 640

Arg Ile Glu Ile Val Pro Glu Gln Pro Ile Pro Ile Ile Pro Gly Asp
                645                 650                 655

Tyr Gln Ile Val Thr Ala Leu Asn Asn Ser Ser Val Phe Asp Leu Asn
            660                 665                 670

Ser Gly Thr Arg Val Thr Leu Trp Ser Asn Asn Arg Gly Ala His Gln
        675                 680                 685

Ile Trp Asn Phe Met Tyr Asp Gln Gln Arg Asn Ala Tyr Val Ile Arg
    690                 695                 700

Asn Val Ser Asn Pro Ser Leu Val Leu Thr Trp Asp Phe Thr Ser Pro
705                 710                 715                 720

Asn Ser Ile Val Phe Ala Ala Pro Phe Ser Pro Gly Arg Gln Glu Gln
                725                 730                 735

Tyr Trp Ile Ala Glu Ser Phe Gln Asn Ser Tyr Val Phe Glu Asn Leu
            740                 745                 750

Arg Asn Thr Asn Met Val Leu Asp Val Ala Gly Gly Ser Thr Ala Ile
        755                 760                 765

Gly Thr Asn Ile Ile Ala Phe Pro Arg His Asn Gly Asn Ala Gln Arg
    770                 775                 780

Phe Phe Ile Arg Arg Pro
785                 790


<210> SEQ ID NO 53
<211> LENGTH: 787
<212> TYPE: PRT
<213> ORGANISM: Bacillus thuringiensis

<400> SEQUENCE: 53

Met Asn Ser Tyr Gln Asn Lys Asn Glu Tyr Glu Ile Leu Asp Ala Ser
1               5                   10                  15

Glu Asn Thr Val Asn Ala Leu Asn Arg Tyr Pro Phe Ala Asn Asn Pro
            20                  25                  30

Tyr Ser Ser Ile Phe Ser Ser Cys Pro Arg Ser Gly Pro Gly Asn Trp
        35                  40                  45

Ile Asn Ile Leu Gly Asn Ala Val Ser Glu Ala Val Ser Ile Ser Gln
    50                  55                  60

Asp Ile Ile Ser Leu Leu Thr Gln Pro Ser Ile Ser Gly Ile Ile Ser
65                  70                  75                  80

Met Ala Phe Ser Leu Leu Ser Arg Met Ile Gly Ser Asn Gly Arg Ser
                85                  90                  95

Ile Ser Glu Leu Ser Met Cys Asp Leu Leu Ala Ile Ile Asp Leu Arg
            100                 105                 110

Val Asn Gln Ser Val Leu Asp Asp Gly Val Ala Asp Phe Asn Gly Ser
        115                 120                 125

Leu Val Ile Tyr Arg Asn Tyr Leu Glu Ala Leu Gln Arg Trp Asn Asn
    130                 135                 140

Asn Pro Asn Pro Ala Asn Ala Glu Glu Val Arg Thr Arg Phe Arg Glu
145                 150                 155                 160
```

```
Ser Asp Thr Ile Phe Asp Leu Ile Leu Thr Gln Gly Ser Leu Thr Asn
                165                 170                 175

Gly Gly Ser Leu Ala Arg Asn Asn Ala Gln Ile Leu Leu Leu Pro Ser
            180                 185                 190

Phe Ala Asn Ala Ala Tyr Phe His Leu Leu Leu Leu Arg Asp Ala Asn
        195                 200                 205

Val Tyr Gly Asn Asn Trp Gly Leu Phe Gly Val Thr Pro Asn Ile Asn
    210                 215                 220

Tyr Glu Ser Lys Leu Leu Asn Leu Ile Arg Leu Tyr Thr Asn Tyr Cys
225                 230                 235                 240

Thr His Trp Tyr Asn Gln Gly Leu Asn Glu Leu Arg Asn Arg Gly Ser
                245                 250                 255

Asn Ala Thr Ala Trp Leu Glu Phe His Arg Phe Arg Arg Asp Met Thr
            260                 265                 270

Leu Met Val Leu Asp Ile Val Ser Ser Phe Ser Ser Leu Asp Ile Thr
        275                 280                 285

Arg Tyr Pro Arg Ala Thr Asp Phe Gln Leu Ser Arg Ile Ile Tyr Thr
    290                 295                 300

Asp Pro Ile Gly Phe Val Asn Arg Ser Asp Pro Ser Ala Pro Arg Thr
305                 310                 315                 320

Trp Phe Ser Phe His Asn Gln Ala Asn Phe Ser Ala Leu Glu Ser Gly
                325                 330                 335

Ile Pro Ser Pro Ser Phe Ser Gln Phe Leu Asp Ser Met Arg Ile Ser
            340                 345                 350

Thr Gly Pro Leu Ser Leu Pro Ala Ser Pro Asn Ile His Arg Ala Arg
        355                 360                 365

Val Trp Tyr Gly Asn Gln Asn Asn Phe Asn Gly Ser Ser Ser Gln Thr
    370                 375                 380

Phe Gly Glu Ile Thr Asn Asp Asn Gln Thr Ile Ser Gly Leu Asn Ile
385                 390                 395                 400

Phe Arg Ile Asp Ser Gln Ala Val Asn Leu Asn Asn Thr Thr Phe Gly
                405                 410                 415

Val Ser Arg Ala Glu Phe Tyr His Asp Ala Ser Gln Gly Ser Gln Arg
            420                 425                 430

Ser Ile Tyr Gln Gly Phe Val Asp Thr Gly Gly Ala Ser Thr Ala Val
        435                 440                 445

Ala Gln Asn Ile Gln Thr Phe Phe Pro Gly Glu Asn Ser Ser Ile Pro
    450                 455                 460

Thr Pro Gln Asp Tyr Thr His Ile Leu Ser Arg Ser Thr Asn Leu Thr
465                 470                 475                 480

Gly Gly Leu Arg Gln Val Ala Ser Gly Arg Arg Ser Ser Leu Val Leu
                485                 490                 495

His Gly Trp Thr His Lys Ser Leu Ser Arg Gln Asn Arg Val Glu Pro
            500                 505                 510

Asn Arg Ile Thr Gln Val Pro Ala Val Lys Ala Ser Ser Pro Ser Asn
        515                 520                 525

Cys Thr Val Ile Ala Gly Pro Gly Phe Thr Gly Gly Asp Leu Val Arg
    530                 535                 540

Met Ser Ser Asn Cys Ser Val Ser Tyr Asn Phe Thr Pro Ala Asp Gln
545                 550                 555                 560

Gln Val Val Ile Arg Leu Arg Tyr Ala Cys Gln Gly Thr Ala Ser Leu
                565                 570                 575
```

Arg Ile Thr Phe Gly Asn Gly Ser Ser Gln Ile Ile Pro Leu Val Ser
580 585 590

Thr Thr Ser Ser Ile Asn Asn Leu Gln Tyr Glu Asn Phe Ser Phe Ala
595 600 605

Ser Gly Pro Asn Ser Val Asn Phe Leu Ser Ala Gly Thr Ser Ile Thr
610 615 620

Ile Gln Asn Ile Ser Thr Asn Ser Asn Val Val Leu Asp Arg Ile Glu
625 630 635 640

Ile Val Pro Glu Gln Pro Ile Pro Ile Ile Pro Gly Asp Tyr Gln Ile
645 650 655

Val Thr Ala Leu Asn Asn Ser Ser Val Phe Asp Leu Asn Ser Gly Thr
660 665 670

Arg Val Thr Leu Trp Ser Asn Asn Arg Gly Ala His Gln Ile Trp Asn
675 680 685

Phe Met Tyr Asp Gln Gln Arg Asn Ala Tyr Val Ile Arg Asn Val Ser
690 695 700

Asn Pro Ser Leu Val Leu Thr Trp Asp Phe Thr Ser Pro Asn Ser Ile
705 710 715 720

Val Phe Ala Ala Pro Phe Ser Pro Gly Arg Gln Glu Gln Tyr Trp Ile
725 730 735

Ala Glu Ser Phe Gln Asn Ser Tyr Val Phe Glu Asn Leu Arg Asn Thr
740 745 750

Asn Met Val Leu Asp Val Ala Gly Gly Ser Thr Ala Ile Gly Thr Asn
755 760 765

Ile Ile Ala Phe Pro Arg His Asn Gly Asn Ala Gln Arg Phe Phe Ile
770 775 780

Arg Arg Pro
785

<210> SEQ ID NO 54
<211> LENGTH: 707
<212> TYPE: PRT
<213> ORGANISM: Bacillus thuringiensis

<400> SEQUENCE: 54

Met Ala Phe Ser Leu Leu Ser Arg Met Ile Gly Ser Asn Gly Arg Ser
1 5 10 15

Ile Ser Glu Leu Ser Met Cys Asp Leu Leu Ala Ile Ile Asp Leu Arg
20 25 30

Val Asn Gln Ser Val Leu Asp Asp Gly Val Ala Asp Phe Asn Gly Ser
35 40 45

Leu Val Ile Tyr Arg Asn Tyr Leu Glu Ala Leu Gln Arg Trp Asn Asn
50 55 60

Asn Pro Asn Pro Ala Asn Ala Glu Glu Val Arg Thr Arg Phe Arg Glu
65 70 75 80

Ser Asp Thr Ile Phe Asp Leu Ile Leu Thr Gln Gly Ser Leu Thr Asn
85 90 95

Gly Gly Ser Leu Ala Arg Asn Asn Ala Gln Ile Leu Leu Leu Pro Ser
100 105 110

Phe Ala Asn Ala Ala Tyr Phe His Leu Leu Leu Leu Arg Asp Ala Asn
115 120 125

Val Tyr Gly Asn Asn Trp Gly Leu Phe Gly Val Thr Pro Asn Ile Asn
130 135 140

Tyr Glu Ser Lys Leu Leu Asn Leu Ile Arg Leu Tyr Thr Asn Tyr Cys
145 150 155 160

```
Thr His Trp Tyr Asn Gln Gly Leu Asn Glu Leu Arg Asn Arg Gly Ser
                165                 170                 175

Asn Ala Thr Ala Trp Leu Glu Phe His Arg Phe Arg Arg Asp Met Thr
            180                 185                 190

Leu Met Val Leu Asp Ile Val Ser Ser Phe Ser Ser Leu Asp Ile Thr
        195                 200                 205

Arg Tyr Pro Arg Ala Thr Asp Phe Gln Leu Ser Arg Ile Ile Tyr Thr
    210                 215                 220

Asp Pro Ile Gly Phe Val Asn Arg Ser Asp Pro Ser Ala Pro Arg Thr
225                 230                 235                 240

Trp Phe Ser Phe His Asn Gln Ala Asn Phe Ser Ala Leu Glu Ser Gly
                245                 250                 255

Ile Pro Ser Pro Ser Phe Ser Gln Phe Leu Asp Ser Met Arg Ile Ser
            260                 265                 270

Thr Gly Pro Leu Ser Leu Pro Ala Ser Pro Asn Ile His Arg Ala Arg
        275                 280                 285

Val Trp Tyr Gly Asn Gln Asn Asn Phe Asn Gly Ser Ser Ser Gln Thr
    290                 295                 300

Phe Gly Glu Ile Thr Asn Asp Asn Gln Thr Ile Ser Gly Leu Asn Ile
305                 310                 315                 320

Phe Arg Ile Asp Ser Gln Ala Val Asn Leu Asn Asn Thr Thr Phe Gly
                325                 330                 335

Val Ser Arg Ala Glu Phe Tyr His Asp Ala Ser Gln Gly Ser Gln Arg
            340                 345                 350

Ser Ile Tyr Gln Gly Phe Val Asp Thr Gly Gly Ala Ser Thr Ala Val
        355                 360                 365

Ala Gln Asn Ile Gln Thr Phe Phe Pro Gly Glu Asn Ser Ser Ile Pro
    370                 375                 380

Thr Pro Gln Asp Tyr Thr His Ile Leu Ser Arg Ser Thr Asn Leu Thr
385                 390                 395                 400

Gly Gly Leu Arg Gln Val Ala Ser Gly Arg Arg Ser Ser Leu Val Leu
                405                 410                 415

His Gly Trp Thr His Lys Ser Leu Ser Arg Gln Asn Arg Val Glu Pro
            420                 425                 430

Asn Arg Ile Thr Gln Val Pro Ala Val Lys Ala Ser Ser Pro Ser Asn
        435                 440                 445

Cys Thr Val Ile Ala Gly Pro Gly Phe Thr Gly Gly Asp Leu Val Arg
    450                 455                 460

Met Ser Ser Asn Cys Ser Val Ser Tyr Asn Phe Thr Pro Ala Asp Gln
465                 470                 475                 480

Gln Val Val Ile Arg Leu Arg Tyr Ala Cys Gln Gly Thr Ala Ser Leu
                485                 490                 495

Arg Ile Thr Phe Gly Asn Gly Ser Ser Gln Ile Ile Pro Leu Val Ser
            500                 505                 510

Thr Thr Ser Ser Ile Asn Asn Leu Gln Tyr Glu Asn Phe Ser Phe Ala
        515                 520                 525

Ser Gly Pro Asn Ser Val Asn Phe Leu Ser Ala Gly Thr Ser Ile Thr
    530                 535                 540

Ile Gln Asn Ile Ser Thr Asn Ser Asn Val Val Leu Asp Arg Ile Glu
545                 550                 555                 560

Ile Val Pro Glu Gln Pro Ile Pro Ile Ile Pro Gly Asp Tyr Gln Ile
                565                 570                 575
```

Val Thr Ala Leu Asn Asn Ser Ser Val Phe Asp Leu Asn Ser Gly Thr
580 585 590

Arg Val Thr Leu Trp Ser Asn Asn Arg Gly Ala His Gln Ile Trp Asn
595 600 605

Phe Met Tyr Asp Gln Gln Arg Asn Ala Tyr Val Ile Arg Asn Val Ser
610 615 620

Asn Pro Ser Leu Val Leu Thr Trp Asp Phe Thr Ser Pro Asn Ser Ile
625 630 635 640

Val Phe Ala Ala Pro Phe Ser Pro Gly Arg Gln Glu Gln Tyr Trp Ile
645 650 655

Ala Glu Ser Phe Gln Asn Ser Tyr Val Phe Glu Asn Leu Arg Asn Thr
660 665 670

Asn Met Val Leu Asp Val Ala Gly Gly Ser Thr Ala Ile Gly Thr Asn
675 680 685

Ile Ile Ala Phe Pro Arg His Asn Gly Asn Ala Gln Arg Phe Phe Ile
690 695 700

Arg Arg Pro
705

<210> SEQ ID NO 55
<211> LENGTH: 699
<212> TYPE: PRT
<213> ORGANISM: Bacillus thuringiensis

<400> SEQUENCE: 55

Met Ile Gly Ser Asn Gly Arg Ser Ile Ser Glu Leu Ser Met Cys Asp
1 5 10 15

Leu Leu Ala Ile Ile Asp Leu Arg Val Asn Gln Ser Val Leu Asp Asp
20 25 30

Gly Val Ala Asp Phe Asn Gly Ser Leu Val Ile Tyr Arg Asn Tyr Leu
35 40 45

Glu Ala Leu Gln Arg Trp Asn Asn Asn Pro Asn Pro Ala Asn Ala Glu
50 55 60

Glu Val Arg Thr Arg Phe Arg Glu Ser Asp Thr Ile Phe Asp Leu Ile
65 70 75 80

Leu Thr Gln Gly Ser Leu Thr Asn Gly Gly Ser Leu Ala Arg Asn Asn
85 90 95

Ala Gln Ile Leu Leu Leu Pro Ser Phe Ala Asn Ala Ala Tyr Phe His
100 105 110

Leu Leu Leu Leu Arg Asp Ala Asn Val Tyr Gly Asn Asn Trp Gly Leu
115 120 125

Phe Gly Val Thr Pro Asn Ile Asn Tyr Glu Ser Lys Leu Leu Asn Leu
130 135 140

Ile Arg Leu Tyr Thr Asn Tyr Cys Thr His Trp Tyr Asn Gln Gly Leu
145 150 155 160

Asn Glu Leu Arg Asn Arg Gly Ser Asn Ala Thr Ala Trp Leu Glu Phe
165 170 175

His Arg Phe Arg Arg Asp Met Thr Leu Met Val Leu Asp Ile Val Ser
180 185 190

Ser Phe Ser Ser Leu Asp Ile Thr Arg Tyr Pro Arg Ala Thr Asp Phe
195 200 205

Gln Leu Ser Arg Ile Ile Tyr Thr Asp Pro Ile Gly Phe Val Asn Arg
210 215 220

Ser Asp Pro Ser Ala Pro Arg Thr Trp Phe Ser Phe His Asn Gln Ala
225 230 235 240

```
Asn Phe Ser Ala Leu Glu Ser Gly Ile Pro Ser Pro Ser Phe Ser Gln
                245                 250                 255

Phe Leu Asp Ser Met Arg Ile Ser Thr Gly Pro Leu Ser Leu Pro Ala
            260                 265                 270

Ser Pro Asn Ile His Arg Ala Arg Val Trp Tyr Gly Asn Gln Asn Asn
        275                 280                 285

Phe Asn Gly Ser Ser Ser Gln Thr Phe Gly Glu Ile Thr Asn Asp Asn
    290                 295                 300

Gln Thr Ile Ser Gly Leu Asn Ile Phe Arg Ile Asp Ser Gln Ala Val
305                 310                 315                 320

Asn Leu Asn Asn Thr Thr Phe Gly Val Ser Arg Ala Glu Phe Tyr His
                325                 330                 335

Asp Ala Ser Gln Gly Ser Gln Arg Ser Ile Tyr Gln Gly Phe Val Asp
            340                 345                 350

Thr Gly Gly Ala Ser Thr Ala Val Ala Gln Asn Ile Gln Thr Phe Phe
        355                 360                 365

Pro Gly Glu Asn Ser Ser Ile Pro Thr Pro Gln Asp Tyr Thr His Ile
    370                 375                 380

Leu Ser Arg Ser Thr Asn Leu Thr Gly Gly Leu Arg Gln Val Ala Ser
385                 390                 395                 400

Gly Arg Arg Ser Ser Leu Val Leu His Gly Trp Thr His Lys Ser Leu
                405                 410                 415

Ser Arg Gln Asn Arg Val Glu Pro Asn Arg Ile Thr Gln Val Pro Ala
            420                 425                 430

Val Lys Ala Ser Ser Pro Ser Asn Cys Thr Val Ile Ala Gly Pro Gly
        435                 440                 445

Phe Thr Gly Gly Asp Leu Val Arg Met Ser Ser Asn Cys Ser Val Ser
    450                 455                 460

Tyr Asn Phe Thr Pro Ala Asp Gln Gln Val Val Ile Arg Leu Arg Tyr
465                 470                 475                 480

Ala Cys Gln Gly Thr Ala Ser Leu Arg Ile Thr Phe Gly Asn Gly Ser
                485                 490                 495

Ser Gln Ile Ile Pro Leu Val Ser Thr Thr Ser Ser Ile Asn Asn Leu
            500                 505                 510

Gln Tyr Glu Asn Phe Ser Phe Ala Ser Gly Pro Asn Ser Val Asn Phe
        515                 520                 525

Leu Ser Ala Gly Thr Ser Ile Thr Ile Gln Asn Ile Ser Thr Asn Ser
    530                 535                 540

Asn Val Val Leu Asp Arg Ile Glu Ile Val Pro Glu Gln Pro Ile Pro
545                 550                 555                 560

Ile Ile Pro Gly Asp Tyr Gln Ile Val Thr Ala Leu Asn Asn Ser Ser
                565                 570                 575

Val Phe Asp Leu Asn Ser Gly Thr Arg Val Thr Leu Trp Ser Asn Asn
            580                 585                 590

Arg Gly Ala His Gln Ile Trp Asn Phe Met Tyr Asp Gln Gln Arg Asn
        595                 600                 605

Ala Tyr Val Ile Arg Asn Val Ser Asn Pro Ser Leu Val Leu Thr Trp
    610                 615                 620

Asp Phe Thr Ser Pro Asn Ser Ile Val Phe Ala Ala Pro Phe Ser Pro
625                 630                 635                 640

Gly Arg Gln Glu Gln Tyr Trp Ile Ala Glu Ser Phe Gln Asn Ser Tyr
                645                 650                 655
```

```
Val Phe Glu Asn Leu Arg Asn Thr Asn Met Val Leu Asp Val Ala Gly
            660                 665                 670

Gly Ser Thr Ala Ile Gly Thr Asn Ile Ile Ala Phe Pro Arg His Asn
        675                 680                 685

Gly Asn Ala Gln Arg Phe Phe Ile Arg Arg Pro
    690                 695


<210> SEQ ID NO 56
<211> LENGTH: 686
<212> TYPE: PRT
<213> ORGANISM: Bacillus thuringiensis

<400> SEQUENCE: 56

Met Cys Asp Leu Leu Ala Ile Ile Asp Leu Arg Val Asn Gln Ser Val
1               5                   10                  15

Leu Asp Asp Gly Val Ala Asp Phe Asn Gly Ser Leu Val Ile Tyr Arg
            20                  25                  30

Asn Tyr Leu Glu Ala Leu Gln Arg Trp Asn Asn Asn Pro Asn Pro Ala
        35                  40                  45

Asn Ala Glu Glu Val Arg Thr Arg Phe Arg Glu Ser Asp Thr Ile Phe
    50                  55                  60

Asp Leu Ile Leu Thr Gln Gly Ser Leu Thr Asn Gly Gly Ser Leu Ala
65                  70                  75                  80

Arg Asn Asn Ala Gln Ile Leu Leu Leu Pro Ser Phe Ala Asn Ala Ala
                85                  90                  95

Tyr Phe His Leu Leu Leu Leu Arg Asp Ala Asn Val Tyr Gly Asn Asn
            100                 105                 110

Trp Gly Leu Phe Gly Val Thr Pro Asn Ile Asn Tyr Glu Ser Lys Leu
        115                 120                 125

Leu Asn Leu Ile Arg Leu Tyr Thr Asn Tyr Cys Thr His Trp Tyr Asn
    130                 135                 140

Gln Gly Leu Asn Glu Leu Arg Asn Arg Gly Ser Asn Ala Thr Ala Trp
145                 150                 155                 160

Leu Glu Phe His Arg Phe Arg Arg Asp Met Thr Leu Met Val Leu Asp
                165                 170                 175

Ile Val Ser Ser Phe Ser Ser Leu Asp Ile Thr Arg Tyr Pro Arg Ala
            180                 185                 190

Thr Asp Phe Gln Leu Ser Arg Ile Ile Tyr Thr Asp Pro Ile Gly Phe
        195                 200                 205

Val Asn Arg Ser Asp Pro Ser Ala Pro Arg Thr Trp Phe Ser Phe His
    210                 215                 220

Asn Gln Ala Asn Phe Ser Ala Leu Glu Ser Gly Ile Pro Ser Pro Ser
225                 230                 235                 240

Phe Ser Gln Phe Leu Asp Ser Met Arg Ile Ser Thr Gly Pro Leu Ser
                245                 250                 255

Leu Pro Ala Ser Pro Asn Ile His Arg Ala Arg Val Trp Tyr Gly Asn
            260                 265                 270

Gln Asn Asn Phe Asn Gly Ser Ser Ser Gln Thr Phe Gly Glu Ile Thr
        275                 280                 285

Asn Asp Asn Gln Thr Ile Ser Gly Leu Asn Ile Phe Arg Ile Asp Ser
    290                 295                 300

Gln Ala Val Asn Leu Asn Asn Thr Thr Phe Gly Val Ser Arg Ala Glu
305                 310                 315                 320

Phe Tyr His Asp Ala Ser Gln Gly Ser Gln Arg Ser Ile Tyr Gln Gly
                325                 330                 335
```

```
Phe Val Asp Thr Gly Gly Ala Ser Thr Ala Val Ala Gln Asn Ile Gln
            340                 345                 350

Thr Phe Phe Pro Gly Glu Asn Ser Ser Ile Pro Thr Pro Gln Asp Tyr
        355                 360                 365

Thr His Ile Leu Ser Arg Ser Thr Asn Leu Thr Gly Gly Leu Arg Gln
    370                 375                 380

Val Ala Ser Gly Arg Arg Ser Ser Leu Val Leu His Gly Trp Thr His
385                 390                 395                 400

Lys Ser Leu Ser Arg Gln Asn Arg Val Glu Pro Asn Arg Ile Thr Gln
                405                 410                 415

Val Pro Ala Val Lys Ala Ser Ser Pro Ser Asn Cys Thr Val Ile Ala
            420                 425                 430

Gly Pro Gly Phe Thr Gly Gly Asp Leu Val Arg Met Ser Ser Asn Cys
        435                 440                 445

Ser Val Ser Tyr Asn Phe Thr Pro Ala Asp Gln Gln Val Val Ile Arg
    450                 455                 460

Leu Arg Tyr Ala Cys Gln Gly Thr Ala Ser Leu Arg Ile Thr Phe Gly
465                 470                 475                 480

Asn Gly Ser Ser Gln Ile Ile Pro Leu Val Ser Thr Thr Ser Ser Ile
                485                 490                 495

Asn Asn Leu Gln Tyr Glu Asn Phe Ser Phe Ala Ser Gly Pro Asn Ser
            500                 505                 510

Val Asn Phe Leu Ser Ala Gly Thr Ser Ile Thr Ile Gln Asn Ile Ser
        515                 520                 525

Thr Asn Ser Asn Val Val Leu Asp Arg Ile Glu Ile Val Pro Glu Gln
    530                 535                 540

Pro Ile Pro Ile Ile Pro Gly Asp Tyr Gln Ile Val Thr Ala Leu Asn
545                 550                 555                 560

Asn Ser Ser Val Phe Asp Leu Asn Ser Gly Thr Arg Val Thr Leu Trp
                565                 570                 575

Ser Asn Asn Arg Gly Ala His Gln Ile Trp Asn Phe Met Tyr Asp Gln
            580                 585                 590

Gln Arg Asn Ala Tyr Val Ile Arg Asn Val Ser Asn Pro Ser Leu Val
        595                 600                 605

Leu Thr Trp Asp Phe Thr Ser Pro Asn Ser Ile Val Phe Ala Ala Pro
    610                 615                 620

Phe Ser Pro Gly Arg Gln Glu Gln Tyr Trp Ile Ala Glu Ser Phe Gln
625                 630                 635                 640

Asn Ser Tyr Val Phe Glu Asn Leu Arg Asn Thr Asn Met Val Leu Asp
                645                 650                 655

Val Ala Gly Gly Ser Thr Ala Ile Gly Thr Asn Ile Ile Ala Phe Pro
            660                 665                 670

Arg His Asn Gly Asn Ala Gln Arg Phe Phe Ile Arg Arg Pro
        675                 680                 685


<210> SEQ ID NO 57
<211> LENGTH: 1172
<212> TYPE: PRT
<213> ORGANISM: Bacillus thuringiensis

<400> SEQUENCE: 57

Met Glu Val Asn Asn Gln Asn Gln Cys Val Pro Tyr Asn Cys Leu Asn
1               5                   10                  15

Asn Pro Glu Ile Glu Ile Leu Gly Gly Glu Arg Ile Ser Val Gly Asn
```

-continued

```
            20                  25                  30

Thr Pro Ile Asp Ile Ser Leu Ser Leu Thr Gln Phe Leu Leu Ser Glu
        35                  40                  45

Phe Val Pro Gly Ala Gly Phe Val Leu Gly Leu Ile Asp Leu Ile Trp
    50                  55                  60

Gly Phe Leu Gly Pro Ser Gln Trp Asp Ala Phe Leu Leu Gln Ile Glu
65                  70                  75                  80

Gln Leu Ile Ser Gln Arg Ile Glu Glu Phe Ala Arg Asn Gln Ala Ile
                85                  90                  95

Ser Arg Leu Glu Gly Leu Ser Asn Leu Tyr Arg Ile Tyr Ala Glu Ala
            100                 105                 110

Phe Arg Ala Trp Glu Ala Asp Pro Thr Asn Leu Ala Leu Arg Glu Glu
        115                 120                 125

Met Arg Thr Gln Phe Asn Asp Met Asn Ser Ala Leu Val Thr Ala Ile
    130                 135                 140

Pro Leu Phe Ser Val Gln Asn Tyr Gln Val Pro Leu Leu Ser Val Tyr
145                 150                 155                 160

Val Gln Ala Ala Asn Leu His Leu Ser Val Leu Arg Asp Val Ser Val
                165                 170                 175

Phe Gly Gln Arg Trp Gly Phe Asp Val Ala Thr Ile Asn Ser Arg Tyr
            180                 185                 190

Asn Asp Leu Thr Arg Leu Ile Gly Glu Tyr Thr Asp Tyr Ala Val Arg
        195                 200                 205

Trp Tyr Asn Thr Gly Leu Asp Arg Leu Arg Gly Ser Asn Phe Gln Asp
    210                 215                 220

Trp Ile Arg Tyr Asn Arg Phe Arg Arg Glu Leu Thr Leu Thr Val Leu
225                 230                 235                 240

Asp Ile Val Ser Val Phe Gln Asn Tyr Asp Ser Arg Leu Tyr Pro Ile
                245                 250                 255

Gln Thr Ser Ser Gln Leu Thr Arg Glu Ile Tyr Ser Asp Leu Leu Leu
            260                 265                 270

Ala Asn Pro Ser Gly Val Gly Ser Phe Ser Asn Val Asp Phe Asp Ser
        275                 280                 285

Ile Leu Ile Arg Gln Pro His Leu Ile Asp Phe Met Arg Val Leu Thr
    290                 295                 300

Ile Tyr Thr Asp Arg His Asn Ala Ser Arg His Asn Ile Tyr Trp Ala
305                 310                 315                 320

Gly His Gln Val Thr Ala Val Asp Thr Ala Asn Arg Thr Ile Val Tyr
                325                 330                 335

Pro Val Asn Gly Ser Ala Ala Asn Leu Glu Pro Pro Arg Thr Leu Arg
            340                 345                 350

Phe Glu Ser Pro Val Val Glu Ile Arg Ser Asn Pro Val Trp Asp Arg
        355                 360                 365

Gly Ser Thr Gly Ile Ala Gly Ser Tyr Glu Phe Phe Gly Val Thr Ser
    370                 375                 380

Ala Leu Phe Ile Thr Ile Leu Gly Phe Gly Tyr Thr Tyr Arg Ser Gly
385                 390                 395                 400

Ser Asn Thr Glu Val Thr Ala Leu Pro Asp His Gln Val Ser His Ile
                405                 410                 415

Gly Tyr Phe Arg Arg Phe Thr Thr Thr Gly Ala Thr Ala Arg Gln Thr
            420                 425                 430

Leu Thr Ser Ala Pro Ile Val Ser Trp Thr His Ser Ser Ala Glu Pro
        435                 440                 445
```

```
Pro Asn Arg Ile Tyr Gln Asn Arg Ile Thr Gln Ile Pro Ala Val Lys
    450                 455                 460

Gly Asn Phe Leu Phe Asn Gly Ala Val Ile Ser Gly Pro Gly Phe Thr
465                 470                 475                 480

Gly Gly Asp Leu Val Arg Leu Asn Arg Asn Asn Asp Asn Ile Gln Asn
                485                 490                 495

Arg Gly Tyr Ile Glu Val Pro Ile Gln Phe Ala Ser Thr Ser Thr Arg
            500                 505                 510

Tyr Arg Val Arg Val Arg Tyr Ala Ser Thr Asn Ala Ile Glu Val Asn
        515                 520                 525

Ile Asn Trp Gly Asn Gly Ser Ile Phe Thr Gly Thr Ala Pro Ala Thr
    530                 535                 540

Ala Thr Ser Leu Asp Asn Leu Gln Ser Asn Asp Phe Gly Tyr Phe Glu
545                 550                 555                 560

Ser Thr Thr Ala Phe Ala Pro Ser Leu Gly Asn Ile Val Gly Val Arg
                565                 570                 575

Asn Phe Ser Ala Asn Ala Asp Val Ile Ile Asp Arg Phe Glu Phe Ile
            580                 585                 590

Pro Val Thr Ala Thr Leu Glu Ala Glu Tyr Asp Leu Glu Arg Ala Glu
        595                 600                 605

Lys Ala Val Asn Ala Leu Phe Thr Ser Thr Thr Gln Leu Gly Leu Lys
    610                 615                 620

Thr Asp Val Thr Asp Tyr His Ile Asp Gln Val Ser Asn Leu Val Glu
625                 630                 635                 640

Cys Leu Ser Asp Glu Phe Cys Leu Asn Glu Lys Arg Glu Leu Ser Glu
                645                 650                 655

Lys Val Lys His Ala Lys Arg Leu Ser Asp Lys Arg Asn Leu Leu Gln
            660                 665                 670

Asp Pro Asn Phe Thr Ser Ile Asn Gly Gln Leu Asp Arg Gly Trp Arg
        675                 680                 685

Gly Ser Thr Asp Ile Thr Ile Gln Gly Gly Asn Asp Val Phe Lys Glu
    690                 695                 700

Asn Tyr Val Thr Leu Pro Gly Thr Phe Asp Glu Cys Tyr Pro Thr Tyr
705                 710                 715                 720

Leu Tyr Gln Lys Ile Asp Glu Ser Gln Leu Lys Ser Tyr Thr Arg Tyr
                725                 730                 735

Gln Leu Arg Gly Tyr Ile Glu Asp Ser Gln Asp Leu Glu Ile Tyr Leu
            740                 745                 750

Ile Arg Tyr Asn Ala Lys His Glu Thr Leu Ser Val Pro Gly Thr Glu
        755                 760                 765

Ser Pro Trp Pro Ser Ser Gly Val Tyr Pro Ile Gly Lys Cys Gly Glu
    770                 775                 780

Pro Asn Arg Cys Ala Pro Arg Ile Glu Trp Asn Pro Asp Leu Gly Cys
785                 790                 795                 800

Ser Cys Arg Tyr Gly Glu Lys Cys Val His His Ser His His Phe Ser
                805                 810                 815

Leu Asp Ile Asp Val Gly Cys Thr Asp Leu Asn Glu Asp Leu Gly Val
            820                 825                 830

Trp Val Ile Phe Lys Ile Lys Thr Gln Asp Gly His Ala Lys Leu Gly
        835                 840                 845

Asn Leu Glu Phe Ile Glu Glu Lys Pro Leu Leu Gly Glu Ala Leu Ser
    850                 855                 860
```

```
Arg Val Lys Arg Ala Glu Lys Lys Trp Lys Asp Lys Cys Glu Lys Leu
865                 870                 875                 880

Gln Leu Glu Thr Gln Arg Val Tyr Thr Glu Ala Lys Glu Ser Val Asp
                885                 890                 895

Ala Leu Phe Ile Asp Ser Gln Tyr Asp Arg Leu Gln Ala Asp Thr Asn
            900                 905                 910

Ile Gly Met Ile His Ala Ala Asp Lys Gln Val His Arg Ile Arg Glu
        915                 920                 925

Ala Tyr Leu Pro Glu Leu His Ala Ile Pro Gly Val Asn Ala Glu Ile
    930                 935                 940

Phe Glu Glu Leu Glu Asn Phe Arg Ile Tyr Thr Ala Phe Ser Leu Tyr
945                 950                 955                 960

Asp Ala Arg Asn Val Ile Lys Asn Gly Asp Phe Asn Asn Gly Leu Ser
                965                 970                 975

Cys Trp Asn Val Lys Gly His Val Asp Val Gln Gln Asn His His Arg
            980                 985                 990

Ser Val Leu Val Leu Ser Glu Trp  Glu Ala Glu Val Ser  Gln Lys Val
        995                 1000                1005

Arg Val  Cys Pro Asp Arg Gly  Tyr Ile Leu Arg Val  Thr Ala Tyr
    1010                1015                1020

Lys Glu  Gly Tyr Gly Glu Gly  Cys Val Thr Ile His  Glu Phe Glu
    1025                1030                1035

Asp Asn  Thr Asp Val Leu Lys  Phe Arg Asn Cys Val  Glu Glu Glu
    1040                1045                1050

Val Tyr  Pro Asn Asn Thr Val  Thr Cys Asn Asp Tyr  Thr Thr Asn
    1055                1060                1065

Gln Ser  Ala Glu Gly Cys Thr  Asp Ala Cys Asn Ser  Tyr Asn Arg
    1070                1075                1080

Gly Tyr  Glu Asp Gly Tyr Gly  Asn Asn Pro Ser Ala  Pro Val Asn
    1085                1090                1095

Tyr Thr  Pro Thr Tyr Glu Glu  Arg Met Tyr Thr Asp  Thr Asp Thr
    1100                1105                1110

Gln Gly  Tyr Asn His Cys Val  Ser Asp Arg Gly Tyr  Arg Asn His
    1115                1120                1125

Thr Pro  Leu Pro Ala Gly Tyr  Val Thr Leu Glu Leu  Glu Phe Phe
    1130                1135                1140

Pro Glu  Thr Glu Gln Val Trp  Ile Glu Ile Gly Glu  Thr Glu Gly
    1145                1150                1155

Thr Phe  Ile Val Asp Ser Val  Glu Leu Phe Leu Met  Glu Glu
    1160                1165                1170
```

<210> SEQ ID NO 58
<211> LENGTH: 594
<212> TYPE: PRT
<213> ORGANISM: Bacillus thuringiensis

<400> SEQUENCE: 58

```
Met Glu Val Asn Asn Gln Asn Gln Cys Val Pro Tyr Asn Cys Leu Asn
1               5                   10                  15

Asn Pro Glu Ile Glu Ile Leu Gly Gly Glu Arg Ile Ser Val Gly Asn
            20                  25                  30

Thr Pro Ile Asp Ile Ser Leu Ser Leu Thr Gln Phe Leu Leu Ser Glu
        35                  40                  45

Phe Val Pro Gly Ala Gly Phe Val Leu Gly Leu Ile Asp Leu Ile Trp
    50                  55                  60
```

Gly Phe Leu Gly Pro Ser Gln Trp Asp Ala Phe Leu Leu Gln Ile Glu
65 70 75 80

Gln Leu Ile Ser Gln Arg Ile Glu Glu Phe Ala Arg Asn Gln Ala Ile
85 90 95

Ser Arg Leu Glu Gly Leu Ser Asn Leu Tyr Arg Ile Tyr Ala Glu Ala
100 105 110

Phe Arg Ala Trp Glu Ala Asp Pro Thr Asn Leu Ala Leu Arg Glu Glu
115 120 125

Met Arg Thr Gln Phe Asn Asp Met Asn Ser Ala Leu Val Thr Ala Ile
130 135 140

Pro Leu Phe Ser Val Gln Asn Tyr Gln Val Pro Leu Leu Ser Val Tyr
145 150 155 160

Val Gln Ala Ala Asn Leu His Leu Ser Val Leu Arg Asp Val Ser Val
165 170 175

Phe Gly Gln Arg Trp Gly Phe Asp Val Ala Thr Ile Asn Ser Arg Tyr
180 185 190

Asn Asp Leu Thr Arg Leu Ile Gly Glu Tyr Thr Asp Tyr Ala Val Arg
195 200 205

Trp Tyr Asn Thr Gly Leu Asp Arg Leu Arg Gly Ser Asn Phe Gln Asp
210 215 220

Trp Ile Arg Tyr Asn Arg Phe Arg Arg Glu Leu Thr Leu Thr Val Leu
225 230 235 240

Asp Ile Val Ser Val Phe Gln Asn Tyr Asp Ser Arg Leu Tyr Pro Ile
245 250 255

Gln Thr Ser Ser Gln Leu Thr Arg Glu Ile Tyr Ser Asp Leu Leu Leu
260 265 270

Ala Asn Pro Ser Gly Val Gly Ser Phe Ser Asn Val Asp Phe Asp Ser
275 280 285

Ile Leu Ile Arg Gln Pro His Leu Ile Asp Phe Met Arg Val Leu Thr
290 295 300

Ile Tyr Thr Asp Arg His Asn Ala Ser Arg His Asn Ile Tyr Trp Ala
305 310 315 320

Gly His Gln Val Thr Ala Val Asp Thr Ala Asn Arg Thr Ile Val Tyr
325 330 335

Pro Val Asn Gly Ser Ala Ala Asn Leu Glu Pro Pro Arg Thr Leu Arg
340 345 350

Phe Glu Ser Pro Val Val Glu Ile Arg Ser Asn Pro Val Trp Asp Arg
355 360 365

Gly Ser Thr Gly Ile Ala Gly Ser Tyr Glu Phe Phe Gly Val Thr Ser
370 375 380

Ala Leu Phe Ile Thr Ile Leu Gly Phe Gly Tyr Thr Tyr Arg Ser Gly
385 390 395 400

Ser Asn Thr Glu Val Thr Ala Leu Pro Asp His Gln Val Ser His Ile
405 410 415

Gly Tyr Phe Arg Arg Phe Thr Thr Thr Gly Ala Thr Ala Arg Gln Thr
420 425 430

Leu Thr Ser Ala Pro Ile Val Ser Trp Thr His Ser Ser Ala Glu Pro
435 440 445

Pro Asn Arg Ile Tyr Gln Asn Arg Ile Thr Gln Ile Pro Ala Val Lys
450 455 460

Gly Asn Phe Leu Phe Asn Gly Ala Val Ile Ser Gly Pro Gly Phe Thr
465 470 475 480

```
Gly Gly Asp Leu Val Arg Leu Asn Arg Asn Asn Asp Asn Ile Gln Asn
                485                 490                 495

Arg Gly Tyr Ile Glu Val Pro Ile Gln Phe Ala Ser Thr Ser Thr Arg
            500                 505                 510

Tyr Arg Val Arg Val Arg Tyr Ala Ser Thr Asn Ala Ile Glu Val Asn
        515                 520                 525

Ile Asn Trp Gly Asn Gly Ser Ile Phe Thr Gly Thr Ala Pro Ala Thr
    530                 535                 540

Ala Thr Ser Leu Asp Asn Leu Gln Ser Asn Asp Phe Gly Tyr Phe Glu
545                 550                 555                 560

Ser Thr Thr Ala Phe Ala Pro Ser Leu Gly Asn Ile Val Gly Val Arg
                565                 570                 575

Asn Phe Ser Ala Asn Ala Asp Val Ile Ile Asp Arg Phe Glu Phe Ile
            580                 585                 590

Pro Val


<210> SEQ ID NO 59
<211> LENGTH: 333
<212> TYPE: PRT
<213> ORGANISM: Unknown
<220> FEATURE:
<223> OTHER INFORMATION: Isolated from soil sample

<400> SEQUENCE: 59

Met Lys Val Tyr Lys Lys Ile Thr Lys Met Ala Pro Ile Met Ala Leu
1               5                   10                  15

Ser Thr Ala Val Leu Leu Ser Pro Gly Ser Thr Phe Ala Ala Glu Lys
            20                  25                  30

Ala Val Val Thr Lys Ser Asn Val Ser Ser Leu Thr Thr Asn Thr Val
        35                  40                  45

Met Gln Ser Gly Ser Ile Ile Gln Gly Tyr Leu Ile Lys Asn Gly Val
    50                  55                  60

Lys Thr Pro Val Tyr Asn Ser Glu Val Gln Thr Arg Ser Thr Ala Val
65                  70                  75                  80

Asn Glu Ala Pro Tyr Pro Glu Leu Ser Ser Asn Pro Asn Asp Pro Val
                85                  90                  95

Pro Ser Lys Gly Ser Ile Thr Ser Glu Ser Gly Asn Val Gly Ser Val
            100                 105                 110

Leu Tyr Phe Ser Lys Phe Asn Ser Gln Lys Leu Gln Asn Thr Ala Glu
        115                 120                 125

Pro Val Tyr Trp Lys Asn Val Tyr Leu Glu Lys Thr Pro Asp Gly Asn
    130                 135                 140

Ile Ile Phe Gly Thr Tyr Asp Pro Thr Thr Leu Lys Arg Thr Pro Asn
145                 150                 155                 160

Leu Val Asn Ile Met Met Thr Pro Ser Lys Val Gln Tyr Tyr Gln Ser
                165                 170                 175

Phe Phe Thr Asp Thr Lys Ile Lys Arg Glu Thr Ala Tyr Glu Lys Ile
            180                 185                 190

Gly Gly Gly Thr Pro Gln Pro Lys Asn Thr Ser Tyr Thr Phe Ser Ser
        195                 200                 205

Ala Val Thr Ser Gly Leu Ser Thr Ser Asp Ala Ile Gly Gly Ser Leu
    210                 215                 220

Thr Leu Gly Tyr Lys Tyr Ser Val Lys Glu Gly Gly Gly Val Leu Pro
225                 230                 235                 240

Val Glu Ala Thr Gln Glu Phe Ser Leu Gln Leu Thr Ala Ser Tyr Asn
```

```
                245                 250                 255

His Thr Ile Thr Val Ser Ser Gln Thr Thr Asn Thr Gln Thr Tyr Ser
            260                 265                 270

Val Ala His Ala Gly Asp Ser Tyr Lys Asn Asp Lys Tyr Val Ala Ala
        275                 280                 285

Met Tyr Gln Leu Lys Ser His Tyr Thr Val Ile Pro Gly Pro Ala Leu
    290                 295                 300

Thr Gln Ser Gly Ser Ile Leu Ala Gln Glu Ala Phe Gln Tyr Asp Asp
305                 310                 315                 320

Ser Ser Leu Tyr Leu Ala Val Thr Pro Gly Ala Gly Ile
                325                 330
```

<210> SEQ ID NO 60
<211> LENGTH: 324
<212> TYPE: PRT
<213> ORGANISM: Unknown
<220> FEATURE:
<223> OTHER INFORMATION: Isolated from soil sample

<400> SEQUENCE: 60

```
Met Ala Pro Ile Met Ala Leu Ser Thr Ala Val Leu Leu Ser Pro Gly
1               5                   10                  15

Ser Thr Phe Ala Ala Glu Lys Ala Val Val Thr Lys Ser Asn Val Ser
            20                  25                  30

Ser Leu Thr Thr Asn Thr Val Met Gln Ser Gly Ser Ile Ile Gln Gly
        35                  40                  45

Tyr Leu Ile Lys Asn Gly Val Lys Thr Pro Val Tyr Asn Ser Glu Val
    50                  55                  60

Gln Thr Arg Ser Thr Ala Val Asn Glu Ala Pro Tyr Pro Glu Leu Ser
65                  70                  75                  80

Ser Asn Pro Asn Asp Pro Val Pro Ser Lys Gly Ser Ile Thr Ser Glu
                85                  90                  95

Ser Gly Asn Val Gly Ser Val Leu Tyr Phe Ser Lys Phe Asn Ser Gln
            100                 105                 110

Lys Leu Gln Asn Thr Ala Glu Pro Val Tyr Trp Lys Asn Val Tyr Leu
        115                 120                 125

Glu Lys Thr Pro Asp Gly Asn Ile Ile Phe Gly Thr Tyr Asp Pro Thr
    130                 135                 140

Thr Leu Lys Arg Thr Pro Asn Leu Val Asn Ile Met Met Thr Pro Ser
145                 150                 155                 160

Lys Val Gln Tyr Tyr Gln Ser Phe Phe Thr Asp Thr Lys Ile Lys Arg
                165                 170                 175

Glu Thr Ala Tyr Glu Lys Ile Gly Gly Gly Thr Pro Gln Pro Lys Asn
            180                 185                 190

Thr Ser Tyr Thr Phe Ser Ser Ala Val Thr Ser Gly Leu Ser Thr Ser
        195                 200                 205

Asp Ala Ile Gly Gly Ser Leu Thr Leu Gly Tyr Lys Tyr Ser Val Lys
    210                 215                 220

Glu Gly Gly Gly Val Leu Pro Val Glu Ala Thr Gln Glu Phe Ser Leu
225                 230                 235                 240

Gln Leu Thr Ala Ser Tyr Asn His Thr Ile Thr Val Ser Ser Gln Thr
                245                 250                 255

Thr Asn Thr Gln Thr Tyr Ser Val Ala His Ala Gly Asp Ser Tyr Lys
            260                 265                 270

Asn Asp Lys Tyr Val Ala Ala Met Tyr Gln Leu Lys Ser His Tyr Thr
```

275 280 285

Val Ile Pro Gly Pro Ala Leu Thr Gln Ser Gly Ser Ile Leu Ala Gln
290 295 300

Glu Ala Phe Gln Tyr Asp Asp Ser Ser Leu Tyr Leu Ala Val Thr Pro
305 310 315 320

Gly Ala Gly Ile

<210> SEQ ID NO 61
<211> LENGTH: 320
<212> TYPE: PRT
<213> ORGANISM: Unknown
<220> FEATURE:
<223> OTHER INFORMATION: Isolated from soil sample

<400> SEQUENCE: 61

Met Ala Leu Ser Thr Ala Val Leu Leu Ser Pro Gly Ser Thr Phe Ala
1 5 10 15

Ala Glu Lys Ala Val Val Thr Lys Ser Asn Val Ser Ser Leu Thr Thr
20 25 30

Asn Thr Val Met Gln Ser Gly Ser Ile Ile Gln Gly Tyr Leu Ile Lys
35 40 45

Asn Gly Val Lys Thr Pro Val Tyr Asn Ser Glu Val Gln Thr Arg Ser
50 55 60

Thr Ala Val Asn Glu Ala Pro Tyr Pro Glu Leu Ser Ser Asn Pro Asn
65 70 75 80

Asp Pro Val Pro Ser Lys Gly Ser Ile Thr Ser Glu Ser Gly Asn Val
85 90 95

Gly Ser Val Leu Tyr Phe Ser Lys Phe Asn Ser Gln Lys Leu Gln Asn
100 105 110

Thr Ala Glu Pro Val Tyr Trp Lys Asn Val Tyr Leu Glu Lys Thr Pro
115 120 125

Asp Gly Asn Ile Ile Phe Gly Thr Tyr Asp Pro Thr Thr Leu Lys Arg
130 135 140

Thr Pro Asn Leu Val Asn Ile Met Met Thr Pro Ser Lys Val Gln Tyr
145 150 155 160

Tyr Gln Ser Phe Phe Thr Asp Thr Lys Ile Lys Arg Glu Thr Ala Tyr
165 170 175

Glu Lys Ile Gly Gly Gly Thr Pro Gln Pro Lys Asn Thr Ser Tyr Thr
180 185 190

Phe Ser Ser Ala Val Thr Ser Gly Leu Ser Thr Ser Asp Ala Ile Gly
195 200 205

Gly Ser Leu Thr Leu Gly Tyr Lys Tyr Ser Val Lys Glu Gly Gly Gly
210 215 220

Val Leu Pro Val Glu Ala Thr Gln Glu Phe Ser Leu Gln Leu Thr Ala
225 230 235 240

Ser Tyr Asn His Thr Ile Thr Val Ser Ser Gln Thr Thr Asn Thr Gln
245 250 255

Thr Tyr Ser Val Ala His Ala Gly Asp Ser Tyr Lys Asn Asp Lys Tyr
260 265 270

Val Ala Ala Met Tyr Gln Leu Lys Ser His Tyr Thr Val Ile Pro Gly
275 280 285

Pro Ala Leu Thr Gln Ser Gly Ser Ile Leu Ala Gln Glu Ala Phe Gln
290 295 300

Tyr Asp Asp Ser Ser Leu Tyr Leu Ala Val Thr Pro Gly Ala Gly Ile
305 310 315 320

<210> SEQ ID NO 62
<211> LENGTH: 285
<212> TYPE: PRT
<213> ORGANISM: Unknown
<220> FEATURE:
<223> OTHER INFORMATION: Isolated from soil sample

<400> SEQUENCE: 62

```
Met Gln Ser Gly Ser Ile Ile Gln Gly Tyr Leu Ile Lys Asn Gly Val
1               5                   10                  15

Lys Thr Pro Val Tyr Asn Ser Glu Val Gln Thr Arg Ser Thr Ala Val
            20                  25                  30

Asn Glu Ala Pro Tyr Pro Glu Leu Ser Ser Asn Pro Asn Asp Pro Val
        35                  40                  45

Pro Ser Lys Gly Ser Ile Thr Ser Glu Ser Gly Asn Val Gly Ser Val
    50                  55                  60

Leu Tyr Phe Ser Lys Phe Asn Ser Gln Lys Leu Gln Asn Thr Ala Glu
65                  70                  75                  80

Pro Val Tyr Trp Lys Asn Val Tyr Leu Glu Lys Thr Pro Asp Gly Asn
                85                  90                  95

Ile Ile Phe Gly Thr Tyr Asp Pro Thr Thr Leu Lys Arg Thr Pro Asn
            100                 105                 110

Leu Val Asn Ile Met Met Thr Pro Ser Lys Val Gln Tyr Tyr Gln Ser
        115                 120                 125

Phe Phe Thr Asp Thr Lys Ile Lys Arg Glu Thr Ala Tyr Glu Lys Ile
    130                 135                 140

Gly Gly Gly Thr Pro Gln Pro Lys Asn Thr Ser Tyr Thr Phe Ser Ser
145                 150                 155                 160

Ala Val Thr Ser Gly Leu Ser Thr Ser Asp Ala Ile Gly Gly Ser Leu
                165                 170                 175

Thr Leu Gly Tyr Lys Tyr Ser Val Lys Glu Gly Gly Gly Val Leu Pro
            180                 185                 190

Val Glu Ala Thr Gln Glu Phe Ser Leu Gln Leu Thr Ala Ser Tyr Asn
        195                 200                 205

His Thr Ile Thr Val Ser Ser Gln Thr Thr Asn Thr Gln Thr Tyr Ser
    210                 215                 220

Val Ala His Ala Gly Asp Ser Tyr Lys Asn Asp Lys Tyr Val Ala Ala
225                 230                 235                 240

Met Tyr Gln Leu Lys Ser His Tyr Thr Val Ile Pro Gly Pro Ala Leu
                245                 250                 255

Thr Gln Ser Gly Ser Ile Leu Ala Gln Glu Ala Phe Gln Tyr Asp Asp
            260                 265                 270

Ser Ser Leu Tyr Leu Ala Val Thr Pro Gly Ala Gly Ile
        275                 280                 285
```

<210> SEQ ID NO 63
<211> LENGTH: 304
<212> TYPE: PRT
<213> ORGANISM: Unknown
<220> FEATURE:
<223> OTHER INFORMATION: Isolated from soil sample

<400> SEQUENCE: 63

```
Met Glu Lys Ala Val Val Thr Lys Ser Asn Val Ser Ser Leu Thr Thr
1               5                   10                  15

Asn Thr Val Met Gln Ser Gly Ser Ile Ile Gln Gly Tyr Leu Ile Lys
```

-continued

```
            20                  25                  30

Asn Gly Val Lys Thr Pro Val Tyr Asn Ser Glu Val Gln Thr Arg Ser
        35                  40                  45

Thr Ala Val Asn Glu Ala Pro Tyr Pro Glu Leu Ser Ser Asn Pro Asn
    50                  55                  60

Asp Pro Val Pro Ser Lys Gly Ser Ile Thr Ser Glu Ser Gly Asn Val
65                  70                  75                  80

Gly Ser Val Leu Tyr Phe Ser Lys Phe Asn Ser Gln Lys Leu Gln Asn
                85                  90                  95

Thr Ala Glu Pro Val Tyr Trp Lys Asn Val Tyr Leu Glu Lys Thr Pro
            100                 105                 110

Asp Gly Asn Ile Ile Phe Gly Thr Tyr Asp Pro Thr Thr Leu Lys Arg
        115                 120                 125

Thr Pro Asn Leu Val Asn Ile Met Met Thr Pro Ser Lys Val Gln Tyr
    130                 135                 140

Tyr Gln Ser Phe Phe Thr Asp Thr Lys Ile Lys Arg Glu Thr Ala Tyr
145                 150                 155                 160

Glu Lys Ile Gly Gly Gly Thr Pro Gln Pro Lys Asn Thr Ser Tyr Thr
                165                 170                 175

Phe Ser Ser Ala Val Thr Ser Gly Leu Ser Thr Ser Asp Ala Ile Gly
            180                 185                 190

Gly Ser Leu Thr Leu Gly Tyr Lys Tyr Ser Val Lys Glu Gly Gly Gly
        195                 200                 205

Val Leu Pro Val Glu Ala Thr Gln Glu Phe Ser Leu Gln Leu Thr Ala
    210                 215                 220

Ser Tyr Asn His Thr Ile Thr Val Ser Ser Gln Thr Thr Asn Thr Gln
225                 230                 235                 240

Thr Tyr Ser Val Ala His Ala Gly Asp Ser Tyr Lys Asn Asp Lys Tyr
                245                 250                 255

Val Ala Ala Met Tyr Gln Leu Lys Ser His Tyr Thr Val Ile Pro Gly
            260                 265                 270

Pro Ala Leu Thr Gln Ser Gly Ser Ile Leu Ala Gln Glu Ala Phe Gln
        275                 280                 285

Tyr Asp Asp Ser Ser Leu Tyr Leu Ala Val Thr Pro Gly Ala Gly Ile
    290                 295                 300


<210> SEQ ID NO 64
<211> LENGTH: 285
<212> TYPE: PRT
<213> ORGANISM: Unknown
<220> FEATURE:
<223> OTHER INFORMATION: Isolated from soil sample

<400> SEQUENCE: 64

Met Gln Ser Gly Ser Ile Ile Gln Gly Tyr Leu Ile Lys Asn Gly Val
1               5                   10                  15

Lys Thr Pro Val Tyr Asn Ser Glu Val Gln Thr Arg Ser Thr Ala Val
            20                  25                  30

Asn Glu Ala Pro Tyr Pro Glu Leu Ser Ser Asn Pro Asn Asp Pro Val
        35                  40                  45

Pro Ser Lys Gly Ser Ile Thr Ser Glu Ser Gly Asn Val Gly Ser Val
    50                  55                  60

Leu Tyr Phe Ser Lys Phe Asn Ser Gln Lys Leu Gln Asn Thr Ala Glu
65                  70                  75                  80

Pro Val Tyr Trp Lys Asn Val Tyr Leu Glu Lys Thr Pro Asp Gly Asn
```

```
                85                  90                  95

Ile Ile Phe Gly Thr Tyr Asp Pro Thr Thr Leu Lys Arg Thr Pro Asn
            100                 105                 110

Leu Val Asn Ile Met Met Thr Pro Ser Lys Val Gln Tyr Tyr Gln Ser
        115                 120                 125

Phe Phe Thr Asp Thr Lys Ile Lys Arg Glu Thr Ala Tyr Glu Lys Ile
    130                 135                 140

Gly Gly Gly Thr Pro Gln Pro Lys Asn Thr Ser Tyr Thr Phe Ser Ser
145                 150                 155                 160

Ala Val Thr Ser Gly Leu Ser Thr Ser Asp Ala Ile Gly Gly Ser Leu
                165                 170                 175

Thr Leu Gly Tyr Lys Tyr Ser Val Lys Glu Gly Gly Gly Val Leu Pro
            180                 185                 190

Val Glu Ala Thr Gln Glu Phe Ser Leu Gln Leu Thr Ala Ser Tyr Asn
        195                 200                 205

His Thr Ile Thr Val Ser Ser Gln Thr Thr Asn Thr Gln Thr Tyr Ser
    210                 215                 220

Val Ala His Ala Gly Asp Ser Tyr Lys Asn Asp Lys Tyr Val Ala Ala
225                 230                 235                 240

Met Tyr Gln Leu Lys Ser His Tyr Thr Val Ile Pro Gly Pro Ala Leu
                245                 250                 255

Thr Gln Ser Gly Ser Ile Leu Ala Gln Glu Ala Phe Gln Tyr Asp Asp
            260                 265                 270

Ser Ser Leu Tyr Leu Ala Val Thr Pro Gly Ala Gly Ile
        275                 280                 285


<210> SEQ ID NO 65
<211> LENGTH: 385
<212> TYPE: PRT
<213> ORGANISM: Unknown
<220> FEATURE:
<223> OTHER INFORMATION: Isolated from soil sample

<400> SEQUENCE: 65

Met Ala Ile Ile Asn Gln Ser Ser Leu Asn Ser Arg Ile His Asp Leu
1               5                   10                  15

Arg Glu Asp Ser Arg Thr Ala Leu Glu Lys Val Tyr Thr Ser Asn Asn
            20                  25                  30

Pro Trp Gly Phe Val Ser Ile His Ser Asp Arg Leu Glu Asn Tyr Gln
        35                  40                  45

Leu Thr Asn Val Asn Val Ser Pro Arg Asn Gln Asp Phe Gln Thr Ile
    50                  55                  60

Pro Arg Leu Gln His Ser Ala Thr Gln Ile Ile Glu Asn Asn Thr Ser
65                  70                  75                  80

Val Thr Gln Ser Gln Thr Ile Ser Phe Asn Glu Arg Thr Thr Asp Thr
                85                  90                  95

Phe Thr Thr Ser Val Thr Thr Gly Phe Lys Thr Gly Thr Ser Val Lys
            100                 105                 110

Ser Thr Thr Lys Phe Lys Ile Ser Val Gly Phe Leu Leu Ala Gly Glu
        115                 120                 125

Leu Glu Gln Ser Val Glu Val Ser Val Asn Phe Glu Tyr Asn Tyr Ser
    130                 135                 140

Ser Thr Thr Thr Glu Thr His Ser Val Glu Arg Gly Trp Thr Ile Ser
145                 150                 155                 160

Gln Pro Ile Ile Ala Pro Pro Arg Thr Arg Val Glu Ala Thr Leu Leu
```

```
                165                 170                 175

Ile Tyr Ala Gly Ser Val Asp Val Pro Ile Asp Leu Asn Ala Thr Ile
            180                 185                 190

Val Gly Asp Pro Ile Pro Trp Pro Ser Trp Gly Pro Ala Val Tyr Ser
        195                 200                 205

Gly Ser Phe Leu Ala Asn Asp Gly Arg Ile Trp Ser Ala Pro Ile Leu
    210                 215                 220

Pro Glu Gln Leu Ser Leu Ala Ser Ser Ala Tyr Thr Thr Val Gly Arg
225                 230                 235                 240

Thr Ala Asn Phe Ser Gly Leu Ala Thr Thr Asn Val Ser Ser Gly Leu
                245                 250                 255

Tyr Ser Ile Val Arg Ile Asp Glu Ser Pro Leu Pro Gly Phe Thr Gly
            260                 265                 270

Glu Thr Arg Arg Tyr Tyr Leu Pro Pro Ser Leu Ala Thr Thr Asn Gln
        275                 280                 285

Ile Leu Ser Thr Asn Ala Leu Gly Asn Asn Val Pro Ile Ile Asn Pro
    290                 295                 300

Val Pro Asn Gly His Cys Lys Lys Asp His Ser Pro Ile Ile Ile His
305                 310                 315                 320

Lys Asn Arg Glu Val Lys Cys Glu His Asn Tyr Asp Glu Val Tyr Pro
                325                 330                 335

Arg His Asp Gln Val Glu Lys Cys Glu His Asn Tyr Asp Glu Val Tyr
            340                 345                 350

Pro Arg His Asp Gln Val Glu Lys Cys Glu His Asp Tyr Asp Glu Val
        355                 360                 365

Tyr Pro Arg His Asp Gln Val Glu Lys Tyr Glu His Asn Tyr Asp Glu
    370                 375                 380

Glu
385


<210> SEQ ID NO 66
<211> LENGTH: 334
<212> TYPE: PRT
<213> ORGANISM: Unknown
<220> FEATURE:
<223> OTHER INFORMATION: Isolated from soil sample

<400> SEQUENCE: 66

Met Ala Ile Ile Asn Gln Ser Ser Leu Asn Ser Arg Ile His Asp Leu
1               5                   10                  15

Arg Glu Asp Ser Arg Thr Ala Leu Glu Lys Val Tyr Thr Ser Asn Asn
            20                  25                  30

Pro Trp Gly Phe Val Ser Ile His Ser Asp Arg Leu Glu Asn Tyr Gln
        35                  40                  45

Leu Thr Asn Val Asn Val Ser Pro Arg Asn Gln Asp Phe Gln Thr Ile
    50                  55                  60

Pro Arg Leu Gln His Ser Ala Thr Gln Ile Ile Glu Asn Asn Thr Ser
65                  70                  75                  80

Val Thr Gln Ser Gln Thr Ile Ser Phe Asn Glu Arg Thr Thr Asp Thr
                85                  90                  95

Phe Thr Thr Ser Val Thr Thr Gly Phe Lys Thr Gly Thr Ser Val Lys
            100                 105                 110

Ser Thr Thr Lys Phe Lys Ile Ser Val Gly Phe Leu Leu Ala Gly Glu
        115                 120                 125

Leu Glu Gln Ser Val Glu Val Ser Val Asn Phe Glu Tyr Asn Tyr Ser
```

130 135 140

Ser Thr Thr Thr Glu Thr His Ser Val Glu Arg Gly Trp Thr Ile Ser
145 150 155 160

Gln Pro Ile Ile Ala Pro Pro Arg Thr Arg Val Glu Ala Thr Leu Leu
165 170 175

Ile Tyr Ala Gly Ser Val Asp Val Pro Ile Asp Leu Asn Ala Thr Ile
180 185 190

Val Gly Asp Pro Ile Pro Trp Pro Ser Trp Gly Pro Ala Val Tyr Ser
195 200 205

Gly Ser Phe Leu Ala Asn Asp Gly Arg Ile Trp Ser Ala Pro Ile Leu
210 215 220

Pro Glu Gln Leu Ser Leu Ala Ser Ser Ala Tyr Thr Thr Val Gly Arg
225 230 235 240

Thr Ala Asn Phe Ser Gly Leu Ala Thr Thr Asn Val Ser Ser Gly Leu
245 250 255

Tyr Ser Ile Val Arg Ile Asp Glu Ser Pro Leu Pro Gly Phe Thr Gly
260 265 270

Glu Thr Arg Arg Tyr Tyr Leu Pro Pro Ser Leu Ala Thr Thr Asn Gln
275 280 285

Ile Leu Ser Thr Asn Ala Leu Gly Asn Asn Val Pro Ile Ile Asn Pro
290 295 300

Val Pro Asn Gly His Cys Lys Lys Asp His Ser Pro Ile Ile Ile His
305 310 315 320

Lys Asn Arg Glu Val Lys Cys Glu His Asn Tyr Asp Glu Glu
325 330

<210> SEQ ID NO 67
<211> LENGTH: 1232
<212> TYPE: PRT
<213> ORGANISM: Bacillus thuringiensis

<400> SEQUENCE: 67

Met Asn Lys Asn Asn Gln Asn Glu Tyr Glu Ile Ile Asp Ala Ser Asn
1 5 10 15

Cys Gly Cys Ala Ser Asp Asp Val Ala Arg Tyr Pro Leu Ala Asn Asn
20 25 30

Pro Tyr Ser Ser Ala Leu Asn Leu Asn Ser Cys Gln Asn Ser Ser Ile
35 40 45

Leu Asn Trp Ile Asn Ile Ile Gly Asn Ala Ala Lys Glu Ala Val Ser
50 55 60

Ile Gly Leu Thr Ile Lys Ser Leu Ile Thr Ala Pro Ser Leu Thr Gly
65 70 75 80

Leu Ile Ser Ile Ala Tyr Asn Leu Leu Gly Lys Val Leu Gly Gly Ser
85 90 95

Ser Gly Gln Ser Ile Ser Asp Leu Ser Ile Cys Asp Leu Leu Ser Ile
100 105 110

Ile Asp Leu Arg Val Asn Gln Ser Val Leu Asn Asp Gly Ile Ala Asp
115 120 125

Phe Asn Gly Ser Leu Ile Leu Tyr Arg Asn Tyr Leu Asp Ala Leu Asn
130 135 140

Ser Trp Asn Glu Asn Pro Asn Ser Asn Arg Ala Glu Glu Leu Arg Ala
145 150 155 160

Arg Phe Arg Ile Ala Asp Ser Glu Phe Asp Arg Ile Leu Thr Arg Gly
165 170 175

```
Ser Leu Thr Asn Gly Gly Ser Leu Ala Arg Gln Asp Ala Gln Ile Leu
            180                 185                 190

Leu Leu Pro Ser Phe Ala Ser Ala Ala Phe Phe His Leu Leu Leu Leu
        195                 200                 205

Arg Asp Ala Ala Arg Tyr Gly Asn Asp Trp Asp Leu Phe Gly Ala Ile
    210                 215                 220

Pro Phe Ile Asn Tyr Gln Ser Lys Leu Val Glu Leu Ile Glu Leu Tyr
225                 230                 235                 240

Thr Asp Tyr Cys Val Asn Trp Tyr Asn Gln Gly Phe Asn Glu Leu Arg
                245                 250                 255

Gln Arg Gly Thr Ser Ala Thr Val Trp Leu Glu Phe His Arg Tyr Arg
            260                 265                 270

Arg Glu Met Thr Leu Thr Val Leu Asp Ile Val Ala Ser Phe Ser Ser
        275                 280                 285

Leu Asp Ile Thr Asn Tyr Pro Ile Glu Thr Asp Phe Gln Leu Ser Arg
    290                 295                 300

Ile Ile Tyr Thr Asp Pro Ile Gly Phe Val His Arg Ser Ser Leu Arg
305                 310                 315                 320

Gly Glu Ser Trp Phe Ser Phe Ile Asn Arg Ala Asn Phe Ser Glu Leu
                325                 330                 335

Glu Asn Ala Ile Pro Asn Pro Arg Pro Ser Trp Phe Leu Asn Asn Met
            340                 345                 350

Ile Ile Ser Thr Gly Ser Leu Thr Leu Pro Val Ser Pro Asn Thr Asp
        355                 360                 365

Arg Ala Arg Val Trp Tyr Gly Ser Arg Asp Arg Ile Ser Pro Ala Asn
    370                 375                 380

Ser Gln Val Ile Ser Glu Leu Ile Ser Gly Gln His Thr Asn Ser Thr
385                 390                 395                 400

Gln Thr Ile Leu Gly Arg Asn Ile Phe Arg Ile Asp Ser Gln Ala Cys
                405                 410                 415

Asn Leu Asn Asp Thr Thr Tyr Gly Val Asn Arg Ala Val Phe Tyr His
            420                 425                 430

Asp Ala Ser Glu Gly Ser Gln Arg Ser Val Tyr Glu Gly Phe Ile Arg
        435                 440                 445

Thr Thr Gly Ile Asp Asn Pro Arg Val Gln Asn Ile Asn Thr Tyr Phe
    450                 455                 460

Pro Gly Glu Asn Ser Asn Ile Pro Thr Pro Glu Asp Tyr Thr His Leu
465                 470                 475                 480

Leu Ser Thr Thr Val Asn Leu Thr Gly Gly Leu Arg Gln Val Ala Asn
                485                 490                 495

Asn Arg Arg Ser Ser Ile Val Ile Tyr Gly Trp Thr His Lys Ser Leu
            500                 505                 510

Thr Arg Asn Asn Thr Ile Asn Pro Gly Ile Ile Thr Gln Ile Pro Met
        515                 520                 525

Val Lys Leu Ser Asn Leu Ser Ser Gly Thr Asn Val Val Arg Gly Pro
    530                 535                 540

Gly Phe Thr Gly Gly Asp Ile Leu Arg Arg Thr Asn Ala Gly Asn Phe
545                 550                 555                 560

Gly Asp Val Arg Val Asn Ile Ala Gly Ser Leu Ser Gln Arg Tyr Arg
                565                 570                 575

Val Arg Ile Arg Tyr Ala Ser Thr Thr Asn Leu Gln Phe His Thr Ser
            580                 585                 590

Ile Asn Gly Arg Ala Ile Asn Gln Ala Asn Phe Pro Ala Thr Met Asn
```

```
        595                 600                 605

Ile Gly Ala Ser Leu Asn Tyr Arg Thr Phe Arg Thr Val Gly Phe Thr
    610                 615                 620

Thr Pro Phe Thr Phe Ser Glu Ala Ser Ser Ile Phe Thr Leu Ser Thr
625                 630                 635                 640

His Ser Phe Ser Ser Gly Asn Ala Val Tyr Ile Asp Arg Ile Glu Phe
                645                 650                 655

Val Pro Ala Glu Val Thr Phe Glu Ala Glu Ser Asp Leu Glu Arg Ala
            660                 665                 670

Gln Lys Ala Val Asn Ala Leu Phe Thr Ser Ser Asn Gln Ile Gly Leu
        675                 680                 685

Lys Thr Asp Val Thr Asp Tyr His Ile Asp Gln Val Ser Asn Leu Val
    690                 695                 700

Ala Cys Leu Ser Asp Glu Phe Cys Leu Asp Glu Lys Arg Glu Leu Ser
705                 710                 715                 720

Glu Lys Val Lys His Ala Lys Arg Leu Ser Asp Glu Arg Asn Leu Leu
                725                 730                 735

Gln Asp Pro Asn Phe Arg Gly Ile Asn Arg Gln Leu Asp Arg Gly Trp
            740                 745                 750

Arg Gly Ser Thr Asp Ile Thr Ile Gln Gly Gly Asp Asp Val Phe Lys
        755                 760                 765

Glu Asn Tyr Val Thr Leu Pro Gly Thr Phe Asp Glu Cys Tyr Pro Thr
    770                 775                 780

Tyr Leu Tyr Gln Lys Ile Asp Glu Ser Lys Leu Lys Ala Tyr Thr Arg
785                 790                 795                 800

Tyr Glu Leu Arg Gly Tyr Ile Glu Asp Ser Gln Asp Leu Glu Val Tyr
                805                 810                 815

Leu Ile Arg Tyr Asn Ala Lys His Glu Thr Leu Asn Val Pro Gly Thr
            820                 825                 830

Gly Ser Leu Trp Pro Leu Ala Ala Glu Ser Ser Ile Gly Arg Cys Gly
        835                 840                 845

Glu Pro Asn Arg Cys Ala Pro His Ile Glu Trp Asn Pro Asp Leu Asp
    850                 855                 860

Cys Ser Cys Arg Asp Gly Glu Lys Cys Ala His His Ser His His Phe
865                 870                 875                 880

Ser Leu Asp Ile Asp Val Gly Cys Thr Asp Leu Asn Glu Asp Leu Gly
                885                 890                 895

Val Trp Val Ile Phe Lys Ile Lys Thr Gln Asp Gly His Ala Arg Leu
            900                 905                 910

Gly Asn Leu Glu Phe Leu Glu Glu Lys Pro Leu Leu Gly Glu Ala Leu
        915                 920                 925

Ala Arg Val Lys Arg Ala Glu Lys Lys Trp Arg Asp Lys Arg Asp Lys
    930                 935                 940

Leu Glu Leu Glu Thr Asn Ile Val Tyr Lys Glu Ala Lys Glu Ser Val
945                 950                 955                 960

Asp Ala Leu Phe Val Asp Ser Gln Tyr Asn Arg Leu Gln Thr Asp Thr
                965                 970                 975

Asn Ile Ala Met Ile His Ala Ala Asp Lys Arg Val His Arg Ile Arg
            980                 985                 990

Glu Ala Tyr Leu Pro Glu Leu Ser  Val Ile Pro Gly Val  Asn Ala Ala
        995                 1000                1005

Ile Phe  Glu Glu Leu Glu Gly  Leu Ile Phe Thr Ala  Phe Ser Leu
    1010                1015                1020
```

Tyr Asp Ala Arg Asn Val Ile Lys Asn Gly Asp Phe Asn His Gly
1025 1030 1035

Leu Ser Cys Trp Asn Val Lys Gly His Val Asp Val Glu Glu Gln
1040 1045 1050

Asn Asn His Arg Ser Val Leu Val Val Pro Glu Trp Glu Ala Glu
1055 1060 1065

Val Ser Gln Glu Val Arg Val Cys Pro Gly Arg Gly Tyr Ile Leu
1070 1075 1080

Arg Val Thr Ala Tyr Lys Glu Gly Tyr Gly Glu Gly Cys Val Thr
1085 1090 1095

Ile His Glu Ile Glu Asp His Thr Asp Glu Leu Lys Phe Arg Asn
1100 1105 1110

Cys Glu Glu Glu Glu Val Tyr Pro Asn Asn Thr Val Thr Cys Asn
1115 1120 1125

Asp Tyr Pro Ala Asn Gln Glu Glu Tyr Lys Gly Ala Tyr Pro Ser
1130 1135 1140

Arg Asn Gly Gly Tyr Glu Asp Thr Tyr Asp Thr Ser Ala Ser Val
1145 1150 1155

His Tyr Asn Thr Pro Thr Tyr Glu Glu Glu Ile Gly Thr Asp Leu
1160 1165 1170

Gln Arg Tyr Asn Gln Cys Glu Asn Asn Arg Gly Tyr Gly Asn Tyr
1175 1180 1185

Thr Pro Leu Pro Ala Gly Tyr Val Thr Lys Glu Leu Glu Tyr Phe
1190 1195 1200

Pro Glu Thr Asp Lys Val Trp Ile Glu Ile Gly Glu Thr Glu Gly
1205 1210 1215

Thr Phe Ile Val Asp Ser Val Glu Leu Leu Leu Met Glu Glu
1220 1225 1230

<210> SEQ ID NO 68
<211> LENGTH: 659
<212> TYPE: PRT
<213> ORGANISM: Bacillus thuringiensis

<400> SEQUENCE: 68

Met Asn Lys Asn Asn Gln Asn Glu Tyr Glu Ile Ile Asp Ala Ser Asn
1 5 10 15

Cys Gly Cys Ala Ser Asp Asp Val Ala Arg Tyr Pro Leu Ala Asn Asn
20 25 30

Pro Tyr Ser Ser Ala Leu Asn Leu Asn Ser Cys Gln Asn Ser Ser Ile
35 40 45

Leu Asn Trp Ile Asn Ile Ile Gly Asn Ala Ala Lys Glu Ala Val Ser
50 55 60

Ile Gly Leu Thr Ile Lys Ser Leu Ile Thr Ala Pro Ser Leu Thr Gly
65 70 75 80

Leu Ile Ser Ile Ala Tyr Asn Leu Leu Gly Lys Val Leu Gly Gly Ser
85 90 95

Ser Gly Gln Ser Ile Ser Asp Leu Ser Ile Cys Asp Leu Leu Ser Ile
100 105 110

Ile Asp Leu Arg Val Asn Gln Ser Val Leu Asn Asp Gly Ile Ala Asp
115 120 125

Phe Asn Gly Ser Leu Ile Leu Tyr Arg Asn Tyr Leu Asp Ala Leu Asn
130 135 140

Ser Trp Asn Glu Asn Pro Asn Ser Asn Arg Ala Glu Glu Leu Arg Ala

-continued

```
145                 150                 155                 160

Arg Phe Arg Ile Ala Asp Ser Glu Phe Asp Arg Ile Leu Thr Arg Gly
                165                 170                 175

Ser Leu Thr Asn Gly Gly Ser Leu Ala Arg Gln Asp Ala Gln Ile Leu
            180                 185                 190

Leu Leu Pro Ser Phe Ala Ser Ala Ala Phe Phe His Leu Leu Leu Leu
        195                 200                 205

Arg Asp Ala Ala Arg Tyr Gly Asn Asp Trp Asp Leu Phe Gly Ala Ile
    210                 215                 220

Pro Phe Ile Asn Tyr Gln Ser Lys Leu Val Glu Leu Ile Glu Leu Tyr
225                 230                 235                 240

Thr Asp Tyr Cys Val Asn Trp Tyr Asn Gln Gly Phe Asn Glu Leu Arg
                245                 250                 255

Gln Arg Gly Thr Ser Ala Thr Val Trp Leu Glu Phe His Arg Tyr Arg
            260                 265                 270

Arg Glu Met Thr Leu Thr Val Leu Asp Ile Val Ala Ser Phe Ser Ser
        275                 280                 285

Leu Asp Ile Thr Asn Tyr Pro Ile Glu Thr Asp Phe Gln Leu Ser Arg
    290                 295                 300

Ile Ile Tyr Thr Asp Pro Ile Gly Phe Val His Arg Ser Ser Leu Arg
305                 310                 315                 320

Gly Glu Ser Trp Phe Ser Phe Ile Asn Arg Ala Asn Phe Ser Glu Leu
                325                 330                 335

Glu Asn Ala Ile Pro Asn Pro Arg Pro Ser Trp Phe Leu Asn Asn Met
            340                 345                 350

Ile Ile Ser Thr Gly Ser Leu Thr Leu Pro Val Ser Pro Asn Thr Asp
        355                 360                 365

Arg Ala Arg Val Trp Tyr Gly Ser Arg Asp Arg Ile Ser Pro Ala Asn
    370                 375                 380

Ser Gln Val Ile Ser Glu Leu Ile Ser Gly Gln His Thr Asn Ser Thr
385                 390                 395                 400

Gln Thr Ile Leu Gly Arg Asn Ile Phe Arg Ile Asp Ser Gln Ala Cys
                405                 410                 415

Asn Leu Asn Asp Thr Thr Tyr Gly Val Asn Arg Ala Val Phe Tyr His
            420                 425                 430

Asp Ala Ser Glu Gly Ser Gln Arg Ser Val Tyr Glu Gly Phe Ile Arg
        435                 440                 445

Thr Thr Gly Ile Asp Asn Pro Arg Val Gln Asn Ile Asn Thr Tyr Phe
    450                 455                 460

Pro Gly Glu Asn Ser Asn Ile Pro Thr Pro Glu Asp Tyr Thr His Leu
465                 470                 475                 480

Leu Ser Thr Thr Val Asn Leu Thr Gly Gly Leu Arg Gln Val Ala Asn
                485                 490                 495

Asn Arg Arg Ser Ser Ile Val Ile Tyr Gly Trp Thr His Lys Ser Leu
            500                 505                 510

Thr Arg Asn Asn Thr Ile Asn Pro Gly Ile Ile Thr Gln Ile Pro Met
        515                 520                 525

Val Lys Leu Ser Asn Leu Ser Ser Gly Thr Asn Val Val Arg Gly Pro
    530                 535                 540

Gly Phe Thr Gly Gly Asp Ile Leu Arg Arg Thr Asn Ala Gly Asn Phe
545                 550                 555                 560

Gly Asp Val Arg Val Asn Ile Ala Gly Ser Leu Ser Gln Arg Tyr Arg
                565                 570                 575
```

```
Val Arg Ile Arg Tyr Ala Ser Thr Thr Asn Leu Gln Phe His Thr Ser
            580                 585                 590

Ile Asn Gly Arg Ala Ile Asn Gln Ala Asn Phe Pro Ala Thr Met Asn
        595                 600                 605

Ile Gly Ala Ser Leu Asn Tyr Arg Thr Phe Arg Thr Val Gly Phe Thr
    610                 615                 620

Thr Pro Phe Thr Phe Ser Glu Ala Ser Ser Ile Phe Thr Leu Ser Thr
625                 630                 635                 640

His Ser Phe Ser Ser Gly Asn Ala Val Tyr Ile Asp Arg Ile Glu Phe
                645                 650                 655

Val Pro Ala


<210> SEQ ID NO 69
<211> LENGTH: 1233
<212> TYPE: PRT
<213> ORGANISM: Bacillus thuringiensis

<400> SEQUENCE: 69

Met Thr Ser Asn Arg Lys Asn Glu Asn Glu Ile Ile Asn Ala Leu Ser
1               5                   10                  15

Ile Pro Ala Val Ser Asn His Ser Ala Gln Met Asp Leu Ser Pro Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Leu Ala Ser
65                  70                  75                  80

Phe Tyr Ser Phe Leu Val Gly Glu Leu Trp Pro Ser Gly Arg Asp Pro
                85                  90                  95

Trp Glu Ile Phe Met Glu His Val Glu Gln Leu Val Arg Gln Gln Ile
            100                 105                 110

Thr Asp Ser Val Arg Asp Thr Ala Ile Ala Arg Leu Glu Gly Leu Gly
        115                 120                 125

Arg Gly Tyr Arg Ser Tyr Gln Gln Ala Leu Glu Thr Trp Leu Asp Asn
    130                 135                 140

Arg Asn Asp Ala Arg Ser Arg Ser Ile Ile Leu Glu Arg Tyr Ile Ala
145                 150                 155                 160

Leu Glu Leu Asp Ile Thr Thr Ala Ile Pro Leu Phe Ser Ile Arg Asn
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Trp Gly Met
        195                 200                 205

Ser Ser Ala Asp Val Asn Gln Tyr Tyr Gln Glu Gln Ile Arg Tyr Thr
    210                 215                 220

Glu Glu Tyr Ser Asn His Cys Val Gln Trp Tyr Asn Thr Gly Leu Asn
225                 230                 235                 240

Asn Leu Arg Gly Thr Asn Ala Glu Ser Trp Val Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Thr Tyr Pro Ile Asn Thr Ser Ala Gln Leu Thr
        275                 280                 285
```

-continued

```
Arg Glu Val Tyr Thr Asp Ala Ile Gly Ala Thr Gly Val Asn Met Ala
    290                 295                 300

Asn Met Asn Trp Tyr Asn Asn Asn Ala Pro Ser Phe Ser Ala Ile Glu
305                 310                 315                 320

Ala Ala Val Ile Arg Ser Pro His Leu Leu Asp Phe Leu Glu Gln Leu
                325                 330                 335

Thr Ile Phe Ser Ala Ser Ser Arg Trp Ser Asn Thr Arg His Met Thr
            340                 345                 350

Tyr Trp Arg Gly His Thr Ile Gln Ser Arg Pro Ile Gly Gly Gly Leu
        355                 360                 365

Asn Thr Ser Thr Tyr Gly Ser Thr Asn Thr Ser Ile Asn Pro Val Thr
    370                 375                 380

Leu Arg Phe Thr Ser Arg Asp Val Tyr Arg Thr Glu Ser Trp Ala Gly
385                 390                 395                 400

Val Leu Leu Trp Gly Ile Tyr Leu Glu Pro Ile His Gly Val Pro Thr
                405                 410                 415

Val Arg Phe Asn Phe Thr Asn Pro Gln Asn Ile Tyr Asp Arg Gly Thr
            420                 425                 430

Ala Asn Tyr Ser Gln Pro Tyr Glu Ser Pro Gly Leu Gln Leu Lys Asp
        435                 440                 445

Ser Glu Thr Glu Leu Pro Pro Glu Thr Thr Glu Arg Pro Asn Tyr Glu
    450                 455                 460

Ser Tyr Ser His Arg Leu Ser His Ile Gly Ile Ile Leu Gln Ser Arg
465                 470                 475                 480

Val Asn Val Pro Val Tyr Ser Trp Thr His Arg Ser Ala Asp Arg Thr
                485                 490                 495

Asn Thr Ile Gly Pro Asn Arg Ile Thr Gln Ile Pro Met Val Lys Ala
            500                 505                 510

Ser Glu Leu Pro Gln Gly Thr Thr Val Val Arg Gly Pro Gly Phe Thr
        515                 520                 525

Gly Gly Asp Ile Leu Arg Arg Thr Asn Thr Gly Gly Phe Gly Pro Ile
    530                 535                 540

Arg Val Thr Val Asn Gly Pro Leu Thr Gln Arg Tyr Arg Ile Gly Phe
545                 550                 555                 560

Arg Tyr Ala Ser Thr Val Asp Phe Asp Phe Phe Val Ser Arg Gly Gly
                565                 570                 575

Thr Thr Val Asn Asn Phe Arg Phe Leu Arg Thr Met Asn Ser Gly Asp
            580                 585                 590

Glu Leu Lys Tyr Gly Asn Phe Val Arg Arg Ala Phe Thr Thr Pro Phe
        595                 600                 605

Thr Phe Thr Gln Ile Gln Asp Ile Ile Arg Thr Ser Ile Gln Gly Leu
    610                 615                 620

Ser Gly Asn Gly Glu Val Tyr Ile Asp Lys Ile Glu Ile Ile Pro Val
625                 630                 635                 640

Thr Ala Thr Phe Glu Ala Glu Tyr Asp Leu Glu Arg Ala Gln Glu Ala
                645                 650                 655

Val Asn Ala Leu Phe Thr Asn Thr Asn Pro Arg Arg Leu Lys Thr Asp
            660                 665                 670

Val Thr Asp Tyr His Ile Asp Gln Val Ser Asn Leu Val Ala Cys Leu
        675                 680                 685

Ser Asp Glu Phe Cys Leu Asp Glu Lys Arg Glu Leu Leu Glu Lys Val
    690                 695                 700
```

-continued

```
Lys Tyr Ala Lys Arg Leu Ser Asp Glu Arg Asn Leu Leu Gln Asp Pro
705                 710                 715                 720

Asn Phe Thr Ser Ile Asn Lys Gln Pro Asp Phe Ile Ser Thr Asn Glu
                725                 730                 735

Gln Ser Asn Phe Thr Ser Ile His Glu Gln Ser Glu His Gly Trp Trp
            740                 745                 750

Gly Ser Glu Asn Ile Thr Ile Gln Glu Gly Asn Asp Val Phe Lys Glu
        755                 760                 765

Asn Tyr Val Thr Leu Pro Gly Thr Phe Asn Glu Cys Tyr Pro Thr Tyr
    770                 775                 780

Leu Tyr Gln Lys Ile Gly Glu Ser Glu Leu Lys Ala Tyr Thr Arg Tyr
785                 790                 795                 800

Gln Leu Arg Gly Tyr Ile Glu Asp Ser Gln Asp Leu Glu Ile Tyr Leu
                805                 810                 815

Ile Arg Tyr Asn Ala Lys Pro Glu Thr Leu Asp Val Pro Gly Thr Glu
            820                 825                 830

Ser Leu Trp Pro Leu Ser Val Glu Ser Pro Ile Gly Arg Cys Gly Glu
        835                 840                 845

Pro Asn Arg Cys Ala Pro His Phe Glu Trp Asn Pro Asp Leu Asp Cys
    850                 855                 860

Ser Cys Arg Asp Gly Glu Lys Cys Ala His His Ser His His Phe Ser
865                 870                 875                 880

Leu Asp Ile Asp Val Gly Cys Thr Asp Leu His Glu Asn Leu Gly Val
                885                 890                 895

Trp Val Val Phe Lys Ile Lys Thr Gln Glu Gly His Ala Arg Leu Gly
            900                 905                 910

Asn Leu Glu Phe Ile Glu Glu Lys Pro Leu Leu Gly Glu Ala Leu Ser
        915                 920                 925

Arg Val Lys Arg Ala Glu Lys Lys Trp Arg Asp Lys Arg Glu Lys Leu
    930                 935                 940

Gln Leu Glu Thr Lys Arg Val Tyr Thr Glu Ala Lys Glu Ala Val Asp
945                 950                 955                 960

Ala Leu Phe Val Asp Ser Gln Tyr Asp Arg Leu Gln Ala Asp Thr Asn
                965                 970                 975

Ile Gly Met Ile His Ala Ala Asp Lys Leu Val His Arg Ile Arg Glu
            980                 985                 990

Ala Tyr Leu Ser Glu Leu Pro Val  Ile Pro Gly Val Asn  Ala Glu Ile
        995                 1000                1005

Phe Glu  Glu Leu Glu Gly His  Ile Ile Thr Ala Ile  Ser Leu Tyr
    1010                1015                1020

Asp Ala  Arg Asn Val Val Lys  Asn Gly Asp Phe Asn  Asn Gly Leu
    1025                1030                1035

Thr Cys  Trp Asn Val Lys Gly  His Val Asp Val Gln  Gln Ser His
    1040                1045                1050

His Arg  Ser Asp Leu Val Ile  Pro Glu Trp Glu Ala  Glu Val Ser
    1055                1060                1065

Gln Ala  Val Arg Val Cys Pro  Gly Cys Gly Tyr Ile  Leu Arg Val
    1070                1075                1080

Thr Ala  Tyr Lys Glu Gly Tyr  Gly Glu Gly Cys Val  Thr Ile His
    1085                1090                1095

Glu Ile  Glu Asn Asn Thr Asp  Glu Leu Lys Phe Lys  Asn Arg Glu
    1100                1105                1110

Glu Glu  Glu Val Tyr Pro Thr  Asp Thr Gly Thr Cys  Asn Asp Tyr
```

```
    1115                1120                1125

Thr Ala  His Gln Gly Thr Ala  Gly Cys Ala Asp Ala  Cys Asn Ser
    1130                1135                1140

Arg Asn  Ala Gly Tyr Glu Asp  Ala Tyr Glu Val Asp  Thr Thr Ala
    1145                1150                1155

Ser Val  Asn Tyr Lys Pro Thr  Tyr Glu Glu Glu Thr  Tyr Thr Asp
    1160                1165                1170

Val Arg  Arg Asp Asn His Cys  Glu Tyr Asp Arg Gly  Tyr Val Asn
    1175                1180                1185

Tyr Pro  Pro Val Pro Ala Gly  Tyr Val Thr Lys Glu  Leu Glu Tyr
    1190                1195                1200

Phe Pro  Glu Thr Asp Thr Val  Trp Ile Glu Ile Gly  Glu Thr Glu
    1205                1210                1215

Gly Lys  Phe Ile Val Asp Ser  Val Glu Leu Leu Leu  Met Glu Glu
    1220                1225                1230


<210> SEQ ID NO 70
<211> LENGTH: 1207
<212> TYPE: PRT
<213> ORGANISM: Bacillus thuringiensis

<400> SEQUENCE: 70

Met Asp Leu Ser Pro Asp Ala Arg Ile Glu Asp Ser Leu Cys Ile Ala
1               5                   10                  15

Glu Gly Asn Asn Ile Asp Pro Phe Val Ser Ala Ser Thr Val Gln Thr
            20                  25                  30

Gly Ile Asn Ile Ala Gly Arg Ile Leu Gly Val Leu Gly Val Pro Phe
        35                  40                  45

Ala Gly Gln Leu Ala Ser Phe Tyr Ser Phe Leu Val Gly Glu Leu Trp
    50                  55                  60

Pro Ser Gly Arg Asp Pro Trp Glu Ile Phe Met Glu His Val Glu Gln
65                  70                  75                  80

Leu Val Arg Gln Gln Ile Thr Asp Ser Val Arg Asp Thr Ala Ile Ala
                85                  90                  95

Arg Leu Glu Gly Leu Gly Arg Gly Tyr Arg Ser Tyr Gln Gln Ala Leu
            100                 105                 110

Glu Thr Trp Leu Asp Asn Arg Asn Asp Ala Arg Ser Arg Ser Ile Ile
        115                 120                 125

Leu Glu Arg Tyr Ile Ala Leu Glu Leu Asp Ile Thr Thr Ala Ile Pro
    130                 135                 140

Leu Phe Ser Ile Arg Asn Gln Glu Val Pro Leu Leu Met Val Tyr Ala
145                 150                 155                 160

Gln Ala Ala Asn Leu His Leu Leu Leu Leu Arg Asp Ala Ser Leu Phe
                165                 170                 175

Gly Ser Glu Trp Gly Met Ser Ser Ala Asp Val Asn Gln Tyr Tyr Gln
            180                 185                 190

Glu Gln Ile Arg Tyr Thr Glu Glu Tyr Ser Asn His Cys Val Gln Trp
        195                 200                 205

Tyr Asn Thr Gly Leu Asn Asn Leu Arg Gly Thr Asn Ala Glu Ser Trp
    210                 215                 220

Val Arg Tyr Asn Gln Phe Arg Arg Asp Leu Thr Leu Gly Val Leu Asp
225                 230                 235                 240

Leu Val Ala Leu Phe Pro Ser Tyr Asp Thr Arg Thr Tyr Pro Ile Asn
                245                 250                 255
```

```
Thr Ser Ala Gln Leu Thr Arg Glu Val Tyr Thr Asp Ala Ile Gly Ala
            260                 265                 270

Thr Gly Val Asn Met Ala Asn Met Asn Trp Tyr Asn Asn Asn Ala Pro
        275                 280                 285

Ser Phe Ser Ala Ile Glu Ala Ala Val Ile Arg Ser Pro His Leu Leu
    290                 295                 300

Asp Phe Leu Glu Gln Leu Thr Ile Phe Ser Ala Ser Ser Arg Trp Ser
305                 310                 315                 320

Asn Thr Arg His Met Thr Tyr Trp Arg Gly His Thr Ile Gln Ser Arg
                325                 330                 335

Pro Ile Gly Gly Gly Leu Asn Thr Ser Thr Tyr Gly Ser Thr Asn Thr
            340                 345                 350

Ser Ile Asn Pro Val Thr Leu Arg Phe Thr Ser Arg Asp Val Tyr Arg
        355                 360                 365

Thr Glu Ser Trp Ala Gly Val Leu Leu Trp Gly Ile Tyr Leu Glu Pro
    370                 375                 380

Ile His Gly Val Pro Thr Val Arg Phe Asn Phe Thr Asn Pro Gln Asn
385                 390                 395                 400

Ile Tyr Asp Arg Gly Thr Ala Asn Tyr Ser Gln Pro Tyr Glu Ser Pro
                405                 410                 415

Gly Leu Gln Leu Lys Asp Ser Glu Thr Glu Leu Pro Pro Glu Thr Thr
            420                 425                 430

Glu Arg Pro Asn Tyr Glu Ser Tyr Ser His Arg Leu Ser His Ile Gly
        435                 440                 445

Ile Ile Leu Gln Ser Arg Val Asn Val Pro Val Tyr Ser Trp Thr His
    450                 455                 460

Arg Ser Ala Asp Arg Thr Asn Thr Ile Gly Pro Asn Arg Ile Thr Gln
465                 470                 475                 480

Ile Pro Met Val Lys Ala Ser Glu Leu Pro Gln Gly Thr Thr Val Val
                485                 490                 495

Arg Gly Pro Gly Phe Thr Gly Gly Asp Ile Leu Arg Arg Thr Asn Thr
            500                 505                 510

Gly Gly Phe Gly Pro Ile Arg Val Thr Val Asn Gly Pro Leu Thr Gln
        515                 520                 525

Arg Tyr Arg Ile Gly Phe Arg Tyr Ala Ser Thr Val Asp Phe Asp Phe
    530                 535                 540

Phe Val Ser Arg Gly Gly Thr Thr Val Asn Asn Phe Arg Phe Leu Arg
545                 550                 555                 560

Thr Met Asn Ser Gly Asp Glu Leu Lys Tyr Gly Asn Phe Val Arg Arg
                565                 570                 575

Ala Phe Thr Thr Pro Phe Thr Phe Thr Gln Ile Gln Asp Ile Ile Arg
            580                 585                 590

Thr Ser Ile Gln Gly Leu Ser Gly Asn Gly Glu Val Tyr Ile Asp Lys
        595                 600                 605

Ile Glu Ile Ile Pro Val Thr Ala Thr Phe Glu Ala Glu Tyr Asp Leu
    610                 615                 620

Glu Arg Ala Gln Glu Ala Val Asn Ala Leu Phe Thr Asn Thr Asn Pro
625                 630                 635                 640

Arg Arg Leu Lys Thr Asp Val Thr Asp Tyr His Ile Asp Gln Val Ser
                645                 650                 655

Asn Leu Val Ala Cys Leu Ser Asp Glu Phe Cys Leu Asp Glu Lys Arg
            660                 665                 670

Glu Leu Leu Glu Lys Val Lys Tyr Ala Lys Arg Leu Ser Asp Glu Arg
```

```
        675                 680                 685

Asn Leu Leu Gln Asp Pro Asn Phe Thr Ser Ile Asn Lys Gln Pro Asp
    690                 695                 700

Phe Ile Ser Thr Asn Glu Gln Ser Asn Phe Thr Ser Ile His Glu Gln
705                 710                 715                 720

Ser Glu His Gly Trp Trp Gly Ser Glu Asn Ile Thr Ile Gln Glu Gly
                725                 730                 735

Asn Asp Val Phe Lys Glu Asn Tyr Val Thr Leu Pro Gly Thr Phe Asn
            740                 745                 750

Glu Cys Tyr Pro Thr Tyr Leu Tyr Gln Lys Ile Gly Glu Ser Glu Leu
        755                 760                 765

Lys Ala Tyr Thr Arg Tyr Gln Leu Arg Gly Tyr Ile Glu Asp Ser Gln
    770                 775                 780

Asp Leu Glu Ile Tyr Leu Ile Arg Tyr Asn Ala Lys Pro Glu Thr Leu
785                 790                 795                 800

Asp Val Pro Gly Thr Glu Ser Leu Trp Pro Leu Ser Val Glu Ser Pro
                805                 810                 815

Ile Gly Arg Cys Gly Glu Pro Asn Arg Cys Ala Pro His Phe Glu Trp
            820                 825                 830

Asn Pro Asp Leu Asp Cys Ser Cys Arg Asp Gly Glu Lys Cys Ala His
        835                 840                 845

His Ser His His Phe Ser Leu Asp Ile Asp Val Gly Cys Thr Asp Leu
    850                 855                 860

His Glu Asn Leu Gly Val Trp Val Val Phe Lys Ile Lys Thr Gln Glu
865                 870                 875                 880

Gly His Ala Arg Leu Gly Asn Leu Glu Phe Ile Glu Glu Lys Pro Leu
                885                 890                 895

Leu Gly Glu Ala Leu Ser Arg Val Lys Arg Ala Glu Lys Lys Trp Arg
            900                 905                 910

Asp Lys Arg Glu Lys Leu Gln Leu Glu Thr Lys Arg Val Tyr Thr Glu
        915                 920                 925

Ala Lys Glu Ala Val Asp Ala Leu Phe Val Asp Ser Gln Tyr Asp Arg
    930                 935                 940

Leu Gln Ala Asp Thr Asn Ile Gly Met Ile His Ala Ala Asp Lys Leu
945                 950                 955                 960

Val His Arg Ile Arg Glu Ala Tyr Leu Ser Glu Leu Pro Val Ile Pro
                965                 970                 975

Gly Val Asn Ala Glu Ile Phe Glu Glu Leu Glu Gly His Ile Ile Thr
            980                 985                 990

Ala Ile Ser Leu Tyr Asp Ala Arg  Asn Val Val Lys Asn  Gly Asp Phe
        995                 1000                1005

Asn Asn  Gly Leu Thr Cys Trp  Asn Val Lys Gly His  Val Asp Val
    1010                1015                1020

Gln Gln  Ser His His Arg Ser  Asp Leu Val Ile Pro  Glu Trp Glu
    1025                1030                1035

Ala Glu  Val Ser Gln Ala Val  Arg Val Cys Pro Gly  Cys Gly Tyr
    1040                1045                1050

Ile Leu  Arg Val Thr Ala Tyr  Lys Glu Gly Tyr Gly  Glu Gly Cys
    1055                1060                1065

Val Thr  Ile His Glu Ile Glu  Asn Asn Thr Asp Glu  Leu Lys Phe
    1070                1075                1080

Lys Asn  Arg Glu Glu Glu Glu  Val Tyr Pro Thr Asp  Thr Gly Thr
    1085                1090                1095
```

```
Cys Asn  Asp Tyr Thr Ala His  Gln Gly Thr Ala Gly  Cys Ala Asp
    1100                 1105                 1110

Ala Cys  Asn Ser Arg Asn Ala  Gly Tyr Glu Asp Ala  Tyr Glu Val
    1115                 1120                 1125

Asp Thr  Thr Ala Ser Val Asn  Tyr Lys Pro Thr Tyr  Glu Glu Glu
    1130                 1135                 1140

Thr Tyr  Thr Asp Val Arg Arg  Asp Asn His Cys Glu  Tyr Asp Arg
    1145                 1150                 1155

Gly Tyr  Val Asn Tyr Pro Pro  Val Pro Ala Gly Tyr  Val Thr Lys
    1160                 1165                 1170

Glu Leu  Glu Tyr Phe Pro Glu  Thr Asp Thr Val Trp  Ile Glu Ile
    1175                 1180                 1185

Gly Glu  Thr Glu Gly Lys Phe  Ile Val Asp Ser Val  Glu Leu Leu
    1190                 1195                 1200

Leu Met  Glu Glu
    1205


<210> SEQ ID NO 71
<211> LENGTH: 1133
<212> TYPE: PRT
<213> ORGANISM: Bacillus thuringiensis

<400> SEQUENCE: 71

Met Glu His Val Glu Gln Leu Val Arg Gln Gln Ile Thr Asp Ser Val
1               5                   10                  15

Arg Asp Thr Ala Ile Ala Arg Leu Glu Gly Leu Gly Arg Gly Tyr Arg
            20                  25                  30

Ser Tyr Gln Gln Ala Leu Glu Thr Trp Leu Asp Asn Arg Asn Asp Ala
        35                  40                  45

Arg Ser Arg Ser Ile Ile Leu Glu Arg Tyr Ile Ala Leu Glu Leu Asp
    50                  55                  60

Ile Thr Thr Ala Ile Pro Leu Phe Ser Ile Arg Asn Gln Glu Val Pro
65                  70                  75                  80

Leu Leu Met Val Tyr Ala Gln Ala Ala Asn Leu His Leu Leu Leu Leu
                85                  90                  95

Arg Asp Ala Ser Leu Phe Gly Ser Glu Trp Gly Met Ser Ser Ala Asp
            100                 105                 110

Val Asn Gln Tyr Tyr Gln Glu Gln Ile Arg Tyr Thr Glu Glu Tyr Ser
        115                 120                 125

Asn His Cys Val Gln Trp Tyr Asn Thr Gly Leu Asn Asn Leu Arg Gly
    130                 135                 140

Thr Asn Ala Glu Ser Trp Val Arg Tyr Asn Gln Phe Arg Arg Asp Leu
145                 150                 155                 160

Thr Leu Gly Val Leu Asp Leu Val Ala Leu Phe Pro Ser Tyr Asp Thr
                165                 170                 175

Arg Thr Tyr Pro Ile Asn Thr Ser Ala Gln Leu Thr Arg Glu Val Tyr
            180                 185                 190

Thr Asp Ala Ile Gly Ala Thr Gly Val Asn Met Ala Asn Met Asn Trp
        195                 200                 205

Tyr Asn Asn Asn Ala Pro Ser Phe Ser Ala Ile Glu Ala Ala Val Ile
    210                 215                 220

Arg Ser Pro His Leu Leu Asp Phe Leu Glu Gln Leu Thr Ile Phe Ser
225                 230                 235                 240

Ala Ser Ser Arg Trp Ser Asn Thr Arg His Met Thr Tyr Trp Arg Gly
```

-continued

```
                245                 250                 255

His Thr Ile Gln Ser Arg Pro Ile Gly Gly Gly Leu Asn Thr Ser Thr
            260                 265                 270

Tyr Gly Ser Thr Asn Thr Ser Ile Asn Pro Val Thr Leu Arg Phe Thr
        275                 280                 285

Ser Arg Asp Val Tyr Arg Thr Glu Ser Trp Ala Gly Val Leu Leu Trp
    290                 295                 300

Gly Ile Tyr Leu Glu Pro Ile His Gly Val Pro Thr Val Arg Phe Asn
305                 310                 315                 320

Phe Thr Asn Pro Gln Asn Ile Tyr Asp Arg Gly Thr Ala Asn Tyr Ser
                325                 330                 335

Gln Pro Tyr Glu Ser Pro Gly Leu Gln Leu Lys Asp Ser Glu Thr Glu
            340                 345                 350

Leu Pro Pro Glu Thr Thr Glu Arg Pro Asn Tyr Glu Ser Tyr Ser His
        355                 360                 365

Arg Leu Ser His Ile Gly Ile Ile Leu Gln Ser Arg Val Asn Val Pro
    370                 375                 380

Val Tyr Ser Trp Thr His Arg Ser Ala Asp Arg Thr Asn Thr Ile Gly
385                 390                 395                 400

Pro Asn Arg Ile Thr Gln Ile Pro Met Val Lys Ala Ser Glu Leu Pro
                405                 410                 415

Gln Gly Thr Thr Val Val Arg Gly Pro Gly Phe Thr Gly Gly Asp Ile
            420                 425                 430

Leu Arg Arg Thr Asn Thr Gly Gly Phe Gly Pro Ile Arg Val Thr Val
        435                 440                 445

Asn Gly Pro Leu Thr Gln Arg Tyr Arg Ile Gly Phe Arg Tyr Ala Ser
    450                 455                 460

Thr Val Asp Phe Asp Phe Phe Val Ser Arg Gly Gly Thr Thr Val Asn
465                 470                 475                 480

Asn Phe Arg Phe Leu Arg Thr Met Asn Ser Gly Asp Glu Leu Lys Tyr
                485                 490                 495

Gly Asn Phe Val Arg Arg Ala Phe Thr Thr Pro Phe Thr Phe Thr Gln
            500                 505                 510

Ile Gln Asp Ile Ile Arg Thr Ser Ile Gln Gly Leu Ser Gly Asn Gly
        515                 520                 525

Glu Val Tyr Ile Asp Lys Ile Glu Ile Ile Pro Val Thr Ala Thr Phe
    530                 535                 540

Glu Ala Glu Tyr Asp Leu Glu Arg Ala Gln Glu Ala Val Asn Ala Leu
545                 550                 555                 560

Phe Thr Asn Thr Asn Pro Arg Arg Leu Lys Thr Asp Val Thr Asp Tyr
                565                 570                 575

His Ile Asp Gln Val Ser Asn Leu Val Ala Cys Leu Ser Asp Glu Phe
            580                 585                 590

Cys Leu Asp Glu Lys Arg Glu Leu Leu Glu Lys Val Lys Tyr Ala Lys
        595                 600                 605

Arg Leu Ser Asp Glu Arg Asn Leu Leu Gln Asp Pro Asn Phe Thr Ser
    610                 615                 620

Ile Asn Lys Gln Pro Asp Phe Ile Ser Thr Asn Glu Gln Ser Asn Phe
625                 630                 635                 640

Thr Ser Ile His Glu Gln Ser Glu His Gly Trp Trp Gly Ser Glu Asn
                645                 650                 655

Ile Thr Ile Gln Glu Gly Asn Asp Val Phe Lys Glu Asn Tyr Val Thr
            660                 665                 670
```

-continued

```
Leu Pro Gly Thr Phe Asn Glu Cys Tyr Pro Thr Tyr Leu Tyr Gln Lys
        675                 680                 685

Ile Gly Glu Ser Glu Leu Lys Ala Tyr Thr Arg Tyr Gln Leu Arg Gly
    690                 695                 700

Tyr Ile Glu Asp Ser Gln Asp Leu Glu Ile Tyr Leu Ile Arg Tyr Asn
705                 710                 715                 720

Ala Lys Pro Glu Thr Leu Asp Val Pro Gly Thr Glu Ser Leu Trp Pro
                725                 730                 735

Leu Ser Val Glu Ser Pro Ile Gly Arg Cys Gly Glu Pro Asn Arg Cys
            740                 745                 750

Ala Pro His Phe Glu Trp Asn Pro Asp Leu Asp Cys Ser Cys Arg Asp
        755                 760                 765

Gly Glu Lys Cys Ala His His Ser His His Phe Ser Leu Asp Ile Asp
    770                 775                 780

Val Gly Cys Thr Asp Leu His Glu Asn Leu Gly Val Trp Val Val Phe
785                 790                 795                 800

Lys Ile Lys Thr Gln Glu Gly His Ala Arg Leu Gly Asn Leu Glu Phe
                805                 810                 815

Ile Glu Glu Lys Pro Leu Leu Gly Glu Ala Leu Ser Arg Val Lys Arg
            820                 825                 830

Ala Glu Lys Lys Trp Arg Asp Lys Arg Glu Lys Leu Gln Leu Glu Thr
        835                 840                 845

Lys Arg Val Tyr Thr Glu Ala Lys Glu Ala Val Asp Ala Leu Phe Val
    850                 855                 860

Asp Ser Gln Tyr Asp Arg Leu Gln Ala Asp Thr Asn Ile Gly Met Ile
865                 870                 875                 880

His Ala Ala Asp Lys Leu Val His Arg Ile Arg Glu Ala Tyr Leu Ser
                885                 890                 895

Glu Leu Pro Val Ile Pro Gly Val Asn Ala Glu Ile Phe Glu Glu Leu
            900                 905                 910

Glu Gly His Ile Ile Thr Ala Ile Ser Leu Tyr Asp Ala Arg Asn Val
        915                 920                 925

Val Lys Asn Gly Asp Phe Asn Asn Gly Leu Thr Cys Trp Asn Val Lys
    930                 935                 940

Gly His Val Asp Val Gln Gln Ser His His Arg Ser Asp Leu Val Ile
945                 950                 955                 960

Pro Glu Trp Glu Ala Glu Val Ser Gln Ala Val Arg Val Cys Pro Gly
                965                 970                 975

Cys Gly Tyr Ile Leu Arg Val Thr Ala Tyr Lys Glu Gly Tyr Gly Glu
            980                 985                 990

Gly Cys Val Thr Ile His Glu Ile  Glu Asn Asn Thr Asp  Glu Leu Lys
        995                 1000                1005

Phe Lys  Asn Arg Glu Glu Glu  Glu Val Tyr Pro Thr  Asp Thr Gly
    1010                1015                1020

Thr Cys  Asn Asp Tyr Thr Ala  His Gln Gly Thr Ala  Gly Cys Ala
    1025                1030                1035

Asp Ala  Cys Asn Ser Arg Asn  Ala Gly Tyr Glu Asp  Ala Tyr Glu
    1040                1045                1050

Val Asp  Thr Thr Ala Ser Val  Asn Tyr Lys Pro Thr  Tyr Glu Glu
    1055                1060                1065

Glu Thr  Tyr Thr Asp Val Arg  Arg Asp Asn His Cys  Glu Tyr Asp
    1070                1075                1080
```

-continued

```
Arg Gly  Tyr Val Asn Tyr Pro  Pro Val Pro Ala Gly  Tyr Val Thr
    1085                1090                1095

Lys Glu  Leu Glu Tyr Phe Pro  Glu Thr Asp Thr Val  Trp Ile Glu
    1100                1105                1110

Ile Gly  Glu Thr Glu Gly Lys  Phe Ile Val Asp Ser  Val Glu Leu
    1115                1120                1125

Leu Leu  Met Glu Glu
    1130


<210> SEQ ID NO 72
<211> LENGTH: 640
<212> TYPE: PRT
<213> ORGANISM: Bacillus thuringiensis

<400> SEQUENCE: 72

Met Thr Ser Asn Arg Lys Asn Glu Asn Glu Ile Ile Asn Ala Leu Ser
1               5                   10                  15

Ile Pro Ala Val Ser Asn His Ser Ala Gln Met Asp Leu Ser Pro Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Leu Ala Ser
65                  70                  75                  80

Phe Tyr Ser Phe Leu Val Gly Glu Leu Trp Pro Ser Gly Arg Asp Pro
                85                  90                  95

Trp Glu Ile Phe Met Glu His Val Glu Gln Leu Val Arg Gln Gln Ile
            100                 105                 110

Thr Asp Ser Val Arg Asp Thr Ala Ile Ala Arg Leu Glu Gly Leu Gly
        115                 120                 125

Arg Gly Tyr Arg Ser Tyr Gln Gln Ala Leu Glu Thr Trp Leu Asp Asn
    130                 135                 140

Arg Asn Asp Ala Arg Ser Arg Ser Ile Ile Leu Glu Arg Tyr Ile Ala
145                 150                 155                 160

Leu Glu Leu Asp Ile Thr Thr Ala Ile Pro Leu Phe Ser Ile Arg Asn
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Trp Gly Met
        195                 200                 205

Ser Ser Ala Asp Val Asn Gln Tyr Tyr Gln Glu Gln Ile Arg Tyr Thr
    210                 215                 220

Glu Glu Tyr Ser Asn His Cys Val Gln Trp Tyr Asn Thr Gly Leu Asn
225                 230                 235                 240

Asn Leu Arg Gly Thr Asn Ala Glu Ser Trp Val Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Thr Tyr Pro Ile Asn Thr Ser Ala Gln Leu Thr
        275                 280                 285

Arg Glu Val Tyr Thr Asp Ala Ile Gly Ala Thr Gly Val Asn Met Ala
    290                 295                 300

Asn Met Asn Trp Tyr Asn Asn Asn Ala Pro Ser Phe Ser Ala Ile Glu
305                 310                 315                 320
```

```
Ala Ala Val Ile Arg Ser Pro His Leu Leu Asp Phe Leu Glu Gln Leu
                325                 330                 335

Thr Ile Phe Ser Ala Ser Ser Arg Trp Ser Asn Thr Arg His Met Thr
            340                 345                 350

Tyr Trp Arg Gly His Thr Ile Gln Ser Arg Pro Ile Gly Gly Gly Leu
        355                 360                 365

Asn Thr Ser Thr Tyr Gly Ser Thr Asn Thr Ser Ile Asn Pro Val Thr
    370                 375                 380

Leu Arg Phe Thr Ser Arg Asp Val Tyr Arg Thr Glu Ser Trp Ala Gly
385                 390                 395                 400

Val Leu Leu Trp Gly Ile Tyr Leu Glu Pro Ile His Gly Val Pro Thr
                405                 410                 415

Val Arg Phe Asn Phe Thr Asn Pro Gln Asn Ile Tyr Asp Arg Gly Thr
            420                 425                 430

Ala Asn Tyr Ser Gln Pro Tyr Glu Ser Pro Gly Leu Gln Leu Lys Asp
        435                 440                 445

Ser Glu Thr Glu Leu Pro Pro Glu Thr Thr Glu Arg Pro Asn Tyr Glu
    450                 455                 460

Ser Tyr Ser His Arg Leu Ser His Ile Gly Ile Ile Leu Gln Ser Arg
465                 470                 475                 480

Val Asn Val Pro Val Tyr Ser Trp Thr His Arg Ser Ala Asp Arg Thr
                485                 490                 495

Asn Thr Ile Gly Pro Asn Arg Ile Thr Gln Ile Pro Met Val Lys Ala
            500                 505                 510

Ser Glu Leu Pro Gln Gly Thr Thr Val Val Arg Gly Pro Gly Phe Thr
        515                 520                 525

Gly Gly Asp Ile Leu Arg Arg Thr Asn Thr Gly Gly Phe Gly Pro Ile
    530                 535                 540

Arg Val Thr Val Asn Gly Pro Leu Thr Gln Arg Tyr Arg Ile Gly Phe
545                 550                 555                 560

Arg Tyr Ala Ser Thr Val Asp Phe Asp Phe Phe Val Ser Arg Gly Gly
                565                 570                 575

Thr Thr Val Asn Asn Phe Arg Phe Leu Arg Thr Met Asn Ser Gly Asp
            580                 585                 590

Glu Leu Lys Tyr Gly Asn Phe Val Arg Arg Ala Phe Thr Thr Pro Phe
        595                 600                 605

Thr Phe Thr Gln Ile Gln Asp Ile Ile Arg Thr Ser Ile Gln Gly Leu
    610                 615                 620

Ser Gly Asn Gly Glu Val Tyr Ile Asp Lys Ile Glu Ile Ile Pro Val
625                 630                 635                 640
```

<210> SEQ ID NO 73
<211> LENGTH: 614
<212> TYPE: PRT
<213> ORGANISM: Bacillus thuringiensis

<400> SEQUENCE: 73

```
Met Asp Leu Ser Pro Asp Ala Arg Ile Glu Asp Ser Leu Cys Ile Ala
1               5                   10                  15

Glu Gly Asn Asn Ile Asp Pro Phe Val Ser Ala Ser Thr Val Gln Thr
            20                  25                  30

Gly Ile Asn Ile Ala Gly Arg Ile Leu Gly Val Leu Gly Val Pro Phe
        35                  40                  45

Ala Gly Gln Leu Ala Ser Phe Tyr Ser Phe Leu Val Gly Glu Leu Trp
```

-continued

```
    50                  55                  60

Pro Ser Gly Arg Asp Pro Trp Glu Ile Phe Met Glu His Val Glu Gln
65                  70                  75                  80

Leu Val Arg Gln Gln Ile Thr Asp Ser Val Arg Asp Thr Ala Ile Ala
                85                  90                  95

Arg Leu Glu Gly Leu Gly Arg Gly Tyr Arg Ser Tyr Gln Gln Ala Leu
            100                 105                 110

Glu Thr Trp Leu Asp Asn Arg Asn Asp Ala Arg Ser Arg Ser Ile Ile
        115                 120                 125

Leu Glu Arg Tyr Ile Ala Leu Glu Leu Asp Ile Thr Thr Ala Ile Pro
    130                 135                 140

Leu Phe Ser Ile Arg Asn Gln Glu Val Pro Leu Leu Met Val Tyr Ala
145                 150                 155                 160

Gln Ala Ala Asn Leu His Leu Leu Leu Leu Arg Asp Ala Ser Leu Phe
                165                 170                 175

Gly Ser Glu Trp Gly Met Ser Ser Ala Asp Val Asn Gln Tyr Tyr Gln
            180                 185                 190

Glu Gln Ile Arg Tyr Thr Glu Glu Tyr Ser Asn His Cys Val Gln Trp
        195                 200                 205

Tyr Asn Thr Gly Leu Asn Asn Leu Arg Gly Thr Asn Ala Glu Ser Trp
    210                 215                 220

Val Arg Tyr Asn Gln Phe Arg Arg Asp Leu Thr Leu Gly Val Leu Asp
225                 230                 235                 240

Leu Val Ala Leu Phe Pro Ser Tyr Asp Thr Arg Thr Tyr Pro Ile Asn
                245                 250                 255

Thr Ser Ala Gln Leu Thr Arg Glu Val Tyr Thr Asp Ala Ile Gly Ala
            260                 265                 270

Thr Gly Val Asn Met Ala Asn Met Asn Trp Tyr Asn Asn Asn Ala Pro
        275                 280                 285

Ser Phe Ser Ala Ile Glu Ala Ala Val Ile Arg Ser Pro His Leu Leu
    290                 295                 300

Asp Phe Leu Glu Gln Leu Thr Ile Phe Ser Ala Ser Ser Arg Trp Ser
305                 310                 315                 320

Asn Thr Arg His Met Thr Tyr Trp Arg Gly His Thr Ile Gln Ser Arg
                325                 330                 335

Pro Ile Gly Gly Gly Leu Asn Thr Ser Thr Tyr Gly Ser Thr Asn Thr
            340                 345                 350

Ser Ile Asn Pro Val Thr Leu Arg Phe Thr Ser Arg Asp Val Tyr Arg
        355                 360                 365

Thr Glu Ser Trp Ala Gly Val Leu Leu Trp Gly Ile Tyr Leu Glu Pro
    370                 375                 380

Ile His Gly Val Pro Thr Val Arg Phe Asn Phe Thr Asn Pro Gln Asn
385                 390                 395                 400

Ile Tyr Asp Arg Gly Thr Ala Asn Tyr Ser Gln Pro Tyr Glu Ser Pro
                405                 410                 415

Gly Leu Gln Leu Lys Asp Ser Glu Thr Glu Leu Pro Pro Glu Thr Thr
            420                 425                 430

Glu Arg Pro Asn Tyr Glu Ser Tyr Ser His Arg Leu Ser His Ile Gly
        435                 440                 445

Ile Ile Leu Gln Ser Arg Val Asn Val Pro Val Tyr Ser Trp Thr His
    450                 455                 460

Arg Ser Ala Asp Arg Thr Asn Thr Ile Gly Pro Asn Arg Ile Thr Gln
465                 470                 475                 480
```

```
Ile Pro Met Val Lys Ala Ser Glu Leu Pro Gln Gly Thr Thr Val Val
                485                 490                 495

Arg Gly Pro Gly Phe Thr Gly Gly Asp Ile Leu Arg Arg Thr Asn Thr
            500                 505                 510

Gly Gly Phe Gly Pro Ile Arg Val Thr Val Asn Gly Pro Leu Thr Gln
        515                 520                 525

Arg Tyr Arg Ile Gly Phe Arg Tyr Ala Ser Thr Val Asp Phe Asp Phe
    530                 535                 540

Phe Val Ser Arg Gly Gly Thr Thr Val Asn Asn Phe Arg Phe Leu Arg
545                 550                 555                 560

Thr Met Asn Ser Gly Asp Glu Leu Lys Tyr Gly Asn Phe Val Arg Arg
                565                 570                 575

Ala Phe Thr Thr Pro Phe Thr Phe Thr Gln Ile Gln Asp Ile Ile Arg
            580                 585                 590

Thr Ser Ile Gln Gly Leu Ser Gly Asn Gly Glu Val Tyr Ile Asp Lys
        595                 600                 605

Ile Glu Ile Ile Pro Val
    610


<210> SEQ ID NO 74
<211> LENGTH: 540
<212> TYPE: PRT
<213> ORGANISM: Bacillus thuringiensis

<400> SEQUENCE: 74

Met Glu His Val Glu Gln Leu Val Arg Gln Gln Ile Thr Asp Ser Val
1               5                   10                  15

Arg Asp Thr Ala Ile Ala Arg Leu Glu Gly Leu Gly Arg Gly Tyr Arg
            20                  25                  30

Ser Tyr Gln Gln Ala Leu Glu Thr Trp Leu Asp Asn Arg Asn Asp Ala
        35                  40                  45

Arg Ser Arg Ser Ile Ile Leu Glu Arg Tyr Ile Ala Leu Glu Leu Asp
    50                  55                  60

Ile Thr Thr Ala Ile Pro Leu Phe Ser Ile Arg Asn Gln Glu Val Pro
65                  70                  75                  80

Leu Leu Met Val Tyr Ala Gln Ala Ala Asn Leu His Leu Leu Leu Leu
                85                  90                  95

Arg Asp Ala Ser Leu Phe Gly Ser Glu Trp Gly Met Ser Ser Ala Asp
            100                 105                 110

Val Asn Gln Tyr Tyr Gln Glu Gln Ile Arg Tyr Thr Glu Glu Tyr Ser
        115                 120                 125

Asn His Cys Val Gln Trp Tyr Asn Thr Gly Leu Asn Asn Leu Arg Gly
    130                 135                 140

Thr Asn Ala Glu Ser Trp Val Arg Tyr Asn Gln Phe Arg Arg Asp Leu
145                 150                 155                 160

Thr Leu Gly Val Leu Asp Leu Val Ala Leu Phe Pro Ser Tyr Asp Thr
                165                 170                 175

Arg Thr Tyr Pro Ile Asn Thr Ser Ala Gln Leu Thr Arg Glu Val Tyr
            180                 185                 190

Thr Asp Ala Ile Gly Ala Thr Gly Val Asn Met Ala Asn Met Asn Trp
        195                 200                 205

Tyr Asn Asn Asn Ala Pro Ser Phe Ser Ala Ile Glu Ala Ala Val Ile
    210                 215                 220

Arg Ser Pro His Leu Leu Asp Phe Leu Glu Gln Leu Thr Ile Phe Ser
```

-continued

```
225                 230                 235                 240

Ala Ser Ser Arg Trp Ser Asn Thr Arg His Met Thr Tyr Trp Arg Gly
                245                 250                 255

His Thr Ile Gln Ser Arg Pro Ile Gly Gly Gly Leu Asn Thr Ser Thr
            260                 265                 270

Tyr Gly Ser Thr Asn Thr Ser Ile Asn Pro Val Thr Leu Arg Phe Thr
        275                 280                 285

Ser Arg Asp Val Tyr Arg Thr Glu Ser Trp Ala Gly Val Leu Leu Trp
    290                 295                 300

Gly Ile Tyr Leu Glu Pro Ile His Gly Val Pro Thr Val Arg Phe Asn
305                 310                 315                 320

Phe Thr Asn Pro Gln Asn Ile Tyr Asp Arg Gly Thr Ala Asn Tyr Ser
                325                 330                 335

Gln Pro Tyr Glu Ser Pro Gly Leu Gln Leu Lys Asp Ser Glu Thr Glu
            340                 345                 350

Leu Pro Pro Glu Thr Thr Glu Arg Pro Asn Tyr Glu Ser Tyr Ser His
        355                 360                 365

Arg Leu Ser His Ile Gly Ile Ile Leu Gln Ser Arg Val Asn Val Pro
    370                 375                 380

Val Tyr Ser Trp Thr His Arg Ser Ala Asp Arg Thr Asn Thr Ile Gly
385                 390                 395                 400

Pro Asn Arg Ile Thr Gln Ile Pro Met Val Lys Ala Ser Glu Leu Pro
                405                 410                 415

Gln Gly Thr Thr Val Val Arg Gly Pro Gly Phe Thr Gly Gly Asp Ile
            420                 425                 430

Leu Arg Arg Thr Asn Thr Gly Gly Phe Gly Pro Ile Arg Val Thr Val
        435                 440                 445

Asn Gly Pro Leu Thr Gln Arg Tyr Arg Ile Gly Phe Arg Tyr Ala Ser
    450                 455                 460

Thr Val Asp Phe Asp Phe Phe Val Ser Arg Gly Gly Thr Thr Val Asn
465                 470                 475                 480

Asn Phe Arg Phe Leu Arg Thr Met Asn Ser Gly Asp Glu Leu Lys Tyr
                485                 490                 495

Gly Asn Phe Val Arg Arg Ala Phe Thr Thr Pro Phe Thr Phe Thr Gln
            500                 505                 510

Ile Gln Asp Ile Ile Arg Thr Ser Ile Gln Gly Leu Ser Gly Asn Gly
        515                 520                 525

Glu Val Tyr Ile Asp Lys Ile Glu Ile Ile Pro Val
    530                 535                 540


<210> SEQ ID NO 75
<211> LENGTH: 4
<212> TYPE: PRT
<213> ORGANISM: Artificial
<220> FEATURE:
<223> OTHER INFORMATION: endoplasmic reticulum targeting peptide

<400> SEQUENCE: 75

Lys Asp Glu Leu
1
```